United States Patent
Shelton, IV et al.

(10) Patent No.: US 11,529,187 B2
(45) Date of Patent: Dec. 20, 2022

(54) SURGICAL EVACUATION SENSOR ARRANGEMENTS

(71) Applicant: Cilag GmbH International, Zug (CH)

(72) Inventors: Frederick E. Shelton, IV, Hillsboro, OH (US); David C. Yates, Morrow, OH (US); Jason L. Harris, Lebanon, OH (US); Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 79 days.

(21) Appl. No.: 16/024,096

(22) Filed: Jun. 29, 2018

(65) Prior Publication Data

US 2019/0201083 A1    Jul. 4, 2019

Related U.S. Application Data

(60) Provisional application No. 62/691,219, filed on Jun. 28, 2018, provisional application No. 62/650,882, (Continued)

(51) Int. Cl.
*A61B 18/14* (2006.01)
*A61B 17/32* (2006.01)
(Continued)

(52) U.S. Cl.
CPC .... *A61B 18/1477* (2013.01); *A61B 17/07207* (2013.01); *A61B 17/320068* (2013.01); (Continued)

(58) Field of Classification Search
CPC ............ A61B 18/1477; A61B 18/1402; A61B 17/320068; A61B 2018/00607; A61B 2217/005; A61B 2018/00642; A61B 2018/00702; A61B 2018/00666; A61B 2018/0063; A61B 2017/07285; A61B 2017/00199; A61B 17/072; A61B 2017/320074; A61B 2017/32007; A61B 34/35; A61B 2218/008;
(Continued)

(56) References Cited

U.S. PATENT DOCUMENTS 1,853,416 A    4/1932    Hall
2,222,125 A    11/1940   Stehlik
(Continued)

FOREIGN PATENT DOCUMENTS

AU    2015201140 A1    3/2015
CA    2795323 A1    5/2014
(Continued)

OTHER PUBLICATIONS

US 10,504,709 B2, 12/2019, Karancsi et al. (withdrawn)
(Continued)

*Primary Examiner* — Lauren P Farrar
*Assistant Examiner* — Hamza A Darb

(57) ABSTRACT

Surgical systems can include evacuation systems for evacuating smoke, fluid, and/or particulates from a surgical site. A surgical evacuation system can be intelligent and may include one or more sensors for detecting one or more properties of the surgical system, evacuation system, surgical procedure, surgical site, and/or patient tissue, for example.

21 Claims, 54 Drawing Sheets

Related U.S. Application Data filed on Mar. 30, 2018, provisional application No. 62/650,877, filed on Mar. 30, 2018, provisional application No. 62/650,898, filed on Mar. 30, 2018, provisional application No. 62/650,887, filed on Mar. 30, 2018, provisional application No. 62/640,417, filed on Mar. 8, 2018, provisional application No. 62/640,415, filed on Mar. 8, 2018, provisional application No. 62/611,341, filed on Dec. 28, 2017, provisional application No. 62/611,340, filed on Dec. 28, 2017, provisional application No. 62/611,339, filed on Dec. 28, 2017.

(51) Int. Cl.

| | | |
|---|---|---|
| *G05B 19/042* | (2006.01) | |
| *G16H 40/63* | (2018.01) | |
| *A61B 18/00* | (2006.01) | |
| *A61B 90/00* | (2016.01) | |
| *A61B 17/072* | (2006.01) | |
| *A61M 1/00* | (2006.01) | |
| *A61B 17/29* | (2006.01) | |
| *A61B 18/12* | (2006.01) | |
| *A61B 34/35* | (2016.01) | |
| *A61B 34/37* | (2016.01) | |
| *A61B 34/20* | (2016.01) | |
| *A61B 17/00* | (2006.01) | |
| *A61N 7/02* | (2006.01) | |

(52) U.S. Cl.
CPC .......... *A61M 1/74* (2021.05); *G05B 19/0428* (2013.01); *G16H 40/63* (2018.01); *A61B 17/072* (2013.01); *A61B 17/29* (2013.01); *A61B 18/1206* (2013.01); *A61B 18/14* (2013.01); *A61B 18/1442* (2013.01); *A61B 34/35* (2016.02); *A61B 34/37* (2016.02); *A61B 90/37* (2016.02); *A61B 2017/00017* (2013.01); *A61B 2017/00022* (2013.01); *A61B 2017/00026* (2013.01); *A61B 2017/00084* (2013.01); *A61B 2017/00199* (2013.01); *A61B 2017/00221* (2013.01); *A61B 2017/00398* (2013.01); *A61B 2017/00734* (2013.01); *A61B 2017/07257* (2013.01); *A61B 2017/07271* (2013.01); *A61B 2017/07285* (2013.01); *A61B 2017/2927* (2013.01); *A61B 2017/32007* (2017.08); *A61B 2017/320074* (2017.08); *A61B 2018/0063* (2013.01); *A61B 2018/00589* (2013.01); *A61B 2018/00595* (2013.01); *A61B 2018/00601* (2013.01); *A61B 2018/00648* (2013.01); *A61B 2018/00702* (2013.01); *A61B 2018/00791* (2013.01); *A61B 2034/2059* (2016.02); *A61B 2090/064* (2016.02); *A61B 2090/066* (2016.02); *A61B 2090/364* (2016.02); *A61B 2217/005* (2013.01); *A61B 2218/007* (2013.01); *A61B 2218/008* (2013.01); *A61M 1/784* (2021.05); *A61N 7/02* (2013.01)

(58) Field of Classification Search
CPC .......... A61B 2018/00601; A61B 2018/00595; A61B 2018/00589; A61B 5/367; A61B 5/0215; A61B 5/7285; A61B 5/7425; A61B 5/0538; A61B 5/341; A61B 5/055; A61B 5/343; A61B 6/503; A61B 5/366; A61B 6/032; A61B 18/14; A61B 5/349; A61B 2034/2048; A61B 2034/105; A61B 2090/376; A61B 2562/0219; G16H 40/63; G06T 7/0012; G06T 17/20; G06T 2210/41; G06T 2207/10072; G06T 2207/30048; A61N 1/365

See application file for complete search history.

(56) References Cited

U.S. PATENT DOCUMENTS

| | | | |
|---|---|---|---|
| 3,082,426 A | 3/1963 | Miles | |
| 3,503,396 A | 3/1970 | Pierie et al. | |
| 3,584,628 A | 6/1971 | Green | |
| 3,626,457 A | 12/1971 | Duerr et al. | |
| 3,633,584 A | 1/1972 | Farrell | |
| 3,759,017 A | 9/1973 | Young | |
| 3,863,118 A | 1/1975 | Lander et al. | |
| 3,898,545 A | 8/1975 | Coppa et al. | |
| 3,912,121 A | 10/1975 | Steffen | |
| 3,915,271 A | 10/1975 | Harper | |
| 3,932,812 A | 1/1976 | Milligan | |
| 4,041,362 A | 8/1977 | Ichiyanagi | |
| 4,052,649 A | 10/1977 | Greenwell et al. | |
| 4,087,730 A | 5/1978 | Goles | |
| 4,157,859 A | 6/1979 | Terry | |
| 4,171,700 A | 10/1979 | Farin | |
| 4,202,722 A | 5/1980 | Paquin | |
| 4,412,539 A | 11/1983 | Jarvik | |
| 4,448,193 A | 5/1984 | Ivanov | |
| 4,523,695 A | 6/1985 | Braun et al. | |
| 4,608,160 A | 8/1986 | Zoch | |
| 4,614,366 A | 9/1986 | North et al. | |
| 4,633,874 A | 1/1987 | Chow et al. | |
| 4,701,193 A * | 10/1987 | Robertson | A61M 1/0066 55/385.1 |
| 4,735,603 A | 4/1988 | Goodson et al. | |
| 4,788,977 A | 12/1988 | Farin et al. | |
| 4,849,752 A | 7/1989 | Bryant | |
| D303,787 S | 10/1989 | Messenger et al. | |
| 4,892,244 A | 1/1990 | Fox et al. | |
| 4,976,173 A | 12/1990 | Yang | |
| 5,010,341 A | 4/1991 | Huntley et al. | |
| 5,026,387 A | 6/1991 | Thomas | |
| 5,035,692 A | 7/1991 | Lyon et al. | |
| 5,042,460 A | 8/1991 | Sakurai et al. | |
| 5,047,043 A | 9/1991 | Kubota et al. | |
| 5,084,057 A | 1/1992 | Green et al. | |
| 5,100,402 A | 3/1992 | Fan | |
| D327,061 S | 6/1992 | Soren et al. | |
| 5,129,570 A | 7/1992 | Schulze et al. | |
| 5,151,102 A | 9/1992 | Kamiyama et al. | |
| 5,156,315 A | 10/1992 | Green et al. | |
| 5,158,585 A | 10/1992 | Saho et al. | |
| 5,171,247 A | 12/1992 | Hughett et al. | |
| 5,189,277 A | 2/1993 | Boisvert et al. | |
| 5,197,962 A | 3/1993 | Sansom et al. | |
| 5,204,669 A | 4/1993 | Dorfe et al. | |
| 5,242,474 A | 9/1993 | Herbst et al. | |
| 5,253,793 A | 10/1993 | Green et al. | |
| 5,271,543 A | 12/1993 | Grant et al. | |
| RE34,519 E | 1/1994 | Fox et al. | |
| 5,275,323 A | 1/1994 | Schulze et al. | |
| 5,318,516 A | 6/1994 | Cosmescu | |
| 5,318,563 A | 6/1994 | Malis et al. | |
| 5,322,055 A | 6/1994 | Davison et al. | |
| 5,342,349 A | 8/1994 | Kaufman | |
| 5,364,003 A | 11/1994 | Williamson, IV | |
| 5,383,880 A | 1/1995 | Hooven | |
| 5,385,544 A | 1/1995 | Edwards et al. | |
| 5,396,900 A | 3/1995 | Slater et al. | |
| 5,397,046 A | 3/1995 | Savage et al. | |
| 5,403,312 A | 4/1995 | Yates et al. | |
| 5,403,327 A | 4/1995 | Thornton et al. | |
| 5,413,267 A | 5/1995 | Solyntjes et al. | |
| 5,415,335 A | 5/1995 | Knodell, Jr. | |
| 5,417,699 A | 5/1995 | Klein et al. | |
| 5,439,468 A | 8/1995 | Schulze et al. | |
| 5,445,304 A | 8/1995 | Plyley et al. | |
| 5,462,545 A | 10/1995 | Wang et al. | |
| 5,465,895 A | 11/1995 | Knodel et al. | |

(56) References Cited

U.S. PATENT DOCUMENTS

| | | |
|---|---|---|
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A * | 10/1999 | Sleister ............... A61B 18/00 604/35 |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 * | 5/2002 | Bodden ............... A61B 18/00 55/DIG. 34 |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |

(56) References Cited

U.S. PATENT DOCUMENTS

| | | |
|---|---|---|
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B2 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |

(56) References Cited

U.S. PATENT DOCUMENTS

| | | |
|---|---|---|
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,468,030 B2 | 6/2013 | Stroup et al. |
| 8,469,973 B2 | 6/2013 | Meade et al. |
| 8,472,630 B2 | 6/2013 | Konrad et al. |
| D687,146 S | 7/2013 | Juzkiw et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |

(56) References Cited

U.S. PATENT DOCUMENTS

| | | |
|---|---|---|
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Frisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Ke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |

(56) References Cited

U.S. PATENT DOCUMENTS

| | | |
|---|---|---|
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Durie |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquln et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |

(56) References Cited

U.S. PATENT DOCUMENTS

| | | |
|---|---|---|
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Res et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zerglebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |

(56) References Cited

U.S. PATENT DOCUMENTS

| | | |
|---|---|---|
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderon! |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |

(56) References Cited

U.S. PATENT DOCUMENTS

| | | |
|---|---|---|
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Wiliams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,413 B2 | 12/2019 | Schepis et al. |

(56) References Cited

U.S. PATENT DOCUMENTS

| | | |
|---|---|---|
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,134 B2 | 6/2020 | Barral et al. |
| 10,716,489 B2 | 7/2020 | Kalvoy et al. |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,751,052 B2 | 8/2020 | Stokes et al. |
| D896,379 S | 9/2020 | Shelton, IV et al. |
| 10,772,630 B2 | 9/2020 | Wixey |
| 10,772,673 B2 | 9/2020 | Allen, IV et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,806,499 B2 | 10/2020 | Castaneda et al. |
| 10,835,247 B2 | 11/2020 | Shelton, IV et al. |
| 10,842,897 B2 | 11/2020 | Schwartz et al. |
| D904,612 S | 12/2020 | Wynn et al. |
| 10,856,768 B2 | 12/2020 | Osadchy et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,446 B2 | 1/2021 | Strobl |
| 10,898,256 B2 | 1/2021 | Yates et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,916,415 B2 | 2/2021 | Karancsi et al. |
| D914,878 S | 3/2021 | Shelton, IV et al. |
| 10,932,784 B2 | 3/2021 | Mozdzierz et al. |
| 10,950,982 B2 | 3/2021 | Regnier et al. |
| 11,000,276 B2 | 5/2021 | Shelton, IV et al. |
| 11,051,817 B2 | 7/2021 | Shelton, IV et al. |
| 11,058,501 B2 | 7/2021 | Tokarchuk et al. |
| 11,071,595 B2 | 7/2021 | Johnson et al. |
| 11,185,325 B2 | 11/2021 | Shelton, IV et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2003/0009111 A1 | 1/2003 | Cory et al. |
| 2003/0018329 A1 | 1/2003 | Hooven |
| 2003/0046109 A1 | 3/2003 | Uchikubo |

(56) References Cited

U.S. PATENT DOCUMENTS

| | | |
|---|---|---|
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1* | 12/2003 | Anstine ............... F04D 27/004 417/18 |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0100867 A1 | 5/2005 | Hilscher et al. |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0156017 A1 | 7/2007 | Lamprecht et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1* | 6/2010 | Duclos ............... F01N 3/0253 60/286 |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2011/0022032 A1 | 1/2011 | Zemlok et al. |
| 2011/0036890 A1 | 2/2011 | Ma |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0112569 A1 | 5/2011 | Friedman et al. |
| 2011/0118708 A1 | 5/2011 | Burbank et al. |

(56) References Cited

U.S. PATENT DOCUMENTS

| | | |
|---|---|---|
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1 | 10/2011 | Faller et al. |
| 2011/0264000 A1 | 10/2011 | Paul et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0105552 A1 | 5/2013 | Weir et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R et al. |
| 2014/0121669 A1 | 5/2014 | Claus |
| 2014/0148729 A1 | 5/2014 | Schmitz et al. |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171923 A1 | 6/2014 | Aranyi |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0303660 A1 | 10/2014 | Boyden et al. |
| 2014/0303990 A1 | 10/2014 | Schoenefeld et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0057675 A1 | 2/2015 | Akeel et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0108198 A1 | 4/2015 | Estrella et al. |
| 2015/0122870 A1 | 5/2015 | Zemlok et al. |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |

(56) References Cited

U.S. PATENT DOCUMENTS

| | | |
|---|---|---|
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2015/0374369 A1 | 12/2015 | Yates et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0113653 A1 | 4/2016 | Zingman |
| 2016/0121143 A1 | 5/2016 | Mumaw et al. |
| 2016/0157717 A1 | 6/2016 | Gaster |
| 2016/0158468 A1* | 6/2016 | Tang .................. A61B 17/3474 604/26 |
| 2016/0166256 A1 | 6/2016 | Baxter, III et al. |
| 2016/0174998 A1 | 6/2016 | Lal et al. |
| 2016/0180045 A1 | 6/2016 | Syed |
| 2016/0184054 A1 | 6/2016 | Lowe |
| 2016/0192960 A1 | 7/2016 | Bueno et al. |
| 2016/0199125 A1 | 7/2016 | Jones |
| 2016/0206202 A1 | 7/2016 | Frangioni |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0253472 A1 | 9/2016 | Pedersen et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310203 A1 | 10/2016 | Gaspredes et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374665 A1 | 12/2016 | DiNardo et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0000554 A1 | 1/2017 | Yates et al. |
| 2017/0020462 A1 | 1/2017 | Brown, III et al. |
| 2017/0027603 A1 | 2/2017 | Pandey |
| 2017/0042604 A1 | 2/2017 | McFarland et al. |
| 2017/0061375 A1 | 3/2017 | Laster et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0151026 A1 | 6/2017 | Panescu et al. |
| 2017/0156076 A1 | 6/2017 | Eom et al. |
| 2017/0156808 A1 | 6/2017 | Auld |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0165725 A1 | 6/2017 | Hersey et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0173262 A1 | 6/2017 | Veltz |
| 2017/0177807 A1 | 6/2017 | Fabian |
| 2017/0181745 A1 | 6/2017 | Penna et al. |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0252095 A1 | 9/2017 | Johnson |
| 2017/0255751 A1 | 9/2017 | Sanmugalingham |
| 2017/0262604 A1 | 9/2017 | Francois |
| 2017/0264644 A1 | 9/2017 | Mihan et al. |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281164 A1 | 10/2017 | Harris et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0290586 A1 | 10/2017 | Wellman |
| 2017/0296169 A1 | 10/2017 | Yates et al. |
| 2017/0296173 A1 | 10/2017 | Shelton, IV et al. |
| 2017/0296177 A1 | 10/2017 | Harris et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325813 A1 | 11/2017 | Aranyi et al. |
| 2017/0325876 A1 | 11/2017 | Nakadate et al. |
| 2017/0325878 A1 | 11/2017 | Messerly et al. |

(56) References Cited

U.S. PATENT DOCUMENTS

| | | |
|---|---|---|
| 2017/0337043 A1 | 11/2017 | Brincat et al. |
| 2017/0354470 A1 | 12/2017 | Farritor et al. |
| 2017/0360358 A1 | 12/2017 | Amiot et al. |
| 2017/0360439 A1 | 12/2017 | Chen et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008260 A1 | 1/2018 | Baxter, III et al. |
| 2018/0008359 A1 | 1/2018 | Randle |
| 2018/0011983 A1 | 1/2018 | Zuhars et al. |
| 2018/0014848 A1 | 1/2018 | Messerly et al. |
| 2018/0042659 A1 | 2/2018 | Rupp et al. |
| 2018/0049817 A1 | 2/2018 | Swayze et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0064498 A1 | 3/2018 | Kapadia et al. |
| 2018/0065248 A1 | 3/2018 | Barral et al. |
| 2018/0078034 A1 | 3/2018 | Savall et al. |
| 2018/0078170 A1 | 3/2018 | Panescu et al. |
| 2018/0097639 A1 | 4/2018 | Gulati et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168600 A1 | 6/2018 | Shelton, IV et al. |
| 2018/0168601 A1 | 6/2018 | Bakos et al. |
| 2018/0168603 A1 | 6/2018 | Morgan et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168632 A1 | 6/2018 | Harris et al. |
| 2018/0168633 A1 | 6/2018 | Shelton, IV et al. |
| 2018/0168639 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0168763 A1 | 6/2018 | Scheib et al. |
| 2018/0177383 A1 | 6/2018 | Noonan et al. |
| 2018/0177557 A1 | 6/2018 | Kapadia et al. |
| 2018/0182475 A1 | 6/2018 | Cossler et al. |
| 2018/0193579 A1 | 7/2018 | Hanrahan et al. |
| 2018/0199995 A1 | 7/2018 | Odermatt et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250080 A1 | 9/2018 | Kopp |
| 2018/0250084 A1 | 9/2018 | Kopp et al. |
| 2018/0250086 A1 | 9/2018 | Grubbs |
| 2018/0263699 A1 | 9/2018 | Murphy et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0310997 A1 | 11/2018 | Peine et al. |
| 2018/0315492 A1 | 11/2018 | Bishop et al. |
| 2018/0317826 A1 | 11/2018 | Muhsin et al. |
| 2018/0317915 A1 | 11/2018 | McDonald, II |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0338806 A1 | 11/2018 | Grubbs |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0358112 A1 | 12/2018 | Sharifi Sedeh et al. |
| 2018/0360449 A1 | 12/2018 | Shelton, IV et al. |
| 2018/0360452 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000465 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0008600 A1 | 1/2019 | Pedros et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |

(56) References Cited

U.S. PATENT DOCUMENTS

| | | |
|---|---|---|
| 2019/0053866 A1 | 2/2019 | Seow et al. |
| 2019/0054620 A1 | 2/2019 | Griffiths et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0090969 A1 | 3/2019 | Jarc et al. |
| 2019/0099180 A1 | 4/2019 | Leimbach et al. |
| 2019/0099221 A1 | 4/2019 | Schmidt et al. |
| 2019/0099227 A1 | 4/2019 | Rockrohr |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125344 A1 | 5/2019 | DiNardo et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125381 A1 | 5/2019 | Scheib et al. |
| 2019/0125382 A1 | 5/2019 | Scheib et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125390 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159777 A1 | 5/2019 | Ehrenfels et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0164285 A1 | 5/2019 | Nye et al. |
| 2019/0167296 A1 | 6/2019 | Tsubuku et al. |
| 2019/0175286 A1 | 6/2019 | Zhou et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201018 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201117 A1 | 7/2019 | Yates et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201122 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |

(56) References Cited

U.S. PATENT DOCUMENTS

| | | |
|---|---|---|
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201593 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |
| 2019/0223291 A1 | 7/2019 | Seow et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cut et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0321157 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054325 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054329 A1 | 2/2020 | Shelton, IV et al. |
| 2020/0054330 A1 | 2/2020 | Harris et al. |
| 2020/0054331 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |

(56) References Cited

U.S. PATENT DOCUMENTS

| | | |
|---|---|---|
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzad et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2509523 A | 7/2014 |
| JP | S5373315 A | 6/1978 |
| JP | 2001029353 A | 2/2001 |
| JP | 2007123394 A | 5/2007 |
| JP | 2010057642 A | 3/2010 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A3 | 11/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and

(56) References Cited

OTHER PUBLICATIONS

Communications Workshops (PERCOM Workshops), IEEE, pp. 479-484, Mar. 13, 2017.
Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.
Yuyi Mao et al., "A Survey on Mobile Edge Computing: The Communication Perspective," IEEE Communications Surveys & Tutorials, pp. 2322-2358, Jun. 13, 2017.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trendbased methods," Computers in Biology and Medic, New York, NY, vol. 27, No. 5, pp. 389-409 (1997).
Stacey et al., "Temporal abstraction in intelligent clinical data analysis: A survey," Artificial Intelligence in Medicine, vol. 39, No. 1, pp. 1-24 (2006).
Zoccali, Bruno, "A Method for Approximating Component Temperatures at Altitude Conditions Based on CFD Analysis at Sea Level Conditions," (white paper), www.tdmginc.com, Decembers, 2018 (9 pages).
Slocinski et al., "Distance measure for impedance spectra for quantified evaluations," Lecture Notes on Impedance Spectroscopy, vol. 3, Taylor and Francis Group (Jul. 2012)—Book Not Attached.
Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Phumzile Malindi, "5. QoS in Telemedicine," "Telemedicine," Jun. 20, 2011, IntechOpen, pp. 119-138.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization% 20And0/o20Removal%200f%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas forTM0n0 operating mode,"Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "ARCM", Video, Sep. 2012, YouTube, 5 screenshots, Retrieved from internet: <https://www.youtube.com/watch?y=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.Mar. 2012 (Revision of IEEE Std 802.Mar. 2008, published Dec. 28, 2012.

(56) References Cited

OTHER PUBLICATIONS

IEEE Std No. 177, "Standard Definitions and Methods of Measurement for Piezoelectric Vibrators," published May 1966, The Institute of Electrical and Electronics Engineers, Inc., New York, N.Y.
Shi et al., An Intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www. cognizant.com/services-resources/150110_IoT_connected_surgical_devices.pdf.
Draijer, Matthijs et al., "Review of laser pseckle contrast techniques for visualizing tissue perfusion," Lasers in Medical Science, Springer-Verlag, LO, vol. 2 4, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column paragraph 3.
"Surgical instrumentation: the true cost of instrument trays and a potential strategy for optimization"; Mhlaba et al.; Sep. 23, 2015 (Year: 2015).

Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

* cited by examiner

SURGICAL EVACUATION SENSOR ARRANGEMENTS

CROSS-REFERENCE TO RELATED APPLICATIONS

This application claims the benefit of priority under 35 U.S.C. § 119(e) to U.S. Provisional Patent Application Ser. No. 62/691,219, titled SURGICAL EVACUATION SENSING AND MOTOR CONTROL, filed Jun. 28, 2018, the disclosure of which is herein incorporated by reference in its entirety.

This application claims the benefit of priority under 35 U.S.C. § 119(e) to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,877, titled SURGICAL SMOKE EVACUATION SENSING AND CONTROLS, filed Mar. 30, 2018, to U.S. Provisional Patent Application Ser. No. 62/650,882, titled SMOKE EVACUATION MODULE FOR INTERACTIVE SURGICAL PLATFORM, filed Mar. 30, 2018, and to U.S. Provisional Patent Application Ser. No. 62/650,898, titled CAPACITIVE COUPLED RETURN PATH PAD WITH SEPARABLE ARRAY ELEMENTS, filed Mar. 30, 2018, the disclosure of each of which is herein incorporated by reference in its entirety.

This application also claims the benefit of priority under 35 U.S.C. § 119(e) to U.S. Provisional Patent Application Ser. No. 62/640,417, titled TEMPERATURE CONTROL IN ULTRASONIC DEVICE AND CONTROL SYSTEM THEREFOR, filed Mar. 8, 2018, and to Provisional Patent Application Ser. No. 62/640,415, titled ESTIMATING STATE OF ULTRASONIC END EFFECTOR AND CONTROL SYSTEM THEREFOR, filed Mar. 8, 2018, the disclosure of each of which is herein incorporated by reference in its entirety.

This application also claims the benefit of priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYTICS, filed Dec. 28, 2017, and to U.S. Provisional Patent Application Ser. No. 62/611,339, titled ROBOT ASSISTED SURGICAL PLATFORM, filed Dec. 28, 2017, the disclosure of each of which is herein incorporated by reference in its entirety.

BACKGROUND

The present invention relates to surgical systems and evacuators thereof. Surgical smoke evacuators are configured to evacuate smoke, as well as fluid and/or particulate, from a surgical site. For example, during a surgical procedure involving an energy device, smoke can be generated at the surgical site.

SUMMARY

In various embodiments, a surgical evacuation system comprises a pump, a motor operably coupled to the pump, a flow path fluidically coupled to the pump, and a sensor system. The sensor system comprises a first pressure sensor and a second pressure sensor. The first pressure sensor is positioned along the flow path. The second pressure sensor is positioned along the flow path upstream of the first pressure sensor. The surgical evacuation system further comprises a control circuit configured to determine a pressure differential between the first pressure sensor and the second pressure sensor. The control circuit is further configured to adjust an operational parameter of the motor based on the pressure differential.

In various embodiments, a surgical evacuation system comprises a pump comprising a motor, a flow path fluidically coupled to the pump, and a sensor system. The sensor system comprises a first pressure sensor and a second pressure sensor. The first pressure sensor is positioned along the flow path to detect a first pressure. The second pressure sensor is positioned along the flow path upstream of the first pressure sensor to detect a second pressure. The surgical evacuation system further comprises a control circuit configured to determine a ratio of the second pressure to the first pressure and determine an operating condition of the surgical evacuation system based on the ratio.

In various embodiments, a non-transitory computer readable medium storing computer readable instructions is disclosed. When executed, the instructions cause a machine to, receive a first signal from a first sensor positioned along a flow path through a surgical evacuation system, receive a second signal from a second sensor positioned along the flow path through the surgical evacuation system, determine an operating condition of the surgical evacuation system based on the first signal and the second signal, and adjust an operational parameter of the surgical evacuation system based on the operating condition.

BRIEF DESCRIPTION OF THE DRAWINGS

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

DETAILED DESCRIPTION

Figure 1:
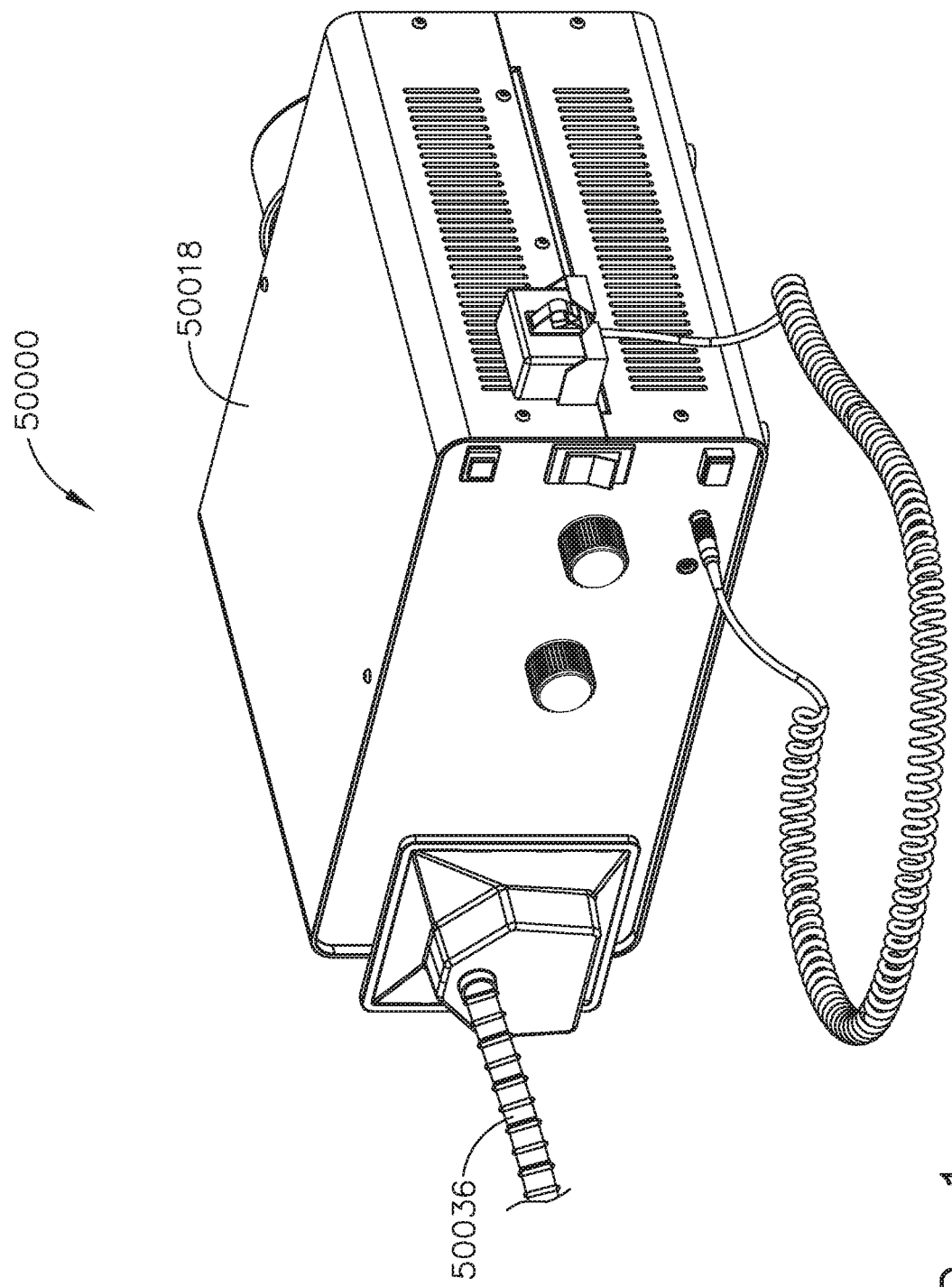
FIG. 1 is perspective view of an evacuator housing for a surgical evacuation system, in accordance with at least one aspect of the present disclosure.

Applicant of the present application owns the following U.S. Patent Applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS, now U.S. Patent Application Publication No. 2019/0201090;

U.S. patent application Ser. No. 16/024,057, titled CONTROLLING A SURGICAL INSTRUMENT ACCORDING TO SENSED CLOSURE PARAMETERS, now U.S. Patent Application Publication No. 2019/0201018;

U.S. patent application Ser. No. 16/024,067, titled SYSTEMS FOR ADJUSTING END EFFECTOR PARAMETERS BASED ON PERIOPERATIVE INFORMATION, now U.S. Pat. No. 10,595,887;

U.S. patent application Ser. No. 16/024,075, titled SAFETY SYSTEMS FOR SMART POWERED SURGICAL STAPLING, now U.S. Patent Application Publication No. 2019/0201146;

U.S. patent application Ser. No. 16/024,083, titled SAFETY SYSTEMS FOR SMART POWERED SURGICAL STAPLING, now U.S. Patent Application Publication No. 2019/0200984;

U.S. patent application Ser. No. 16/024,094, titled SURGICAL SYSTEMS FOR DETECTING END EFFECTOR TISSUE DISTRIBUTION IRREGULARITIES, now U.S. Patent Application Publication No. 2019/0201020;

U.S. patent application Ser. No. 16/024,138, titled SYSTEMS FOR DETECTING PROXIMITY OF SURGICAL END EFFECTOR TO CANCEROUS TISSUE, now U.S. Patent Application Publication No. 2019/0200985;

U.S. patent application Ser. No. 16/024,150, titled SURGICAL INSTRUMENT CARTRIDGE SENSOR ASSEMBLIES, now U.S. Patent Application Publication No. 2019/0200986;

U.S. patent application Ser. No. 16/024,160, titled VARIABLE OUTPUT CARTRIDGE SENSOR ASSEMBLY, now U.S. Patent Application Publication No. 2019/0200987;

U.S. patent application Ser. No. 16/024,124, titled SURGICAL INSTRUMENT HAVING A FLEXIBLE ELECTRODE, No. 2019/0201079;

U.S. patent application Ser. No. 16/024,132, titled SURGICAL INSTRUMENT HAVING A FLEXIBLE CIRCUIT, now U.S. Patent Application Publication No. 2019/0201021;

U.S. patent application Ser. No. 16/024,141, titled SURGICAL INSTRUMENT WITH A TISSUE MARKING ASSEMBLY, now U.S. Patent Application Publication No. 2019/0201159;

U.S. patent application Ser. No. 16/024,162, titled SURGICAL SYSTEMS WITH PRIORITIZED DATA TRANSMISSION CAPABILITIES, U.S. Patent Application Publication No. 2019/0200988;

U.S. patent application Ser. No. 16/024,066, titled SURGICAL EVACUATION SENSING AND MOTOR CONTROL, now U.S. Patent Application Publication No. 2019/0201082;

U.S. patent application Ser. No. 16/024,116, titled SURGICAL EVACUATION FLOW PATHS, now U.S. Patent Application Publication No. 2019/0201084;

U.S. patent application Ser. No. 16/024,149, titled SURGICAL EVACUATION SENSING AND GENERATOR CONTROL, now U.S. Patent Application Publication No. 2019/0201085;

U.S. patent application Ser. No. 16/024,180, titled SURGICAL EVACUATION SENSING AND DISPLAY, now U.S. Patent Application Publication No. 2019/0201086;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, now U.S. Patent Application Publication No. 2019/0201593;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM, now U.S. Patent Application Publication No. 2019/0201087;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE, now U.S. Patent Application Publication No. 2019/0201088; and U.S. patent application Ser. No. 16/024,273, titled DUAL IN-SERIES LARGE AND SMALL DROPLET FILTERS, now U.S. Patent Application Publication No. 2019/0201597.

Applicant of the present application owns the following U.S. Provisional Patent Applications, filed on Jun. 28, 2018, the disclosure of each of which is herein incorporated by reference in its entirety:

U.S. Provisional Patent Application Ser. No. 62/691,228, titled A METHOD OF USING REINFORCED FLEX CIRCUITS WITH MULTIPLE SENSORS WITH ELECTROSURGICAL DEVICES;

U.S. Provisional Patent Application Ser. No. 62/691,227, titled CONTROLLING A SURGICAL INSTRUMENT ACCORDING TO SENSED CLOSURE PARAMETERS;

U.S. Provisional Patent Application Ser. No. 62/691,230, titled SURGICAL INSTRUMENT HAVING A FLEXIBLE ELECTRODE;

U.S. Provisional Patent Application Ser. No. 62/691,219, titled SURGICAL EVACUATION SENSING AND MOTOR CONTROL;

U.S. Provisional Patent Application Ser. No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. Provisional Patent Application Ser. No. 62/691,262, titled SURGICAL EVACUATION SYSTEM WITH A COMMUNICATION CIRCUIT FOR COMMUNICATION BETWEEN A FILTER AND A SMOKE EVACUATION DEVICE; and U.S. Provisional Patent Application Ser. No. 62/691,251, titled DUAL IN-SERIES LARGE AND SMALL DROPLET FILTERS.

Applicant of the present application owns the following U.S. Patent Applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY; and U.S. patent application Ser. No. 15/940,742, titled DUAL CMOS ARRAY IMAGING.

Applicant of the present application owns the following U.S. Patent Applications, filed on Mar. 29, 2018, the disclosure of each of which is herein incorporated by reference in its entirety:

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK; and U.S. patent application Ser. No. 15/940,675, titled CLOUD INTERFACE FOR COUPLED SURGICAL DEVICES.

Applicant of the present application owns the following U.S. Patent Applications, filed on Mar. 29, 2018, the disclosure of each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional Patent Applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional Patent Application, filed on Apr. 19, 2018, the disclosure of each of which is herein incorporated by reference in its entirety:

U.S. Provisional Patent Application Ser. No. 62/659,900, titled METHOD OF HUB COMMUNICATION.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Energy Devices and Smoke Evacuation

The present disclosure relates to energy devices and intelligent surgical evacuation systems for evacuating smoke and/or other fluids and/or particulates from a surgical site. Smoke is often generated during a surgical procedure that utilizes one or more energy devices. Energy devices use energy to affect tissue. In an energy device, the energy is supplied by a generator. Energy devices include devices with tissue-contacting electrodes, such as an electrosurgical device having one or more radio frequency (RF) electrodes, and devices with vibrating surfaces, such as an ultrasonic device having an ultrasonic blade. For an electrosurgical device, a generator is configured to generate oscillating electric currents to energize the electrodes. For an ultrasonic device, a generator is configured to generate ultrasonic vibrations to energize the ultrasonic blade. Generators are further described herein.

Ultrasonic energy can be utilized for coagulation and cutting tissue. Ultrasonic energy coagulates and cuts tissue by vibrating an energy-delivery surface (e.g. an ultrasonic blade) in contact with tissue. The ultrasonic blade can be coupled to a waveguide that transmits the vibrational energy from an ultrasonic transducer, which generates mechanical vibrations and is powered by a generator. Vibrating at high frequencies (e.g., 55,500 times per second), the ultrasonic blade generates friction and heat between the blade and the tissue, i.e. at the blade-tissue interface, which denatures the proteins in the tissue to form a sticky coagulum. Pressure exerted on the tissue by the blade surface collapses blood vessels and allows the coagulum to form a hemostatic seal. The precision of cutting and coagulation can be controlled by the clinician's technique and by adjusting the power level, blade edge, tissue traction, and blade pressure, for example.

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, which can desirably minimize patient trauma. The cutting action is typically realized by an end effector, or blade tip, at the distal end of the ultrasonic instrument. The ultrasonic end effector transmits the ultrasonic energy to tissue brought into contact with the end effector. Ultrasonic instruments of this nature can be configured for open surgical use, laparoscopic surgical procedures, or endoscopic surgical procedures, including robotic-assisted procedures, for example.

Electrical energy can also be utilized for coagulation and/or cutting. An electrosurgical device typically includes a handpiece and an instrument having a distally-mounted end effector (e.g., one or more electrodes). The end effector can be positioned against and/or adjacent to the tissue such that electrical current is introduced into the tissue. Electrosurgery is widely-used and offers many advantages including the use of a single surgical instrument for both coagulation and cutting.

The electrode or tip of the electrosurgical device is small at the point of contact with the patient to produce an RF current with a high current density in order to produce a surgical effect of coagulating and/or cutting tissue through cauterization. The return electrode carries the same RF signal back to the electrosurgical generator after it passes through the patient, thus providing a return path for the RF signal.

Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on or against a patient's body. Heat generated by the current flowing through the tissue may form hemostatic seals within the tissue and/or between tissues and, thus, may be particularly useful for sealing blood vessels, for example. The end effector of an electrosurgical device also may include a cutting member that is movable relative to the tissue and the electrodes to transect the tissue.

In application, an electrosurgical device can transmit low frequency RF current through tissue, which causes ionic agitation, or friction (in effect resistive heating), thereby increasing the temperature of the tissue. Because a boundary is created between the affected tissue and the surrounding tissue, clinicians can operate with a high level of precision and control, without sacrificing un-targeted adjacent tissue.

The low operating temperature of RF energy is useful for removing, shrinking, or sculpting soft tissue while simultaneously sealing blood vessels. RF energy can work particularly well on connective tissue, which is primarily comprised of collagen and shrinks when contacted by heat. Other electrosurgical instruments include, without limitation, irreversible and/or reversible electroporation, and/or microwave technologies, among others. The techniques disclosed herein are applicable to ultrasonic, bipolar and/or monopolar RF (electrosurgical), irreversible and/or reversible electroporation, and/or microwave based surgical instruments, among others.

Electrical energy applied by an electrosurgical device can be transmitted to the instrument from a generator. The generator is configured to convert electricity to high frequency waveforms comprised of oscillating electric currents, which are transmitted to the electrodes to affect tissue. The current passes through tissue to fulgurate (a form of coagulation in which a current arc over the tissue creates tissue charring), desiccate (a direct energy application that drives water of the cells), and/or cut (an indirect energy application that vaporizes cellular fluid causing cellular explosions) tissue. The tissue's response to the current is a function of the resistance of the tissue, the current density passing through the tissue, the power output, and the duration of current application. In certain instances, as further described herein, the current waveform can be adjusted to affect a different surgical function and/or accommodate tissue of different properties. For example, different types of tissue—vascular tissue, nerve tissue, muscles, skin, fat and/or bone—can respond differently to the same waveform.

The electrical energy may be in the form of RF energy that may be in a frequency range described in EN 60601-2-2: 2009+A11:2011, Definition 201.3.218—HIGH FREQUENCY. For example, the frequencies in monopolar RF applications are typically restricted to less than 5 MHz to minimize the problems associated with high frequency leakage current. Frequencies above 200 kHz can be typically used for monopolar applications in order to avoid the unwanted stimulation of nerves and muscles that would result from the use of low frequency current.

In bipolar RF applications, the frequency can be almost anything. Lower frequencies may be used for bipolar techniques in certain instances, such as if a risk analysis shows that the possibility of neuromuscular stimulation has been mitigated to an acceptable level. It is generally recognized that 10 mA is the lower threshold of thermal effects on tissue. Higher frequencies may also be used in the case of bipolar techniques.

In certain instances, a generator can be configured to generate an output waveform digitally and provide it to a surgical device such that the surgical device may utilize the waveform for various tissue effects. The generator can be a monopolar generator, a bipolar generator, and/or an ultrasonic generator. For example, a single generator can supply energy to a monopolar device, a bipolar device, an ultrasonic device, or a combination electrosurgery/ultrasonic device. The generator can promote tissue-specific effects via wave-shaping, and/or can drive RF and ultrasonic energy simultaneously and/or sequentially to a single surgical instrument or multiple surgical instruments.

In one instance, a surgical system can include a generator and various surgical instruments usable therewith, including an ultrasonic surgical instrument, an RF electrosurgical instrument, and a combination ultrasonic/RF electrosurgical instrument. The generator can be configurable for use with the various surgical instruments as further described in U.S.

patent application Ser. No. 15/265,279, titled TECHNIQUES FOR OPERATING GENERATOR FOR DIGITALLY GENERATING ELECTRICAL SIGNAL WAVEFORMS AND SURGICAL INSTRUMENTS, filed Sep. 14, 2016, now U.S. Patent Application Publication No. 2017/0086914, which is herein incorporated by reference in its entirety.

As described herein, medical procedures of cutting tissue and/or cauterizing blood vessels are often performed by utilizing RF electrical energy, which is produced by a generator and transmitted to a patient's tissue through an electrode that is operated by a clinician. The electrode delivers an electrical discharge to cellular matter of the patient's body adjacent to the electrode. The discharge causes the cellular matter to heat up in order to cut tissue and/or cauterize blood vessels.

The high temperatures involved in electrosurgery can cause thermal necrosis of the tissue adjacent to the electrode. The longer time at which tissue is exposed to the high temperatures involved with electrosurgery, the more likely it is that the tissue will suffer thermal necrosis. In certain instances, thermal necrosis of the tissue can decrease the speed of cutting the tissue and increase post-operative complications, eschar production, and healing time, as well as increasing incidences of heat damage to the tissue positioned away from the cutting site.

The concentration of the RF energy discharge affects both the efficiency with which the electrode is able to cut tissue and the likelihood of tissue damage away from the cutting site. With a standard electrode geometry, the RF energy tends to be uniformly distributed over a relatively large area adjacent to the intended incision site. A generally uniform distribution of the RF energy discharge increases the likelihood of extraneous charge loss into the surrounding tissue, which may increase the likelihood of unwanted tissue damage in the surrounding tissue.

Typical electrosurgical generators generate various operating frequencies of RF electrical energy and output power levels. The specific operating frequency and power output of a generator varies based upon the particular electrosurgical generator used and the needs of the physician during the electrosurgical procedure. The specific operating frequency and power output levels can be manually adjusted on the generator by a clinician or other operating room personnel. Properly adjusting these various settings requires great knowledge, skill, and attention from the clinician or other personnel. Once the clinician has made the desired adjustments to the various settings on the generator, the generator can maintain those output parameters during electrosurgery. Generally, wave generators used for electrosurgery are adapted to produce RF waves with an output power in the range of 1-300 W in a cut mode and 1-120 W in coagulation mode, and a frequency in the range of 300-600 kHz. Typical wave generators are adapted to maintain the selected settings during the electrosurgery. For example, if the clinician were to set the output power level of the generator to 50 W and then touch the electrode to the patient to perform electrosurgery, the power level of the generator would quickly rise to and be maintained at 50 W. While setting the power level to a specific setting, such as 50 W, will allow the clinician to cut through the patient's tissue, maintaining such a high power level increases the likelihood of thermal necrosis of the patient's tissue.

In some forms, a generator is configured to provide sufficient power to effectively perform electrosurgery in connection with an electrode that increases the concentration of the RF energy discharge, while at the same time limiting unwanted tissue damage, reducing post-operative complications, and facilitating quicker healing. For example, the waveform from the generator can be optimized by a control circuit throughout the surgical procedure. The subject matter claimed herein, however, is not limited to aspects that solve any disadvantages or that operate only in environments such as those described above. Rather, this background is only provided to illustrate one example of a technology area where some aspects described herein may be practiced.

As provided herein, energy devices delivery mechanical and/or electrical energy to target tissue in order to treat the tissue (e.g. to cut the tissue, cauterize blood vessels and/or coagulate the tissue within and/or near the targeted tissue). The cutting, cauterization, and/or coagulation of tissue can result in fluids and/or particulates being released into the air. Such fluids and/or particulates emitted during a surgical procedure can constitute smoke, for example, which can comprise carbon particles and/or other particles suspended in air. In other words, a fluid can comprise smoke and/or other fluidic matter. Approximately 90% of endoscopic and open surgical procedures generate some level of smoke. The smoke can be unpleasant to the olfactory senses of the clinician(s), the assistant(s), and/or the patient(s), may obstruct the clinician(s)'s view of the surgical site, and may be unhealthy to inhale in certain instances. For example, smoke generated during an electrosurgical procedure can contain toxic chemicals including acrolein, acetonitrile, acrylonitrile, acetylene, alkyl benzenes, benzene, butadiene, butene, carbon monoxide, creosols, ethane, ethylene, formaldehyde, free radicals, hydrogen cyanide, isobutene, methane, phenol, polycyclic aromatic hydrocarbons, propene, propylene, pyridene, pyrrole, styrene, toluene, and xylene, as well as dead and live cellular material (including blood fragments), and viruses. Certain material that has been identified in surgical smoke has been identified as known carcinogens. It is estimated that one gram of tissue cauterized during an electrosurgical procedure can be equivalent to the toxins and carcinogens of six unfiltered cigarettes. Additionally, exposure to the smoke released during an electrosurgical procedure has been reported to cause eye and lung irritation to health care workers.

In addition to the toxicity and odors associated with the material in surgical smoke, the size of particulate matter in surgical smoke can be harmful to the respiratory system of the clinician(s), the assistant(s), and/or the patient(s). In certain instances, the particulates can be extremely small. Repeated inhalation of extremely small particulate matter can lead to acute and chronic respiratory conditions in certain instances.

Many electrosurgical systems employ a surgical evacuation system that captures the resultant smoke from a surgical procedure, and directs the captured smoke through a filter and an exhaust port away from the clinician(s) and/or from the patient(s). For example, an evacuation system can be configured to evacuate smoke that is generated during an electrosurgical procedure. The reader will appreciate that such an evacuation system can be referred to as a "smoke evacuation system" though such evacuation systems can be configured to evacuate more than just smoke from a surgical site. Throughout the present disclosure, the "smoke" evacuated by an evacuation system is not limited to just smoke. Rather, the smoke evacuation systems disclosed herein can be used to evacuate a variety of fluids, including liquids, gases, vapors, smoke, steam, or combinations thereon. The fluids can be biologic in origin and/or can be introduced to the surgical site from an external source during a procedure. The fluids can include water, saline, lymph, blood, exudate, and/or pyogenic discharge, for example. Moreover, the fluids can include particulates or other matter (e.g. cellular matter or debris) that is evacuated by the evacuation system. For example, such particulates can be suspended in the fluid.

Evacuation systems often include a pump and a filter. The pump creates suction that draws the smoke into the filter. For example, suction can be configured to draw smoke from the surgical site into a conduit opening, through an evacuation conduit, and into an evacuator housing of the evacuation system. An evacuator housing 50018 for a surgical evacuation system 50000 is shown in FIG. 1. In one aspect of the present disclosure, a pump and a filter are positioned within the evacuator housing 50018. Smoke drawn into the evacuator housing 50018 travels to the filter via a suction conduit 50036, and harmful toxins and offensive smells are filtered out of the smoke as it moves through the filter. The suction conduit can also be referred to as vacuum and/or evacuation conduit and/or tube, for example. Filtered air may then exit the surgical evacuation system as exhaust. In certain instances, various evacuation systems disclosed herein can also be configured to deliver fluids to a desired location, such as a surgical site.

Figure 2:
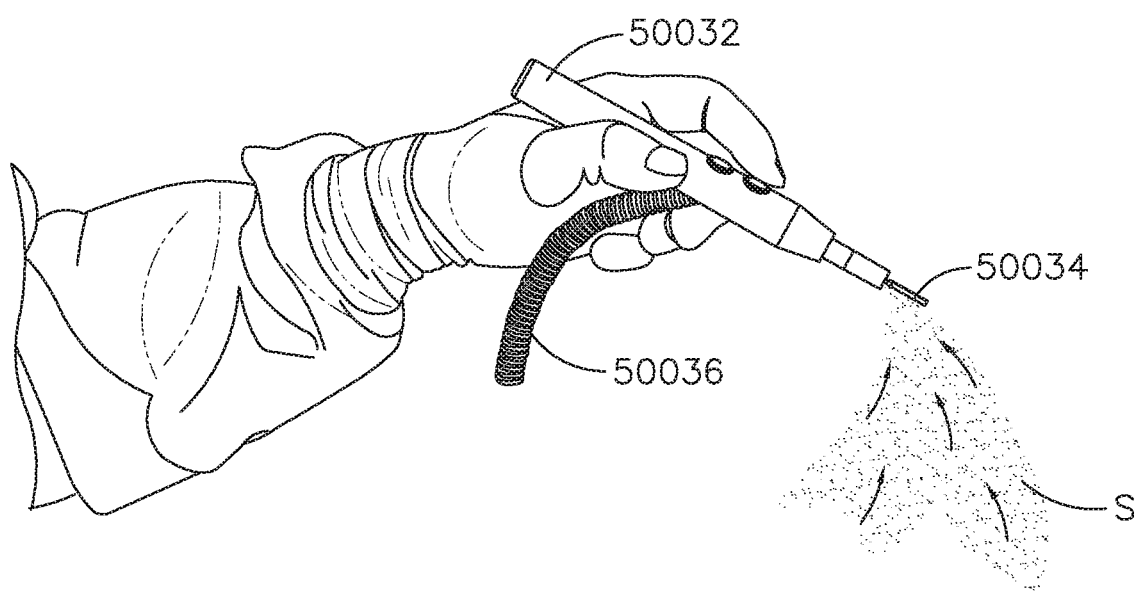
FIG. 2 is a perspective view of a surgical evacuation electrosurgical tool, in accordance with at least one aspect of the present disclosure.

Referring now to FIG. 2, the suction conduit 50036 from the evacuator housing 50018 (FIG. 1) may terminate at a hand piece, such as the handpiece 50032. The handpiece 50032 comprises an electrosurgical instrument that includes an electrode tip 50034 and an evacuation conduit opening near and/or adjacent to the electrode tip 50034. The evacuation conduit opening is configured to capture the fluid and/or particulates that are released during a surgical procedure. In such an instance, the evacuation system 50000 is integrated into the electrosurgical instrument 50032. Referring still to FIG. 2, smoke S is being pulled into the suction conduit 50036.

Figure 3:
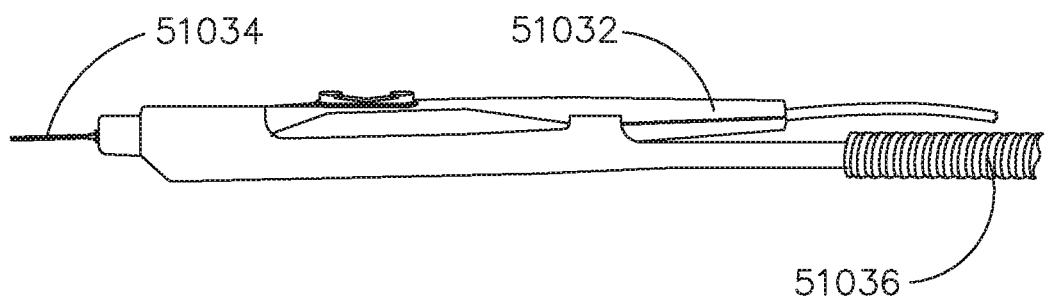
FIG. 3 is an elevation view of a surgical evacuation tool releasably secured to an electrosurgical pencil, in accordance with at least one aspect of the present disclosure.

In certain instances, the evacuation system 50000 can include a separate surgical tool that comprises a conduit opening and is configured to suck the smoke out into the system. In still other instances, a tool comprising the evacuation conduit and opening can be snap fit onto an electrosurgical tool as depicted in FIG. 3. For example, a portion of a suction conduit 51036 can be positioned around (or adjacent to) an electrode tip 51034. In one instance, the suction conduit 51036 can be releasably secured to a handpiece 51032 of an electrosurgical tool comprising the electrode tip 51034 with clips or other fasteners.

Figure 4:
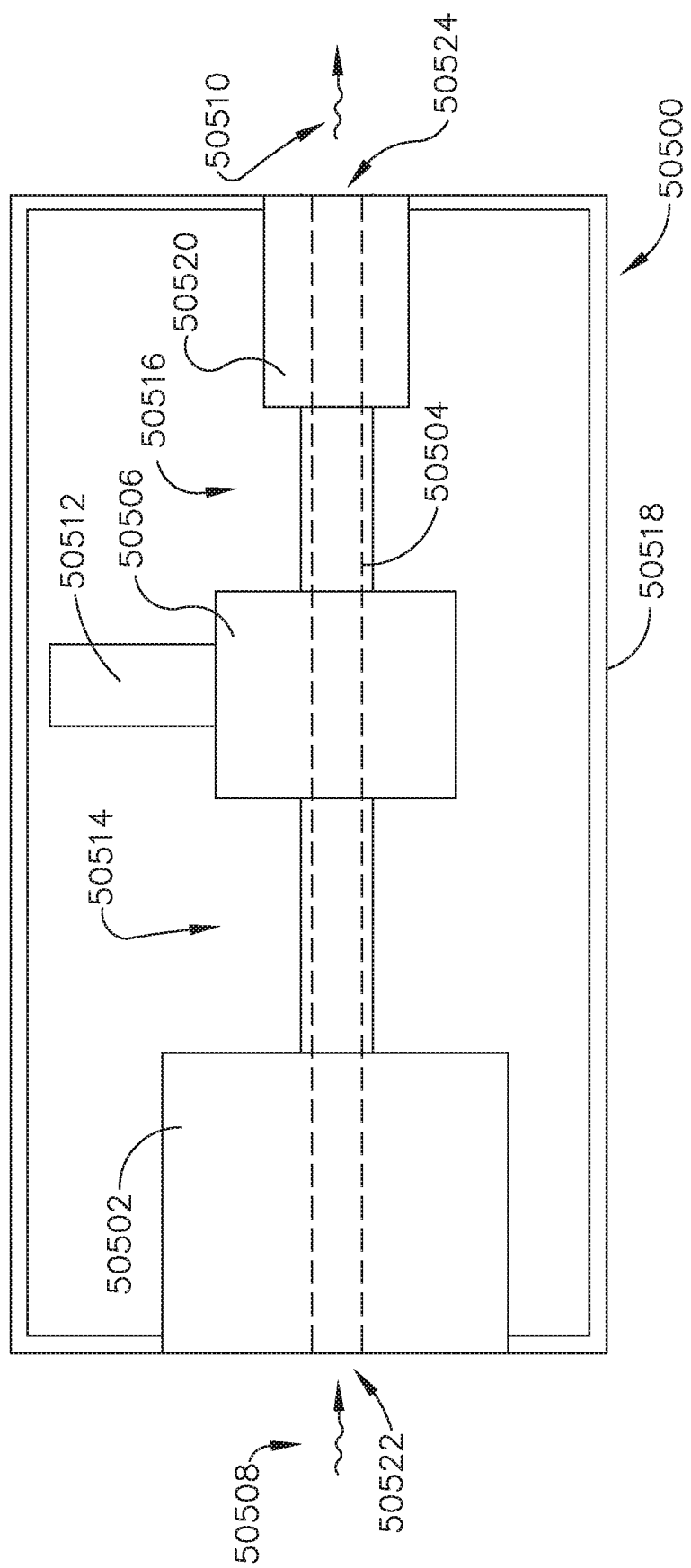
FIG. 4 is a schematic depicting internal components within an evacuator housing for a surgical evacuation system, in accordance with at least one aspect of the present disclosure.

Various internal components of an evacuator housing 50518 are shown in FIG. 4. In various instances, the internal components in FIG. 4 can also be incorporated into the evacuator housing 50018 of FIG. 1. Referring primarily to FIG. 4, an evacuation system 50500 includes the evacuator housing 50518, a filter 50502, an exhaust mechanism 50520, and a pump 50506. The evacuation system 50500 defines a flow path 50504 through the evacuator housing 50518 having an inlet port 50522 and an outlet port 50524. The filter 50502, the exhaust mechanism 50520, and the pump 50506 are sequentially arranged in-line with the flow path 50504 through the evacuator housing 50518 between the inlet port 50522 and the outlet port 50524. The inlet port 50522 can be fluidically coupled to a suction conduit, such as the suction conduit 50036 in FIG. 1, for example, which can comprise a distal conduit opening positionable at the surgical site.

The pump 50506 is configured to produce a pressure differential in the flow path 50504 by a mechanical action. The pressure differential is configured to draw smoke 50508 from the surgical site into the inlet port 50522 and along the flow path 50504. After the smoke 50508 has moved through the filter 50502, the smoke 50508 can be considered to be filtered smoke, or air, 50510, which can continue through the flow path 50504 and is expelled through the outlet port 50524. The flow path 50504 includes a first zone 50514 and a second zone 50516. The first zone 50514 is upstream from the pump 50506; the second zone 50516 is downstream from the pump 50506. The pump 50506 is configured to pressurize the fluid in the flow path 50504 so that the fluid in the second zone 50516 has a higher pressure than the fluid in the first zone 50514. A motor 50512 drives the pump 50506. Various suitable motors are further described herein. The exhaust mechanism 50520 is a mechanism that can control the velocity, the direction, and/or other properties of the filtered smoke 50510 exiting the evacuation system 50500 at the outlet port 50524.

The flow path 50504 through the evacuation system 50500 can be comprised of a tube or other conduit that substantially contains and/or isolates the fluid moving through the flow path 50504 from the fluid outside the flow path 50504. For example, the first zone 50514 of the flow path 50504 can comprise a tube through which the flow path 50504 extends between the filter 50502 and the pump 50506. The second zone 50516 of the flow path 50504 can also comprise a tube through which the flow path 50504 extends between the pump 50506 and the exhaust mechanism 50520. The flow path 50504 also extends through the filter 50502, the pump 50506, and the exhaust mechanism 50520 so that the flow path 50504 extends continuously from the inlet port 50522 to the outlet port 50524.

In operation, the smoke 50508 can flow into the filter 50502 at the inlet port 50522 and can be pumped through the flow path 50504 by the pump 50506 such that the smoke 50508 is drawn into the filter 50502. The filtered smoke 50510 can then be pumped through the exhaust mechanism 50520 and out the outlet port 50524 of the evacuation system 50500. The filtered smoke 50510 exiting the evacuation system 50500 at the outlet port 50524 is the exhaust, and can consist of filtered gases that have passed through the evacuation system 50500.

Figure 41:
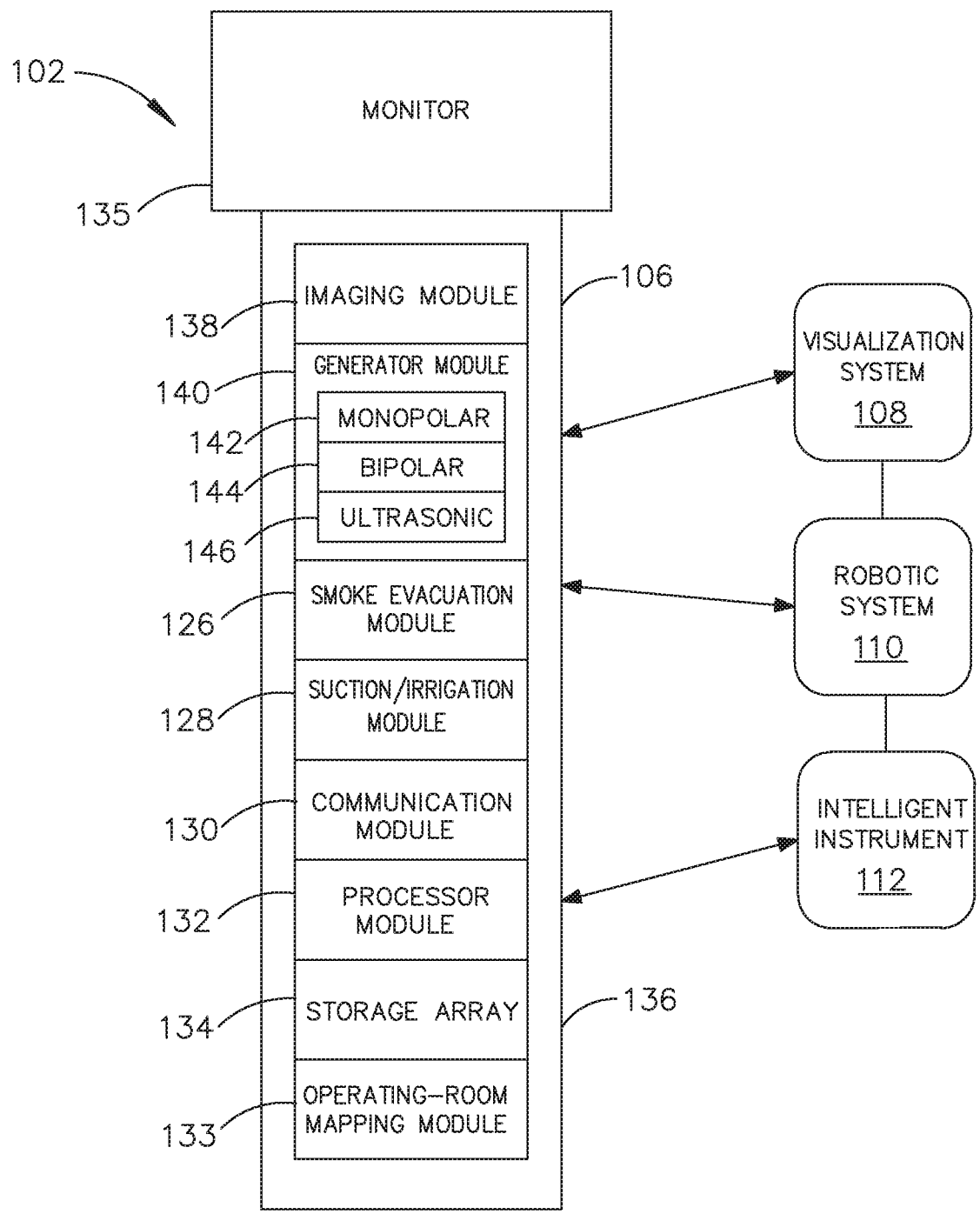
FIG. 41 is a surgical hub paired with a visualization system, a robotic system, and an intelligent instrument, in accordance with at least one aspect of the present disclosure.

In various instances, the evacuation systems disclosed herein (e.g. the evacuation system 50000 and the evacuation system 50500) can be incorporated into a computer-implemented interactive surgical system, such as the system 100 (FIG. 39) or the system 200 (FIG. 47), for example. In one aspect of the present disclosure, for example, the computer-implemented surgical system 100 can include at least one hub 106 and a cloud 104. Referring primarily to FIG. 41, the hub 106 includes a smoke evacuation module 126. Operation of the smoke evacuation module 126 can be controlled by the hub 106 based on its situational awareness and/or feedback from the components thereof and/or based on information from the cloud 104. The computer-implemented surgical systems 100 and 200, as well as situational awareness therefor, are further described herein.

Situational awareness encompasses the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g. a smoke evacuation system) that are connected to it and provide contextualized information or suggestions to the clinician during the course of the surgical procedure. Situational awareness is further described herein and in U.S.

Provisional Patent Application Ser. No. 62/611,341, entitled INTERACTIVE SURGICAL PLATFORM, filed Dec. 28, 2017, which is incorporated by reference herein in its entirety.

Figure 5:
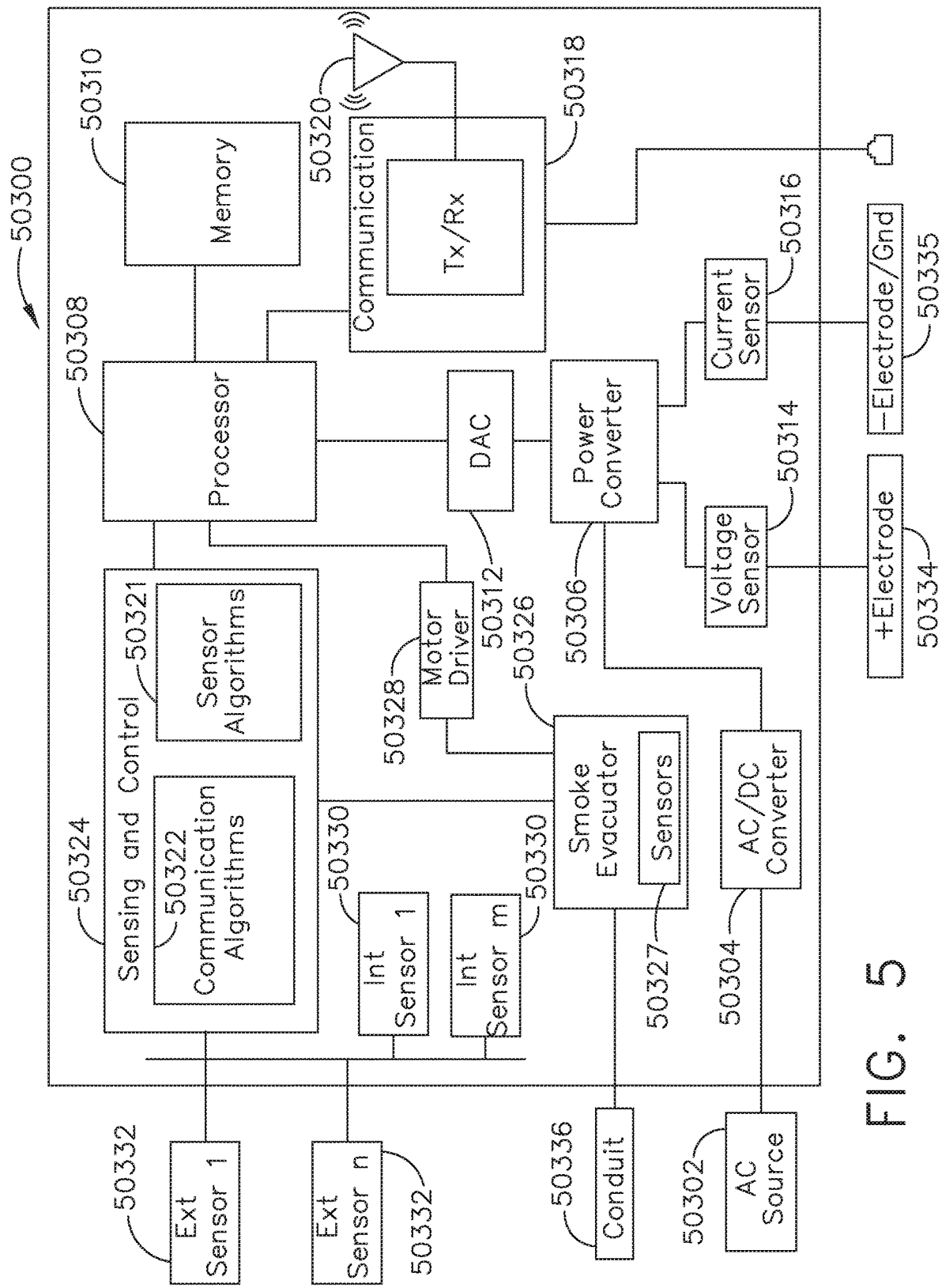
FIG. 5 is a schematic of an electrosurgical system including a smoke evacuator, in accordance with at least one aspect of the present disclosure.

In various instances, the surgical systems and/or evacuation systems disclosed herein can include a processor. The processor can be programmed to control one or more operational parameters of the surgical system and/or the evacuation system based on sensed and/or aggregated data and/or one or more user inputs, for example. FIG. 5 is a schematic representation of an electrosurgical system 50300 including a processor 50308. The electrosurgical system 50300 is powered by an AC source 50302, which provides either 120 V or 240 V alternating current. The voltage supplied by the AC source 50302 is directed to an AC/DC converter 50304, which converts the 120 V or 240 V of alternating current to 360 V of direct current. The 360 V of direct current is then directed to a power converter 50306 (e.g., a buck converter). The power converter 50306 is a step-down DC to DC converter. The power converter 50306 is adapted to step-down the incoming 360 V to a desired level within a range between 0-150 V.

The processor 50308 can be programmed to regulate various aspects, functions, and parameters of the electrosurgical system 50300. For instance, the processor 50308 can determine the desired output power level at an electrode tip 50334, which can be similar in many respects to the electrode tip 50034 in FIG. 2 and/or the electrode tip 51034 in FIG. 3, for example, and direct the power converter 50306 to step-down the voltage to a specified level so as to provide the desired output power. The processor 50308 is coupled to a memory 50310 configured to store machine executable instructions to operate the electrosurgical system 50300 and/or subsystems thereof.

Connected between the processor 50308 and the power converter 50306 is a digital-to-analog converter ("DAC") 50312. The DAC 50312 is adapted to convert a digital code created by the processor 50308 to an analog signal (current, voltage, or electric charge) which governs the voltage step-down performed by the power converter 50306. Once the power converter 50306 steps-down the 360 V to a level that the processor 50308 has determined will provide the desired output power level, the stepped-down voltage is directed to the electrode tip 50334 to effectuate electrosurgical treatment of a patient's tissue and is then directed to a return or ground electrode 50335. A voltage sensor 50314 and a current sensor 50316 are adapted to detect the voltage and current present in the electrosurgical circuit and communicate the detected parameters to the processor 50308 so that the processor 50308 can determine whether to adjust the output power level. As noted herein, typical wave generators are adapted to maintain the selected settings throughout an electrosurgical procedure. In other instances, the operational parameters of a generator can be optimized during a surgical procedure based on one or more inputs to the processor 5308, such as inputs from a surgical hub, cloud, and/or situational awareness module, for example, as further described herein.

The processor 50308 is coupled to a communication device 50318 to communicate over a network. The communication device includes a transceiver 50320 configured to communicate over physical wires or wirelessly. The communication device 50318 may further include one or more additional transceivers. The transceivers may include, but are not limited to cellular modems, wireless mesh network transceivers, Wi-Fi® transceivers, low power wide area (LPWA) transceivers, and/or near field communications transceivers (NFC). The communication device 50318 may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers 50320 may be configured to receive serial transmit data via respective UARTs from the processor 50308, to modulate the serial transmit data onto an RF carrier to produce a transmit RF signal and to transmit the transmit RF signal via respective antennas. The transceiver(s) are further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth are related to the operating frequency range(s) of the transceiver(s) 50320. Each channel bandwidth is further related to the wireless communication standard and/or protocol with which the transceiver(s) 50320 may comply. In other words, each transceiver 50320 may correspond to an implementation of a selected wireless communication standard and/or protocol, e.g., IEEE 802.11 a/b/g/n for Wi-Fi® and/or IEEE 802.15.4 for wireless mesh networks using Zigbee routing.

The processor 50308 is coupled to a sensing and intelligent controls device 50324 that is coupled to a smoke evacuator 50326. The smoke evacuator 50326 can include one or more sensors 50327, and can also include a pump and a pump motor controlled by a motor driver 50328. The motor driver 50328 is communicatively coupled to the processor 50308 and a pump motor in the smoke evacuator 50326. The sensing and intelligent controls device 50324 includes sensor algorithms 50321 and communication algorithms 50322 that facilitate communication between the smoke evacuator 50326 and other devices to adapt their control programs. The sensing and intelligent controls device 50324 is configured to evaluate extracted fluids, particulates, and gases via an evacuation conduit 50336 to improve smoke extraction efficiency and/or reduce device smoke output, for example, as further described herein. In certain instances, the sensing and intelligent controls device 50324 is communicatively coupled to one or more sensors 50327 in the smoke evacuator 50326, one or more internal sensors 50330 and/or one or more external sensors 50332 of the electrosurgical system 50300.

In certain instances, a processor can be located within an evacuator housing of a surgical evacuation system. For example, referring to FIG. 6, a processor 50408 and a memory 50410 therefor are positioned within an evacuator housing 50440 of a surgical evacuation system 50400. The processor 50408 is in signal communication with a motor driver 50428, various internal sensors 50430, a display 50442, the memory 50410, and a communication device 50418. The communication device 50418 is similar in many respects to the communication device 50318 described above with respect to FIG. 5. The communication device 50418 can allow the processor 50408 in the surgical evacuation system 50400 to communicate with other devices within a surgical system. For example, the communication device 50418 can allow wired and/or wireless communication to one or more external sensors 50432, one or more surgical devices 50444, one or more hubs 50448, one or more clouds 50446, and/or one or more additional surgical systems and/or tools. The reader will readily appreciate that the surgical evacuation system 50400 of FIG. 6 can be incorporated into the electrosurgical system 50300 of FIG. 5 in certain instances. The surgical evacuation system 50400 also includes a pump 50450, including a pump motor 50451 thereof, an evacuation conduit 50436, and an exhaust 50452. Various pumps, evacuation conduits and exhausts are further described herein. The surgical evacuation system 50400 can also include a sensing and intelligent controls device, which can be similar in many respects to the sensing and intelligent controls device 50324, for example. For example, such a sensing and intelligent controls device can be in signal communication with the processor 50408 and/or one or more of the sensors 50430 and/or external sensors 50432.

The electrosurgical system 50300 (FIG. 5) and/or the surgical evacuation system 50400 (FIG. 6) can be programmed to monitor one or more parameters of a surgical system and can affect a surgical function based on one or more algorithms stored in a memory in signal communication with the processor 50308 and/or 50408. Various exemplary aspects disclosed herein can be implemented by such algorithms, for example.

In one aspect of the present disclosure, a processor and sensor system, such as the processors 50308 and 50408 and respective sensor systems in communication therewith (FIGS. 5 and 6), are configured to sense the airflow through a vacuum source in order to adjust parameters of the smoke evacuation system and/or external devices and/or systems that are used in tandem with the smoke evacuation system, such as an electrosurgical system, energy device, and/or generator, for example. In one aspect of the present disclosure, the sensor system may include multiple sensors positioned along the airflow path of the surgical evacuation system. The sensors can measure a pressure differential within the evacuation system, in order to detect a state or status of the system between the sensors. For example, the system between two sensors can be a filter, and the pressure differential can be used to increase the speed of the pump motor as flow through the filter is reduced, in order to maintain a flow rate through the system. As another example, the system can be a fluid trap of the evacuation system, and the pressure differential can be used to determine an airflow path through the evacuation system. In still another example, the system can be the inlet and outlet (or exhaust) of the evacuation system, and the pressure differential can be used to determine the maximum suction load in the evacuation system in order to maintain the maximum suction load below a threshold value.

In one aspect of the present disclosure, a processor and sensor system, such as the processors 50308 and 50408 and respective sensor systems in communication therewith (FIGS. 5 and 6), are configured to detect the ratio of an aerosol or carbonized particulate, i.e. smoke, in the fluid extracted from a surgical site. For example, the sensing system may include a sensor that detects the size and/or the composition of particles, which is used to select an airflow path through the evacuation system. In such instances, the evacuation system can include a first filtering path, or first filtering state, and a second filtering path, or second filtering state, which can have different properties. In one instance, the first path includes only a particulate filter, and the second path includes both a fluid filter and the particulate filter. In certain instances, the first path includes a particulate filter, and the second path includes the particulate filter and a finer particulate filter arranged in series. Additional and/or alternative filtering paths are also envisioned.

In one aspect of the present disclosure, a processor and sensor system, such as the processors 50308 and 50408 and respective sensor systems in communication therewith (FIGS. 5 and 6), are configured to perform a chemical analysis on the particles evacuated from within the abdomen cavity of a patient. For example, the sensing and intelligent controls device 50324 may sense the particle count and type in order to adjust the power level of the ultrasonic generator in order to induce the ultrasonic blade to produce less smoke. In another example, the sensor systems may include sensors for detecting the particle count, the temperature, the fluid content, and/or the contamination percentage of the evacuated fluid, and can communicate the detected property or properties to a generator in order to adjust its output. For example, the smoke evacuator 50326 and/or the sensing and intelligent controls device 50324 therefor can be configured to adjust the evacuation flow rate and/or the pump's motor speed and, at a predefined particulate level, may operably affect the output power or waveform of the generator to lower the smoke generated by the end effector.

In one aspect of the present disclosure, a processor and sensor system, such as the processors 50308 and 50408 and respective sensor systems therewith (FIGS. 5 and 6), are configured to evaluate particle count and contamination in the operating room by evaluating one or more properties in the ambient air and/or the exhaust from the evacuator housing. The particle count and/or the air quality can be displayed on the smoke evacuation system, such as on the evacuator housing, for example, in order to communicate the information to a clinician and/or to establish the effectiveness of the smoke evacuation system and filter(s) thereof.

In one aspect of the present disclosure, a processor, such as the processor 50308 or the processor 50408 (FIGS. 5 and 6), for example, is configured to compare a sample rate image obtained from an endoscope to the evacuator particle count from the sensing system (e.g. the sensing and intelligent controls device 50324) in order to determine a correlation and/or to adjust the rate of the pump's revolutions-per-minute (RPM). In one instance, the activation of the generator can be communicated to the smoke evacuator such that an anticipated, required rate of smoke evacuation can be implemented. The generator activation can be communicated to the surgical evacuation system through a surgical hub, cloud communication system, and/or direct connection, for example.

In one aspect of the present disclosure, sensor systems and algorithms for a smoke evacuation system (see, e.g. FIGS. 5 and 6) can be configured to control the smoke evacuator, and can adapt motor parameters thereof to adjust the filtering efficiency of the smoke evacuator based on the needs of the surgical field at a given time. In one instance, an adaptive airflow pump speed algorithm is provided to automatically change the motor pump speed based on the sensed particulate into the inlet of the smoke evacuator and/or out of the outlet or exhaust of the smoke evacuator. For example, the sensing and intelligent controls device 50324 (FIG. 5) can include a user-selectable speed and an auto-mode speed, for example. In the auto-mode speed, the airflow through the evacuation system can be scalable based on the smoke into the evacuation system and/or a lack of filtered particles out of the smoke evacuation system. The auto-mode speed can provide automatic sensing and compensation for laparoscopic mode in certain instances.

In one aspect of the present disclosure, the evacuation system can include an electrical and communication architecture (see, e.g. FIGS. 5 and 6) that provides data collection and communication features, in order to improve interactivity with a surgical hub and a cloud. In one example, a surgical evacuation system and/or processor therefor, such as the processor 50308 (FIG. 5) and the processor 50408 (FIG. 6), for example, can include a segmented control circuit that is energized in a staged method to check for errors, shorts, and/or safety checks of the system. The segmented control circuit may also be configured to have a portion energized and a portion not energized until the energized portion performs a first function. The segmented control circuit can include circuit elements to identify and display status updates to the user of attached components. The segmented control circuit also includes circuit elements for running the motor in a first state, in which the motor is activated by the user, and in a second state, in which the motor has not been activated by the user but runs the pump in a quieter manner and at a slower rate. A segmented control circuit can allow the smoke evacuator to be energized in stages, for example.

The electrical and communication architecture for the evacuation system (see, e.g. FIGS. 5 and 6) can also provide interconnectivity of the smoke evacuator with other components within the surgical hub for interactions, as well as communication of data with a cloud. Communication of surgical evacuation system parameters to a surgical hub and/or cloud can be provided to affect the output or operation of other attached devices. The parameters can be operational or sensed. Operational parameters include airflow, pressure differentials, and air quality. Sensed parameters include particulate concentration, aerosol percentage, and chemical analysis.

In one aspect of the present disclosure, the evacuation system, such as the surgical evacuation system 50400, for example, can also include an enclosure and replaceable components, controls, and a display. Circuit elements are provided for communicating the security identification (ID) between such replaceable components. For example, communication between a filter and the smoke evacuation electronics can be provided to verify authenticity, remaining life of the component, to update parameters in the component, to log errors, and/or to limit the number and/or the type of components that can be identified by the system. In various instances, the communication circuit can authenticate features for enabling and/or disabling of configuration parameters. The communication circuit can employ encryption and/or error handling schemes to manage security and proprietary relationships between the component and the smoke evacuation electronics. Disposable/re-useable components are included in certain instances.

In one aspect of the present disclosure, the evacuation systems can provide fluid management and extraction filters and airflow configurations. For example, a surgical evacuation system including a fluid capture mechanism is provided where the fluid capture mechanism has a first and a second set of extraction or airflow control features, which are in series with each other to extract large and small fluid droplets, respectively. In certain instances, the airflow path can contain a recirculation channel or secondary fluid channel back to the primary reservoir from downstream of the exhaust port of the main fluid management chamber.

In one aspect of the present disclosure, an advanced pad can be coupled to the electrosurgical system. For example, the ground electrode 50335 of the electrosurgical system 50300 (FIG. 5) can include an advanced pad having localized sensing that is integrated into the pad while maintaining the capacitive coupling. For example, the capacitive coupling return path pad can have small separable array elements, which can be used to sense nerve control signals and/or movement of select anatomic locations, in order to detect the proximity of the monopolar tip to a nerve bundle.

Figure 7:
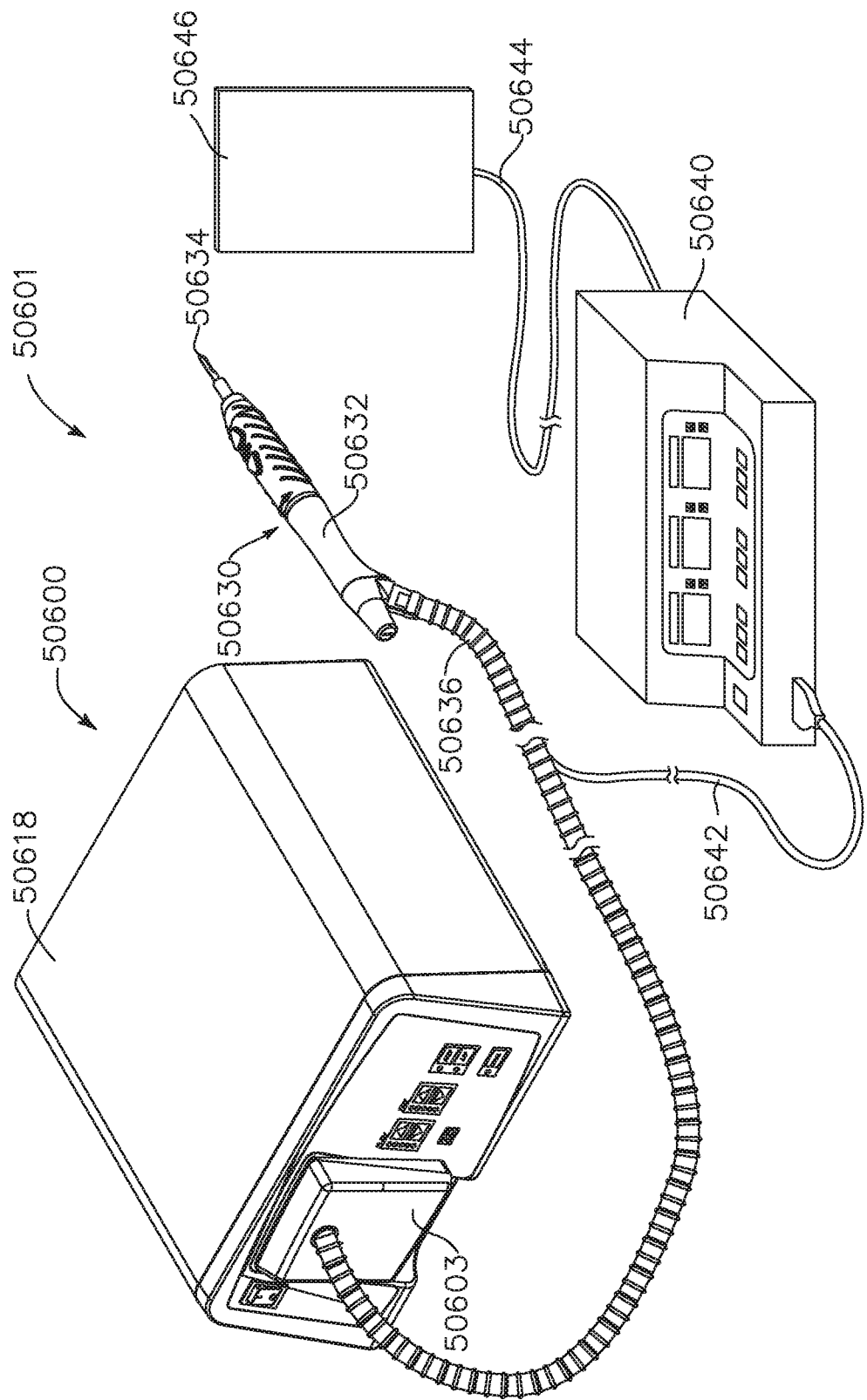
FIG. 7 is a perspective view of a surgical system including a surgical evacuation system, in accordance with at least one aspect of the present disclosure.

An electrosurgical system can includes a signal generator, an electrosurgical instrument, a return electrode, and a surgical evacuation system. The generator may be an RF wave generator that produces RF electrical energy. Connected to the electrosurgical instrument is a utility conduit. The utility conduit includes a cable that communicates electrical energy from the signal generator to the electrosurgical instrument. The utility conduit also includes a vacuum hose that conveys captured/collected smoke and/or fluid away from a surgical site. Such an exemplary electrosurgical system 50601 is shown in FIG. 7. More specifically, the electrosurgical system 50601 includes a generator 50640, an electrosurgical instrument 50630, a return electrode 50646, and an evacuation system 50600. The electrosurgical instrument 50630 includes a handle 50632 and a distal conduit opening 50634 that is fluidically coupled to a suction hose 50636 of the evacuation system 50600. The electrosurgical instrument 50630 also includes an electrode that is powered by the generator 50640. A first electrical connection 50642, e.g., a wire, extends from the electrosurgical instrument 50630 to the generator 50640. A second electrical connection 50644, e.g., a wire, extends from the electrosurgical instrument 50630 to electrode, i.e., the return electrode 50646. In other instances, the electrosurgical instrument 50630 can be a bipolar electrosurgical instrument. The distal conduit opening 50634 on the electrosurgical instrument 50630 is fluidically coupled to the suction hose 50636 that extends to a filter end cap 50603 of a filter that is installed in an evacuator housing 50618 of the evacuation system 50600.

In other instances, the distal conduit opening 50634 for the evacuation system 50600 can be on a handpiece or tool that is separate from the electrosurgical instrument 50630. For example, the evacuation system 50600 can include a surgical tool that is not coupled to the generator 50640 and/or does not include tissue-energizing surfaces. In certain instances, the distal conduit opening 50634 for the evacuation system 50600 can be releasably attached to an electrosurgical tool. For example, the evacuation system 50600 can include a clip-on or snap-on conduit terminating at a distal conduit opening, which can be releasably attached to a surgical tool (see, e.g., FIG. 3).

The electrosurgical instrument 50630 is configured to deliver electrical energy to target tissue of a patient to cut the tissue and/or cauterize blood vessels within and/or near the target tissue, as described herein. Specifically, an electrical discharge is provided by the electrode tip to the patient in order to cause heating of cellular matter of the patient that is in close contact with or adjacent to electrode tip. The tissue heating takes place at an appropriately high temperature to allow the electrosurgical instrument 50630 to be used to perform electrosurgery. The return electrode 50646 is either applied to or placed in close proximity to the patient (depending on the type of return electrode), in order to complete the circuit and provide a return electrical path to the generator 50640 for energy that passes into the patient's body.

The heating of cellular matter of the patient by the electrode tip, or cauterization of blood vessels to prevent bleeding, often results in smoke being released where the cauterization takes place, as further described herein. In such instances, because the evacuation conduit opening 50634 is near the electrode tip, the evacuation system 50600 is configured to capture the smoke that is released during a surgical procedure. Vacuum suction may draw the smoke into the conduit opening 50634, through the electrosurgical instrument 50630, and into the suction hose 50636 toward the evacuator housing 50618 of the evacuation system 50600.

Figure 8:
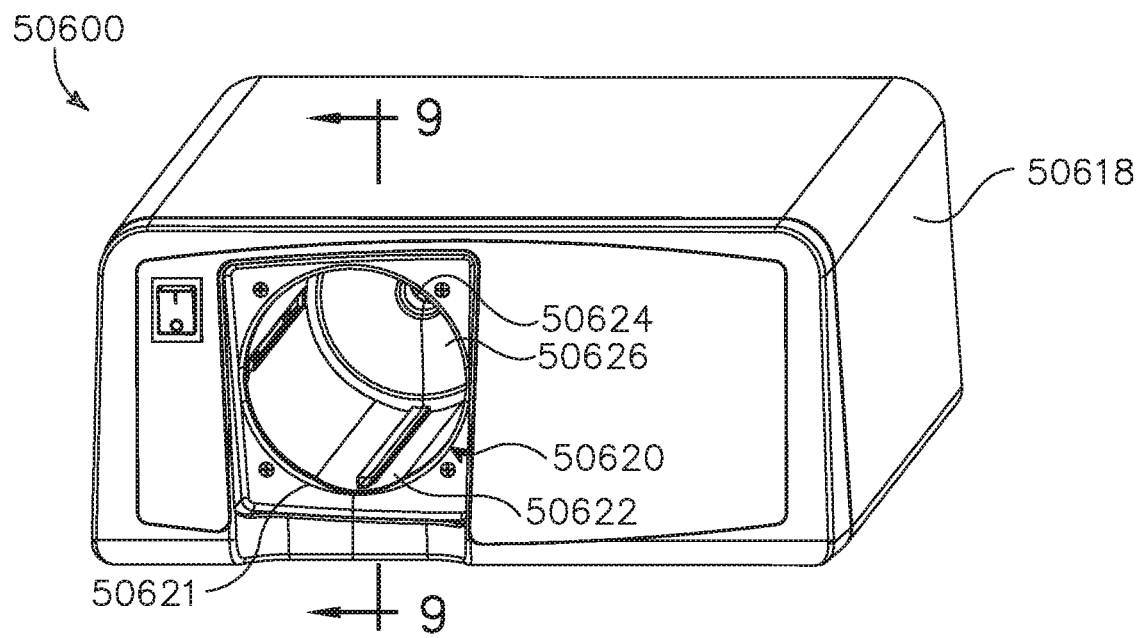
FIG. 8 is a perspective view of an evacuator housing of the surgical evacuation system of FIG. 7, in accordance with at least one aspect of the present disclosure.

Referring now to FIG. 8, the evacuator housing 50618 of the evacuation system 50600 (FIG. 7) is depicted. The evacuator housing 50618 includes a socket 50620 that is dimensioned and structured to receive a filter. The evacuator housing 50618 can completely or partially encompass the internal components of the evacuator housing 50618. The socket 50620 includes a first receptacle 50622 and a second receptacle 50624. A transition surface 50626 extends between the first receptacle 50622 and the second receptacle 50624.

Figure 9:
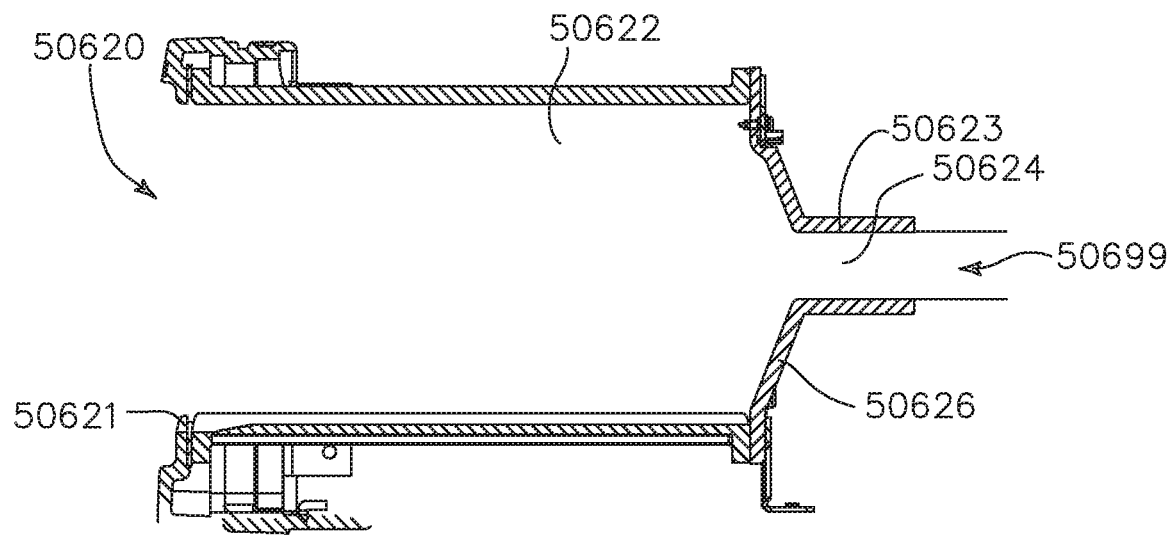
FIG. 9 is an elevation, cross-section view of a socket in the evacuator housing of FIG. 8 along the plane indicated in FIG. 8, in accordance with at least one aspect of the present disclosure.

Referring primarily now to FIG. 9, the socket 50620 is depicted along a cross sectional plane indicated in FIG. 8. The socket 50620 includes a first end 50621 that is open to receive a filter and a second end 50623 in communication with a flow path 50699 through the evacuator housing 50618. A filter 50670 (FIGS. 10 and 11) may be removably positioned with the socket 50620. For example, the filter 50670 can be inserted and removed from the first end 50621 of the socket 50620. The second receptacle 50624 is configured to receive a connection nipple of the filter 50670.

Surgical evacuation systems often use filters to remove unwanted pollutants from the smoke before the smoke is released as exhaust. In certain instances, the filters can be replaceable. The reader will appreciate that the filter 50670 depicted in FIGS. 10 and 11 can be employed in various evacuation systems disclosed herein. The filter 50670 can be a replaceable and/or disposable filter.

The filter 50670 includes a front cap 50672, a back cap 50674, and a filter body 50676 disposed therebetween. The front cap 50672 includes a filter inlet 50678, which, in certain instances, is configured to receive smoke directly from the suction hose 50636 (FIG. 7) or other smoke source. In some aspects of the present disclosure, the front cap 50672 can be replaced by a fluid trap (e.g. the fluid trap 50760 depicted in FIGS. 14-17) that directs the smoke directly from the smoke source, and after removing at least a portion of the fluid therefrom, passes the partially processed smoke into the filter body 50676 for further processing. For example, the filter inlet 50678 can be configured to receive smoke via a fluid trap exhaust port, such as a port 50766 in a fluid trap 50760 (FIGS. 14-17) to communicate partially processed smoke into the filter 50670.

Once the smoke enters the filter 50670, the smoke can be filtered by components housed within the filter body 50676. The filtered smoke can then exit the filter 50670 through a filter exhaust 50680 defined in the back cap 50674 of the filter 50670. When the filter 50670 is associated with an evacuation system, suction generated in the evacuator housing 50618 of the evacuation system 50600 can be communicated to the filter 50670 through the filter exhaust 50680 to pull the smoke through the internal filtering components of the filter 50670. A filter often includes a particulate filter and a charcoal filter. The particulate filter can be a high-efficiency particulate air (HEPA) filter or an ultra-low penetration air (ULPA) filter, for example. ULPA filtration utilizes a depth filter that is similar to a maze. The particulate can be filtered using at least one of the following methods: direct interception (in which particles over 1.0 micron are captured because they are too large to pass through the fibers of the media filter), inertial impaction (in which particles between 0.5 and 1.0 micron collide with the fibers and remain there, and diffusional interception (in which particles less than 0.5 micron are captured by the effect of Brownian random thermal motion as the particles "search out" fibers and adhere to them).

The charcoal filter is configured to remove toxic gases and/or odor generated by the surgical smoke. In various instances, the charcoal can be "activated" meaning it has been treated with a heating process to expose the active absorption sites. The charcoal can be from activated virgin coconut shells, for example.

Figure 11:
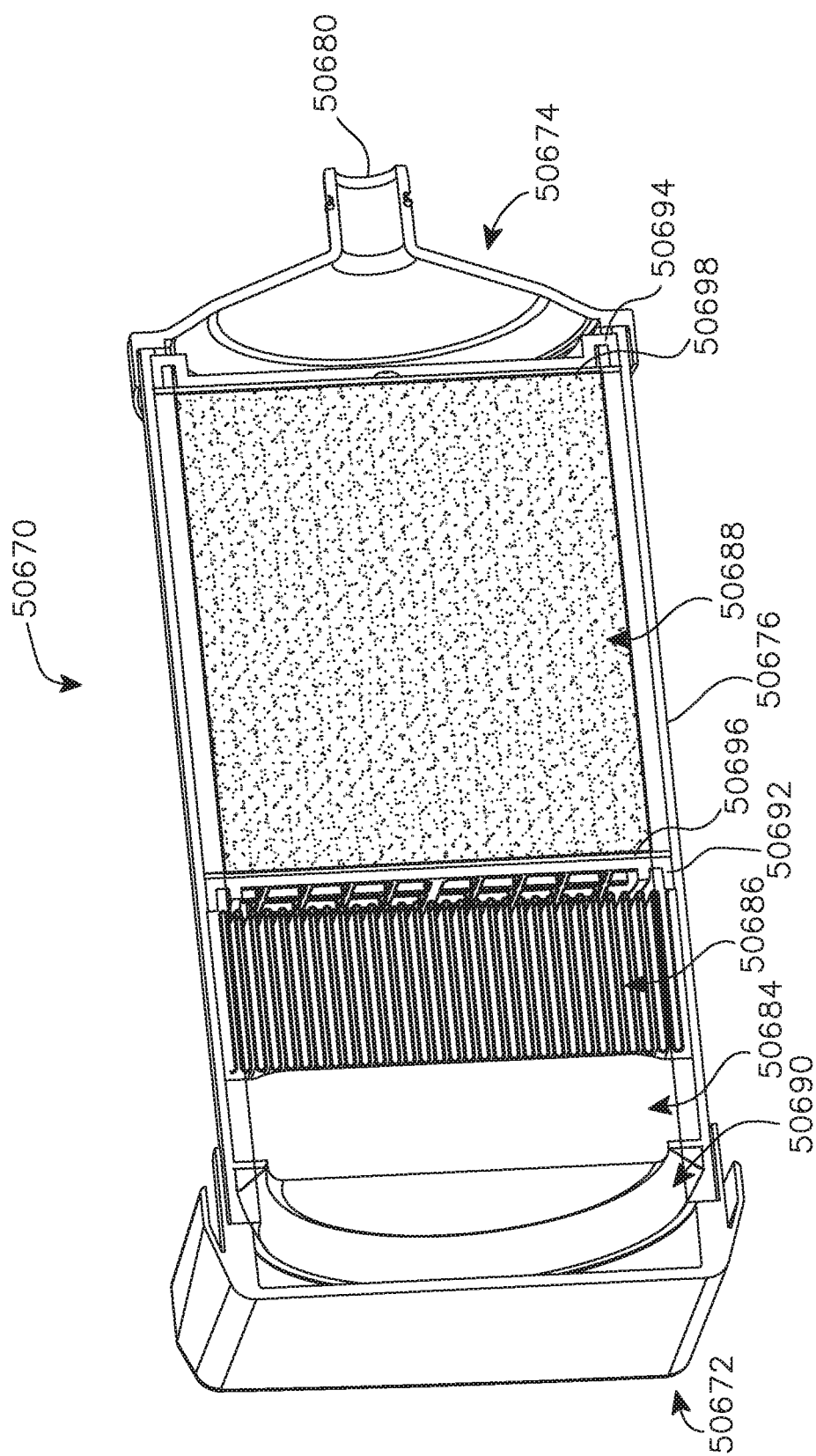
FIG. 11 is a perspective, cross-section view of the filter of FIG. 10 taken along a central longitudinal plane of the filter, in accordance with at least one aspect of the present disclosure.

Referring now to FIG. 11, the filter 50670 includes a coarse media filter layer 50684 followed by a fine particulate filter layer 50686. In other instances, the filter 50670 may consist of a single type of filter. In still other instances, the filter 50670 can include more than two filter layers and/or more than two different types of filter layers. After the particulate matter is removed by the filter layers 50684 and 50686, the smoke is drawn through a carbon reservoir 50688 in the filter 50670 to remove gaseous contaminants within the smoke, such as volatile organic compounds, for example. In various instances, the carbon reservoir 50688 can comprise a charcoal filter. The filtered smoke, which is now substantially free of particulate matter and gaseous contaminants, is drawn through the filter exhaust 50680 and into the evacuation system 50600 for further processing and/or elimination.

The filter 50670 includes a plurality of dams between components of the filter body 50676. For example, a first dam 50690 is positioned intermediate the filter inlet 50678 (FIG. 10) and a first particulate filter, such as the coarse media filter 50684, for example. A second dam 50692 is positioned intermediate a second particulate filter, such as the fine particulate filter 50686, for example, and the carbon reservoir 50688. Additionally, a third dam 50694 is positioned intermediate the carbon reservoir 50688 and the filter exhaust 50680. The dams 50690, 50692, and 50694 can comprise a gasket or O-ring, which is configured to prevent movement of the components within the filter body 50676. In various instances, the size and shape of the dams 50690, 50692, and 50694 can be selected to prevent distention of the filter components in the direction of the applied suction.

The coarse media filter 50684 can include a low-air-resistant filter material, such as fiberglass, polyester, and/or pleated filters that are configured to remove a majority of particulate matter larger than 10 µm, for example. In some aspects of the present disclosure, this includes filters that remove at least 85% of particulate matter larger than 10 µm, greater than 90% of particulate matter larger than 10 µm, greater than 95% of particular matter larger than 10 µm, greater than 99% of particular matter larger than 10 µm, greater than 99.9% particulate matter larger than 10 µm, or greater than 99.99% particulate matter larger than 10 µm.

Additionally or alternatively, the coarse media filter 50684 can include a low-air-resistant filter that removes the majority of particulate matter greater than 1 µm. In some aspects of the present disclosure, this includes filters that remove at least 85% particulate matter larger than 1 µm, greater than 90% of particulate matter larger than 1 µm, greater than 95% of particular matter larger than 1 µm, greater than 99% of particular matter larger than 1 µm, greater than 99.9% particulate matter larger than 1 µm, or greater than 99.99% particulate matter larger than 1 µm.

The fine particulate filter 50686 can include any filter of higher efficiency than the coarse media filter 50684. This includes, for example, filters that are capable of filtering a higher percentage of the same sized particles as the coarse media filter 50684 and/or capable of filtering smaller sized particles than the coarse media filter 50684. In some aspects of the present disclosure, the fine particulate filter 50686 can include a HEPA filter or an ULPA filter. Additionally or alternatively, the fine particulate filter 50686 can be pleated to increase the surface area thereof. In some aspects of the present disclosure, the coarse media filter 50684 includes a pleated HEPA filter and the fine particulate filter 50686 includes a pleated ULPA filter.

Subsequent to particulate filtration, smoke enters a downstream section of the filter 50670 that includes the carbon reservoir 50688. The carbon reservoir 50688 is bounded by porous dividers 50696 and 50698 disposed between the intermediate and terminal dams 50692 and 50694, respectively. In some aspects of the present disclosure, the porous dividers 50696 and 50698 are rigid and/or inflexible and define a constant spatial volume for the carbon reservoir 50688.

The carbon reservoir 50688 can include additional sorbents that act cumulatively with or independently from the carbon particles to remove gaseous pollutants. The additional sorbents can include, for example, sorbents such as magnesium oxide and/or copper oxide, for example, which can act to adsorb gaseous pollutants such as carbon monoxide, ethylene oxide, and/or ozone, for example. In some aspects of the present disclosure, additional sorbents are dispersed throughout the reservoir 50688 and/or are positioned in distinct layers above, below, or within the reservoir 50688.

Figure 10:
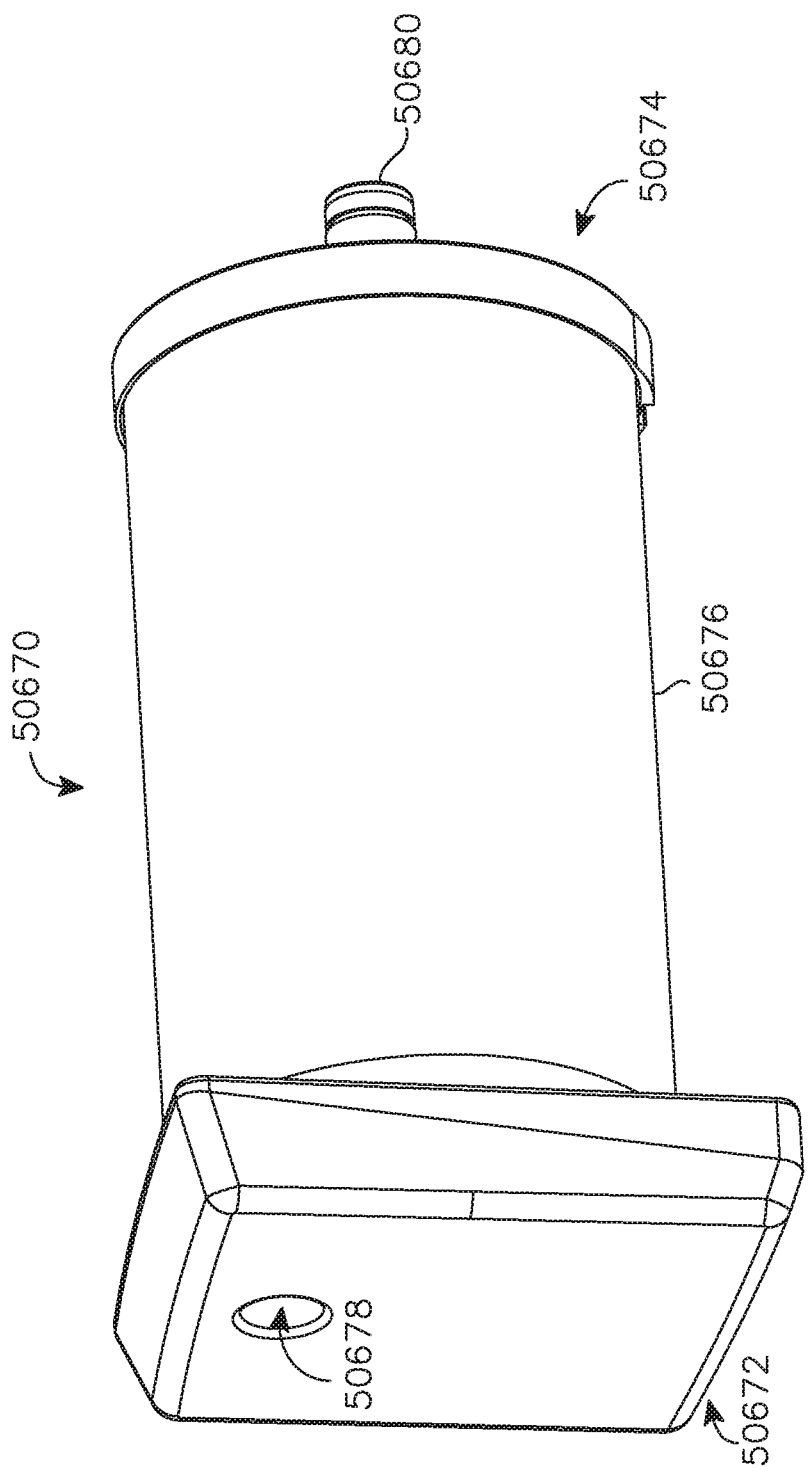
FIG. 10 is a perspective view of a filter for an evacuation system, in accordance with at least one aspect of the present disclosure.

Referring again to FIG. 4, the evacuation system 50500 includes the pump 50506 within the evacuator housing 50518. Similarly, the evacuation system 50600 depicted in FIG. 7 can include a pump located in the evacuator housing 50618, which can generate suction to pull smoke from the surgical site, through the suction hose 50636 and through the filter 50670 (FIGS. 10 and 11). In operation, the pump can create a pressure differential within the evacuator housing 50618 that causes the smoke to travel into the filter 50670 and out an exhaust mechanism (e.g. exhaust mechanism 50520 in FIG. 4) at the outlet of the flow path. The filter 50670 is configured to extract harmful, foul, or otherwise unwanted particulates from the smoke.

The pump can be disposed in-line with the flow path through the evacuator housing 50618 such that the gas flowing through the evacuator housing 50618 enters the pump at one end and exits the pump at the other end. The pump can provide a sealed positive displacement flow path. In various instances, the pump can produce the sealed positive displacement flow path by trapping (sealing) a first volume of gas and decreasing that volume to a second smaller volume as the gas moves through the pump. Decreasing the volume of the trapped gas increases the pressure of the gas. The second pressurized volume of gas can be released from the pump at a pump outlet. For example, the pump can be a compressor. More specifically, the pump can comprise a hybrid regenerative blower, a claw pump, a lobe compressor, and/or a scroll compressor. Positive displacement compressors can provide improved compression ratios and operating pressures while limiting vibration and noise generated by the evacuation system 50600. Additionally or alternatively, the evacuation system 50600 can include a fan for moving fluid therethrough.

Figure 12:
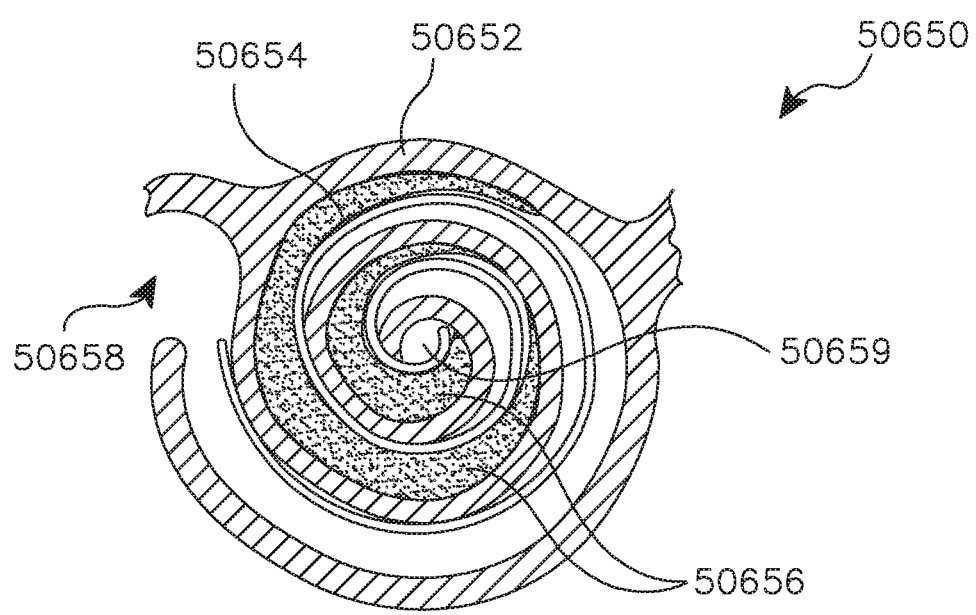
FIG. 12 is a pump for a surgical evacuation system, such as the surgical evacuation system of FIG. 7, in accordance with at least one aspect of the present disclosure.

An example of a positive displacement compressor, e.g. a scroll compressor pump 50650, is depicted in FIG. 12. The scroll compressor pump 50650 includes a stator scroll 50652 and a moving scroll 50654. The stator scroll 50652 can be fixed in position while the moving scroll 50654 orbits eccentrically. For example, the moving scroll 50654 can orbit eccentrically such that it rotates about the central longitudinal axis of the stator scroll 50652. As depicted in FIG. 12, the central longitudinal axes of the stator scroll 50652 and the moving scroll 50654 extend perpendicular to the viewing plane of the scrolls 50652, 50654. The stator scroll 50652 and the moving scroll 50654 are interleaved with each other to form discrete sealed compression chambers 50656.

In use, a gas can enter the scroll compressor pump 50650 at an inlet 50658. As the moving scroll 50654 orbits relative to the stator scroll 50652, the inlet gas is first trapped in the compression chamber 50656. The compression chamber 50656 is configured to move a discrete volume of gas along the spiral contour of the scrolls 50652 and 50654 toward the center of the scroll compressor pump 50650. The compression chamber 50656 defines a sealed space in which the gas resides. Moreover, as the moving scroll 50654 moves the captured gas toward the center of the stator scroll 50652, the compression chamber 50656 decreases in volume. This decrease in volume increases the pressure of the gas inside the compression chamber 50656. The gas inside the sealed compression chamber 50656 is trapped while the volume decreases, thus pressurizing the gas. Once the pressurized gas reaches the center of the scroll compressor pump 50650, the pressurized gas is released through an outlet 50659.

Figure 13:
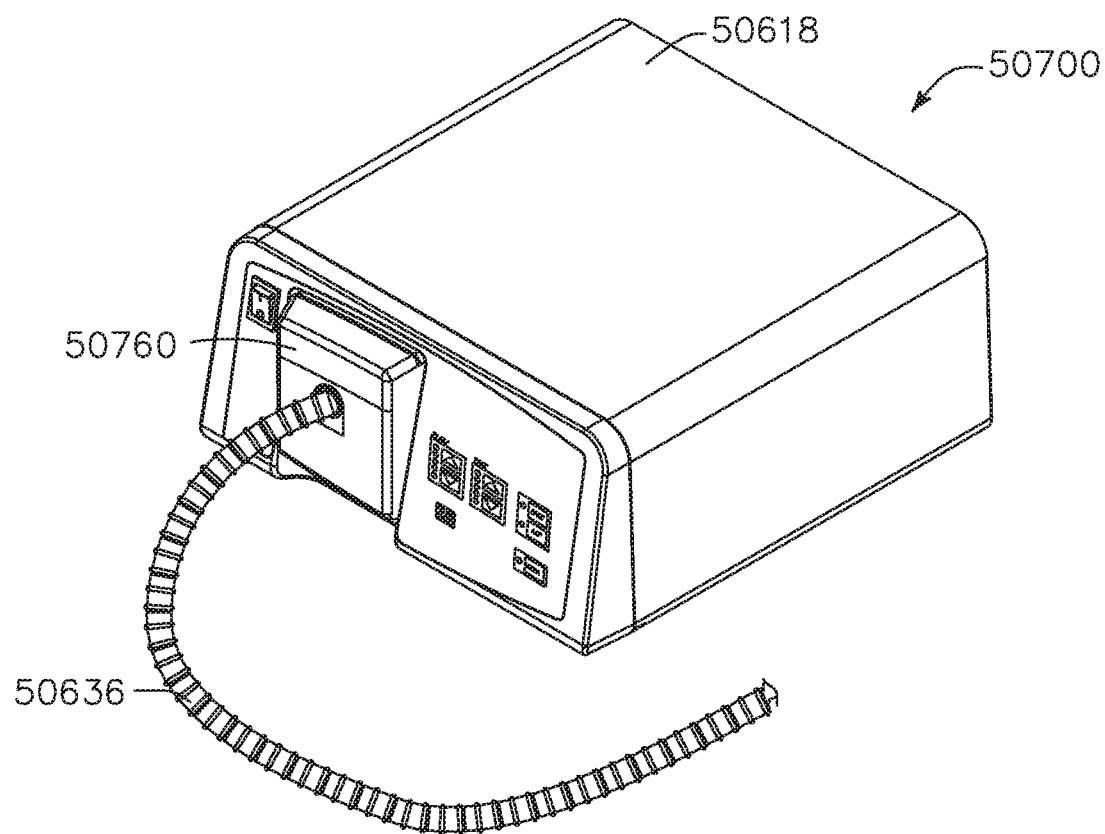
FIG. 13 is a perspective view of a portion of a surgical evacuation system, in accordance with at least one aspect of the present disclosure.
Figure 14:
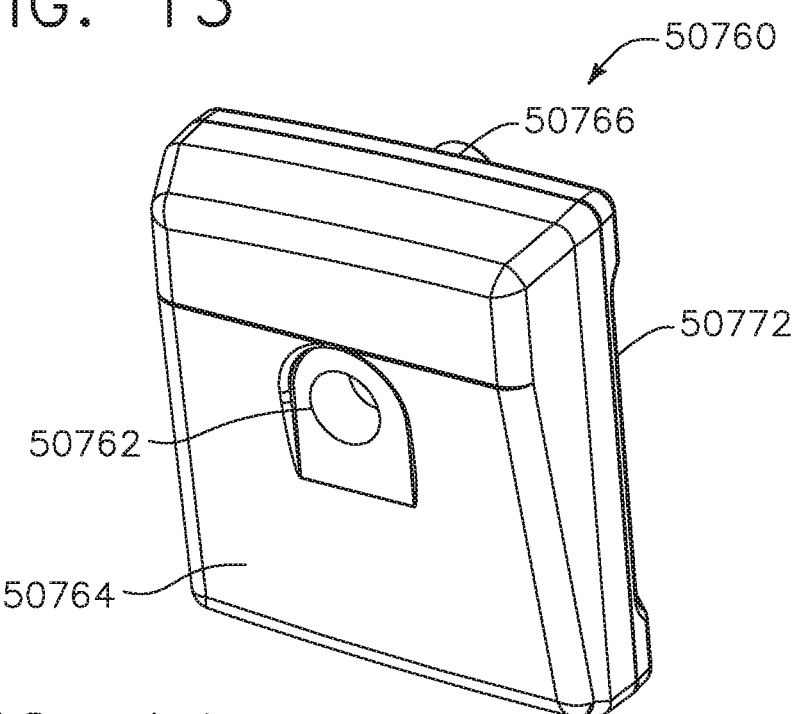
FIG. 14 is a front perspective view of a fluid trap of the surgical evacuation system of FIG. 13, in accordance with at least one aspect of the present disclosure.
Figure 15:
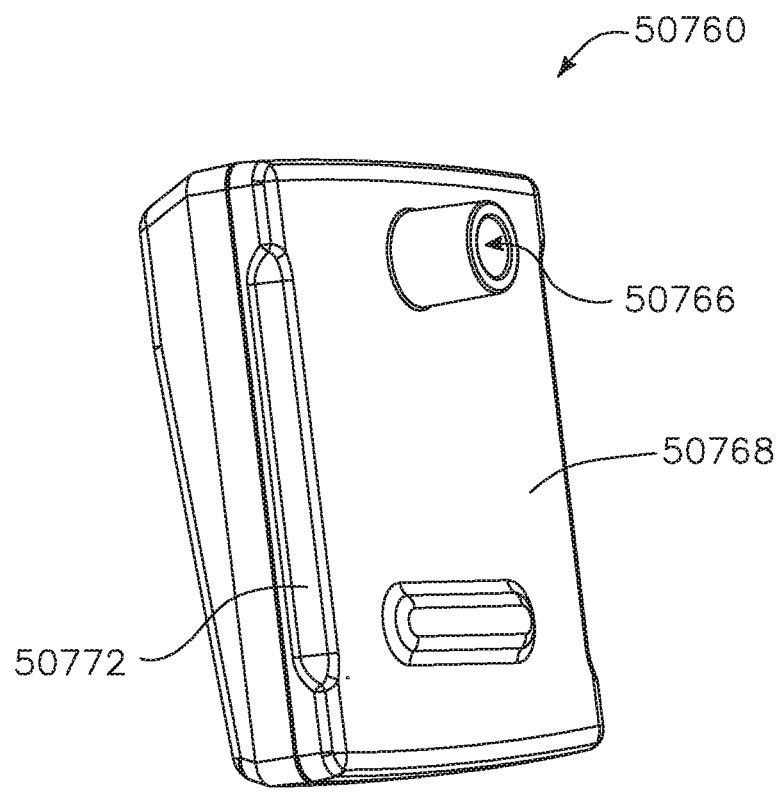
FIG. 15 is a rear perspective view of the fluid trap of FIG. 14, in accordance with at least one aspect of the present disclosure.

Referring now to FIG. 13, a portion of an evacuation system 50700 is depicted. The evacuation system 50700 can be similar in many respects to the evacuation system 50600 (FIG. 7). For example, the evacuation system 50700 includes the evacuator housing 50618 and the suction hose 50636. Referring again to FIG. 7, the evacuation system 50600 is configured to produce suction and thereby draw smoke from the distal end of the suction hose 50636 into the evacuator housing 50618 for processing. Notably, the suction hose 50636 is not connected to the evacuator housing 50618 through the filter end cap 50603 in FIG. 13. Rather, the suction hose 50636 is connected to the evacuator housing 50618 through the fluid trap 50760. A filter, similar to the filter 50670 can be positioned within the socket of the evacuator housing 50618 behind the fluid trap 50760.

The fluid trap 50760 is a first processing point that extracts and retains at least a portion of the fluid (e.g. liquid) from the smoke before relaying the partially-processed smoke to the evacuation system 50700 for further processing and filtration. The evacuation system 50700 is configured to process, filter, and otherwise clean the smoke to reduce or eliminate unpleasant odors or other problems associated with smoke generation in the surgical theater (or other operating environment), as described herein. By extracting liquid droplets and/or aerosol from the smoke before it is further processed by the evacuation system 50700, the fluid trap 50760 can, among other things, increase the efficiency of the evacuation system 50700 and/or increase the life of filters associated therewith, in certain instances.

Referring primarily to FIGS. 14-17, the fluid trap 50760 is depicted detached from the evacuator housing 50618 (FIG. 13). The fluid trap 50760 includes an inlet port 50762 defined in a front cover or surface 50764 of the fluid trap 50760. The inlet port 50762 can be configured to releasably receive the suction hose 50636 (FIG. 13). For example, an end of the suction hose 50636 can be inserted at least partially within the inlet port 50762 and can be secured with an interference fit therebetween. In various instances, the interference fit can be a fluid tight and/or airtight fit so that substantially all of the smoke passing through the suction hose 50636 is transferred into the fluid trap 50760. In some instances, other mechanisms for coupling or joining the suction hose 50636 to the inlet port 50762 can be employed such as a latch-based compression fitting, an O-ring, threadably coupling the suction hose 50636 with the inlet port 50762, for example, and/or other coupling mechanisms.

In various instances, a fluid tight and/or airtight fit between the suction hose 50636 and the fluid trap 50760 is configured to prevent fluids and/or other materials in the evacuated smoke from leaking at or near the junction of these components. In some instances, the suction hose 50636 can be associated with the inlet port 50762 through an intermediate coupling device, such as an O-ring and/or adaptor, for example, to further ensure an airtight and/or fluid tight connection between the suction hose 50636 and the fluid trap 50760.

As discussed above, the fluid trap 50760 includes the exhaust port 50766. The exhaust port extends away from a rear cover or surface 50768 of the fluid trap 50760. The exhaust port 50766 defines an open channel between an interior chamber 50770 of the fluid trap 50760 and the exterior environment. In some instances, the exhaust port 50766 is sized and shaped to tightly associate with a surgical evacuation system or components thereof. For example, the exhaust port 50766 can be sized and shaped to associate with and communicate at least partially processed smoke from the fluid trap 50760 to a filter housed within an evacuator housing 50618 (FIG. 13). In certain instances, the exhaust port 50766 can extend away from the front plate, a top surface, or a side surface of the fluid trap 50760.

In certain instances, the exhaust port 50766 includes a membrane, which spaces the exhaust port 50766 apart from the evacuator housing 50618. Such a membrane can act to prevent water or other liquid collected in the fluid trap 50760 from being passed through the exhaust port 50766 and into the evacuator housing 50618 while permitting air, water and/or vapor to freely pass into the evacuator housing 50618. For example, a high flow rate microporous polytetrafluoroethylene (PTFE) can be positioned downstream of the exhaust port 50766 and upstream of a pump to protect the pump or other components of the evacuation system 50700 from damage and/or contamination.

The fluid trap 50760 also includes a gripping region 50772, which is positioned and dimensioned to assist a user in handling the fluid trap 50760 and/or connecting the fluid trap 50760 with the suction hose 50636 and/or the evacuator housing 50618. The gripping region 50772 is depicted as being an elongate recess; however, the reader will readily appreciate that the gripping region 50772 may include at least one recess, groove, protrusion, tassel, and/or ring, for example, which can be sized and shaped to accommodate a user's digits or to otherwise provide a gripping surface.

Figure 16:
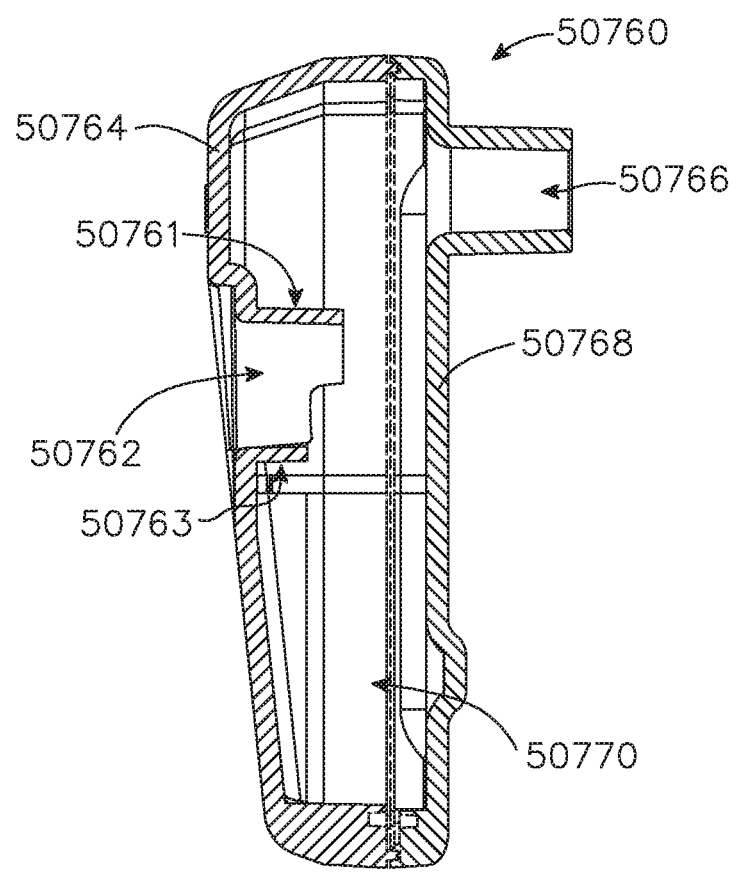
FIG. 16 is an elevation, cross-section view of the fluid trap of FIG. 14, in accordance with at least one aspect of the present disclosure.
Figure 17:
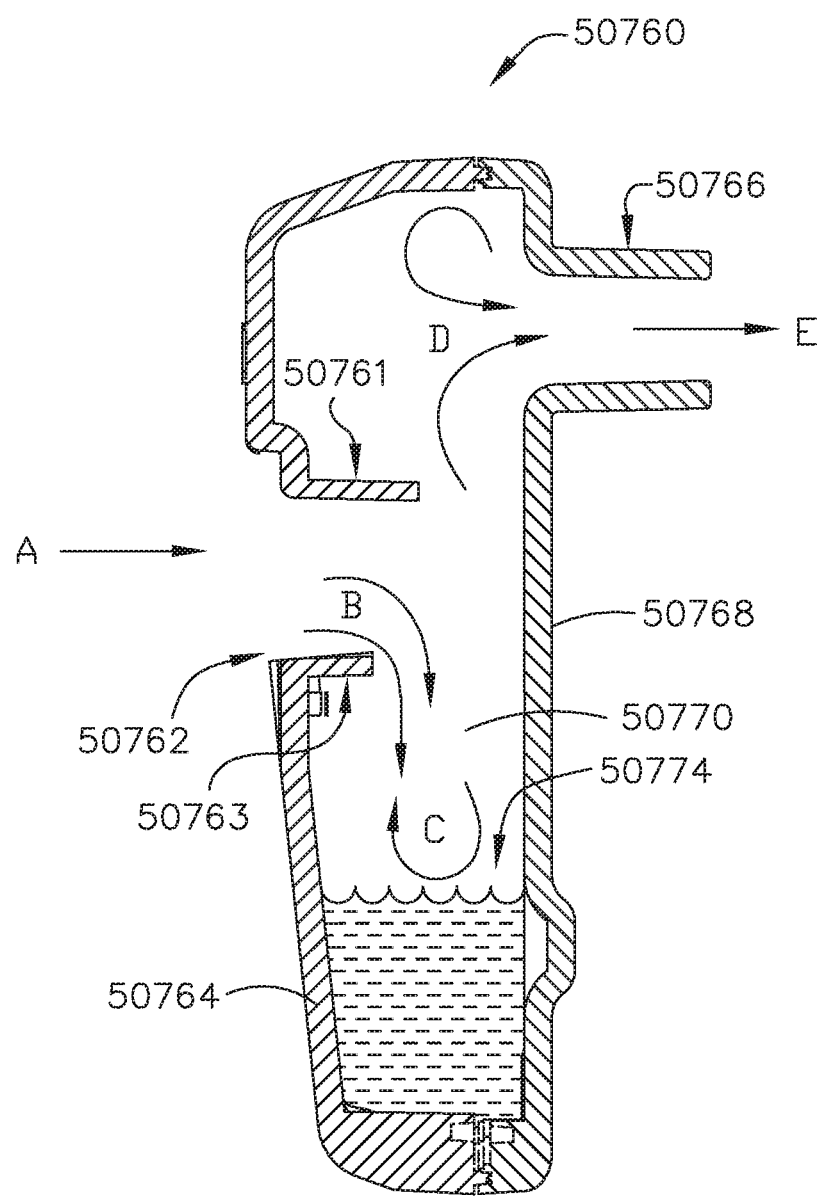
FIG. 17 is an elevation, cross-section view of the fluid trap of FIG. 14 with portions removed for clarity and depicting liquid captured within the fluid trap and smoke flowing through the fluid trap, in accordance with at least one aspect of the present disclosure.

Referring primarily now to FIGS. 16 and 17, the interior chamber 50770 of the fluid trap 50760 is depicted. The relative positioning of the inlet port 50762 and the exhaust port 50766 is configured to promote the extraction and the retention of fluid from the smoke as it passes into the fluid trap 50760. In certain instances, the inlet port 50762 can comprise a notched cylindrical shape, which can direct the smoke and the accompanying fluid towards a fluid reservoir 50774 of the fluid trap 50760 or otherwise directionally away from the exhaust port 50766. An example of such a fluid flow is depicted with arrows A, B, C, D, and E in FIG. 17.

As shown, smoke enters the fluid trap 50760 through the inlet port 50762 (illustrated by the arrow A) and exits the fluid trap 50760 through the exhaust port 50766 (illustrated by the arrow E). At least partially due to the geometry of the inlet port (e.g., a longer, upper sidewall 50761 and a shorter, lower sidewall 50763), the smoke entering the inlet port 50762 is initially directed primarily downward into the fluid reservoir 50774 of the fluid trap 50760 (illustrated by the arrows B). As smoke continues to be pulled downward into the fluid trap 50760 along the arrows A and B, the smoke that was initially directed downward, tumbles downward, and is directed laterally away from its source to travel in a substantially opposite but parallel path towards the upper portion of the fluid trap 50760 and out of the exhaust port 50766 (illustrated by the arrows D and E).

The directional flow of smoke through the fluid trap 50760 can ensure that liquids within the smoke are extracted and retained within the lower portion (e.g. the fluid reservoir 50774) of the fluid trap 50760. Furthermore, the relative positioning of the exhaust port 50766 vertically above the inlet port 50762 when the fluid trap 50760 is in an upright position is configured to discourage liquid from inadvertently being carried through the exhaust port 50766 by the flow of smoke while not substantially hindering fluid flow into and out of the fluid trap 50760. Additionally, in certain instances, the configuration of the inlet port 50762 and the outlet port 50766 and/or the size and shape of the fluid trap 50760 itself, can enable the fluid trap 50760 to be spill resistant.

Figure 6:
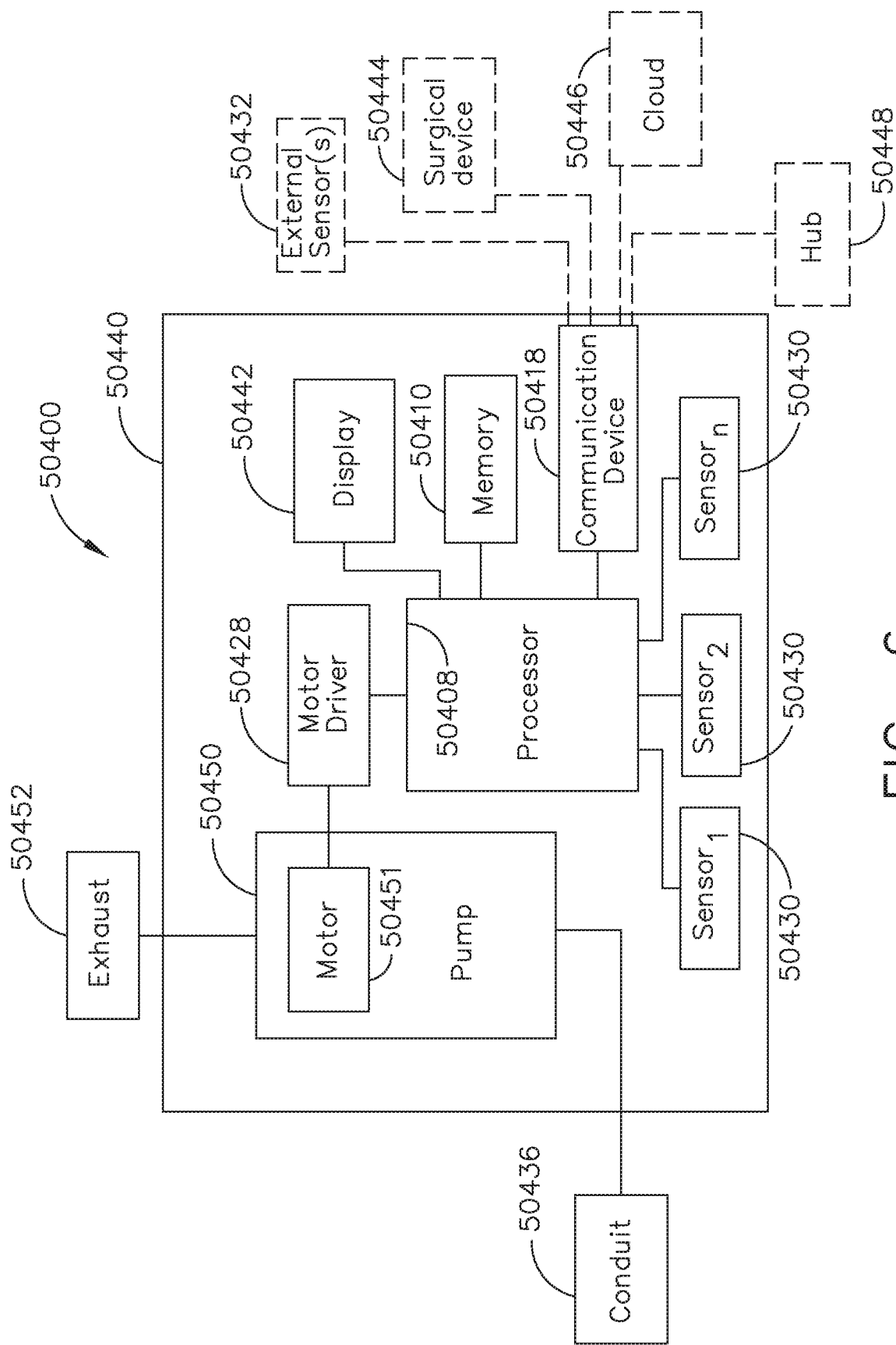
FIG. 6 is a schematic of a surgical evacuation system, in accordance with at least one aspect of the present disclosure.

In various instances, an evacuation system can include a plurality of sensors and intelligent controls, as further described herein with respect to FIGS. 5 and 6, for example. In one aspect of the present disclosure, an evacuation system can include one or more temperatures sensors, one or more fluid detection sensors, one or more pressure sensors, one or more particle sensors, and/or one or more chemical sensors. A temperature sensor can be positioned to detect the temperature of a fluid at the surgical site, moving through a surgical evacuation system, and/or being exhaust into a surgical theater from a surgical evacuation system. A pressure sensor can be positioned to detect a pressure within the evacuation system, such as within the evacuator housing. For example, a pressure sensor can be positioned upstream of the filter, between the filter and the pump, and/or downstream of the pump. In certain instances, a pressure sensor can be positioned to detect a pressure in the ambient environment outside of the evacuation system. Similarly, a particle sensor can be positioned to detect particles within the evacuation system, such as within the evacuator housing. A particle sensor can be upstream of the filter, between the filter and the pump, and/or downstream of the pump, for example. In various instances, a particle sensor can be positioned to detect particles in the ambient environment in order to determine the air quality in the surgical theater, for example.

Figure 18:
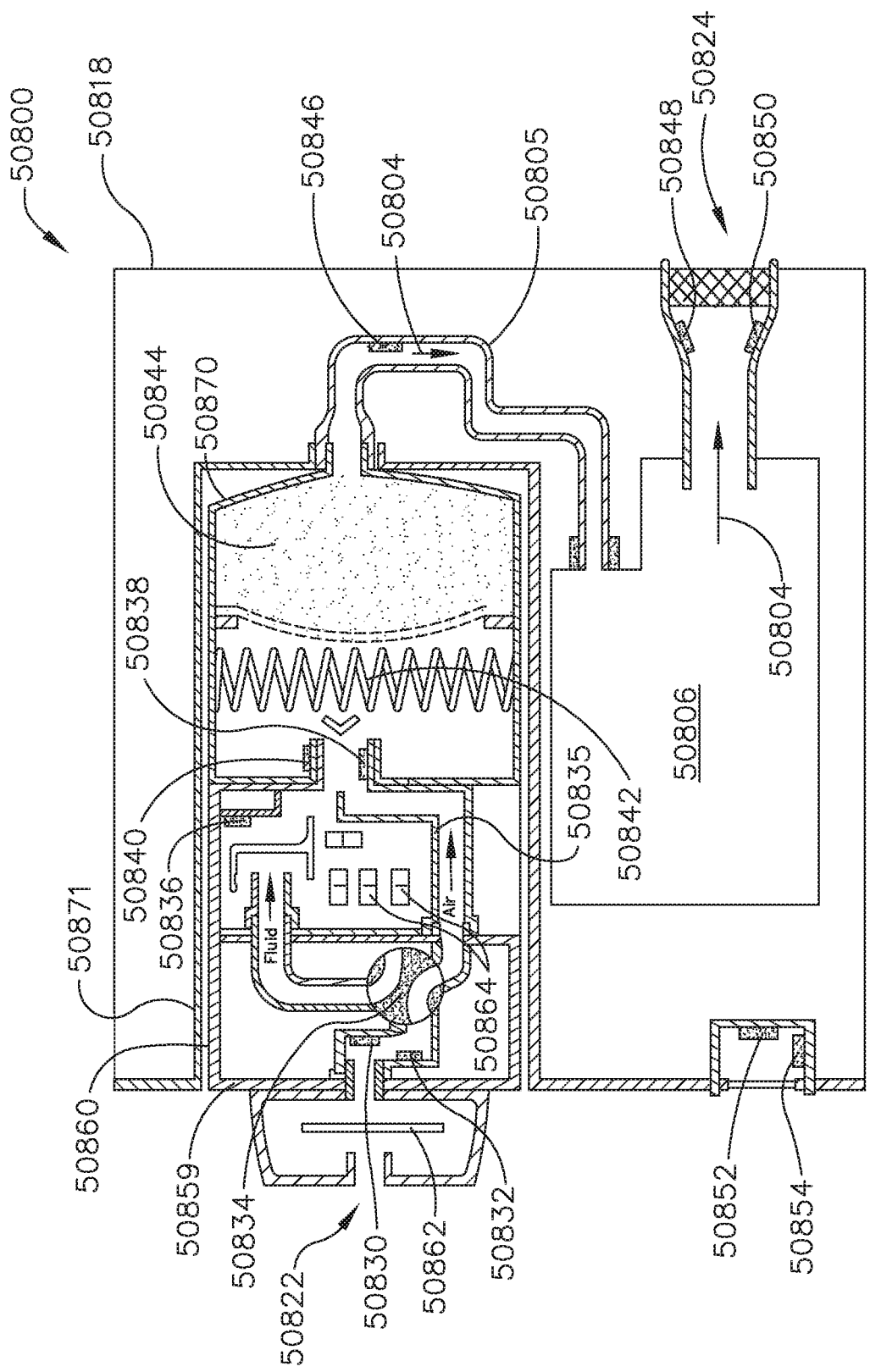
FIG. 18 is a schematic of an evacuator housing of an evacuation system, in accordance with at least one aspect of the present disclosure.

An evacuator housing 50818 for an evacuation system 50800 is schematically depicted in FIG. 18. The evacuator housing 50818 can be similar in many respects to the evacuator housings 50018 and/or 50618, for example, and/or can be incorporated into various evacuation systems disclosed herein. The evacuator housing 50818 includes numerous sensors, which are further described herein. The reader will appreciate that certain evacuator housings may not include each sensor depicted in FIG. 18 and/or may include additional sensor(s). Similar to the evacuator housings 50018 and 50618 disclosed herein, the evacuator housing 50818 of FIG. 18 includes an inlet 50822 and an outlet 50824. A fluid trap 50860, a filter 50870, and a pump 50806 are sequentially aligned along a flow path 50804 through the evacuator housing 50818 between the inlet 50822 and the outlet 50824.

An evacuator housing can include modular and/or replaceable components, as further described herein. For example, an evacuator housing can include a socket or a receptacle 50871 dimensioned to receive a modular fluid trap and/or a replaceable filter. In certain instances, a fluid trap and a filter can be incorporated into a single interchangeable module 50859, as depicted in FIG. 18. More specifically, the fluid trap 50860 and the filter 50870 form the interchangeable module 50859, which can be modular and/or replaceable, and can be removably installed in the receptacle 50871 in the evacuator housing 50818. In other instances, the fluid trap 50860 and the filter 50870 can be separate and distinct modular components, which can be assembled together and/or separately installed in the evacuator housing 50818.

Referring still to the evacuator housing 50818, the evacuator housing 50818 includes a plurality of sensors for detecting various parameters therein and/or parameters of the ambient environment. Additionally or alternatively, one or more modular components installed in the evacuator housing 50818 can include one or more sensors. For example, referring still to FIG. 18, the interchangeable module 50859 includes a plurality of sensors for detecting various parameters therein.

In various instances, the evacuator housing 50818 and/or a modular component(s) compatible with the evacuator housing 50818 can include a processor, such as the processor 50308 and 50408 (FIGS. 5 and 6, respectively), which is configured to receive inputs from one or more sensors and/or to communicate outputs to one more systems and/or drivers. Various processors for use with the evacuator housing 50818 are further described herein.

In operation, smoke from a surgical site can be drawn into the inlet 50822 to the evacuator housing 50818 via the fluid trap 50860. The flow path 50804 through the evacuator housing 50818 in FIG. 18 can comprise a sealed conduit or tube 50805 extending between the various in-line components. In various instances, the smoke can flow past a fluid detection sensor 50830 and a chemical sensor 50832 to a diverter valve 50834, which is further described herein. A fluid detection sensor, such as the sensor 50830, can detect fluid particles in the smoke. In one instance, the fluid detection sensor 50830 can be a continuity sensor. For example, the fluid detection sensor 50830 can include two spaced-apart electrodes and a sensor for detecting the degree of continuity therebetween. When no fluid is present, the continuity can be zero, or substantially zero, for example. The chemical sensor 50832 can detect the chemical properties of the smoke.

At the diverter valve 50834, fluid can be directed into a condenser 50835 of the fluid trap 50860 and the smoke can continue toward the filter 50870. Baffles 50864 are positioned within the condenser 50835 to facilitate the condensation of fluid droplets from the smoke into a reservoir in the fluid trap 50860. A fluid detection sensor 50836 can ensure any fluid in the evacuator housing is entirely, or at least substantially, captured within the fluid trap 50860.

Referring still to FIG. 18, the smoke can then be directed to flow into the filter 50870 of the interchangeable module 50859. At the inlet to the filter 50870, the smoke can flow past a particle sensor 50838 and a pressure sensor 50840. In one form, the particle sensor 50838 can comprise a laser particle counter, as further described herein. The smoke can be filtered via a pleated ultra-low penetration air (ULPA) filter 50842 and a charcoal filter 50844, as depicted in FIG. 18.

Upon exiting the filter, the filtered smoke can flow past a pressure sensor 50846 and can then continue along the flow path 50804 within the evacuator housing 50818 toward the pump 50806. Upon moving through the pump 50806, the filtered smoke can flow past a particle sensor 50848 and a pressure sensor 50850 at the outlet to the evacuator housing 50818. In one form, the particle sensor 50848 can comprise a laser particle counter, as further described herein. The evacuator housing 50818 in FIG. 18 also includes an air quality particle sensor 50852 and an ambient pressure sensor 50854 to detect various properties of the ambient environment, such as the environment within the surgical theater. The air quality particle sensor, or external/ambient air particle sensor, 50852 can comprise a laser particle counter in at least one form. The various sensors depicted in FIG. 18 are further described herein. Moreover, in various instances, alternative sensing means can be utilized in the smoke evacuation systems disclosed herein. For example, alternative sensors for counting particles and/or determining particulate concentration in a fluid are further disclosed herein.

In various instances, the fluid trap 50860 depicted in FIG. 18 can be configured to prevent spillage and/or leakage of the captured fluid. For example, the geometry of the fluid trap 50860 can be selected to prevent the captured fluid from spilling and/or leaking. In certain instances, the fluid trap 50860 can include baffles and/or splatter screens, such as the screen 50862, for preventing the captured fluid from splashing out of the fluid trap 50860. In one or more instances, the fluid trap 50860 can include sensors for detecting the volume of fluid within the fluid trap and/or determining if the fluid trap 50860 is filled to capacity. The fluid trap 50860 may include a valve for empty the fluid therefrom. The reader will readily appreciate that various alternative fluid trap arrangements and geometries can be employed to capture fluid drawn into the evacuator housing 50818.

In certain instances, the filter 50870 can include additional and/or fewer filtering levels. For example, the filter 50870 can include one or more filtering layers selected from the following group of filters: a course media filter, a fine media filter, and a sorbent-based filter. The course media filter can be a low-air-resistant filter, which can be comprised of fiberglass, polyester, and/or pleated filters, for example. The fine media filter can be a high efficiency particulate air (HEPA) filter and/or ULPA filter. The sorbent-based filter can be an activated-carbon filter, for example. The reader will readily appreciate that various alternative filter arrangements and geometries can be employed to filter smoke drawn along the flow path through the evacuator housing 50818.

In one or more instances, the pump 50806 depicted in FIG. 18 can be replaced by and/or used in combination with another compressor and/or pump, such as a hybrid regenerative blower, a claw pump, and/or a lobe compressor, for example. The reader will readily appreciate that various alternative pumping arrangements and geometries can be employed to generate suction within the flow path 50804 to draw smoke into the evacuator housing 50818.

The various sensors in an evacuation system, such as the sensors depicted in FIG. 18, can communicate with a processor. The processor can be incorporated into the evacuation system and/or can be a component of another surgical instrument and/or a surgical hub. Various processors are further described herein. An on-board processor can be configured to adjust one or more operational parameters of the evacuator system (e.g. a motor for the pump 50806) based on input from the sensor(s). Additionally or alternatively, an on-board processor can be configured to adjust one or more operational parameters of another device, such as an electrosurgical tool and/or imaging device based on input from the sensor(s).

Figure 19:
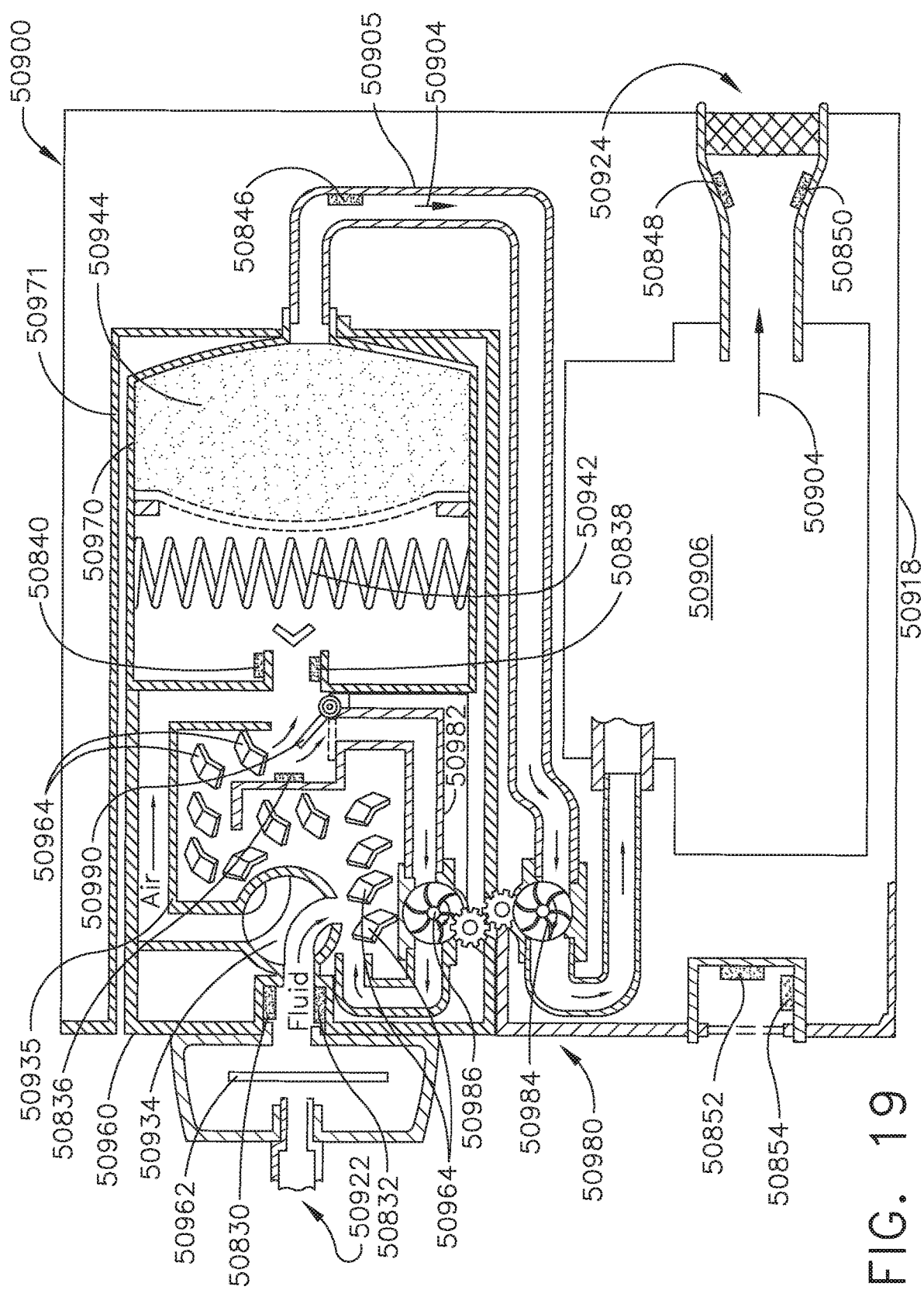
FIG. 19 is a schematic of an evacuator housing of another evacuation system, in accordance with at least one aspect of the present disclosure.

Referring now to FIG. 19, another evacuator housing 50918 for an evacuation system 50900 is depicted. The evacuator housing 50918 in FIG. 19 can be similar in many respects to the evacuator housing 50818 in FIG. 18. For example, the evacuator housing 50918 defines a flow path 50904 between an inlet 50922 to the evacuator housing 50918 and an outlet 50924 to the evacuator housing 50918. Intermediate the inlet 50922 and the outlet 50924, a fluid trap 50960, a filter 50970, and a pump 50906 are sequentially arranged. The evacuator housing 50918 can include a socket or a receptacle 50971 dimensioned to receive a modular fluid trap and/or a replaceable filter, similar to the receptacle 50871, for example. At a diverter valve 50934, fluid can be directed into a condenser 50935 of the fluid trap 50960 and the smoke can continue toward the filter 50970. In certain instances, the fluid trap 50960 can include baffles, such as the baffles 50964, and/or splatter screens, such as the screen 50962, for example, for preventing the captured fluid from splashing out of the fluid trap 50960. The filter 50970 includes a pleated ultra-low penetration air (ULPA) filter 50942 and a charcoal filter 50944. A sealed conduit or tube 50905 extends between the various in-line components. The evacuator housing 50918 also includes the sensors 50830, 50832, 50836, 50838, 50840, 50846, 50848, 50850, 50852, and 50854 which are further described herein and shown in FIG. 18 and FIG. 19.

Referring still to FIG. 19, the evacuator housing 50918 also includes a centrifugal blower arrangement 50980 and a recirculating valve 50990. The recirculating valve 50990 can selectively open and close to recirculate fluid through the fluid trap 50960. For example, if the fluid detection sensor 50836 detects a fluid, the recirculating valve 50990 can be opened such that the fluid is directed back away from the filter 50970 and back into the fluid trap 50960. If the fluid detection sensor 50836 does not detect a fluid, the valve 50990 can be closed such that the smoke is directed into the filter 50970. When fluid is recirculated via the recirculating valve 50990, the fluid can be drawn through a recirculation conduit 50982. The centrifugal blower arrangement 50980 is engaged with the recirculation conduit 50982 to generate a recirculating suction force in the recirculation conduit 50982. More specifically, when the recirculating valve 50990 is open and the pump 50906 is activated, the suction force generated by the pump 50906 downstream of the filter 50970 can generate rotation of the first centrifugal blower, or squirrel cage, 50984, which can be transferred to the second centrifugal blower, or squirrel cage, 50986, which draws the recirculated fluid through the recirculating valve 50990 and into the fluid trap 50960.

In various aspects of the present disclosure, the control schematics of FIGS. 5 and 6 can be utilized with the various sensor systems and evacuator housings of FIGS. 18 and 19.

Smoke evacuated from a surgical site can include liquids, aerosols, and/or gases, and/or can include material of different chemical and/or physical properties, such as particulate matter and particles of different sizes and/or densities, for example. The different types of materials evacuated from a surgical site can affect the efficiency of the surgical evacuation system and the pump thereof. Moreover, certain types of material can require the pump to draw excessive power and/or can risk damaging the motor for the pump.

The power supplied to the pump can be modulated to control the flowrate of smoke through the evacuation system based on input from one or more sensors along the flow path. Output from the sensors can be indicative of a state or quality of the smoke evacuation system and/or one or more properties of the evacuated smoke such as the type(s) and ratios of matter, chemical properties, density, and/or size of particulates, for example. In one aspect of the present disclosure, a pressure differential between two pressure sensors in the evacuation system can indicate the state of the region therebetween such as the state of a filter, a fluid trap, and/or the overall system, for example. Based on the sensor input, an operational parameter of the motor for the pump can be adjusted by changing the current supplied to the motor and/or the duty cycle, which is configured to change the motor speed.

In one aspect of the present disclosure, by modulating the flowrate of smoke through the evacuation system, the efficiency of the filter can be improved and/or the motor can be protected from burnout.

A surgical evacuation system can include one or more particle counters, or particle sensors, for detecting the size and/or concentration of particulate within the smoke. Referring again to FIGS. 18 and 19, the particle sensors 50838 and 50848 are depicted. The reader will readily appreciate that various particle measurement means are possible. For example, a particle sensor can be an optical sensor, a laser sensor, a photoelectric sensor, an ionization sensor, an electrostatic sensor, and/or combinations thereof. Various particle sensors are further described herein.

In various instances, the speed of the motor and, thus, the speed of the pump can be adjusted based on the particulate concentration detected by the one or more particle sensors in a surgical evacuation system. For example, when the particle sensor(s) detects an increased concentration of particulate in the flow path, which can correspond to an increased quantity of smoke in the flow path, the speed of the motor can be increased to increase the speed of the pump and to draw more fluid into the smoke evacuation system from the surgical site. Similarly, when the particle sensor(s) detects a decreased concentration of particulate in the flow path, which can correspond to a decreased quantity of smoke in the flow path, the speed of the motor can be decreased to decrease the speed of the pump and to reduce suction from the surgical site. Additional and alternative adjustment algorithms for the surgical evacuation system are further described herein. Moreover, in certain instances, based on the sensor data from the smoke evacuation system, a generator in the surgical system can be controlled to adjust the amount of smoke generated at the surgical site, as further described herein.

In addition to particle sensors positioned along the flow path of the surgical evacuation system, the system can include one or more sensors for detecting the particulate concentration in the ambient room, for example, in the operating room or surgical theater. Referring again to FIGS. 18 and 19, the air quality particle sensor 50852 is installed on an external surface of the evacuator housing 50818. Alternative locations for the air quality particle sensor 50852 are also envisioned.

In at least one instance, a particle sensor can be positioned downstream of the filter and, in certain instances, can be positioned at or near the outlet of the filter. For example, the particle sensor 50848 is positioned downstream of the filter 50870 and the pump 50806 in the smoke evacuation system 50800 and is positioned downstream of the filter 50970 and the pump 50906 in the smoke evacuation system 50900. Because the particle sensor 50848 is positioned downstream of the filter(s) 50870, 50970, the particle sensor is configured to confirm that the filter(s) 50870, 50970 have removed sufficient particulate from the smoke. In various instances, such a sensor can be adjacent to the exhaust outlet 50824, 50924 of the evacuator housing 50818, 50918, respectively. In one aspect of the present disclosure, an electrostatic particle sensor can be utilized. For example, the exhaust outlet 50824, 50924 can include an electrostatic particulate sensor that the exhaust flows past downstream of the filtration system and prior to being exhaust into the surgical theater.

The particulate concentration detected by one or more sensors of the surgical evacuation system can be communicated to a clinician in a number of different ways. For example, the evacuator housing 50818, 50918 and/or the evacuation device (e.g. the electrosurgical instrument 50032 in FIG. 2) can include an indicator, such as one or more lights and/or display screens. For example, an LED on the evacuator housing 50818, 50819 may change color (e.g. from blue to red) depending on the volume of particulate detected by the sensor(s). In other instances, the indicator can include an alarm or warning, which can be tactile, auditory, and/or visual, for example. In such instances, when the particulate concentration in the ambient air detected by the air quality sensor (e.g. the particle sensor 50852) exceeds a threshold amount, the clinician(s) in the surgical theater can be notified by the indicator(s).

In certain instances, a surgical evacuation system can include an optical sensor. The optical sensor can include an electronic sensor that coverts light, or a change in the light, into an electronic signal. The optical sensor can utilize a light scattering method to detect and count particles in the smoke to determine the concentration of particles in the smoke. In various instances, the light is laser-based. For example, in one instance, a laser light source is configured to illuminate particles as the particles move through a detection chamber. As the particles pass through the laser's beam, the light source becomes obscured, redirected, and/or absorbed. The scattered light is recorded by a photo detector, and the recorded light is analyzed. For example, the recorded light can be converted to an electrical signal indicative of the size and quantity of the particles, which corresponds to the particulate concentration in the smoke. The particulate concentration in the smoke can be calculated in real time by a laser optical sensor, for example. In one aspect of the present disclosure, at least one of the particle sensors 50838, 50848, 50852 are laser optical sensors.

Figure 20:
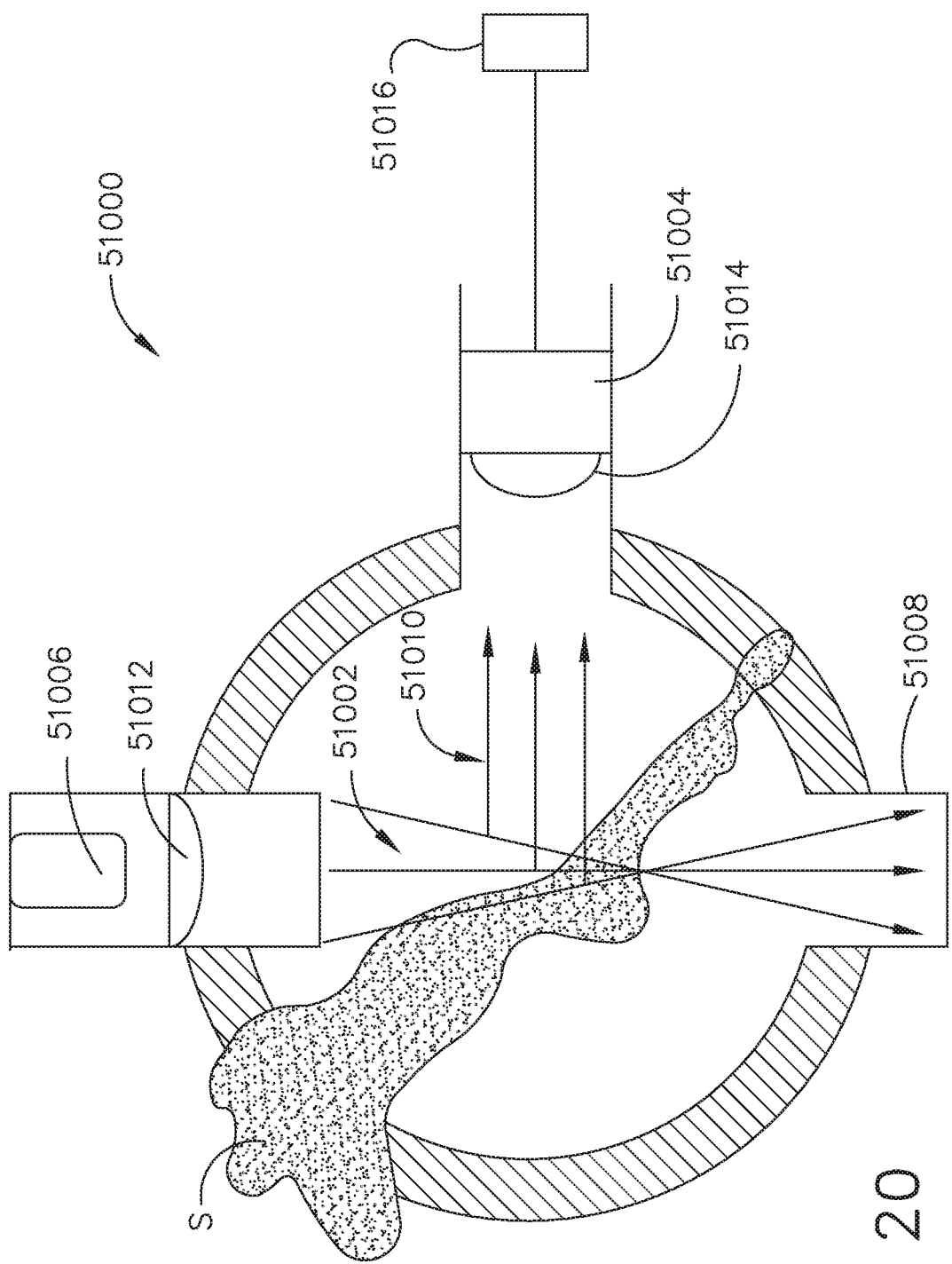
FIG. 20 is a schematic of a photoelectric sensor for a surgical evacuation system, in accordance with at least one aspect of the present disclosure.

A photoelectric sensor for detecting particles in the smoke can be a pass-through beam sensor, reflective sensor, or a diffuse sensor. A reflective photoelectric sensor 51000 is depicted in FIG. 20. Referring to FIG. 20, the reflective photoelectric sensor 51000 is a light-scattering sensor in which a light beam 51002 emitted from a light source 51006 through a lens 51012 is offset from a photo detector, or photo cell, 51004. For example, the photo detector 51004 in FIG. 20 is 90-degrees offset from the light source 51006. When smoke S obscures the light beam 51002 intermediate the light source 51006 and a light catcher 51008, the light is reflected and the reflected light 51010 is scattered toward a lens 51014 and onto the photo detector 51004. The photo detector 51004 converts the light into an electrical signal (current) that corresponds to the particulate concentration in the smoke S. The output signal can be provided to a processor 51016, which can be similar in many respects to the processor 50308 and/or 50408 depicted in FIGS. 5 and 6, respectively, which can affect an operational parameter of the motor based on the electrical signal and corresponding particulate concentration. For example, the output signal from the reflective photoelectric sensor 51000 can be an input to a control algorithm for the motor and/or an input to a surgical hub.

Figure 21:
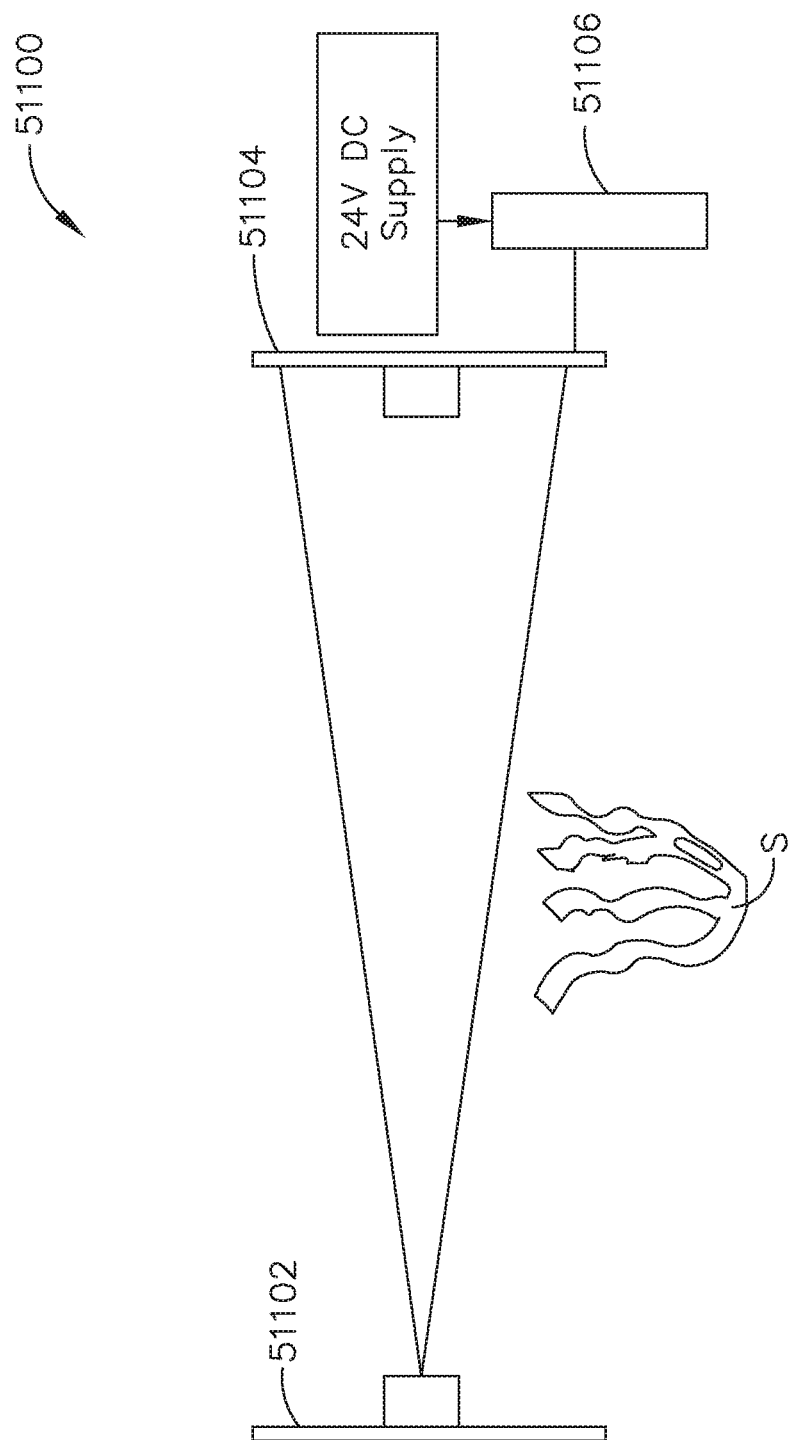
FIG. 21 is a schematic of another photoelectric sensor for a surgical evacuation system, in accordance with at least one aspect of the present disclosure.

A pass-through photoelectric sensor 51100 is depicted in FIG. 21. As depicted in FIG. 21, a line of sight extends between the light source 51102 and the photo detector 51104. In such instances, the intensity of the light reaching the photo detector 51104 can be converted to an electrical signal (current) that corresponds to the particulate concentration in the smoke S. The output signal can be provided to a processor 51106 coupled to a 24 V direct current supply, which can be similar in many respects to the processors 50308 and/or 50408 depicted in FIGS. 5 and 6. The processor 51106 can affect an operational parameter of the motor based on the electrical signal and corresponding particulate concentration. For example, the output signal from the photoelectric sensor 51100 can be an input to a control algorithm for the motor and/or an input to a surgical hub.

In a photoelectric sensor for a surgical evacuation system, such as the sensor 51000 in FIG. 20 and/or the sensor 51100 in FIG. 21, the wavelength of the light can be selected to tune the sensor 51000 for specific types of smoke while ignoring other types of smoke. In certain instances, multiple sensors and/or multiple wavelengths can be used to dial the sensor 51000 into the right combination(s). Water vapor, even thick water vapor, absorbs light of a certain wavelength. For example, water vapor absorbs infrared light instead of reflecting it. Due to these absorption properties of water vapor, infrared light can be useful in the presence of water vapor to accurately count particles in the fluid in a surgical evacuation system.

In certain instances, an ionization sensor can be used to detect particles in smoke. An ionization sensor includes two electrodes and radioactive material, which converts air molecules into positive and negative ions. The positive ions move toward the negative electrode, and the negative ions move toward the positive electrode. If smoke passes between the electrodes, the smoke bonds with the ions, which breaks the circuit. Drops in the current through the circuit can be converted into an electrical signal (current) that corresponds to the volume of smoke passing between the electrodes.

Figure 22:
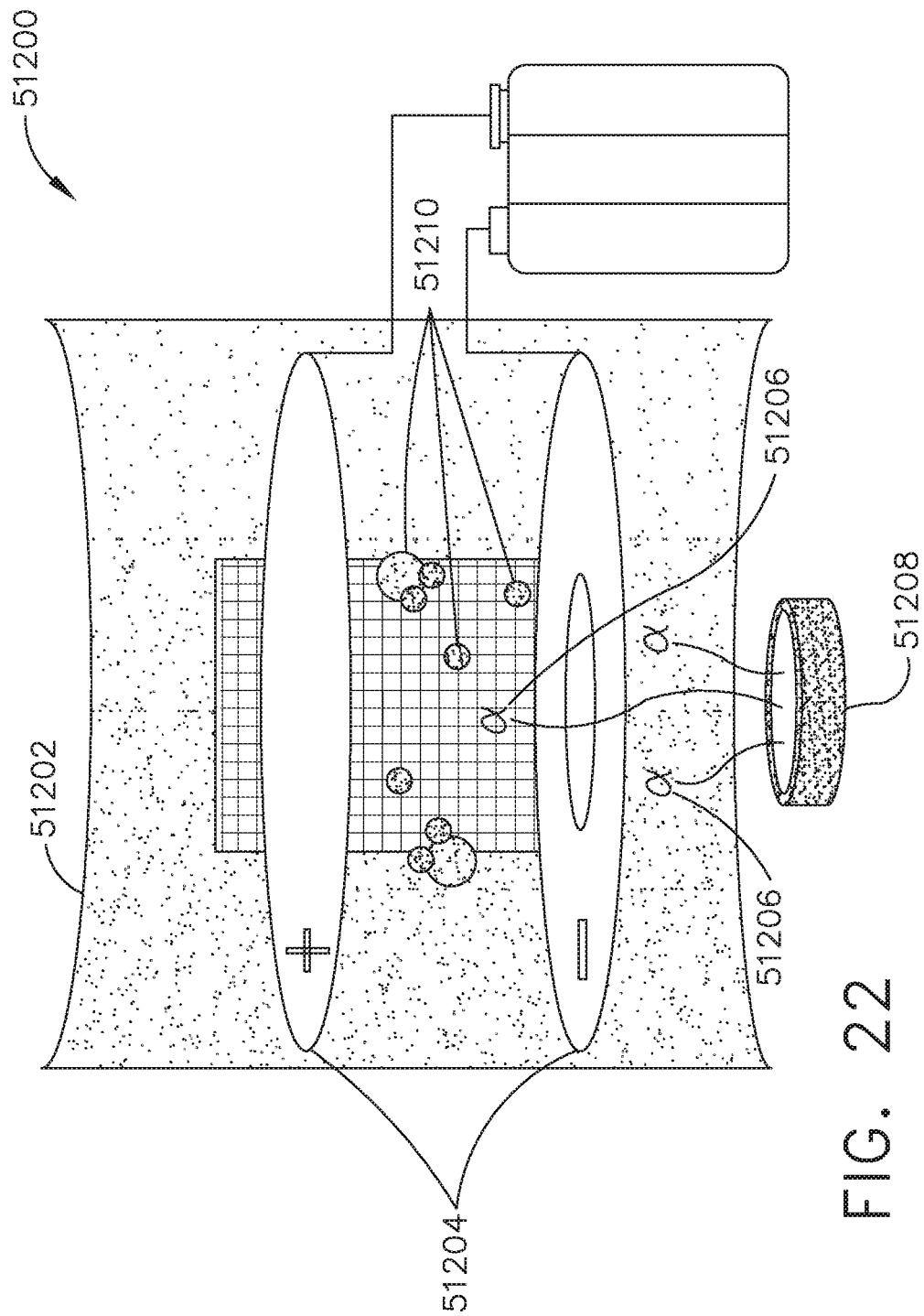
FIG. 22 is a schematic of an ionization sensor for a surgical evacuation system, in accordance with at least one aspect of the present disclosure.

An ionization sensor 51200 is depicted in FIG. 22. The ionization sensor 51200 utilizes Americium-241 to ionize air in a confined area. The sensor 51200 includes a small ionization chamber 51202 having two electrodes 51204 spaced apart. The ionization chamber 51202 can be made of polyvinylchloride or polystyrene, for example, and the electrodes 51204 can be spaced about 1 cm apart within the ionization chamber 51202, for example. An Americium-241 source 51208 can provide the Americium-241 to the ionization chamber 51202. About 0.3 µg of Americium-241 can be embedded within a gold foil matrix that is sandwiched between a silver backing and a 2-micro thick layer of palladium laminate, for example. The Americium-241 can have a half-life of 432 years and decay by emitting alpha rays 51206. The gold foil matrix is configured to retain the radioactive material while still allowing the alpha rays 51206 to pass through. In various instances, alpha rays are preferred over beta rays and gamma waves because they easily ionize air particles, have low penetrative power, and can be easily contained.

During ionization, electrons are knocked off the oxygen and nitrogen molecules, which produce charged ions. The charged ions are attracted to oppositely-charged electrodes and, thus, form a current in the chamber. Because smoke particulate 51210 is larger than air molecules, the ionized particles collide and combine with the smoke particulates. The combined particles act as recombination centers and neutralize the ions, which reduces the amount of ionized particles in the ionization chamber 51202 and reduces the overall current. Drops in the current can be converted to an electrical signal corresponding to the volume of smoke passing between the electrodes 51204. The output signal can be provided to a processor, such as the processor 50308 and/or the processor 50408 depicted in FIGS. 5 and 6, respectively, for example, which can affect an operational parameter of the motor. For example, the output signal from the ionization sensor 51200 can be an input to a control algorithm for the motor and/or an input to a surgical hub, as further described herein.

In various instances, dual ionization chambers can be used. A first chamber, which acts as a sensing chamber, can be open to the atmosphere and affected by particulate matter, humidity, and atmospheric pressure. A second chamber can be insulated from the smoke and particulate matter. Though positioned outside of the smoke flow path, the second chamber is still affected by humidity and atmospheric pressure. By using two chambers, humidity and atmospheric pressure changes can be minimized because the output from both chambers are affected equally and cancel each other out. Because humidity and pressure can vary significantly during a surgical procedure—depending on the type of surgical procedure, the surgical device(s) employed, and the type of tissue encountered, for example—a dual ionization chamber can be helpful in a smoke evacuation system to compensate for the changes in pressure and humidity.

In certain instances, a combination approach can be utilized for determining the particulate concentration in the smoke. For example, multiple different types of smoke detectors or sensors can be utilized. Such sensors can be arranged in series in-line with the flow path. For example, a plurality of particle sensors can be positioned along the flow path 50804 in FIG. 18 and/or the flow path 50904 in FIG. 19. The various sensors can provide inputs to a pump motor control algorithm, such as the various adjustment algorithms described herein.

In certain instances, the surgical evacuation system can be configured to tune the sensor parameters to more accurately detect particulate within the smoke. Tuning of the sensor parameters can depend on the type of surgical device, type of surgical procedure, and/or the type of tissue. Surgical devices often create a predictable type of smoke. For example, in certain procedures, a predictable type of smoke can be a smoke with a high water vapor content. In such instances, an infrared photoelectric sensor can be employed because infrared light is substantially absorbed and not reflected by water vapor. Additionally or alternatively, a predictable type of smoke can be a smoke having particles of a certain size or concentration. Based on the expected size of the particles, the sensor can be tuned to more accurately determine particulate concentration in the smoke.

In certain instances, situational awareness can facilitate tuning of the sensor parameters. Information relevant to situational awareness can be provided to a surgical evacuation system by a clinician, intelligent electrosurgical instrument in signal communication with the surgical evacuation system, robotic system, hub, and/or cloud. For example, a hub can include a situational awareness module, which can aggregate data from various sensor systems and/or input systems, including a smoke evacuation system, for example. Sensors and/or inputs throughout a computer-implemented interactive surgical system can be employed to determine and/or confirm the surgical device utilized in the surgical procedure, the type and/or step of the surgical procedure, and/or the type of tissue, for example. In certain instances, situational awareness can predict the type of smoke that will result at a particular time. For example, a situational awareness module can determine the type of surgical procedure and the step therein to determine what kind of smoke will likely be produced. Based on the expected type of smoke, the sensors can be tuned.

In certain instances, one or more of the particle sensors disclosed herein can be a fluid detection sensors. For example, the particle sensor can be positioned and configured to determine if aerosols and/or liquid droplets are present in the evacuated smoke. In one aspect of the present disclosure, the size and/or concentration of the detected particles can correspond to aerosol, liquid droplets, solid matter, and/or a combination thereof. In certain instances, situational awareness can determine and/or confirm whether the detected particles are an aerosol or solid matter. For example, a situational awareness module in signal communication with the processor (e.g. the processor 50308 in FIG. 5 and/or the processor 50408 in FIG. 6) can inform the identification of particles in the fluid.

Figure 23:
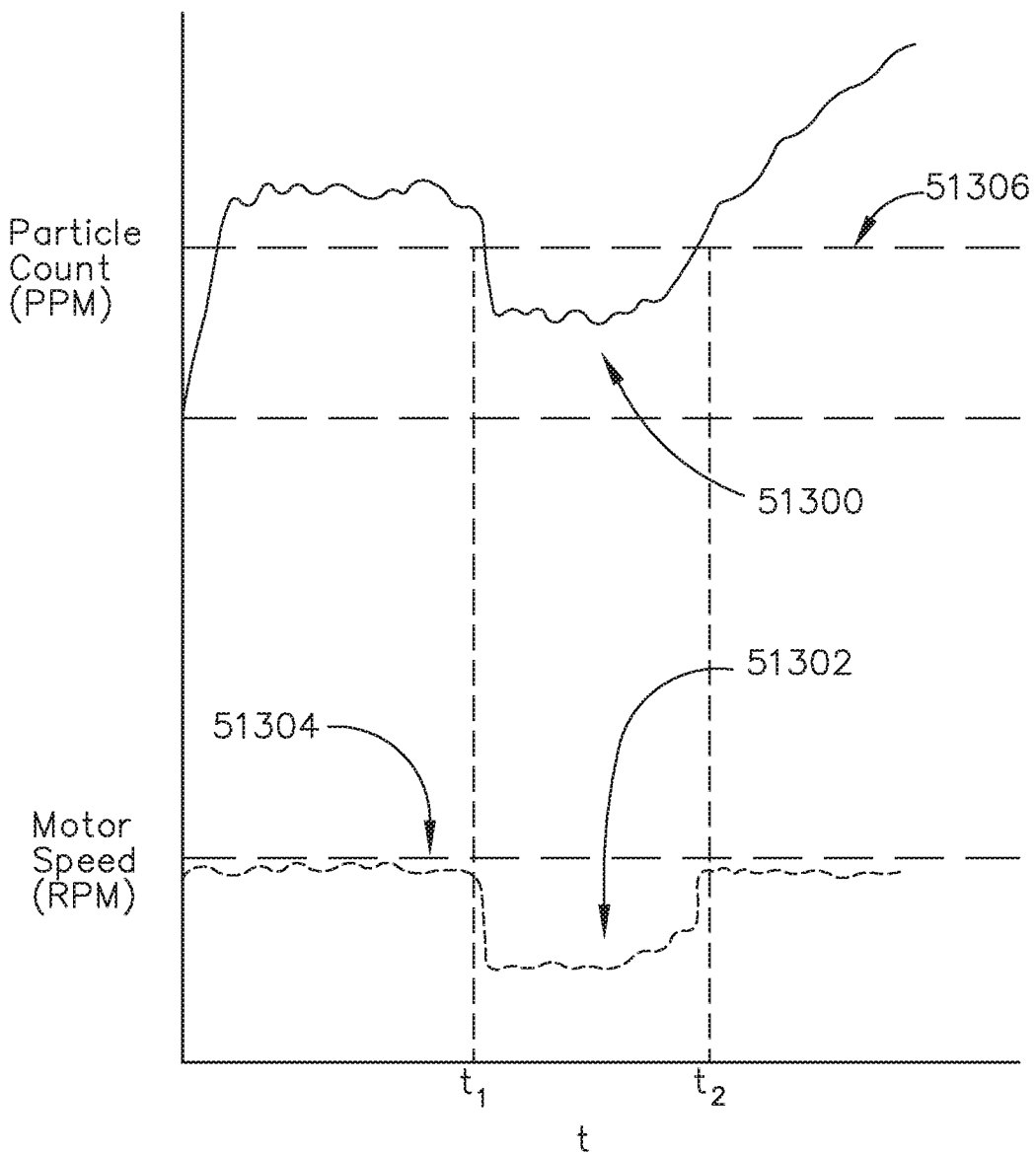
FIG. 23 is (A) a graphical representation of particle count over time and (B) a graphical representation of motor speed over time for a surgical evacuation system, in accordance with at least one aspect of the present disclosure.

Referring now to FIG. 23, a graphical representation of particle count 51300 and motor speed 51302 over time for a surgical evacuation system, such as the surgical evacuation system 50400 (FIG. 6), for example, is depicted. A target motor speed 51304 can be predefined and stored in the memory of the processor that is in signal communication with the motor (see, e.g., FIGS. 5 and 6). In various instances, the processor can be configured to maintain the target motor speed 51304 under normal operating conditions. For example, the target motor speed 51304 can be stored in the memory 50410 (FIG. 6), and the processor 50408 (FIG. 6) can be configured to maintain the target motor speed 51304 under normal operating conditions. In such instances, when the surgical evacuation system 50400 (FIG. 6) is activated, the motor 50451 can be operated at the target motor speed 51304 and can continue operating at the target motor speed 51304 unless one or more conditions are detected and/or communicated to the processor 50408.

In certain instances, the processor 50408 can be in signal communication with a particle sensor, which is configured to detect the particulate concentration in the intake smoke in real time. Various examples of particulate concentration sensors, such as a laser particle counter sensor, is described herein. In one aspect of the present disclosure, the particle sensor 50838 (FIGS. 18 and 19), which is positioned at the inlet to the filter 50870 in FIG. 18 and the inlet to the filter 50970 in FIG. 19, can be in signal communication with the processor 50408 (FIG. 6). For example, the laser particle sensor 50838 can correspond to one of the sensors 50430 in FIG. 6.

In various instances, when the particle sensor 50838 (FIGS. 18 and 19) detects that the particulate concentration (e.g. part-per-million of particulate matter in the fluid) drops below a threshold amount 51306, the processor 50408 can direct the motor driver 50428 to reduce the speed of the motor 50451. For example, at time $t_1$ in FIG. 23, the particle count, or particulate concentration, 51300 drops below the threshold amount 51306. Because the particle count 51300 has dropped below the threshold amount 51306, the motor speed 51302 can be reduced to below the target motor speed 51304. Thereafter, if the particle sensor 50838 (FIGS. 18 and 19) detects that the particle count 51300 again exceeds the threshold amount 51306, such as at time $t_2$, the processor 50408 can direct the motor driver 50428 to increase the speed of the motor 50451 to resume the target motor speed 51304. The particulate concentration can correspond to the size of particles in the smoke. For example, the smoke can contain smaller particles between time $t_1$ and time $t_2$. By reducing the speed of the motor 50451, the suction generated by the pump 50450 can be reduced, which can ensure that smaller particles are not sucked through the filter of the surgical evacuation system 50400. For example, reducing the motor speed or reducing the pressure of the pump can ensure the filtration system has adequate time and capacity to capture particulate and ensure the fine media filters can capture the smaller particles. Stated differently, the slower speed can improve the filtering efficiency of the surgical evacuation system 50400.

In certain instances, the speed of the motor 50451 driving the pump 50450 can be adjusted based on a particle sensor positioned downstream of the filter. For example, referring again to FIGS. 18 and 19, the particle sensor 50848 is positioned downstream of the filter 50870 in FIG. 18 and downstream of the filter 50970 in FIG. 19. Because the particle sensor 50848 is positioned downstream of the filter assembly, the particle sensor 50848 is configured to detect particulate in the exhaust from the surgical evacuation system 50800 or evacuation system 50900, for example. In other words, such a particle sensor 50848 is configured to detect particulate that has passed through the evacuator housing 50818, 50918 and is being expelled into the ambient air. The particle sensor 50848 is positioned adjacent to the outlet 50824, 50924 to the evacuator housing 50818, 50918, respectively. In one instance, when the particulate concentration in the exhaust (e.g. the particulate concentration detected by the particle sensor 50848) exceeds a predefined threshold amount, the processor 50308 (FIG. 5) and/or the processor 50408 (FIG. 6) can implement an adjustment to the pump. For example, referring again to FIG. 6, the speed of the motor 50451 can be adjusted to improve the filtering efficiency of the surgical evacuation system 50400.

The motor speed can be adjusted by limiting the current supplied to the motor and/or changing the duty cycle of the motor. For example, a pulse modulation circuit can employ pulse width modulation and/or pulse frequency modulation to adjust the length and/or frequency of the pulses.

Additionally or alternatively, the exhausted fluid can be redirected through one or more filters in the surgical evacuation system if the particle count in the exhaust exceeds a predefined threshold amount that may be dangerous or hazardous to the operator(s) and clinician(s) in the operating room. For example, if the particle sensor 50838 detects a particle count in the exhaust above a threshold amount, the processor 50308 (FIG. 5) and/or the processor 50408 (FIG. 6) can open a valve downstream of the filter, which can recirculate the exhaust and inject the recirculated exhaust into the flow path upstream of the filter. In certain instances, the valve can inject the recirculated exhaust into an alternative flow path that includes one or more additional and/or different filters, for example.

In certain instances, the surgical evacuation system can include an override option in which the evacuation system continues to operate and/or continues to operate a predefined power level despite exceeding a set threshold. For example, in an override mode, the surgical evacuation system can continue to operate and exhaust particles even if the particle sensor downstream of the filter detects a particulate concentration that exceeds the threshold amount. An operator in the surgical theater can activate the override feature or override mode by activating a switch, a toggle, a button, or other actuator on the evacuator housing and/or an input to the surgical hub, for example.

Figure 27:
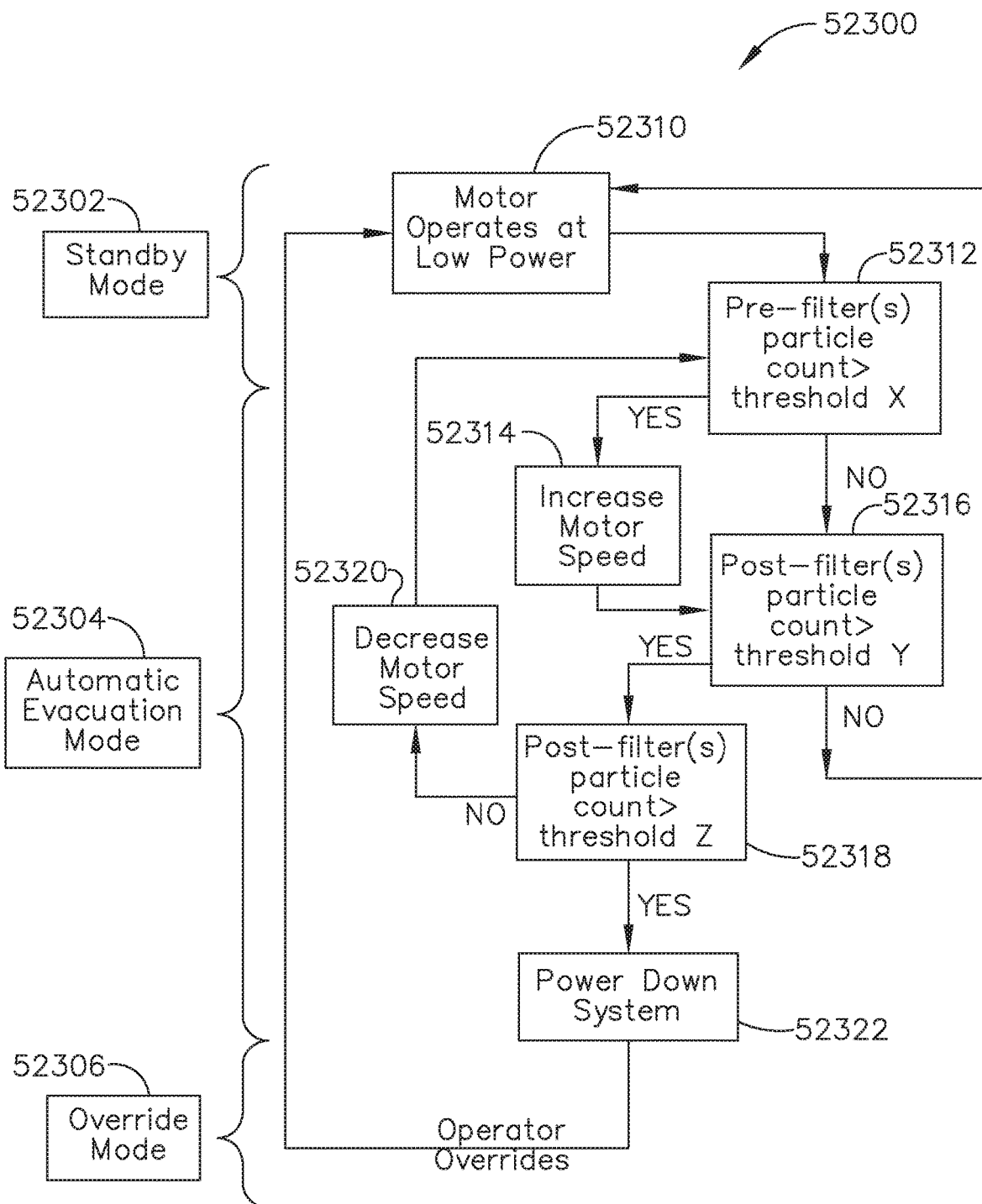
FIG. 27 is a flowchart depicting an adjustment algorithm for a surgical evacuation system, in accordance with at least one aspect of the present disclosure.

Referring now to FIG. 27, a flowchart depicting an adjustment algorithm 52300 for a surgical evacuation system is depicted. Various surgical evacuation systems disclosed herein can utilize the adjustment algorithm 52300 of FIG. 27. Moreover, the reader will readily appreciate that the adjustment algorithm 52300 can be combined with one or more additional adjustment algorithms described herein in certain instances. The adjustments to the surgical evacuation system can be implemented by a processor, which is in signal communication with the motor of the evacuator pump (see, e.g. the processors and pumps in FIGS. 5 and 6). For example, the processor 50408 can implement the adjustment algorithm 52300. Such a processor can also be in signal communication with one or more sensors in the surgical evacuation system.

In various instances, a surgical evacuation system can initially operate in a standby mode 52302, as depicted in FIG. 27, in which the motor is operated at a low power, as indicated in block 52310, in order to sample fluid from the surgical site. For example, in the standby mode 52302, a small sample of fluid can be evacuated from the surgical site by the surgical evacuation system. The standby mode 52302 can be the default mode of the evacuation system.

If a particle sensor upstream of the filter (e.g. the particle sensor 50838) detects a particle count, or particulate concentration, that is greater than a threshold value X, as indicated in block 52312, the surgical evacuation system can enter an automatic evacuation mode 52304. In the automatic evacuation mode 52304, the motor speed can be increased at block 52314 to draw additional smoke from the surgical site. For example, the particle count, or particulate concentration, may increase above the threshold amount X when an electrosurgical procedure commences or when a particular electrosurgical power level is activated. In certain instances, the speed of the motor can be adjusted during the automatic evacuation mode 52304 based on the detected particulate concentration. For example, as the particulate concentration detected by the particle sensor 50838 increases, the motor speed can correspondingly increase. In certain instances, predefined motors speeds can correspond to a predefined range of a particulate concentration detected by the particle sensor 50838.

Referring still to FIG. 27, if a particle sensor downstream of the filter (e.g. the particle sensor 50848) detects a particle count, or particulate concentration, that is less than a threshold amount Y at block 52316, the motor can resume a low power mode at block 52310 and/or be further adjusted at block 52314, as provided herein. Moreover, if the downstream particle sensor 50848 detects a particle count, or particulate concentration, that is greater than a threshold amount Y and less than a threshold amount Z at block 52318, the motor speed can be decreased at block 52320 to improve the efficiency of the filters. For example, a particulate concentration detected by the particle sensor 50848 between thresholds Y and Z can correspond to small particles that are passing through the filter of the smoke evacuation system.

Referring still to FIG. 27, if the particle sensor 50848 downstream of the filter detects a particle count that is greater than the threshold amount Z at block 52318, the motor can be turned off at block 52322 to terminate the evacuation procedure and the surgical evacuation system can enter an override mode 52306. For example, the threshold Z can correspond to an air quality risk to clinicians and/or other personnel in the surgical theater. In certain instances, the operator can selectively override the shutdown function, as further provided herein, such that the motor continues to operate at block 52310. For example, the surgical evacuation system can return to the standby mode 52302, in which samples of fluid are evacuated from the surgical site and monitored by the surgical evacuation system.

In certain instances, the power level of the pump can be a function of a pressure differential across at least a portion of the surgical evacuation system. For example, a surgical evacuation system can include at least two pressure sensors. Referring again to FIGS. 18 and 19, the ambient pressure sensor 50854 is configured to detect the pressure in the ambient room. The pressure sensor 50840 is configured to detect the pressure in the flow path 50804 intermediate the fluid trap 50860 and the filter, or filtering system, 50870 in FIG. 18, and to detect the pressure in the flow path 50904 intermediate the fluid trap 50960 and the filter system 50970 in FIG. 19. Additionally, the pressure sensor 50846 is configured to detect the pressure in the flow path 50804 intermediate the filtering system 50870 and the pump 50806 in FIG. 18, and in the flow path 50904 intermediate the filtering system 50970 and the pump 50906 in FIG. 19. Finally, the pressure sensor 50850 is configured to detect the pressure in the flow path 50804 and 50904 at the exhaust port or outlet 50824 and 50924, respectively. The reader will readily appreciate that certain smoke evacuation system can include less than or more than the four pressure sensors 50840, 50846, 50850, and 50854 depicted in FIGS. 18 and 19. Moreover, pressure sensors can be positioned at alternative locations throughout the surgical evacuation system. For example, one or more pressure sensors can be positioned in a smoke evacuator device, along the evacuation conduit extending between the evacuator and the housing, and within the housing, such as upstream of the fluid trap and/or intermediate different layers of the filtering system, for example.

Figure 28:
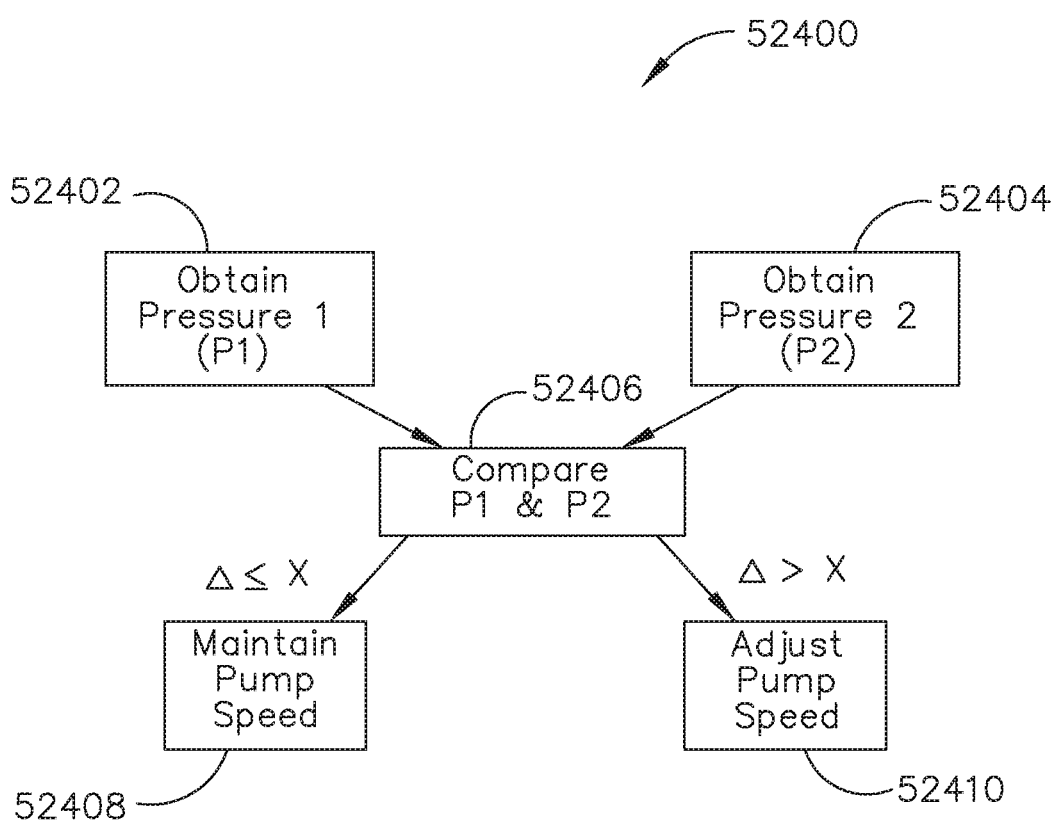
FIG. 28 is a flowchart depicting an adjustment algorithm for a surgical evacuation system, in accordance with at least one aspect of the present disclosure.

Referring now to FIG. 28, a flowchart depicting an adjustment algorithm 52400 for a surgical evacuation system is depicted. In various instances, the surgical evacuation systems disclosed herein can utilize the adjustment algorithm of FIG. 28. Moreover, the reader will readily appreciate that the adjustment algorithm 52400 of FIG. 28 can be combined with one or more additional adjustment algorithms described herein in certain instances. The adjustments to the surgical evacuation system can be implemented by a processor, which is in signal communication with the motor of the evacuator pump (see, e.g. the processors and pumps in FIGS. 5 and 6). For example, the processor 50408 can implement the adjustment algorithm 52400. The processor can also be in signal communication with one or more pressure sensors in the surgical evacuation system.

In various instance, the processor 50408 is configured to obtain a pressure measurement P1 from a first pressure sensor at block 52402, and a second pressure measurement P2 from a second pressure sensor at block 52404. The first and second pressure sensors can be provided by the sensors 50430 in FIG. 6, for example. The processor 50408 is configured to compare the measurements P1 and P2 at block 52406 to determine a pressure differential between the first pressure sensor and the second pressure sensor. In one instance, if the pressure differential is less than or equal to a threshold amount X, such as at block 52408, the speed of the pump can be maintained. Conversely, if the pressure differential is greater than the threshold amount X, such as at block 52410, the speed of the pump can be adjusted. An adjustment to an operational parameter of the motor is configured to adjust the speed of the pump. The adjustment algorithm 52400 can be repeated continuously and/or at regular intervals. In certain instances, a clinician can trigger implementation of the adjustment algorithm 52400.

The flowrate of smoke through the evacuation system can be a function of the pressure differential. In one instance, if a pressure differential across an evacuation system increases significantly, the flowrate through the system may also increase. The actual flow rate can be predicted based on the pressure differential and the motor speed. Therefore, by monitoring the pressure differential, the flowrate can be more accurately determined.

Additionally, occlusions in the flow path can correspond to increases in the pressure differential. For example, as the filter captures particles from smoke, the pressure differential across the filter can increase for a given pump speed. In response to a predefined pressure drop across the filter, the speed of the motor, and the corresponding speed of the pump, can be increased to maintain the flowrate of smoke through the system despite the occlusions in the filter. For example, referring again to FIGS. 18 and 19, a first pressure sensor can be positioned upstream of the filter (e.g. the pressure sensor 50840) and a second pressure sensor can be positioned downstream of the filter (e.g. the pressure sensor 50846). The pressure differential between the pressure sensor 50840 and the pressure sensor 50846 can correspond to the pressure drop across the filter. As the filter captures particles in the smoke, the captured particles can obstruct the flow path, which can increase the pressure differential across the filter. In response to the increased pressure differential, the processor can adjust an operational parameter of the motor to maintain the flowrate across the system. For example, the speed of the motor, and the corresponding speed of the pump, can be increased to compensate for the partially obstructed filter in the flow path.

In other instances, a predefined pressure drop can correspond to a blockage in the evacuation conduit. In one example, to avoid tissue damage when the evacuation conduit becomes blocked with tissue, for example, the speed of the motor, and the corresponding speed of the pump, can be decreased. Decreasing the speed of the pump in such instances can be configured to avoid potential tissue trauma.

In another instance, a first pressure sensor can be positioned upstream of the fluid trap and a second pressure sensor can be positioned downstream of the fluid trap (e.g., the pressure sensor 50840). The pressure differential between the sensors can correspond to the pressure drop across the fluid trap, which can correspond to the flowrate and/or flow path through the fluid trap. The pressure differential across the fluid trap can also be estimated by other sensors in the fluid evacuation system. In certain instances, it is desirable to reduce the flow rate through the fluid trap to ensure the sufficient removal of liquid from the smoke before it enters the downstream filter(s) and pump. In such instances, the pressure differential can be reduced by reducing the speed of the motor, and the corresponding speed of the pump.

In still other instances, a first pressure sensor can be positioned at the inlet to the surgical evacuation system, or evacuator housing thereof, and a second pressure sensor can be positioned at the outlet to the surgical evacuation system (e.g. the pressure sensor 50850). The pressure differential between the sensors can correspond to the pressure drop across the surgical evacuation system. In certain instances, the maximum suction load of the system can be maintained below a threshold value by monitoring the pressure drop across the system. When the pressure drop exceeds a threshold amount, the processor can adjust an operational parameter of the motor (e.g. slow down the motor) to reduce the pressure differential.

In one instance, the chemical sensor 50832 can detect the pH of matter in physical contact with the sensor such as fluid splattered onto the sensor 50832, for example. In one aspect of the present disclosure, the chemical sensor 50832 can detect glucose and/or oxygen content in the fluid. The chemical sensor 50382 can be configured to detect cancerous byproducts in certain instances. If cancerous byproducts are detected, the parameters of the evacuation system can be adjusted to reduce the likelihood that such byproducts would enter the surgical theater. In one instances, the pump speed can be reduced to improve the efficiency of a filter in the evacuation system, for example. In other instances, the evacuation system can be powered down to ensure the cancerous byproducts are not exhausted into the surgical theater.

The fluid extracted from a surgical site by a surgical evacuation system may contain liquid and various particulates. The combination of different types and/or states of matter in the evacuated fluid can make the evacuated fluid difficult to filter. Additionally or alternatively, certain types and/or states of matter can be detrimental to certain filters. For example, the presence of liquid droplets in the smoke can damage certain filters and the presence of larger particulates in the smoke can block certain fine particulate filters.

Sensors can be configured to detect a parameter of a fluid moving through the evacuation system. Based on the parameter detected by the sensor(s), the surgical evacuation system can direct the evacuated fluid along an appropriate flow path. For example, fluid containing a percentage of liquid droplets above a certain threshold parameter can be directed through a fluid trap. As another example, fluid containing particulates above a threshold size can be directed through a coarse media filter, and fluid containing particulates below the threshold size can bypass the coarse media filter and be directed to a fine media filter.

By providing alternative flow paths through a surgical evacuation system, the surgical evacuation system and filter(s) thereof may operate more efficiently and be less prone to damage and/or blockages. The usable life of the filters may also be extended. As provided herein a filter can include one or more filtering layers and, in certain instances, a filtering system can include one or more filters.

Figure 24A:
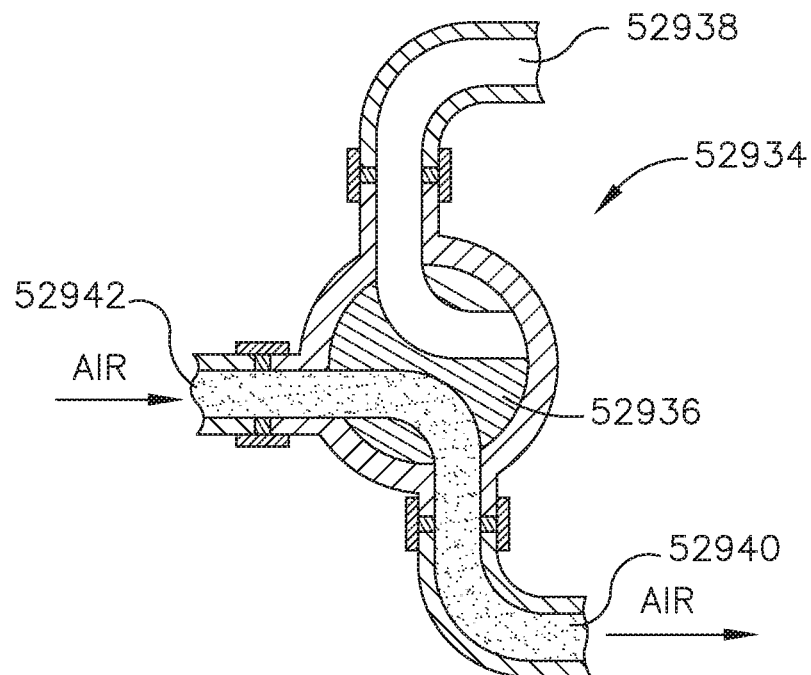
FIG. 24A is a cross-section view of a diverter valve for a surgical evacuation system, depicting the diverter valve in a first position, in accordance with at least one aspect of the present disclosure.
Figure 24B:
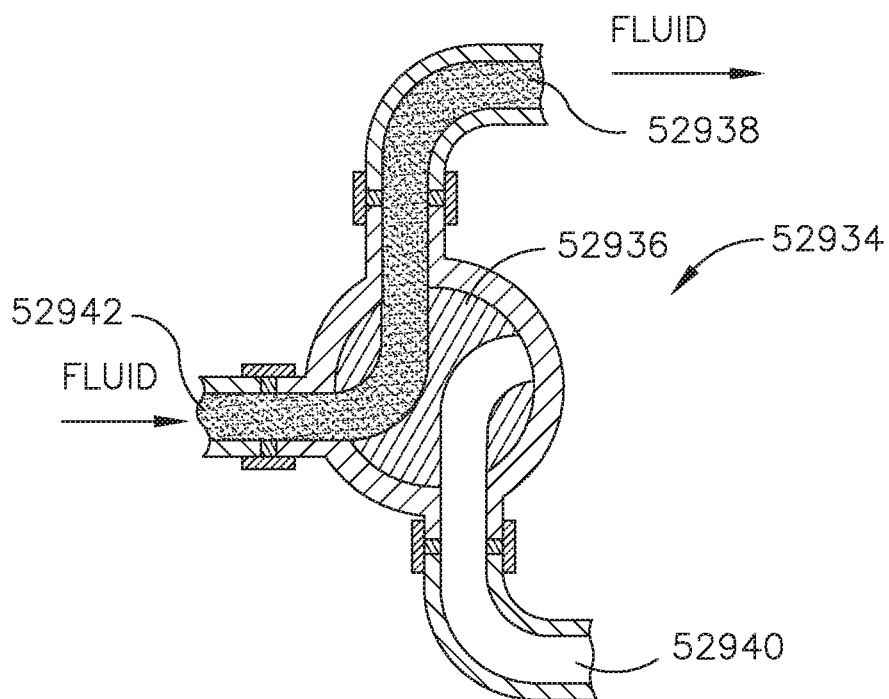
FIG. 24B is a cross-section view of the diverter valve of FIG. 24A in a second position, in accordance with at least one aspect of the present disclosure.

A diverter valve 52934 for a surgical evacuation system is depicted in detail in FIGS. 24A and 24B. In one aspect of the present disclosure, the diverter valves 50834 and 50934 depicted in the surgical evacuation systems 50800 and 50900 in FIGS. 18 and 19, respectively, can comprise the diverter valve 52934. The diverter valve 52934 comprises a ball valve 52396, which is operably structured to direct a fluid from an inlet path 52942 along either a first path 52940 or a second path 52938. In various instances, the ball valve 52396 can be an electrically-actuated ball valve comprising a controller. For example, a processor for the surgical evacuation system, such as the processor 50408 (FIG. 6), can send a signal to the ball valve controller to initiate rotation of the ball valve 52396 to change the flow path of the smoke therethrough. When the diverter valve 52934 is in a first position (FIG. 24A), smoke intake through the diverter valve 52934 is directed along the first path 52940. When the diverter valve 52934 is in a second position (FIG. 24B), smoke intake through the diverter valve 52934 is directed along the second path 52938.

The first path 52940 can correspond to a flow path when no liquid has been detected within the smoke or when the detected liquid-to-gas ratio or aerosol percentage is below a threshold value. The second path 52938 can correspond to a flow path when liquid has been detected within the smoke, e.g. aerosol, or when the detected liquid-to-gas ratio or aerosol percentage is equal to or above the threshold value. In certain aspects of the present disclosure, the first path 52940 can bypass a fluid trap and the second path 52938 can direct the smoke through the fluid trap to capture fluid from the smoke before the smoke is directed into the filter. By selecting a flow path based on the aerosol percentage, the efficiency of the surgical evacuation system can be improved.

In other instances, the diverter valve 52934 can include more than two fluid path outlets. Moreover, the fluid paths can bypass/recirculate fluid with respect to a fluid trap and/or direct the smoke along different filtering paths including different arrangements of fluid traps, condensers, and/or particulate filters depending on the detected parameters of the fluid.

Referring again to FIGS. 18 and 19, the fluid detection sensor 50830 is configured to detect the presence of aerosol, or the liquid-to-gas ratio, in the smoke. For example, the fluid detection sensor 50830 in FIG. 18 is positioned at the inlet 50822 to the evacuator housing 50818. In other instances, the fluid detection sensor 50830 can be positioned near the inlet 50822 and/or at a location upstream of the filter 50870 and/or of a socket for receiving the filter 50870. Examples of fluid detection sensors are further described herein. For example, the fluid detection sensor 50830 can include one or more of the particle sensors further disclosed herein. Additionally or alternatively, in one aspect of the present disclosure, the fluid detection sensor 50830 includes a continuity sensor.

In one instance, if the fluid detection sensor 50830 detects a liquid-to-gas ratio equal to or above a threshold value, the intake can be diverted into a condenser before entering the particulate filter. The condenser can be configured to condense small liquid droplets in the flow path. In various instances, the condenser can include a honey-comb structure. The condenser can include a plurality of baffles or other structures, upon which the liquid is configured to condensate. As smoke flows past the condenser, the liquid can condensate on the baffles therein, and can be directed to drip downward into a fluid reservoir.

Referring primarily to FIG. 18, the diverter valve 50834 therein is positioned to direct the smoke intake to bypass the condenser 50835 such that the smoke flows directly to the filter 50870. In bypassing the condenser 50835, the surgical evacuation system 50800 can require less power from the motor that drives the pump (see, e.g. the motor 50451 and the pump 50450 in FIG. 6). Referring now to FIG. 19, the diverter valve 50934 is positioned to direct the smoke into the condenser 50935 within the fluid trap 50960 before the smoke flows into the filter 50970. Conversely, if the fluid detection sensor 50830 detects a liquid-to-gas ratio below the threshold value, the intake can bypass the condenser 50935 and be directed directly to the filter 50970.

In various instances, the fluid detection sensor 50830 can detect the presence of smoke in the flow path. For example, the fluid detection sensor 50830 can comprise a particle sensor. Detection of particles, or detection of a particulate concentration above a threshold value, can indicate that smoke is present in the flow path. In certain instances, the fluid detection sensor may not distinguish between solid particles (e.g. carbon) and aerosol particles. In other instances, the fluid detection sensor 50830 can also detect the presence of aerosols. For example, the fluid detection sensor can include a continuity sensor, as described herein, which can determine whether the detected particles are aerosol, for example.

In various instances, the surgical evacuation system can include additional or alternative flow paths. For example, the surgical evacuation system can include a high-particulate flow path and a low-particulate flow path. When a particle sensor such as the particle sensor 50838 (FIGS. 18 and 19), for example, detects a particulate concentration equal to or above a threshold valve, the intake smoke can be diverted into a particulate filter. Conversely, if the laser particle sensor detects a particulate concentration below the threshold value, the intake smoke can bypass the particulate filter. Similarly, different flow paths can correspond to different sizes and/or types of particles. For example, if larger particles are detected by the particle sensor 50838, the smoke can be directed along a different path than if smaller particles are detected. For example, a surgical evacuation system can include different types of particulate filters (e.g. large media and fine media filters) and can utilize different filtering methods such as direct interception, inertial impaction, and diffusional interception based on the detected size (or size range) of the particles. Different flow paths can be selected to optimize fluid extraction and/or particulate filtering of the smoke while minimizing the power draw and/or stress on the motor. In certain instances, a default flow path can be a more direct flow path and, upon detecting a fluid parameter that exceeds a threshold limit, the fluid can be diverted to the less direct flow path. The less direct flow path can require more power.

In various instances, the motor for the surgical evacuation system can be adjusted based on properties of the intake smoke and/or the filter installed in the surgical evacuation system. Referring again to the schematic depicted in FIG. 6, the processor 50408 is in signal communication with the motor driver 50428, which is coupled to the motor 50451 for the pump 50450. The processor 50408 can be configured to adjust the motor 50451 based on the properties of the smoke and/or the installed filter. In one instance, the processor 50408 can receive inputs corresponding to the liquid volume within a flow path including the volume of aerosol suspended within the smoke and/or the volume of liquid droplets in contact with or resting on the tubing of the surgical evacuation system. Various sensors for detecting fluid density of the intake smoke, such as continuity sensors, for example, are further described herein.

The liquid-to-gas ratio of the smoke can affect the efficiency of a smoke evacuation pump. For example, liquid(s) within the smoke can be less compressible than gas within the smoke, which can affect the efficiency of the pump. Additionally, different types of pumps may perform differently in the presence of aerosols. In certain instances, the pump speed can be accelerated and, in other instances, the pump speed can be decelerated. To optimize the pump's efficiency for a respective liquid-to-gas ratio, the processor can be configured to adjust the motor that drives the pump. In other words, a control program for the motor can operably adjust the pump speed based on the detected liquid-to-gas ratio in the flow path.

Certain pumps may efficiently handle fluids having a high liquid-to-gas ratio such that the efficiency of the pump either stays the same or increases. For example, certain scroll pumps can handle aerosols in the smoke path. In such instances, the pump's rotational velocity may be decreased with the incompressible (or less compressible) fluids increasing the air handling of the vacuum. Other pumps may be more sensitive to fluids with a high liquid-to-gas ratio and, thus, can be slowed down to limit the pressure differential through the fluid trap.

In various instances, a sensor can be configured to detect the flow rate through a surgical evacuation system. For example, an optical sensor can be configured to measure the flowrate of particles within the surgical evacuation system. In certain instances, the detected flow rate through the surgical evacuation system can be utilized to manage the suction rate of the compressor. An algorithm can determine the appropriate suction rate based on the flow rate and/or one or more detected parameters of the smoke (e.g. particulate concentration, liquid-to-gas ratio, etc.). For example, when smoke having a high liquid-to-gas ratio enters the surgical evacuation system, the motor speed can be reduced to reduce the flow rate through the surgical evacuation system including the fluid trap thereof such that more liquid can be extracted from the smoke before the smoke enters the pump. Liquid can damage certain pumps. For example, lobe pumps and regenerative blows can be damaged if liquid within the smoke is allowed to enter.

Figure 25:
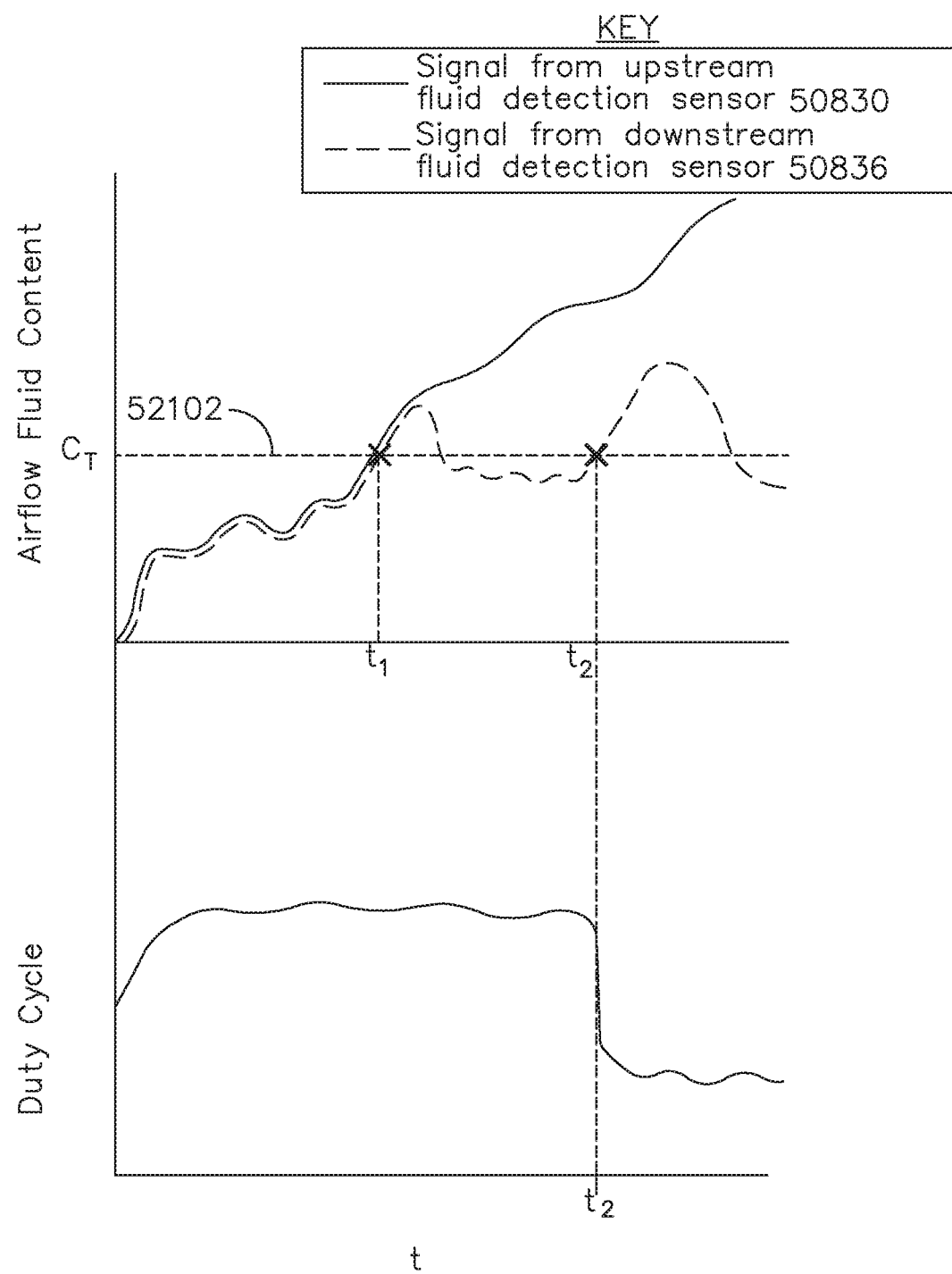
FIG. 25 is a graphical representation of (A) airflow fluid content over time and (B) duty cycle over time for a surgical evacuation system, in accordance with at least one aspect of the present disclosure.

FIG. 25 depicts a graphical representation of airflow fluid content and duty cycle over time for a surgical evacuation system, such as the surgical evacuation systems 50800 (FIG. 18) and/or 50900 (FIG. 19). The fluid content can include aerosol and liquid droplets within the evacuation system, and can be detected by the fluid detection sensors 50830 and 50836 (FIGS. 18 and 19), for example. Referring again to FIG. 25, at the outset of the procedure, the fluid detection sensors 50830 and 50836 detect the same, or substantially the same, content of fluid in the smoke. Stated differently, the fluid content upstream of the respective fluid trap 50860, 50960 is the same, or substantially the same, as the fluid content downstream of the respective fluid trap 50860, 50960. The fluid content detected by both sensors 50830 and 50836 continues to rise as the procedure continues.

At time $t_1$, the fluid content detected by both sensors 50830 and 50836 exceeds a fluid content threshold ($C_T$) 52102 and, to prevent damage to the filtering system, the smoke is redirected through the fluid trap, such as the fluid traps 50860 and/or 50960. The fluid content threshold $C_T$ 52102 can correspond to a volume or fluid and/or aerosol percentage that would be detrimental to the filtering system. Referring primarily to the evacuation system 50900 in FIG. 19, the recirculating valve 50990 can be opened (as shown in FIG. 19), such that the fluid can be redirected back into the condenser 50935 of the fluid trap 50960 before entering the filter 50970. By recirculating the fluid, additional liquid droplets can be removed therefrom. As a result, referring again to FIG. 25, the fluid content detected by the fluid detection sensor 50836, positioned upstream of the filter 50970, can decrease to below the fluid content threshold $C_T$ 52102. In various instances, through the airflow path through the evacuator housing is adjusted at time $t_1$, the duty cycle of the motor can be maintained, as shown in FIG. 25.

Referring still to the graphical representations in FIG. 25, as the smoke is recirculated through the fluid trap, which captures some of the aerosol and/or liquid droplets, the downstream fluid detection sensor 50836 begins to detect less liquid content in the smoke. However, the upstream fluid detection sensor 50830 continues to detect an increasing amount of liquid in the smoke. Moreover, at time $t_2$, the downstream fluid detection sensor 50836 again detects a fluid content that exceeds the fluid content threshold $C_T$ 52102. To address the increasing fluid content despite recirculation of the smoke through the fluid trap, the duty cycle for the pump motor is decreased at time $t_2$ to reduce the velocity of the pump, such that more liquid can be extracted from the smoke before the smoke enters the pump. As the pump adjusts to the reduced duty cycle, the fluid trap can more effectively capture aerosol and/or liquid droplets within the smoke and the fluid content detected by the fluid detection sensor 50836 eventually begins to decrease to below the fluid content threshold $C_T$ 52102.

In certain instances, the volume of fluid in the fluid trap and/or the levelness of the housing can be utilized to determine if the fluid level therein is approaching a threshold limit, which can correspond to reaching the spill-prevention baffles and/or the exit port of the fluid trap to the particulate filter. Liquid can damage the particulate filter and/or reduce the efficiency thereof, as further described herein. To prevent liquid from entering the particulate filter, the processor can adjust the motor to minimize the likelihood of drawing liquid into the particulate filter. For example, when a predefined volume of liquid enters the fluid trap and/or when the liquid within the trap reaches a set marker or level within the housing that exceeds a predefined safe level, the processor can direct the motor to slow down.

In various instances, the control program for the motor can be further affected by using the pressure differential between pressure sensors in an evacuation system, such as the pressure sensors 50840 and 50846 in the surgical evacuation system 50900 (FIG. 19). For example, based on the pressure differential across the filter 50970 and the speed of the motor for the pump 50906, a processor for the surgical evacuation system 50900 can be configured to predict the actual flowrate through the filter 50970. Moreover, the flowrate can be adjusted (by adjusting the motor speed, for example) to limit the flowrate and reduce the likelihood that fluid will be drawn out of a reservoir in the fluid trap 50960 and into the filter 50970.

As set forth herein, the surgical evacuation system can include one or more sensors configured to detect the presence of aerosol within the smoke (e.g. a liquid-to-gas ratio) and one or more sensors configured to detect the presence of carbonized particulate within the smoke (e.g. a parts-per-million measurement). By determining whether the extracted fluid is primarily steam, primarily smoke, and/or the respective ratio of each, the surgical evacuation system can provide valuable information to a clinician, an intelligent electrosurgical instrument, a robotic system, a hub, and/or a cloud. For example, the ratio of steam to smoke can indicate the extent of tissue welding and/or collagen cauterization. In various instances, the energy algorithm of an electrosurgical instrument and generator therefor can be tuned based on the steam-to-smoke ratio.

Figure 58:
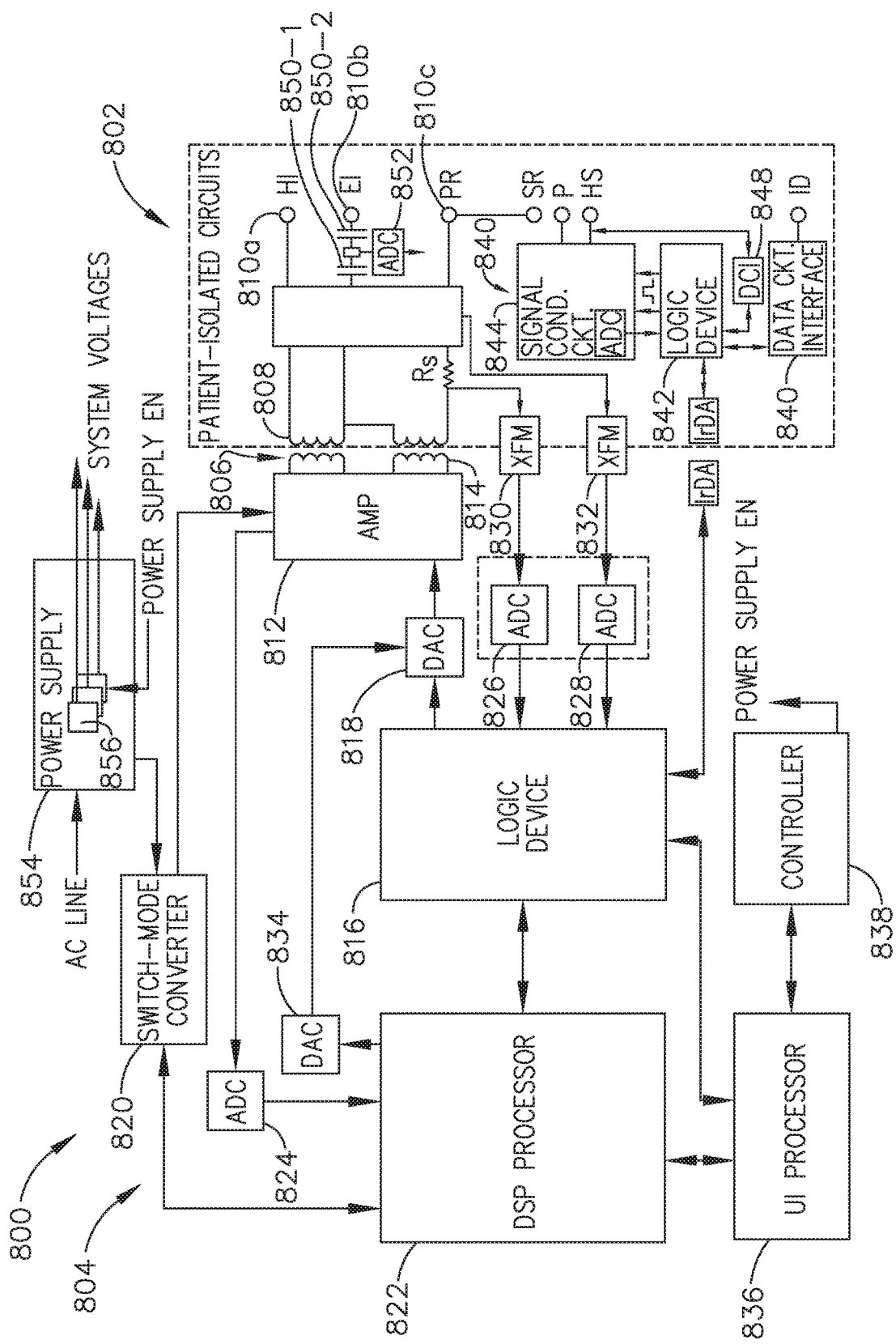
FIG. 58 is a simplified block diagram of a generator configured to provide inductorless tuning, among other benefits, in accordance with at least one aspect of the present disclosure.

In one aspect of the present disclosure, when the extracted fluid is primarily steam or comprises a high aerosol percentage, a processor can adjust the amplitude and/or power of an ultrasonic generator, such as the generator 800 (FIG. 58). For example, a processor for a smoke evacuation system can be communicatively coupled to the generator 800. In one instance, excessive steam or aerosols may be generated when the power is too high for a particular surgical scenario. In such instances, the power level of the generator can be decreased to reduce the generation of steam/aerosols by the energy tool. In other instances, for higher particulate ratios, a processor can adjust the power level of the generator. For example, the power level can be decreased for particulate ratios above a threshold value. In certain instances, the voltage can be adjusted to reduce the particulate generated by the energy tool.

Figure 26:
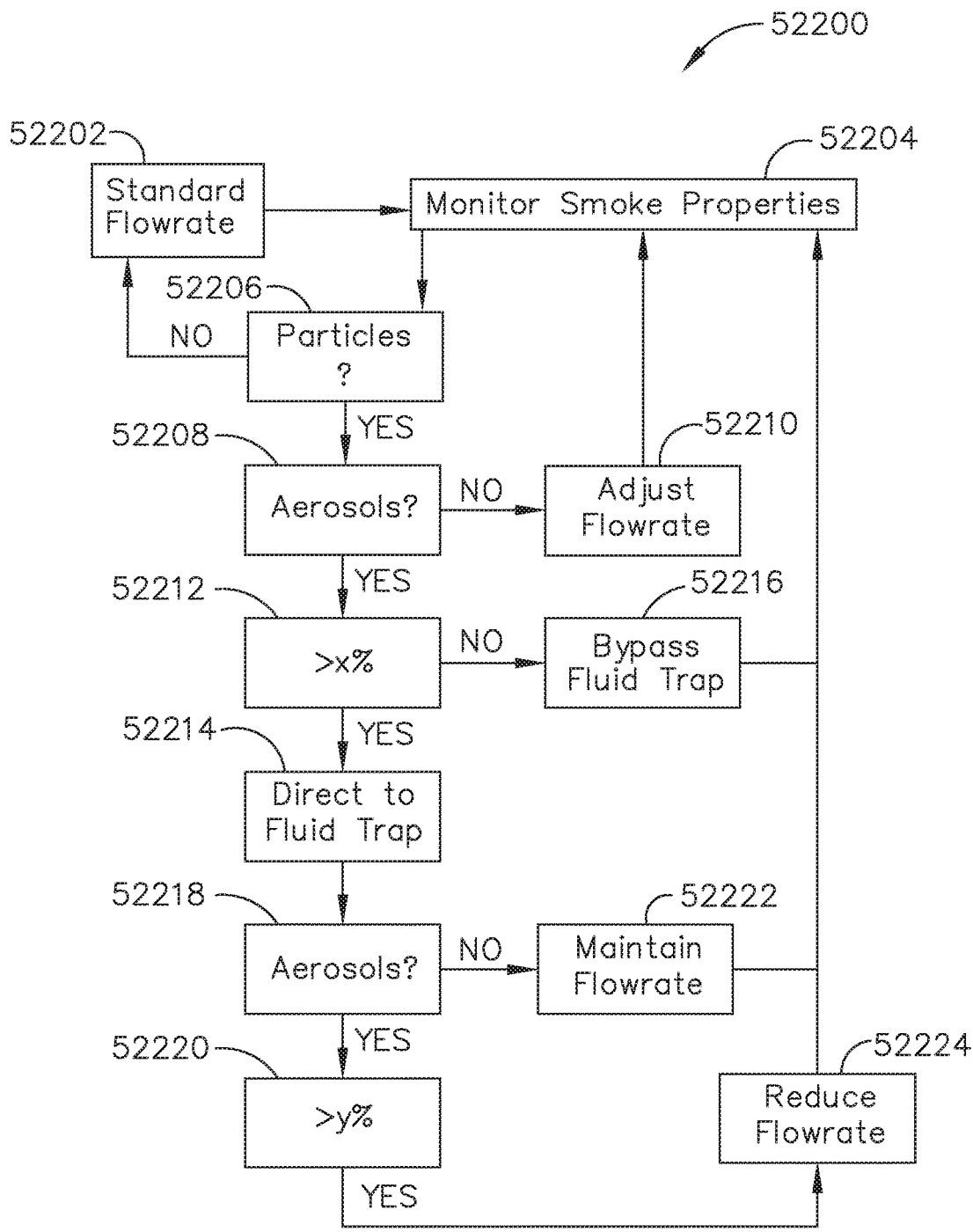
FIG. 26 is a flowchart depicting an adjustment algorithm for a surgical evacuation system, in accordance with at least one aspect of the present disclosure.

Referring now to FIG. 26, an adjustment algorithm 52200 for a surgical evacuation system is depicted. Various surgical evacuation systems disclosed herein can utilize the adjustment algorithm 52200. Moreover, the reader will readily appreciate that the adjustment algorithm 52200 can be combined with one or more additional adjustment algorithms described herein in certain instances. The adjustments to the surgical evacuation system can be implemented by a processor, which is in signal communication with the motor of the evacuator pump (see, e.g. the processors and pumps in FIGS. 5 and 6). For example, the adjustment algorithm 52200 can be implemented by the processor 50408 in signal communication with the motor driver 50428 and/or a controller for a diverter valve, as further described herein. The processor is configured to utilize various sensors to monitor properties of the evacuated smoke. In one aspect of the present disclosure, referring to FIG. 26, the processor is configured to determine if the intake smoke includes particles and aerosols above a threshold value.

At the outset of the adjustment algorithm 52200, a standard flowrate can commence at block 52202 and one or more properties of the intake smoke can be monitored at block 52204. At block 52206, a sensor can be configured to check for particles in the fluid. If no particles are detected by the sensor, the standard flowrate and/or the power level can be maintained at block 52202. In one instance, the standard flowrate can be a minimum flowrate, or idle flowrate, as further described herein. If particles are detected at block 52206 and the particles are determined not to be aerosol particles at block 52208, a first adjustment to the flowrate and/or the power level can be implemented at block 52210. For example, the flowrate and the power level can be increased to increase the evacuation of the particles, i.e. smoke, from the surgical site. In certain instances, if the particles are determined to be aerosol particles at block 52208, or if a portion of the particles are aerosol particles, a second adjustment can be implemented.

In one aspect of the present disclosure, the second adjustment can depend on the aerosol percentage in the smoke. For example, if the aerosol percentage is determined to be greater than a first threshold amount, such as X % in block 52212 in FIG. 26, the smoke can be directed to a fluid trap at block 52214. Conversely, if the aerosol concentration in the smoke is less than or equal to the threshold amount X %, the smoke can be directed to bypass the fluid trap at block 52216. Conduits and valves for directing the fluid flow within a smoke evacuation system are further described herein. In certain instances, the flowrate and/or the power level can be adjusted to sufficiently draw the fluid along the selected flow path, such as toward the fluid trap and/or around the fluid trap, for example. In one aspect of the present disclosure, additional power and/or suction can be required to draw the fluid into the fluid trap.

Referring still to FIG. 26, upon exiting the fluid trap, if aerosol particles are still detected in the smoke at block 52218, and if the aerosol concentration is greater than a second threshold amount at block 52220, such as Y % in FIG. 26, the flowrate can be reduced at block 52224 to ensure adequate extraction of the aerosol from the smoke. Conversely, if the aerosol concentration downstream of the fluid trap is less than or equal to the second threshold amount, Y %, the flowrate can be maintained at block 52222. As indicated in FIG. 26, upon redirected the flow path and/or adjusting and/or maintain the flowrate in the adjustment algorithm 52200, the adjustment algorithm can return to block 52204 to continue monitoring one or more parameters of the smoke evacuation system. In certain instances, the adjustment algorithm 52200 can cycle continuously such that the smoke properties are continuously being monitored and/or transmitted to the processor in real-time, or near real-time. In other instances, the adjustment algorithm 52200 can repeat a predefined times and/or intervals.

In certain instances, the surgical evacuation system can further include a chemical sensor, such as the chemical sensor 50832 (FIGS. 18 and 19). The chemical sensor 50832 is located near the inlet 50822 to the surgical evacuation system 50800 and near the inlet 50922 to the surgical evacuation system 50900. The chemical sensor 50832 is configured to detect chemical properties of particles evacuated by the surgical evacuation system. For example, the chemical sensor 50832 can identify the chemical composition of particles in smoke evacuated from an abdomen cavity of a patient during an electrosurgical procedure. Different types of chemical sensors can be utilized to determine the type of material extracted by the surgical evacuation system. In certain instances, the smoke evacuation system can be controlled based on what is being extracted from the surgical site, such as by what is being detected by the chemical sensor 50832.

A chemical analysis of the extracted fluids and/or particles can be utilized to adjust a generator function, such as a function of the generator 800 (FIG. 58). For example, the generator function can be adjusted based on the detection of cancerous material by the chemical sensor 50832. In certain instances, when cancerous material is no longer detected by the chemical sensor 50832, the clinician can be alerted that all cancerous material has been removed and/or the generator can cease operation of the energy device. Alternatively, when cancerous material is detected by the chemical sensor 50832, the clinician can be alerted and the generator can optimize operation of the energy device to remove the cancerous material.

Figure 29:
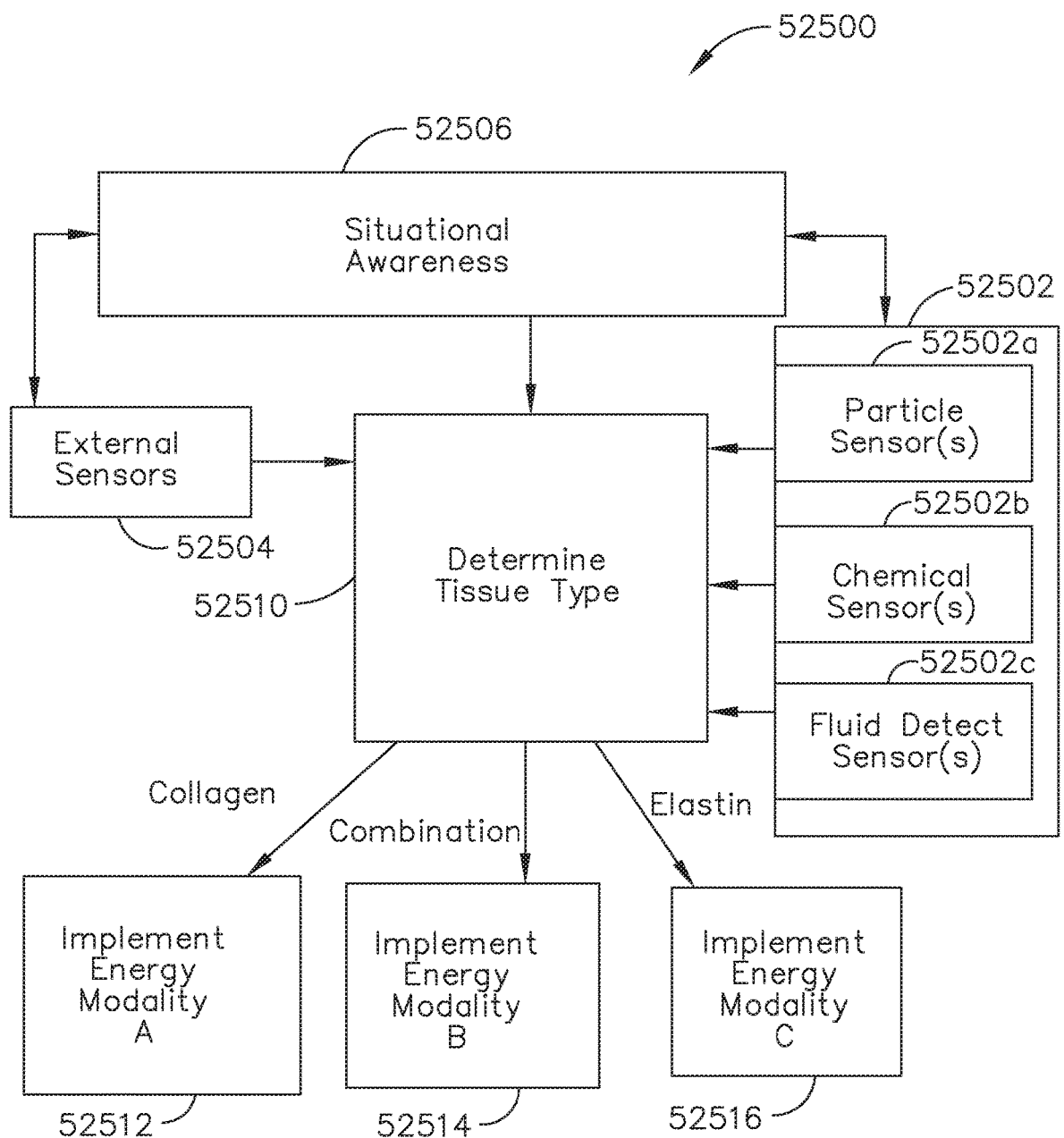
FIG. 29 is a flowchart depicting an adjustment algorithm for a surgical system, in accordance with at least one aspect of the present disclosure.

In certain instances, a generator function can be adjusted based on the tissue properties detected by a surgical system. Referring primarily to FIG. 29, a flowchart depicting an adjustment algorithm 52500 for a surgical system is depicted. Various surgical systems disclosed herein can utilize the adjustment algorithm 52500. Moreover, the reader will readily appreciate that the adjustment algorithm 52500 can be combined with one or more additional adjustment algorithms described herein in certain instances. The adjustments to the surgical system can be implemented by a processor (see, e.g. the processor 50308 in FIG. 5). In various aspects of the present disclosure, to determine the type of tissue, the processor 50308 (FIG. 5) can be configured to receive information from a plurality of sources.

Referring still to FIG. 29, one or more sensors 52502 in a surgical evacuation system can provide information to the processor 50308 (FIG. 5). Referring primarily still to FIG. 28, particle sensor(s) 52502a, chemical sensor(s) 52502b, and/or fluid detection sensor(s) 52502c of the surgical evacuation system, which can be similar to the sensors depicted in FIGS. 18 and 19, for example, can provide data to the processor 50308 that is indicative of the tissue type. Additionally, external sensor(s) 52504 can provide information to the processor 50308. The external sensors 52504 can be remote to the surgical evacuation system, but positioned on other surgical devices involved with the surgical procedure. For example, one or more external sensor(s) 52504 can be positioned on a surgical instrument, robotic tool, and/or an endoscope. In certain instances, the internal and external sensors 52502, 52504 can provide information to a situational awareness module or surgical hub, which can provide situational awareness 52506 to the various sensors 52502, 52504. Moreover, the situational awareness 52506 can inform the processor 50308 regarding the various sensor data. Based on the situational awareness 52506 and data from the sensors 52502, 52504, the tissue type can be ascertained by the processor 50308 (FIG. 5) at block 52510.

In certain instances, the elastin-to-collagen ratio of the extracted material can be determined from the tissue type. For example, elastin can correspond to a first melt temperature and collagen can correspond to a second melt temperature, which is higher than the first melt temperature. In instances in which the external sensor 52504 is configured to detect the speed of a clamp arm and/or a parameter of an electric motor that corresponds to the clamping speed, the external sensor 52504 can indicate the melt temperature of the tissue and, thus, the elastin-to-collagen ratio. Elastin and collagen also define different refractivity and absorptions. In certain instances, an infrared spectrometer and/or refractive camera sensor can be utilized to determine and/or confirm the tissue type.

In certain instances, the energy modality can be adjusted based on the detected tissue type (elastin, collagen, and/or elastin-to-collagen ratio). For example, certain energy devices are more efficient at melting collagen than elastin, but can be adjusted to better melt the elastin by adjusting the energy modality. In other instances, it can be desirable to melt the collagen and retain the elastin. Additionally or alternatively, the elastin-to-collagen ratio can indicate a type of physical structure, such as a vein or an artery, which can inform the situational awareness 52506 of the system. For example, energy modality A can be implemented at block 52512 if collagen is detected at block 52510. In other instances, energy modality C can be implemented at block 52516 if elastin is detected at block 52510. In still other instances, when a combination of collagen and elastic is detected at block 52510, energy modality B can be implemented at block 52514. The reader will readily appreciate that additional and/or alternative energy modalities are envisioned. For example, different modalities can be utilized depending on the specific ratio of elastin-to-collagen and/or based on the surgical procedure being performed and/or step thereof.

In various surgical procedures that employ energy devices to treat tissue, fluids and/or particles can be released, thereby contaminating the atmosphere in and/or around a surgical site, as further described herein. In an effort to improve visibility of the atmosphere in the surgical site, for example, the contaminants can be drawn into a smoke evacuation system. Moreover, as the contaminants are directed along an airflow path in the smoke evacuation system, the suspended fluids and/or particles can be filtered out to improve air quality. Depending on the efficiency of the smoke evacuation system and/or the amount of smoke and/or contaminants produced following activation of an electrosurgical instrument, smoke can accumulate in the atmosphere in and/or surrounding the surgical site. Such a build-up of contaminants can, for example, prevent the clinician from being able to see the surgical site.

In one aspect of the present disclosure, the surgical system can comprise a smoke evacuation system including a particle sensor, an electrosurgical instrument, and a generator. Such a smoke evacuation system can monitor a particulate concentration as an electrosurgical instrument applies energy to tissue during the surgical procedure. For example, as a clinician requests power to be supplied to the electrosurgical instrument, the generator is configured to supply the requested power. A processor within the surgical system is configured to analyze the monitored particulate concentration and the clinician-requested power from the generator. If the clinician requested power produces contaminants that drive the particulate concentration above a pre-determined threshold, the processor can prevent the generator from supplying the requested power. Instead, in such instances, the generator can supply power at a level that brings the particulate concentration back under the predetermined threshold.

In such instances, the clinician(s) and/or assistant(s) do not have to individually monitor the particulate concentration and adjust the energy modality in response. Instead, the instruments and devices of the surgical system can communicate amongst themselves to direct the generator to supply a particular power level in a particular situation based on input from the sensors in the smoke evacuation system. The reader will readily appreciate that situational awareness can further inform the decision-making process of the generator. Various algorithms are implementing the foregoing monitoring process and/or adjustments are further disclosed herein.

A surgical system can include an electrosurgical device, a generator configured to supply the electrosurgical device with power, and a smoke evacuation system. A smoke evacuation system can include a sensor system configured to monitor the size and/or concentration of particulates within the smoke and/or intake evacuation conduit. Referring again to FIGS. 18 and 19, the particle sensor 50838 is depicted. The particle sensor 50838 is an interior sensor that is located at a position along the flow path 50804 (FIG. 18) and the flow path 50904 (FIG. 19). In various instances, the particle sensor 50838 is positioned at a point on the flow path 50804, 50904 prior to filtration by the filter system 50870, 50970, respectively; however, the interior particle sensor 50838 can be positioned at any suitable location along the flow path 50804, 50904 to monitor the contaminated air flowing in from the surgical site. In various instances, the smoke evacuation system 50800 and/or 50900 can comprise more than one interior particle sensor 50838 positioned at various locations along the flow path 50804 and/or 50904, respectively. The reader will readily appreciate that various particle measurement means are possible. For example, a particulate concentration sensor can be an optical sensor, a laser sensor, a photoelectric sensor, an ionization sensor, an electrostatic sensor, and/or any suitable combinations thereof. Various sensors are further described herein.

Electrosurgical generators are a key component in an electrosurgical circuit, as they produce electrosurgical waveforms. The generator is configured to convert electricity to high frequency waveforms and creates the voltage for the flow of electrosurgical current. In various instances, the generator is configured to produce a variety of waveforms, wherein each waveform produces a different effect on tissue. A "cutting current" will cut the tissue but provide little hemostasis. A "coagulation current" provides coagulation with limited tissue dissection and creates an increased depth of heating. A "blend current" is an intermediate current between the cutting and coagulation currents, however, the blend current is generally not a combination of cutting and coagulation currents. Rather, a blend current can be a cutting current in which the time that current is actually flowing is reduced from 100 percent to approximately 50 percent of the time. In various instances, the generator can automatically monitor tissue impedance and adjusts a power output to the energy device in order to reduce tissue damage, resulting in an efficient and accurate cutting effect at the lowest possible setting.

An additional mode of electrosurgical cutting, known as the Advanced Cutting Effect (ACE), provides a clinician with a scalpel-like cutting effect that provides little to no thermal necrosis and no hemostasis. When a generator is placed in the ACE mode, a constant voltage is maintained at the tip of an electrode on an end effector. The active electrode on the end of the end effector delivers an RF current from the generator to the surgical site. By utilizing the ACE mode, the clinician has the ability to use electrosurgical devices on the skin and achieve equivalent wound healing results often without the use of certain surgical instruments, such as scalpels, needles, and/or any surgical instrument that could cause wounds and/or punctures to the patient and/or any personnel handling them.

In various aspects of the present disclosure, the electrosurgical device comprises an ACE cutting system.

Throughout the duration of a surgical procedure, contaminants and/or smoke can be produced. If the atmosphere in and/or around the surgical site is not efficiently filtered by a smoke evacuation system, the contaminants aggregate in the atmosphere, making it hard for a clinician and/or assistant to see the surgical site. Additional concerns regarding smoke in the surgical theater are further disclosed herein. In various instances, a processor within the surgical system can store information in a memory that is specific to the amount of smoke and/or contaminants produced when a clinician uses a particular surgical instrument for a specific duration. Such information can be stored directly in the memory of the processor, in a centralized hub, and/or in a cloud. In various instances, the processors and memories depicted in FIGS. 5 and 6 can be employed to store such information.

In various instances, communication pathways are established between the smoke evacuation system and the generator in order to control the power supplied to the electrosurgical instrument. Such power is controlled in order to effectively induce the electrosurgical instrument to produce less smoke and/or release fewer contaminants and to allow the surgical site to be efficiently filtered. In various instances the components of the surgical system can directly communicate with one another. In various instances, the components of the surgical system are in communication with each other through a centralized hub, as further described herein with respect to FIGS. 39-60, for example. The reader will readily appreciate that any suitable communication pathway can be used.

As the surgical procedure begins and the electrosurgical instrument is activated, a sensor within the smoke evacuation system is configured to monitor a parameter regarding air quality. Such parameters can include, for example, particle count and/or concentration, temperature, fluid content, and/or contamination percentage. The sensor is configured to communicate the monitored parameter to the processor. In various instances, the sensor automatically communicates the monitored parameter after detection. In various instances, the sensor communicates the monitored parameter to the processor after the sensor has been interrogated; however, the reader will appreciate that any suitable manner of communicating the monitored information can be used. In various instances, the sensor continuously communicates the monitored information to the processor; however, the reader will appreciate that any suitable sample rate can be used. The monitored information can be communicated in real-time or nearly real-time, for example.

In various instances, the processor stores information regarding a predetermined threshold. The predetermined threshold varies based on the parameter monitored by the sensor of the smoke evacuation system. For example, when the sensor is monitoring particle count and/or concentration, such a threshold can indicate a level of particles within the atmosphere of the surgical site that effectively and/or unsafely occludes the clinician's vision within the surgical site. In other instances, the threshold can correspond to the filtration system in the evacuator housing and the capability of the filtration system to adequately filter particles. For example, if the particulate concentration exceeds a particular threshold, the filtration can be unable to sufficiently filter the particulate from the smoke and toxins may pass through the evacuation system and/or obstruct and/or clog the filter thereof. As the processor receives information regarding the monitored parameter from the sensor(s) of the smoke evacuation system, the processor is configured to compare the monitored parameter(s) against predetermined threshold(s) to ensure that the threshold(s) have not been exceeded.

In various instances, if the processor recognizes that the predetermined threshold has been exceeded and/or is close to being exceeded, the processor can control various motor functions of the smoke evacuation system. The processor can adjust the flow rate of the smoke evacuation system by increasing or decreasing the speed of the motor to more efficiently filter the contaminants from the surgical site. For example, if the sensor communicates information to the processor that suggests the particle threshold has been reached, the processor can increase the speed of the motor to draw more fluid, and likely more contaminants, from the surgical site into the smoke evacuation system for filtration.

In various instances, if the processor recognizes that the predetermined threshold has been exceeded and/or is close to being exceeded, the processor can vary the power supplied by the generator to the electrosurgical instrument. For example, if the sensor communicates information to the processor that suggests the particle threshold has been reached, the processor will prevent the generator from supplying any additional requested power to the handheld electrosurgical instrument. When the smoke evacuation system filters the contaminants out of the atmosphere to a level that falls underneath the particle threshold, the processor can then allow the generator to supply the handheld electrosurgical instrument with the requested power.

Figure 33:
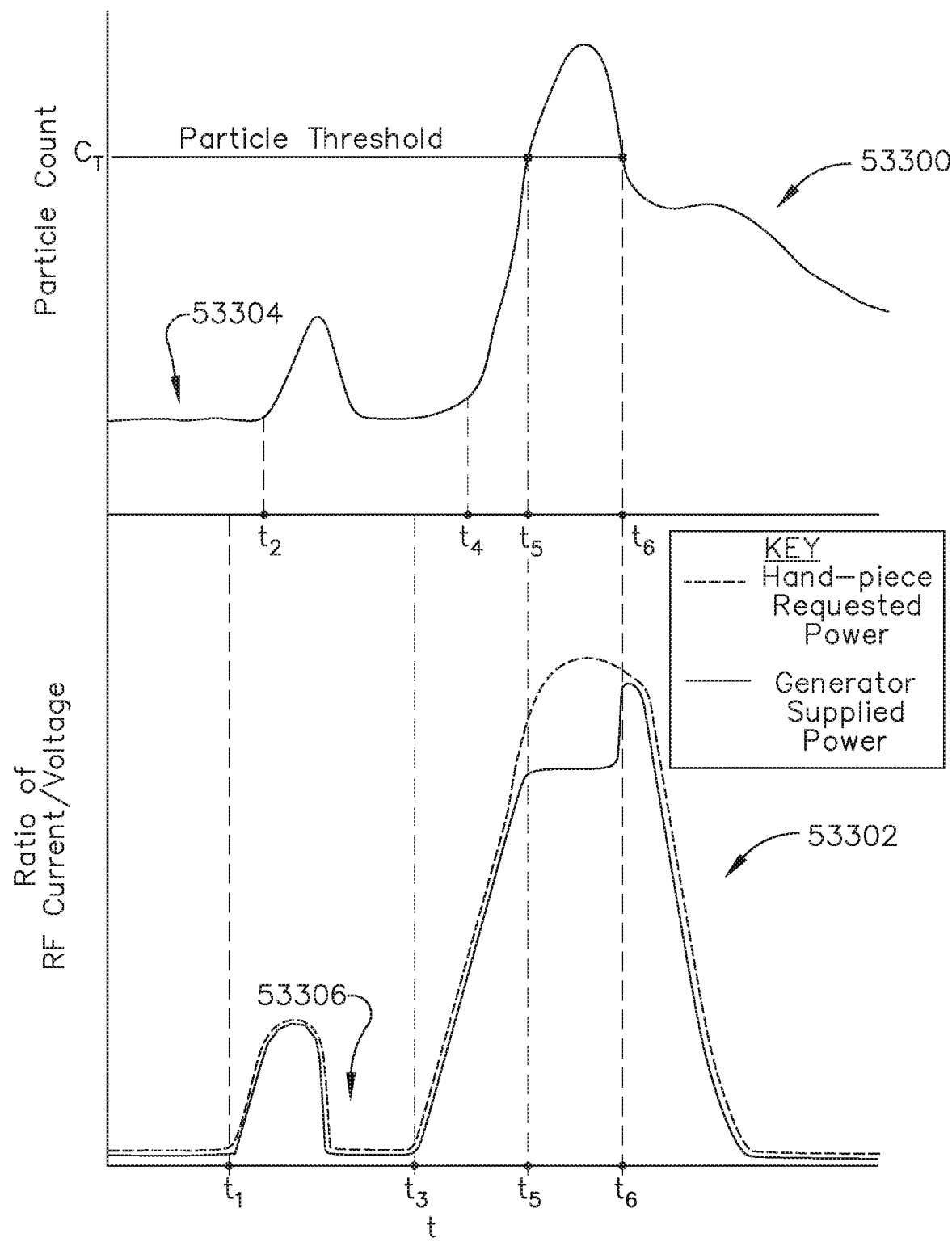
FIG. 33 is a graphical representation of (A) particle count over time and (B) the ratio of RF current-to-voltage over time for a surgical system, in accordance with at least one aspect of the present disclosure.

FIG. 33 is a graphical representation of a correlation between detected particle count and the power level over a period of time during a surgical procedure. The top graph 53300 represents the particle count and/or particulate concentration detected by the interior particle sensor 50838 (FIGS. 18 and 19) as particles and contaminants are filtered into a smoke evacuation system 50800 and/or 50900 from a surgical site. A particulate concentration $C_T$ is representative of a predetermined particle count and/or concentration threshold within a volume of evacuated fluid. The bottom graph 53302 represents the power level(s) reached during the surgical procedure, including the power requested by the clinician through a handheld electrosurgical instrument (the dashed line), and the power actually supplied by the generator of the surgical system (the solid line). The power level(s) are defined as the ratio of RF-current-to-voltage for the electrosurgical system.

Prior to the start of a surgical procedure at time $t<t_1$, a baseline particulate concentration 53304 is detected. When the clinician and/or assistant activates the electrosurgical instrument at time $t_1$, the clinician and/or assistant requests a particular power level to be supplied in order to perform a particular function. Such functions include dissecting and/or cutting through tissue within a surgical site. Application of power to the tissue creates smoke and/or contaminants that can be directed into the smoke evacuation system to improve visibility within the surgical site, for example. At time $t_1$, the generator supplies the requested power. The detected particulate concentration is below the threshold $C_T$; however, the interior particle sensor 50838 begins to detect an increase in particulate concentration at time $t_2$ after the activation of the electrosurgical instrument at time $t_1$.

In the graphical representation of FIG. 33, the clinician does not request additional power until time $t_3$. The "off" time 53306 between $t_1$ and $t_3$ can allow the tissue to cool creating a degree of hemostasis, for example. As can be seen in FIG. 33, the detected particulate concentration and the power level decrease between time $t_2$ and time $t_3$. At time $t_3$, the clinician requests a high power level that, when supplied by the generator, creates an increase in particulate concentration at time $t_4$. Ultimately, the clinician requests a power level that creates a particulate concentration that rises about the predetermined threshold $C_T$ at time $t_5$. In some instances, exceeding the threshold $C_T$ can indicate low visibility within the surgical site due to a buildup of contaminants and/or particles, an inefficient smoke evacuation system, and/or an inoperable smoke evacuation system.

In response to the particulate concentration exceeding the particle threshold $C_T$ at time $t_5$, the processor of the surgical system is configured to adjust the supplied power of the generator to bring the particulate concentration back below the particle threshold $C_T$. As shown in FIG. 33, the generator supplied power differs from the hand-piece requested power when the particle threshold $C_T$ has been reached and/or exceeded due to the high hand-piece requested power. As the particulate concentration returns to the threshold $C_T$ and/or dips below the threshold $C_T$, such as at time $t_6$, the generator once again supplies a power level as requested by the handheld electrosurgical instrument. Moreover, as the hand-piece requested power declines after time $t_6$, the particulate concentration detected by the particle sensor 50838 also decreases.

Figure 34:
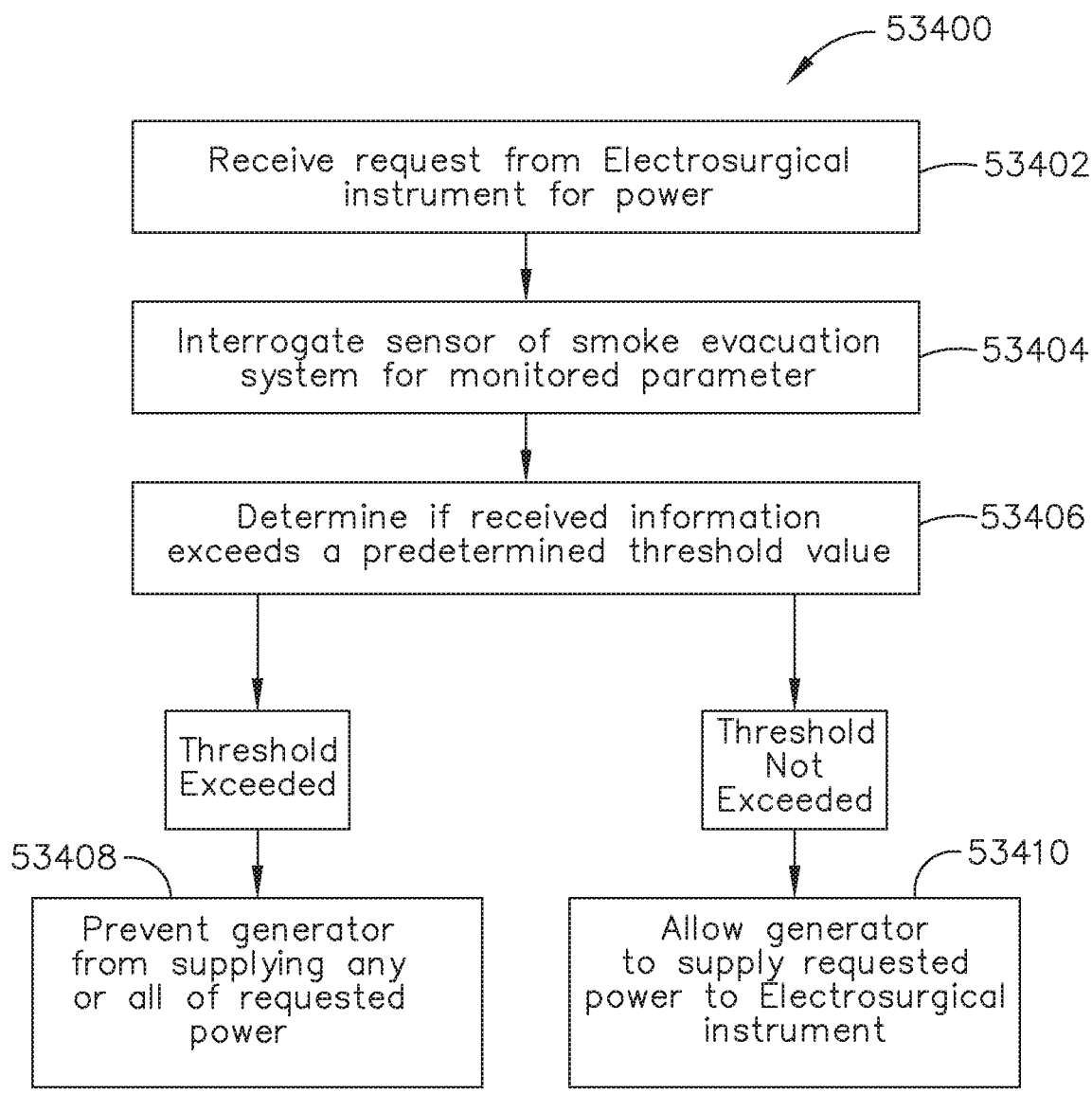
FIG. 34 is a flowchart depicting an adjustment algorithm for a surgical system, in accordance with at least one aspect of the present disclosure.

FIG. 34 shows a representation of instructions 53400 stored by a memory of a surgical system, such as the memory in FIGS. 5 and 6, for example. In various instances, the surgical systems disclosed herein can utilize the instructions 53400. For example, the instructions 53400 can comprise adjustment algorithms for the surgical systems. Moreover, the reader will readily appreciate that the instructions 53400 can be combined with one or more additional algorithms and/or instructions described herein in certain instances. The instructions 53400 can be implemented by a processor, such as the processor 50308 in FIG. 5, for example.

At block 53402 in the instructions 53400, a processor can receive a request from an electrosurgical instrument for power. For example, the electrosurgical instrument can comprise a handheld device and/or robotic tool. The requested power can be user-provided via controls and/or a control console, for example. As discussed above, a sensor is configured to monitor a parameter relating to the fluid passing through the evacuation system. Such a parameter can include, for example, particle size, temperature, fluid content, and/or contamination percentage. The processor is configured to receive the monitored parameter from the sensor. In various instances, the processor receives such information in response to interrogating the sensor, as indicated in block 53404. In various instances, the sensor automatically communicates the information upon detection. The processor then determines if the received information exceeds a predetermined threshold value at block 53406. If the threshold value has been exceeded and/or is close to being exceeded, the processor is configured to prevent the generator from supplying any or all of the requested power to the electrosurgical instrument at block 53408. In other instances, the generator waveform can be adjusted to reduce the smoke generated by the surgical device at block 53410, as further described herein.

In various instances, the generator can supply power at a level that will not cause the threshold value to be exceeded. If the threshold value has not been exceeded, the processor is configured to allow the generator to supply the electrosurgical instrument with the requested power at block 53410. In various instances, the processor is configured to receive information from the sensor of the smoke evacuation system throughout the duration of the surgical procedure, or at least as long as the processor is receiving requests from the electrosurgical instrument for the delivery of power.

In various surgical procedures, radio frequency (RF) power can be used to cut tissue and coagulate bleeding. As RF power is used to treat tissue, fluids and/or particulates can be released, thereby contaminating the air in and/or around a surgical site. In an effort to improve the visibility of the surgical site for a clinician, for example, the contaminated air inside of the surgical site can be drawn into a smoke evacuation system. As the contaminated air is directed along an airflow path, the suspended fluids and/or particulates can be filtered out of the contaminated air. The filtered air ultimately exits the smoke evacuation system through an outlet port and is released into the atmosphere of the operating room. Depending on the efficiency and/or efficacy of the smoke evacuation system, the filtered air may still contain fluids and/or particulates when it is released into the operating room atmosphere. The remaining contaminants can be, for example, unpleasant to the olfactory senses of the clinician(s), the assistant(s), and/or the patient(s), and the contaminants can be unhealthy to inhale in certain instances.

The smoke evacuation system can comprise a sensor system configured to monitor the detected size and/or concentration of particulates in the air at various points along the airflow path, including locations that are external to the evacuation system and internal to the evacuation system. In one aspect of the present disclosure, the smoke evacuation system can determine the efficiency of the evacuation system based on comparing the particulate concentration external to the evacuation system and internal to the evacuation system and/or by monitoring the particulate concentration over time. Moreover, the smoke evacuation system can alert the clinician(s) of contaminated air in the operating room through a display.

The clinician(s) can be made aware of the level of contaminants, such as fluids and/or particulates, suspended in the atmosphere of the operating room. An indication of contaminants in the air can indicate the air quality in the operating room and alert the clinician(s) and/or assistant(s) that the smoke evacuation system requires adjustment and/or maintenance.

A smoke evacuation system can include a sensor system configured to monitor the size and/or concentration of particles within the air. Referring again to FIGS. 18 and 19, the particle sensors 50838 and 50852 are depicted. The particle sensor 50838 is an interior sensor that is located at a position along the flow path. In various instances, the particle sensor 50838 is positioned at a point on the flow path 50804 (FIG. 18), 50904 (FIG. 19) prior to filtration; however, the interior particle sensor 50838 can be positioned at any suitable location along the respective flow path 50804, 50904 to monitor the contaminated air flowing in from the surgical site. In various instances, the smoke evacuation system 50800, 50900 can include more than one interior particle sensor 50838 positioned at various locations along the flow path 50804, 50904, respectively.

The particle sensor 50852 is an exterior sensor that is positioned on an exterior surface of the smoke evacuation system 50800 (FIG. 18), 50900 (FIG. 19). In various instances, the smoke evacuation system 50800, 50900 can include more than one exterior particle sensor 50852. In various instances, the exterior particle sensor 50852 is located within a recess of the housing of the smoke evacuation system 50800, 50900; however, the exterior particle sensor 50852 can be positioned on any suitable surface to detect the air quality in the operating room. In various instances, the exterior particle sensor 50852 is located near the inlet 50822 (FIG. 18), 50922 (FIG. 19) of the smoke evacuation system 50800, 50900, respectively, to ensure that unfiltered air is not leaking into the operating room atmosphere from the surgical site. In various instances, the exterior particle sensor 50852 is located near an outlet port 50824 (FIG. 18), 50924 (FIG. 19) of the smoke evacuation system 50800, 50900, respectively, to analyze the air flowing out of the smoke evacuation system 50800, 50900.

The reader will readily appreciate that the exterior particle sensor(s) 50852 can be located at any suitable location to appropriately monitor the atmosphere of the operating room. In addition, the reader will readily appreciate that various particle measurement means are possible. For example, the particle sensor 50852 can be any suitable particulate concentration sensor such as an optical sensor, a laser sensor, a photoelectric sensor, an ionization sensor, an electrostatic sensor, and/or any suitable combinations thereof. Various sensors are further described herein.

In various instances, a sensor system for the smoke evacuation system is configured to evaluate particle size and/or concentration of the operating room contamination and to display the detected air quality. The display of such information can communicate the effectiveness of the smoke evacuation system, for example. In various instances, the communicated information includes detailed information about the filter(s) within the smoke evacuation system, and can prevent contaminated air and/or smoke from accumulating in the atmosphere of the operating room. The smoke evacuation system can be configured to sense particulate concentration, temperature, fluid content, and/or contamination percent, for example, and communicate it to a generator to adjust its output, as further described herein. In one aspect of the present disclosure, the smoke evacuation system may be configured to adjust its flow rate and/or motor speed, and at a predefined particulate level, operably affect the output power or waveform of the generator to reduce the amount of smoke generated by the end effector.

In various instances, the sensor system, as described herein, can be used to detect whether the contaminants and/or smoke in the air are being properly and efficiently removed by the filter(s) in the smoke evacuation system. By detecting the air quality level(s) of the operating room, the smoke evacuation system is configured to prevent a high level of contamination from accumulating in the operating room atmosphere. The parameters monitored by the sensor system can be used to inform a clinician if the smoke evacuation system is functioning and/or performing its intended purpose. In various instances, the monitored parameters can be used by a clinician and/or assistant to determine that a filter within the smoke evacuation system needs to be repaired and/or replaced. For example, if the external sensor 50852 (FIGS. 18 and 19) detects a contaminant particle size and/or concentration above a predetermined and/or acceptable threshold, the clinician is directed to check if a filter within the smoke evacuation system needs to be repaired and/or replaced.

In various instances, as described above, a processor within the smoke evacuation system compares the detected parameters of the external sensor to the parameters detected by an internal sensor. In various instances, the smoke evacuation system comprises multiple internal sensors located at various points along the flow path, such as after each individual filter, for example. The reader will understand that the internal sensors can be positioned at any point throughout the flow path to provide meaningful comparisons for filter efficiency. Using this detected information, a clinician can determine that a filter at a particular location is failing to effectively remove contaminants and/or smoke from the air. In such instances, the clinician is directed to a precise location of the filter (or filtering layer) that needs attention for repair and/or replacement.

In various instances, the sensor system is configured to assess the dilution of the contaminants and/or particles within the atmosphere of the operating room. As discussed herein, the internal sensor(s) can be located at any suitable position along the flow path. When an internal sensor is located near an outlet port of the smoke evacuation system and downstream of the filter(s), the internal sensor is effectively measuring the size and/or concentration of the particles that are emitted into the atmosphere of the operating system. In other words, the internal sensor is configured to detect the particles and/or contaminants that were not captured during the filtration process. The external sensor is configured to monitor the concentration and/or size of particles diluted throughout the atmosphere of the operating room. The differential between readings of the internal sensor and the external sensor may be important to determine the air quality of the particular operating room.

The size and/or concentration of the particles emitted into the atmosphere can have varying impacts on the air quality in the operating room based on parameters, such as, the size of the operating room and/or ventilation in the operating room, for example. In one instance, the size and/or concentration of particles emitted can have a more detrimental impact on the air quality if emitted in a smaller operating room than if the same size and/or concentration of particles were emitted into a larger operating room. In various instances, the presence and/or efficiency of a ventilation system in the operating room can impact how the air quality fluctuates in response to the emission of particles from the smoke evacuation system. For example, in operating rooms without a ventilation system or operating rooms with an inefficient ventilation system, the emitted particles from the smoke evacuation system can more quickly accumulate to a potentially hazardous level, creating an unsatisfactory air quality within the operating room.

In various instances, the information detected by the sensor system can be used to control one or more motor functions of the smoke evacuation system. Prior to the start of a surgical procedure, the exterior sensor can detect an initial air quality level. The air quality is able to be continuously monitored throughout the surgical procedure; however, the reader will understand that the air quality can be monitored at any suitable rate. The exterior sensor communicates the detected information to a processor (e.g. the processors 50308 and 50408 in FIGS. 5 and 6, respectively) of the smoke evacuation system. The processor uses the initial air quality level as a baseline to compare against the continuously detected air quality levels. When the processor determines that the air quality level(s) detected by the exterior sensor 50852 exhibits signs of a higher contaminant particle size and/or concentration within the operating room atmosphere, the processor directs the motor to run at a higher level. With the motor running at an increased speed, more contaminated air and/or smoke is pulled into the smoke evacuation system 50800, 50900 from the surgical site for filtering. In various instances, the processor stores instructions to increase the flow rate of contaminated air and/or smoke directed into the smoke evacuation system 50800, 50900 during the procedure when the internal sensor 50838 determines that a cautery device and/or other electrosurgical device that creates smoke is active. By detecting the activation of smoke-creating surgical devices, the smoke evacuation system 50800, 50900 prevents a high level of contamination from accumulating in the operating room atmosphere through motor control.

In various instances, the motor speed level is controlled automatically when the processor determines that the operating room atmosphere possesses an unacceptable air quality level. In various instances, the motor speed level is controlled automatically when the processor determines that a smoke-creating surgical device has been activated. For example, when the exterior sensor 50852 detects a level of contamination in the operating room atmosphere that exceeds a predetermined threshold, the processor can automatically direct the motor to operate at a faster speed. Then, when the exterior sensor 50852 detects a level of contamination that dips below the predetermined threshold, the processor automatically decreases the speed of the motor. In various instances, the motor speed level is controlled manually after a clinician is notified of an unacceptable air quality level. In various instances, the motor speed level is controlled manually after a clinician activates a smoke-creating surgical device. The reader will understand that any suitable combination of automatic and/or manual controls can be implemented and/or incorporated into a control algorithm for the smoke evacuation systems 50800, 50900.

In various instances, the processor of the smoke evacuation system can recognize when the exterior sensor 50852 detects an unacceptable and/or increased contamination level of the operating room atmosphere. Such detection is indicative that the smoke evacuation system 50800, 50900 is inefficient. The detected inefficiency can indicate that one or more filters are failing and/or need to be replaced. When the clinician is notified of a failing filter, the clinician can ensure that replacement filters are in stock for future maintenance to prevent delay(s).

Figure 47:
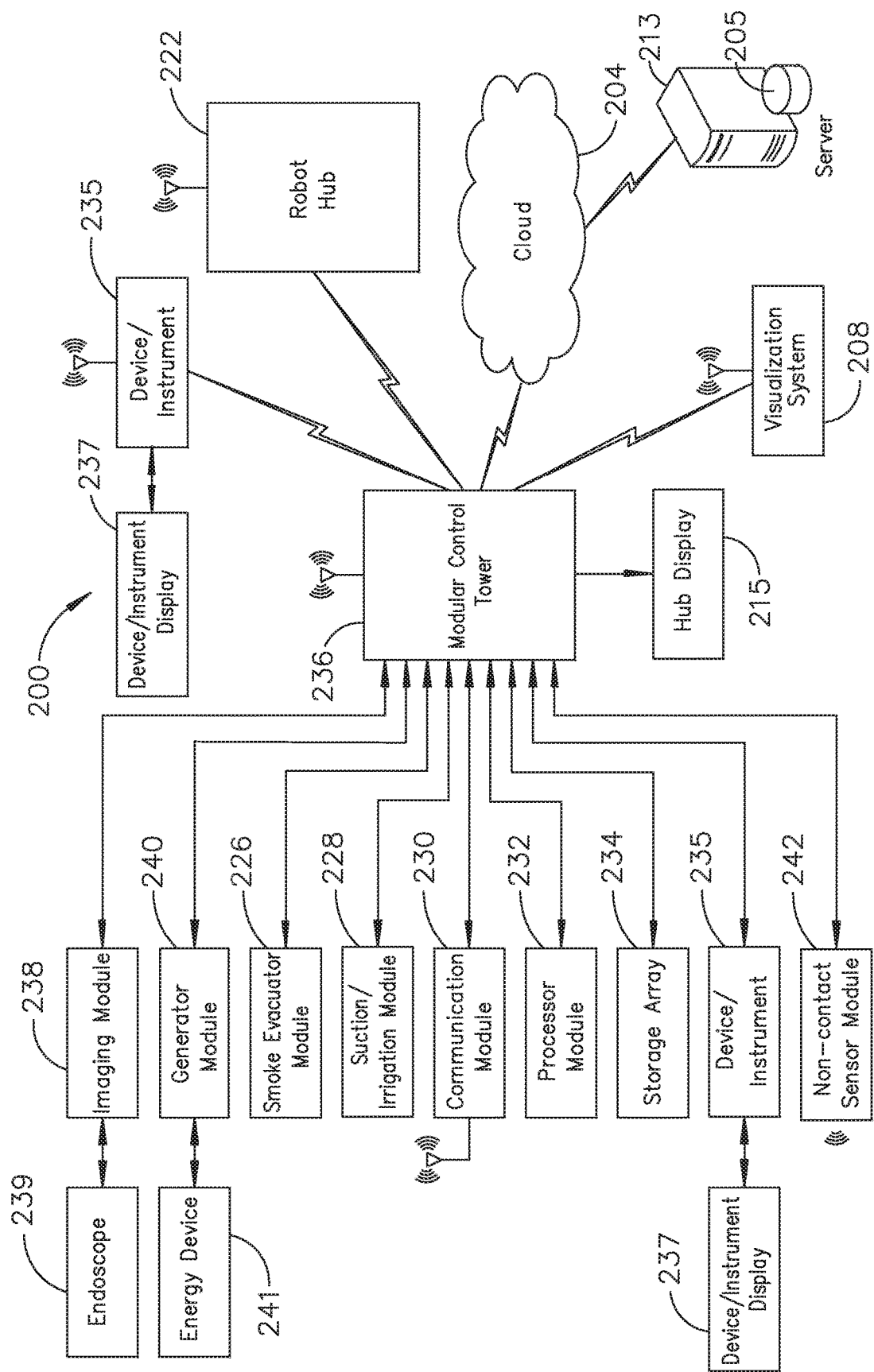
FIG. 47 illustrates a computer-implemented interactive surgical system, in accordance with at least one aspect of the present disclosure.

In various instances, a smoke evacuation system can be used in combination with a camera scope during a surgical procedure to efficiently manage contaminant and/or smoke evacuation from a surgical site. For example, the smoke evacuation systems 50800, 50900 can be used in combination with the imaging module 238 and endoscope 239 (FIG. 47). In one aspect of the present disclosure, a surgical hub, such as the hub 206 (FIG. 48), can coordinate communication between the imaging module 238 and a surgical evacuation system, such as the smoke evacuator 226 (FIG. 48), for example. The camera scope is configured to monitor the visual occlusion in the air by capturing a series of images at a particular sample rate. The collected images are sent to a processor (e.g. the processors 50308, 50408 in FIGS. 5 and 6, respectively) for evaluation. In various instances, the processor is also configured to receive monitored data from the sensor system, which can include the internal sensor 50838 and/or the external sensor 50852, as described herein. The processor is configured to compare the images received from the camera scope with the particulate count and/or concentration received from the sensor system to determine correlation(s) to improve the efficiency of evacuation of smoke and/or contamination from the surgical site and/or the operating room atmosphere.

In such instances, the visual occlusion determined by the camera scope and the particulate count and/or concentration determined by the sensor system are compared in order to tune the particle count measure to the speed of the motor of the smoke evacuation system. Upon comparison of the collected data from the sensor system and the camera scope, the processor can take any of a number of steps. For example, based on the comparison, the processor can decide to: turn on the smoke evacuation system; increase the motor speed of the smoke evacuation system; decrease the motor speed of the smoke evacuation system; and/or turn off the smoke evacuation system. In various instances, the comparison is done automatically; however, the reader will appreciate that such comparison can occur after manual activation.

In various instances, the images captured by the camera scope and the detected particulate count and/or concentration by the sensor system can be stored in a memory as a baseline comparison. In future surgical procedures, the clinician and/or assistant can use the images collected by the camera scope alone to confirm a smoke and/or contaminant density. In such instances, the visual occlusion detected by the camera scope is associated with a particular particulate count and/or concentration. After the processor has analyzed the air, the processor can take any of a number of steps. For example, based on the analyzed images captured by the camera scope in light of the stored baseline comparison, the processor can decide to: turn on the smoke evacuation system; increase the motor speed of the smoke evacuation system; decrease the motor speed of the smoke evacuation system; and/or turn off the smoke evacuation system.

In various instances, situational awareness can further inform the decision making process described herein. For example, the images from a scope can be meaningful in the context of a particular surgical procedure and/or step thereof, which can be configured and/or determined based on the situational awareness of a smoke evacuation system and/or hub in communication therewith. More smoke may be expected during certain surgical procedures and/or particular steps thereof and/or when treating particular types of tissue, for example.

In various instances, the smoke evacuation system is in wireless communication with other surgical devices and/or hubs located in the operating room to improve the efficiency of smoke evacuation during a surgical procedure. For example, activation of a generator of a surgical device can be communicated to a centralized hub that forwards the information on to the smoke evacuation system. The centralized hub can detect current through a surgical energy device and/or sense a change in the power draw of the generator for communication to the smoke evacuation system. In various instances, the centralized hub can store information relevant to the surgical procedure and/or the activated surgical device. Such information can include, for example, the anticipated amount of smoke produced during the particular surgical procedure and may use the particular surgical device and/or information relevant to a particular patient's tissue composition to determine the anticipated amount. Receiving such information can allow the smoke evacuation system to anticipate a particular rate of smoke evacuation to more efficiently move smoke and/or contaminants out of the surgical site. The reader will appreciate that the various surgical devices can communicate information directly to the smoke evacuation system and/or indirectly through the centralized hub. The centralized hub can be a surgical hub, such as the surgical hub 206 (FIG. 48), for example.

In various instances, the smoke evacuation system is in wired communication with other surgical devices and/or hubs located in the operating room to improve the efficiency of smoke evacuation during a surgical procedure. Such wired communication can be established through a cable interconnection between a generator and the smoke evacuation system for communication of generator activation. For example, an activation indication signal cable can be connected between the generator of a surgical device and the smoke evacuation system. When the generator is activated and a signal is received via the wired connection, the smoke evacuation system is automatically activated.

Wireless and/or wired communication between the generator of a surgical device and/or a centralized hub and/or the smoke evacuation system can include information about the activated surgical device. Such information can include, for example, a current operating mode of the surgical device and/or information regarding the intensity of a particular energy setting and/or delivery. In various instances, once such information is communicated from the surgical device, the memory of the centralized hub and/or the smoke evacuation system is configured to store such information for future use. For example, the centralized hub can store information regarding the surgical device used during a particular procedure and the average smoke and/or contaminant count and/or concentration. In future surgical procedures, when the same (or a similar) surgical device is activated in the same (or a similar) surgical procedure treating the same (or a similar) type of tissue, the centralized hub can communicate such information to the smoke evacuation system prior to a buildup of smoke and/or contaminants.

In various instances, the smoke evacuation system is configured to inform a clinician of a detected level of contamination in the atmosphere of the operating room. The smoke evacuation system can utilize the sensor system to monitor a differential between a particle size and/or concentration of particles detected by a first interior sensor and a second exterior sensor. In various instances, the monitored parameters of the sensor system can be used to alert a clinician and/or an assistant when a detected level of contamination exceeds a predetermined threshold.

In various instances, the processor directs a display to show the parameters monitored by the sensor system. In various instances, the display is located on the exterior of the housing of the smoke evacuation system. The processor can also communicate the monitored parameters with other surgical instruments located in the operating room and/or hubs to assist in the situational awareness of the interactive surgical system. In this manner, the other surgical instruments and/or hubs can be used more efficiently together. In circumstances where the monitored parameters are communicated throughout the operating room, clinicians and/or assistants can see the contamination alert from various displays around the operating room. The monitored parameters can be displayed on multiple monitors in the operating room in addition to the display on the smoke evacuation system. The reader will appreciate that any suitable combination of displays can be used to communicate the detected air quality in the operating room.

Figure 30:
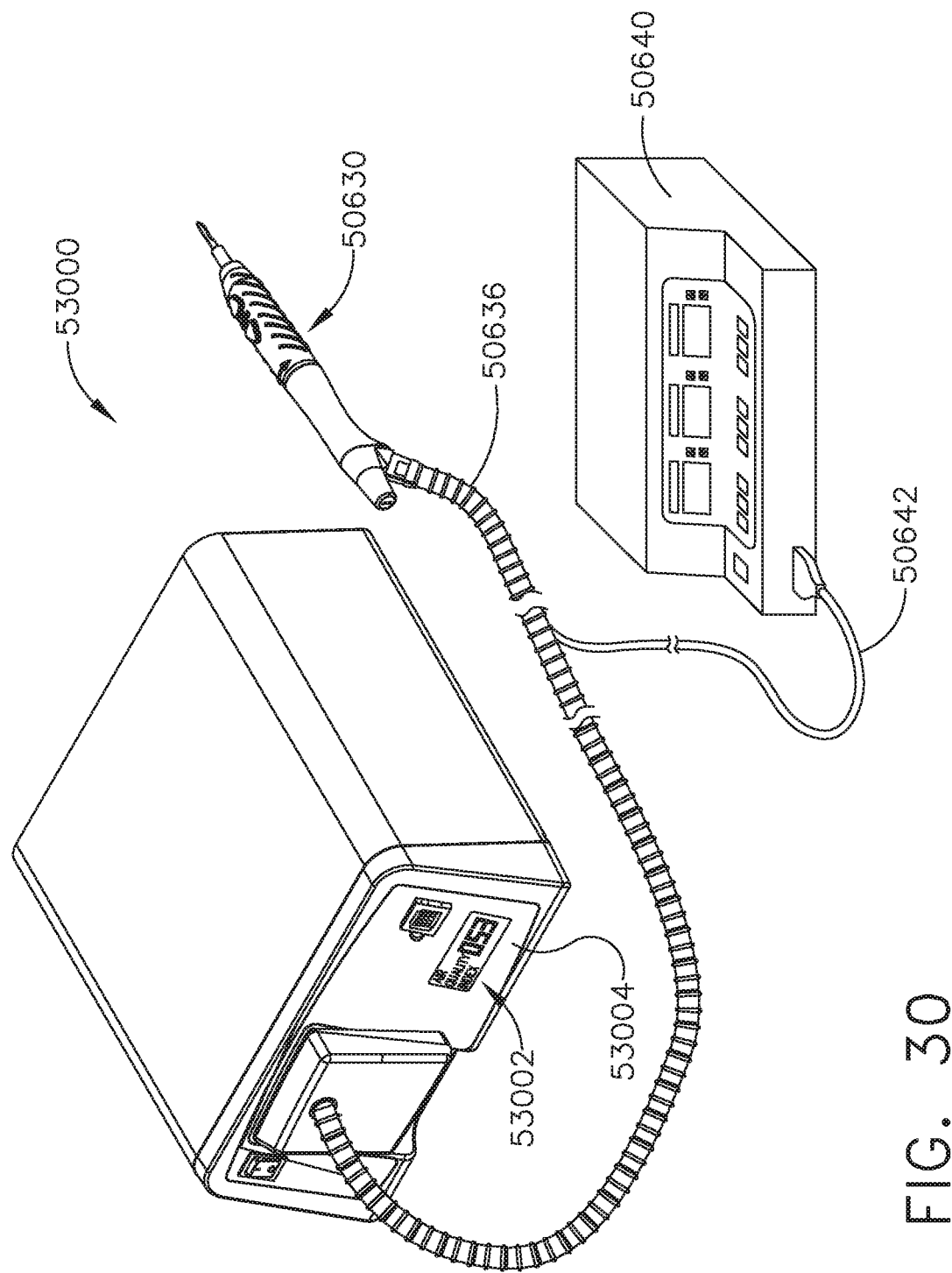
FIG. 30 is a perspective view of a surgical system, in accordance with at least one aspect of the present disclosure.

FIG. 30 depicts a smoke evacuation system 53000 configured to monitor the air quality of the operating room atmosphere and alert a clinician when the detected air quality surpasses a predetermined threshold and/or becomes potentially harmful. The smoke evacuation system 53000 is similar in many respects to the smoke evacuation system 50600 (FIG. 7). For example, the smoke evacuation system 53000 includes the generator 50640, the first electrical connection 50642, the surgical instrument 50630, and the suction hose 50636. As shown in FIG. 30, in various instances, the smoke evacuation system 53000 comprises a display or an air quality index screen 53002. The air quality index screen 53002 is configured to display the information detected by a sensor system, such as a sensor system comprising one of more of the sensors 50830, 50832, 50836, 50838, 50840, 50846, 50848, 50850, 50852, which are further described herein and shown in FIGS. 18 and 19. A processor, such as the processor 50308 and/or 50408 (FIGS. 5 and 6) can be in signal communication with the sensor system and the air quality index screen 53002. In various instances, the air quality index screen 53002 is configured to display a contaminant particle count monitored by the external sensor 50852 to verify that the contaminants are not being circulated into the operating room atmosphere at a hazardous level.

In various instances, the smoke evacuation system 53000 comprises a latch door 53004 accessible by the clinician to replace and/or interchange a filter housed in the evacuator housing of the smoke evacuation system 53000. For example, by monitoring the particulate concentration through the smoke evacuation system 53000, a processor therefor can determine that one or more filters are substantially obstructed and approaching the end of their useful life and, thus, need to be replaced. In such instances, the clinician can open the latch door 53004 to replace the one more filters. As further described herein, based on the relative placement of the internal sensors in the smoke evacuation system 53000, the specific filter and/or filter(s) that need to be replaced can be identified.

In various instances, a processor, such as the processor 50308 and/or 50408 (FIGS. 5 and 6), is configured to communicate smoke parameters such as the detected particle size and/or concentration to the display 53002. The display 53002 is configured to display such detected information in any suitable manner. For example, the display 53002 can show the level of contamination detected by each sensor, internal and external, throughout the sensor system. In various instances, the display 53002 is configured to display information only when the air quality does not meet a predetermined threshold. In various instances, the display 53002 comprises a touch screen that permits the clinician to determine what information is displayed and/or the location where the information is displayed.

In various instances, the display 53002 comprises a graphical interface, an LCD screen, and/or a touch screen. The reader will appreciate that any suitable means of displaying the detected information and/or combinations thereof can be used in the smoke evacuation system 53000. For example, a LED light can be used as the display 53002. When the processor 50308 and/or 50408 (FIGS. 5 and 6) determines that an unacceptable air quality is present in the operating room, the processor 50308 and/or 50408 is configured to activate the LED light.

Figure 31:
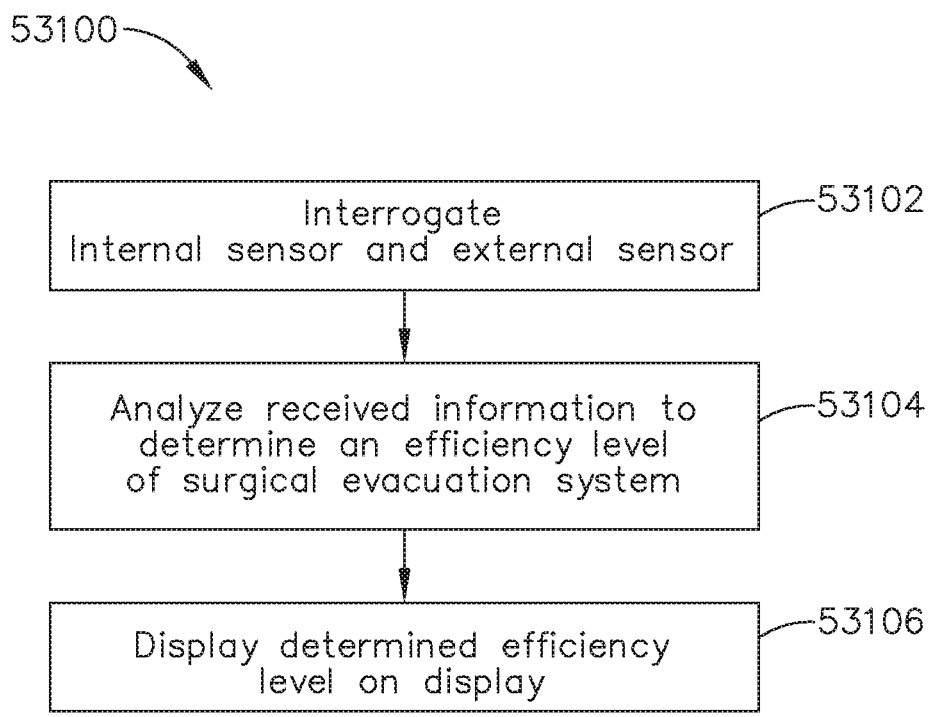
FIG. 31 is a flowchart depicting an algorithm for displaying efficiency data of a surgical evacuation system, in accordance with at least one aspect of the present disclosure.

FIG. 31 shows a representation of instructions 53100 stored by a memory for a surgical evacuation system, such as the memory 50310 and 50410 in FIGS. 5 and 6, for example. In various instances, the surgical evacuation systems disclosed herein can utilize the instructions 53100 of FIG. 31. Moreover, the reader will readily appreciate that the instructions 53100 of FIG. 31 can be combined with one or more additional algorithms and/or instructions described herein in certain instances. The instructions 53100 stored in the memory can be implemented by a processor, such as the processors 50308 and/or 50408 in FIGS. 5 and 6, for example.

Referring still to FIG. 31, as discussed above, an internal sensor, such as the sensor 50838 (FIGS. 18 and 19), is configured to monitor an internal parameter, such as the particle size and/or concentration of a fluid. As the fluid flows through a flow path, particles and/or contaminants are filtered out prior to the fluid exiting the surgical evacuation system. An external sensor, such as the sensor 50852 (FIGS. 18 and 19), located on the exterior housing of the surgical evacuation system, is configured to monitor an external parameter as the filtered fluid exits the surgical evacuation system. Such an external parameter includes, for example, the particle size and/or concentration of particles in the atmosphere in an operating room.

At block 53102 in the instructions 53100, the processor is configured to interrogate the internal sensor and the external sensor for the detected internal parameter and the detected external parameter, respectively. In various instances, the processor continuously interrogates the internal and external sensors for this information; however, any suitable sample rate can be used. The processor is then configured to analyze the received information from the internal and external sensors to determine an efficiency level of the surgical evacuation system at block 53104. After determining the efficiency level of the surgical evacuation system, the processor is configured to display the determined efficiency level on a display at block 53106. Such a display can include the raw information received from the internal and external sensors, the efficiency level determined by the processor, and/or an alert to the clinician if the efficiency level falls below a predetermined threshold. Falling below the predetermined threshold can indicate, for example, that a filter needs to be replaced and/or that the particles are not being efficiently filtered out and are accumulating in the atmosphere of the operating room.

Figure 32:
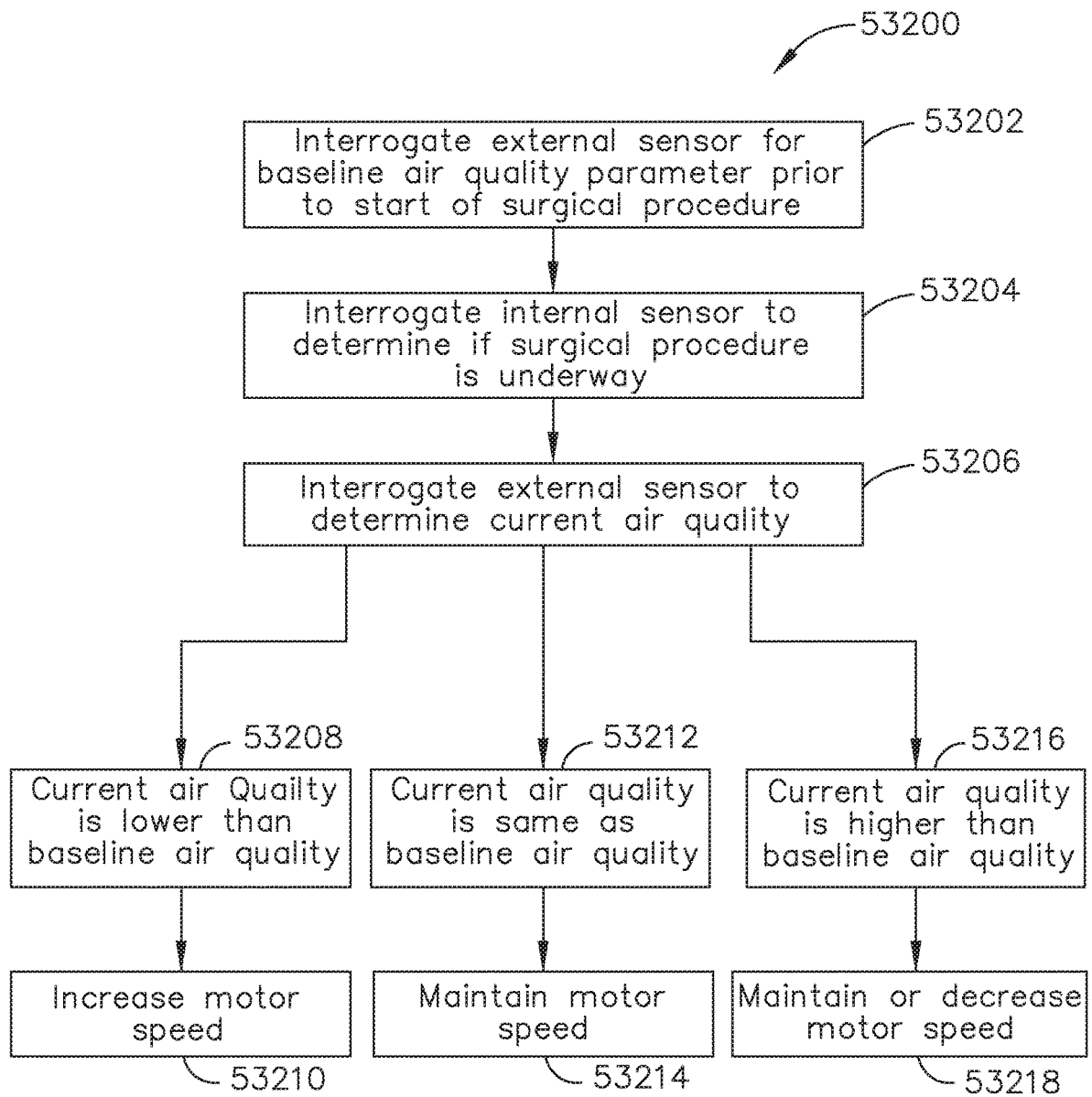
FIG. 32 is a flowchart depicting an adjustment algorithm for a surgical evacuation system, in accordance with at least one aspect of the present disclosure.

FIG. 32 shows a representation of instructions 53200 stored by a memory for a surgical evacuation system, similar to those represented in FIG. 31. In various instances, the surgical evacuation systems disclosed herein can utilize the instructions of FIG. 32. Moreover, the reader will readily appreciate that the instructions of FIG. 32 can be combined with one or more additional algorithms and/or instructions described herein in certain instances. The instructions can be stored in a memory and executed by a processor, such as the memory 50310 and/or 50410 and/or the processors 50308 and/or 50408 in FIGS. 5 and 6, for example.

Referring still to FIG. 32, prior to the start of a surgical procedure at block 53202, the processor is configured to interrogate an external sensor, such as the sensor 50852 (FIGS. 18 and 19) for a baseline air quality parameter. The baseline air quality parameter is indicative of the air quality of the operating room prior to the surgical procedure. At block 53204, the processor is configured to continuously interrogate the internal sensor in order to recognize that the surgical procedure is underway. After the processor has determined that a surgical procedure is occurring, the processor continuously interrogates the external sensor at block 53206. When the processor determines that the air quality detected by the external sensor is deteriorating, such as at block 53208, for example, the processor is configured to increase the speed of the motor at block 53210 to direct more fluid into the surgical evacuation system. If the detected air quality is the same as the baseline air quality, such as at block 53212, the processor is configured to maintain the speed of the motor at block 53214. If the detected air quality has improved from the baseline air quality, such as block 53216, for example, the processor is configured to maintain or decrease the speed of the motor at block 53218. In various instances, the processor continuously interrogates the internal and external sensors for information; however, any suitable sample rate can be used.

Smoke evacuation systems serve an important role in electrosurgical systems by removing harmful toxins and/or offensive smells from the surgical theater. However, controls and adjustability of certain smoke evacuation systems may be lacking, which can lead to a decreased motor life span and/or poor filter longevity, for example.

In one aspect of the present disclosure, sensors can be positioned and configured to detect a presence of particulate in a fluid moving through various points in a flow path of an evacuation system. In some aspects of the present disclosure, a control circuit can be utilized to modify a speed of a motor that drives a pump of the evacuation system based on the detected particulate concentration at the various points along the flow path. Additionally or alternatively, the control circuit can be utilized to modify the speed of the motor based on detected pressures at the various points in the flow path.

The efficient regulation of an evacuation system's motor speed can increase the motor's life span and/or increase filter longevity. Further benefits include potential energy savings and less noise in the surgical theater, for example.

As described herein, electrosurgical instruments can deliver energy to target tissue of a patient to cut the tissue and/or cauterize the blood vessels within and/or near the target tissue. The cutting and cauterization can result in smoke being released into the air. In various instances, the smoke can be unpleasant, obstructive to the view of a practitioner, and unhealthy to inhale, as further described herein. Electrosurgical systems can employ an evacuation system that captures the resulting smoke, directs the captured smoke through one or more filters, and exhausts the filtered smoke. More specifically, the smoke can travel through the evacuation system via a vacuum tube. Harmful toxins and offensive smells can be filtered out of the smoke as it moves through one or more of the filters in the evacuation system. The filtered air can then exit the evacuation system as exhaust through an exhaust port.

In various aspects of the present disclosure, an evacuation system includes a filter receptacle or socket. The filter receptacle is configured to receive a filter. The evacuation system also includes a pump that has a sealed positive displacement flow path and a motor that drives the pump. The sealed positive displacement flow path of the pump can comprise one or more circulation paths of a fluid within the pump. In one aspect of the present disclosure, the pump has a first operating pressure and a second operating pressure. In certain instances, the pump can compress an incoming fluid to create a pressure difference along the flow path, as further described herein.

As illustrated in FIG. 4, the evacuation system 50500 includes the pump 50506 coupled to and driven by the motor 50512. As described herein, the pump 50506 can be a positive displacement pump such as a reciprocating positive displacement pump, a rotary positive displacement pump, or a linear positive displacement pump, for example. In various instances, the pump 50506 can be a hybrid regenerative blower, a claw pump, a lobe compressor, or a scroll compressor, for example. In one aspect of the present disclosure, the motor 50512 can be a permanent magnet synchronous direct current (DC) motor. Some aspects can include a brushless DC motor.

According to aspects of the present disclosure, the motor 50512 can be regulated and/or controlled for various reasons including to maintain flow rates, increase motor efficiency, increase motor lifespan, increase pump lifespan, increase filter longevity, and/or conserve energy, for example. Once a control circuit for the evacuation system (see e.g. the control schematics in FIGS. 5 and 6) becomes aware of a particular condition, such as an obstruction in the flow path, an undesired pressure, and/or undesired particulate count, for example, the control circuit can regulate the motor 50512 to adjust or maintain the flow rate, which may increase motor efficiency, increase motor lifespan, increase pump lifespan, increase filter longevity, and/or conserve energy, for example.

In one aspect of the present disclosure, referring to FIG. 6, a processor can be internal to the evacuation system. For example, the processor 50408 can be internal to the evacuator housing 50618 in FIG. 7. In other aspects of the present disclosure, the processor can by external to the evacuation system 50600. The external processor 50308 is depicted in FIG. 5, for example. The external processor can be the processor of a surgical hub. In yet another aspect, an internal processor and an external processor can communicate to cooperatively control the motor 50512.

According to one aspect of the present disclosure, the motor 50512 can be regulated by a control circuit to increase motor efficiency. For example, referring to the evacuation systems in FIGS. 18 and 19, the fluid detection sensor 50830 is positioned upstream of the filter(s) and of the filter receptacle. In various instance, the fluid detection sensor 50830 is configured to detect a fluid upstream of the filter(s). For example, the fluid detection sensor 50830 is configured to detect whether aerosol or liquid droplets are present in the evacuated smoke. Based on output from the fluid detection sensor 50830, the control circuit can adjust a control parameter of the smoke evacuation system, such adjusting valves and/or power to the motor, for example.

In certain instances, the evacuation system can detect whether a fluid (e.g. smoke) is present in the flow path. In certain instances, the fluid detection sensor 50830 can automatically scan for fluid, or a particular type of fluid, when a clinician begins treating patient tissue using an electrosurgical instrument, such as when the electrosurgical instrument 50630 (FIG. 7) is activated by the generator 50640 (FIG. 7), for example. Alternatively, or in combination with the fluid detection sensor 50830, a separate sensor can be configured to detect fluid(s) at the surgical site, such as an end effector of a surgical instrument or imaging device, for example. In one instance, the separate sensor can be positioned near the tip of the electrosurgical instrument 50630. When the fluid detected at one or more of the fluid detection sensor(s) is below a threshold value, the control circuit can regulate the motor speed of the pump to a level sufficient to monitor for the presence of a fluid, or a particular type of fluid. The motor speed in such instances can be a minimum motor speed, or idle motor speed, that allows an accurate reading at the fluid detection sensor(s). Alternatively, the motor speed can be reduced to zero and periodically increased to the minimum motor speed, or idle motor speed, to monitor for the presence of a fluid, or a particular type of fluid.

Upon the detection of a fluid by the fluid detection sensor, or a fluid level above a threshold value, the control circuit can regulate the speed of the motor 50512 to a level that is sufficient to fully evacuate the fluid from the surgical site. In one example, a cloud, such as the cloud 104 (FIG. 39) and/or the cloud 204 (FIG. 46), can track and/or store motor speed levels that have been established as sufficient to efficiently evacuate fluids for the same or a similar surgical procedure. In such an example, the control circuit can access and/or reference the historical motor speed levels stored in the cloud when setting an appropriate motor speed level for that surgical procedure.

Additionally or alternatively, the speed of the motor can be adjusted based on a particulate concentration detected along the flow path. For example, referring again to FIGS. 18 and 19, the evacuation systems 50800 and 50900 include laser particle sensors 50838 and 50848 along the respective flow paths 50804 and 50904. The particle sensor 50838 is positioned upstream of the filters 50842, 50844 and the receptacle 50871 in the surgical evacuation system 50800, and upstream of the filters 50942, 50944 and the receptacle 50971 in the surgical evacuation system 50900. The particle sensor 50838 is configured to detect and/or count particles upstream of the filter(s). The particle sensor 50848 is positioned downstream of the filter(s) 50842, 50844 and the receptacle 50871 in the surgical evacuation system 50800, and downstream of the filter(s) 50942, 50944 and the receptacle 50971 in the surgical evacuation system 50900. The particle sensor 50848 is configured to detect and/or count particles downstream of the filter(s).

In such instances, the evacuation system 50800, 50900 can detect (e.g., via the laser particle counter sensors) whether a fluid (e.g., a smoke comprising particulate matter) is present. For example, the sensor(s) can detect a particulate concentration in smoke. In certain instances, the laser particle counter sensor(s) can automatically scan and count particles when a practitioner begins treating patient tissue using an electrosurgical instrument, such as when the electrosurgical instrument 50630 is activated by the generator 50640, for example.

When the particulate concentration detected by the particle sensor 50838 is below a threshold value, the control circuit can regulate the motor speed to a level sufficient to sample the particulate concentration of the flow path. For example, the motor speed can be set at a minimum or idle motor speed that permits an accurate reading at the sensors. In an alternative aspect, the motor speed can be reduced to zero and periodically increased to the minimum or idle motor speed level that is sufficient to monitor for the presence of a fluid (e.g., a particulate concentration in smoke above a threshold value). In such aspects, upon detection of a particulate concentration above a threshold value, the control circuit can regulate the motor 50512 (FIG. 4) speed to a level sufficient to fully evacuate the smoke and filter the particulates from the surgical site. Again, a cloud can track and/or store motor speed levels that have been established as sufficient to efficiently evacuate fluids for a same or a similar surgical procedure based on the particulate concentration detected by the sensors. In such an example, the control circuit can access and/or reference such historical motor speed levels when setting an appropriate motor speed level for that surgical procedure.

In one aspect of the present disclosure, the motor 50512 is more efficient because it will either be off (i.e., zero motor speed) or running at a predetermined minimum or idle speed unless a fluid and/or a threshold particulate concentration is detected. In such instances, energy can be saved and noise in the surgical theater can be minimized. Furthermore, if a fluid and/or a threshold particulate concentration is detected, the motor 50512 can be operated at an efficient motor speed, i.e. at a motor speed that is established as being sufficient to efficiently evacuate the fluid and/or particles based on historical data. This is an improvement over otherwise manual methods of setting motor speed levels based on a subjective assessment (e.g., a particular clinician's experience) and/or simply turning an evacuation system on and/or increasing the motor speed levels upon visual and/or olfactory cues (e.g., seeing and/or smelling smoke).

In accordance with various aspects of the present disclosure, motor parameters such as the speed of the motor, for example, are adaptable to adjust (e.g., increase) the efficiency of an evacuation system and a filter thereof based on the needs at the surgical site. As described herein, if the smoke detected at the surgical site is below a threshold value, it can be inefficient for the evacuation system to be unnecessarily filtering volumes of air. In such an instance, the motor speed could be decreased, reduced to zero, or maintained at zero such that the volume of air being filtered by the evacuation box is decreased, reduced to zero, or maintained at zero, respectively. Efficient use of an evacuation system ultimately prolongs the useful life of the evacuation system and/or the components thereof (e.g., fluid trap, filter, motor, pump, etc.) and reduces associated repair and/or replacement costs of the evacuation system and/or components thereof. Stress and wear caused by running the motor at full speed or at more than a sufficient speed at all times is avoided. Furthermore, the motor that drives the pump in an evacuation system can produce various levels of running and/or vibratory noise. Such running and/or vibratory noise may not be desired in the surgical theater and/or environment because it can inhibit communications between the surgical staff and/or annoy and/or distract the surgical staff, for example.

In certain instances, it may not be desirable to reduce the motor speed to zero. An electric motor, such as a permanent magnet synchronous DC motor, for example, can require a large starting torque from a fully stopped condition for use with the various pumps described herein. Here, referring again to FIG. 4, the pump 50506 creates a pressure differential between a fluid entering the pump 50506 and a fluid exiting the pump 50506. This pressure differential, or compression ratio, of the pump 50506 can result in a high starting torque of the motor 50512 in order to initiate the motor 50512 to rotate the pump 50506. In one example, the pump 50506 can comprise a blower (e.g., a hybrid regenerative blower). In such an aspect, the blower can operate at a compression ratio between about 1.1 and 1.2 to deliver a higher volume of fluid (e.g., relative to a fan or a compressor) at an operational pressure between about 1.5 psig and 1.72 psig, for example. In another example, the pump 50506 can comprise a compressor (e.g., scroll compressor pump 50650 in FIG. 12). In such an aspect, the compressor can operate at a compression ratio greater than about 2 to deliver a lower volume of fluid (e.g., relative to a fan or a blower) at an operational pressure greater than about 2.72 psig, for example.

Aspects of the present disclosure are directed to systems and methods for improving filter assembly longevity. The filter assembly can include a plurality of filtering layers. For example, referring again to FIG. 11, the filter assembly includes a coarse media filter 50684, a fine particulate filter 50686, and a carbon reservoir 50688.

According to various aspects of the present disclosure, a first pressure sensor (e.g., the pressure sensor 50840 in FIGS. 18 and 19) can be positioned upstream of the filter receptacle within the flow path and a second pressure sensor (e.g., the pressure sensor 50846 in FIGS. 18 and 19) can be positioned downstream of the filter receptacle within the flow path. In such instances, the first pressure sensor is configured to detect a first pressure and transmit a signal indicative of the first pressure to the control circuit. Similarly, the second pressure sensor is configured to detect a second pressure and transmit a signal indicative of the second pressure to the control circuit. Furthermore, the control circuit receiving the signal indicative of the first pressure and the signal indicative of the second pressure is configured to calculate the pressure differential between the first pressure sensor and the second pressure sensor. The control circuit can utilize the computed pressure differential in various ways. In a first instance, the control circuit can adjust the motor speed based on the pressure differential. In a second instance, the control circuit can indicate that maintenance is needed based on the pressure differential. For example, an indicator can appear on an evacuation system interface and/or a surgical hub interface. The control circuit can calculate the pressure differential continuously, in real time, periodically, or when system computational resources are available.

Referring again to FIG. 4, in certain instances, particles that enter the flow path 50504 of the evacuation system 50500 can cause obstructions therein. For example, particles can at least partially clog and/or block a portion of the flow path 50504. In one instance, the filter 50502 can become obstructed with particles. An obstruction can occur abruptly or over time as the evacuation system is operated. Obstructions within the evacuation system 50500 can cause a pressure differential in the flow path 50504 to rise as flow is impeded. In order to maintain a desired flow rate and compensate for the obstruction, the pump 50506 and/or the motor 50512 can require more power and/or an increased speed. However, an increased speed and/or power may diminish the efficiency of the motor 50512 and/or the pump 50506. Moreover, operating the motor 50512 and/or the pump 50506 at an increased speed to compensate for an obstruction may decrease their lifespan. In other instances, to compensate for an obstruction, the control circuit can adjust the motor 50512, as further described herein.

In one aspect of the present disclosure, the control circuit can send a drive signal to supply an adjusted current to the motor 50512. The desired supply of current can be accomplished by varying a pulse width modulation duty cycle of an electrical input to the motor 50512. In such an aspect, increasing the duty cycle of the current input to the motor can increase the motor speed and decreasing the duty cycle of the current input to the motor can decrease the motor speed.

In one aspect of the present disclosure, the evacuation system can comprise a relief valve within the flow path to relieve excessive resistance pressures in the evacuation system. The relief valve can be in fluidic communication with the ambient surroundings, for example. Relief of excessive resistance pressures, via such a relief valve, can prevent the motor 50512 from having to, or attempting to, compensate for an excessive resistance pressure. In various aspects of the present disclosure, such a relief valve is configured to be operated (e.g., opened and/or closed) upon receiving a signal from the control circuit.

Figure 46:
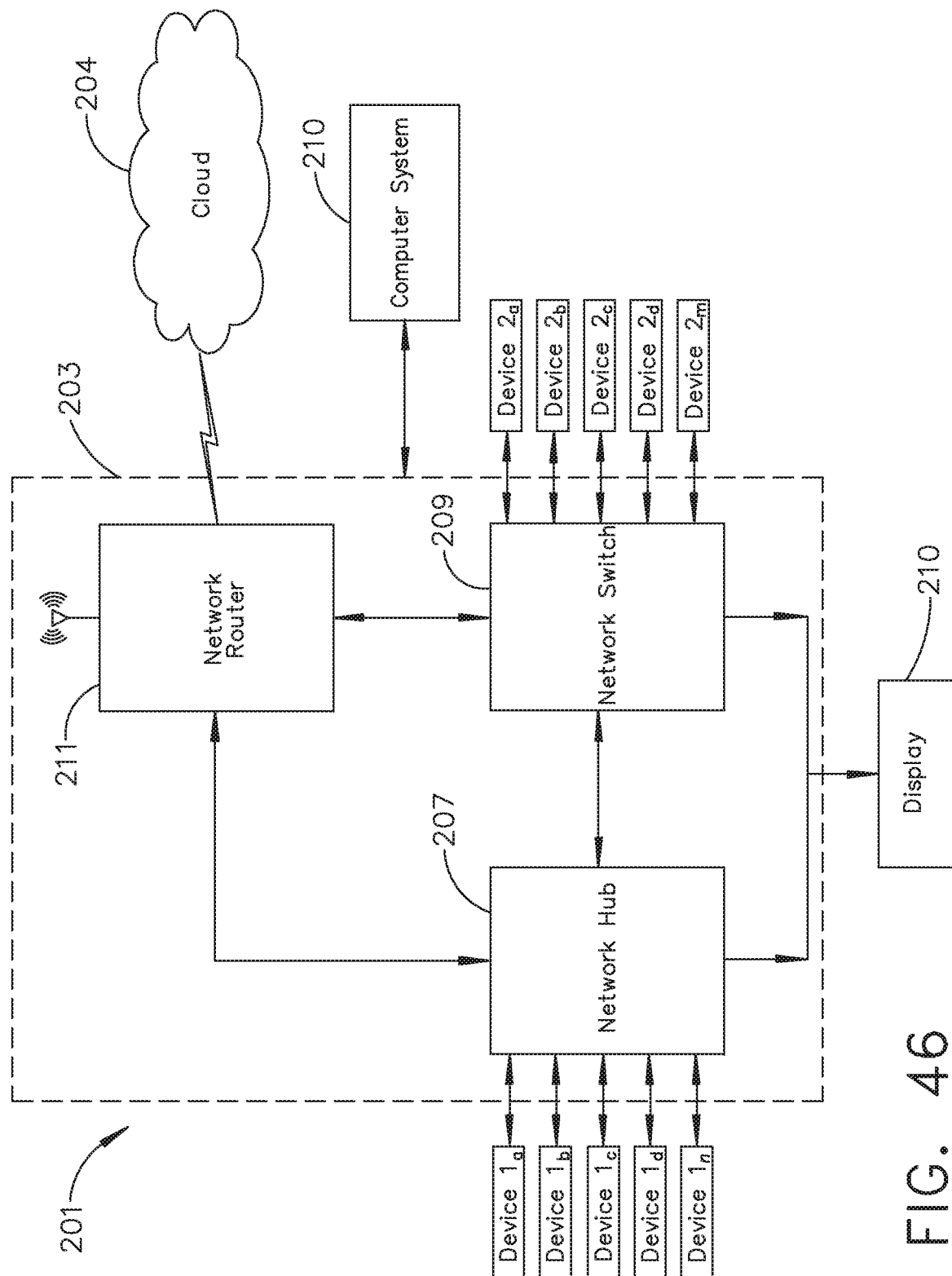
FIG. 46 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

In various aspects of the present disclosure, the control circuit can become aware of an obstruction based on sensors positioned within the evacuation system. For example, referring again to FIGS. 18 and 19, the pressure sensor 50840 is positioned and configured to detect a pressure upstream of one or more filter(s), and the pressure sensor 50846 is positioned and configured to detect a pressure downstream of the one or more filter(s). The pressure sensor 50840 is further configured to transmit a signal indicative of the pressure detected to the control circuit. Similarly, the pressure sensor 50846 is configured to transmit a signal indicative of the pressure detected to the control circuit. In such an instance, the control circuit can determine that a portion of the filter assembly is at least partially obstructed based upon the pressure detected at 50846 and/or the pressure differential calculated between 50840 and 50846. In various aspects of the present disclosure, the control circuit can determine that the filter assembly is obstructed if, for example, (A) the pressure detected at the pressure sensor 50846 is above a certain threshold, (B) the calculated pressure differential between the pressure sensor 50840 and the pressure sensor 50846 is above a certain threshold, (C) the pressure detected at the pressure sensor 50846 is above a certain threshold established for the filter(s), and/or (D) the computed pressure differential between the pressure sensor 50840 and the pressure sensor 50846 is above a certain threshold established for the filter(s). In one instance, the control circuit is configured to access and/or reference expected pressures for the filter(s) based on historical data stored in a cloud, such as the cloud 104 (FIG. 39) and/or the cloud 204 (FIG. 46).

Referring again to FIGS. 18 and 19, the pressure sensor 50850 is positioned and configured to detect a pressure at or near the outlet of the evacuation system. Additionally, the pressure sensor 50850 is configured to transmit a signal indicative of the pressure detected at or near the outlet to the control circuit. In such instances, the control circuit can determine that the flow path through the evacuation system downstream of the filter(s) is at least partially obstructed based upon the pressure detected at the pressure sensor 50846 and/or a pressure differential calculated between the pressure sensor 50846 and the pressure sensor 50850. In various aspects of the present disclosure, the control circuit can determine that the flow path is obstructed if, for example, the pressure detected at the pressure sensor 50846 is above a certain threshold and/or the pressure differential between the pressure sensor 50846 and the pressure sensor 50850 is above a certain threshold. The pressure differential generated by the pump can be considered when comparing the pressure differential of the pressure sensor 50846 and the pressure sensor 50850. In one instance, the control circuit can access and/or reference expected pressures for the flow path based on historical data stored in a cloud, such as the cloud 104 (FIG. 39) and/or the cloud 204 (FIG. 46).

The speed of the motor 50512 can correspond to the current being supplied to the motor 50512. In one aspect of the present disclosure, the control circuit can decrease the pulse width modulation (PWM) duty cycle of the current input to the motor 50512 to decrease the rotational speed of the pump 50506 and/or can increase the PWM duty cycle of the current input to the motor 50512 to increase the rotational speed of the pump 50506. As described herein, the adjustments to the PWM duty cycle can be configured to keep the flow rate substantially constant across a range of inlet pressures (e.g. measured at the pressure sensor 50840) and/or a range of outlet pressures (e.g., measured at the pressure sensor 50850).

Figure 37:
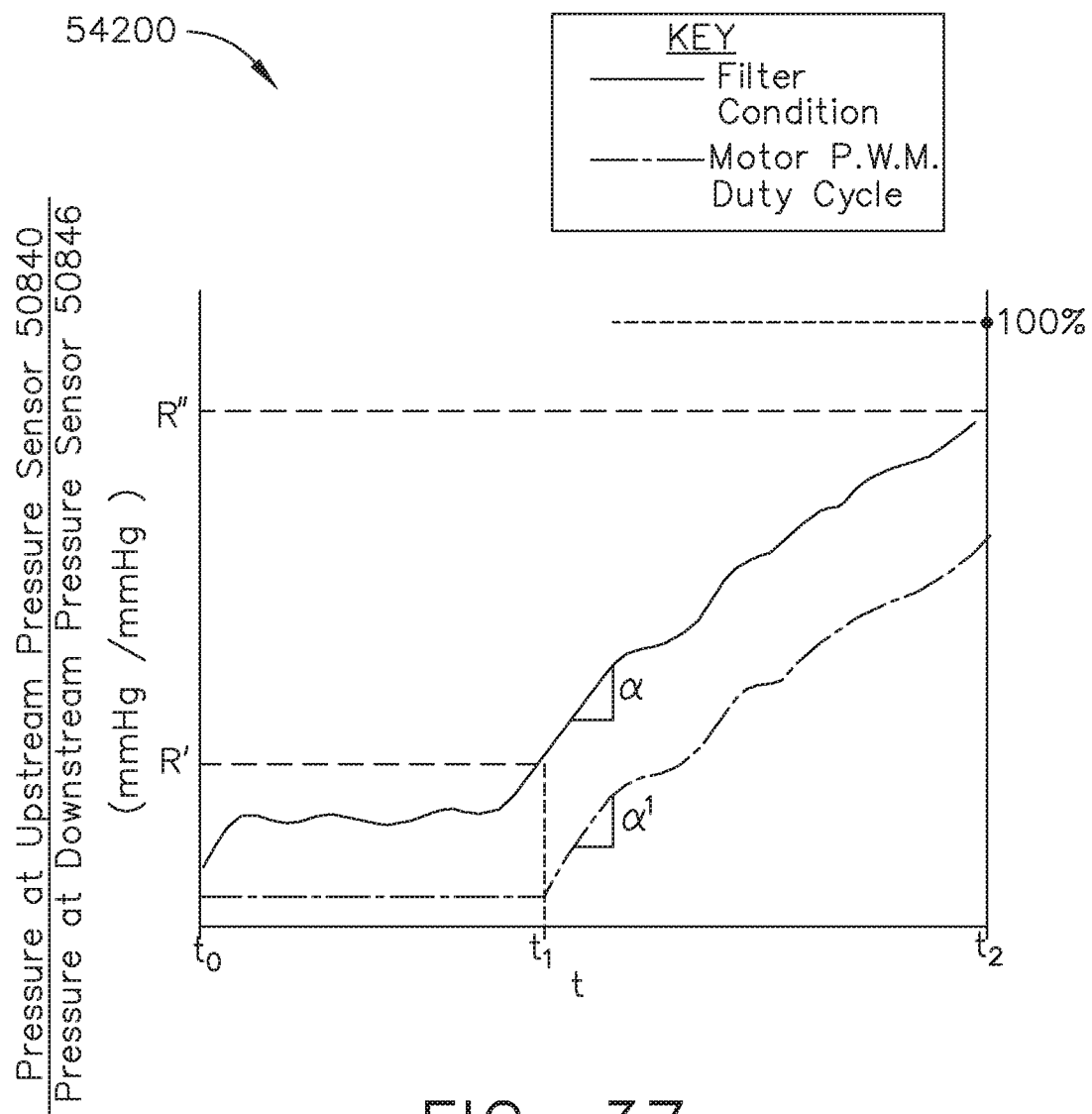
FIG. 37 is a graphical representation of the ratio of a pressure detected at a first sensor to a pressure detected at a second sensor and a pulse width modulation duty cycle of a motor of an evacuation system over time, in accordance with at least one aspect of the present disclosure.

Referring now to FIG. 37, a control circuit can track and/or plot a ratio of the pressure detected at the upstream pressure sensor 50840 to the pressure detected at the downstream pressure sensor 50846 (upstream-to-downstream pressure ratio) over time. For example, a control circuit comprising the processor 50308 and/or 50408 (FIGS. 5 and 6) can determine a pressure ratio and implement various adjustments to the surgical evacuation system based on the pressure ratio.

In one instance, referring to the graphical representation 54200 in FIG. 37, the pressure differential between the upstream pressure sensor 50840 and the downstream pressure sensor 50846 can increase as the filter becomes occluded. In one aspect of the present disclosure, the pressure ratio can increase as the downstream pressure measured by the pressure sensor 50846 decreases and/or the upstream pressure measured by the pressure sensor 50840 increases. The pressure at the pressure sensor 50840 can be equal to, or substantially equal to, the pressure at the surgical site (e.g. within a patient's body). The pressure at the pressure sensor 50846 can be the pressure drawn by the pump. An increase of the pressure ratio can correspond to an obstruction between the downstream pressure sensor 50846 and the upstream pressure sensor 50840, such as an obstruction in the filter(s). For example, as the filter becomes occluded, the pressure at the pressure sensor 50840 can remain the same or substantially the same (the pressure at the surgical site) and the pressure at the pressure sensor 50846 can decrease as the pump continues to draw a vacuum.

The ratio of upstream-to-downstream pressure can be indicative of filter life. For example, a low ratio can indicate that the filter does not need replaced and a high ratio can indicate that the filter needs to be replaced.

The progression from a new and unobstructed filter at time $t_0$ to a mostly blocked filter at time $t_2$ is depicted in FIG. 37. As shown in FIG. 37, the ratio of upstream-to-downstream pressure (the pressure at the upstream pressure sensor 50840 to the pressure at the downstream pressure sensor 50846) begins at a non-zero ratio, which can be due to a baseline pressure difference from air flow through the filter components and materials. The ratio remains relatively constant from time $t_0$ to just before time $t_1$. At time $t_1$, the upstream-to-downstream pressure ratio increases at a relatively steady rate with a slope of a until the upstream-to-downstream pressure ratio reaches a replacement ratio R". Upon reaching and/or exceeding the replacement ratio R", the filter is considered to be substantially blocked and should be replaced to avoid damaging the motor and/or pump, for example. In one instance, the control circuit can access and/or reference a replacement ratio R" for a given filter that is installed or positioned in the filter receptacle of the evacuation system via the cloud. For example, the replacement ratio R" can be stored in the memory 50410 accessible to the processor 50408 in FIG. 6. Alternatively, the replacement ratio R" can be user-defined and/or based on a history of local and/or global pressure data in the cloud. In various aspects of the present disclosure, the control circuit can utilize the tracked and/or plotted ratios to display a filter life metric (e.g., 40% remaining) on an evacuation system and/or surgical hub user interface.

Referring still to FIG. 37, the control circuit can further track and/or plot the pulse width modulation (PWM) duty cycle of the motor of the evacuation system over time. For example, when the filter(s) are considered to be relatively new after time $t_0$ until just before time $t_1$, the PWM duty cycle of the motor is set at a relatively low constant duty cycle or percentage. At time $t_1$, which corresponds to a partial blockage ratio R', the control circuit is configured to increase the PWM duty cycle of the motor at a relatively steady rate with a slope of $\alpha^1$. The increased duty cycle can be selected to compensate for the filter blockage. As obstructions in the filter continue to accumulate during use, the duty cycle can correspondingly increase to compensate for the filter blockage. In various instances, the slope $\alpha^1$ can track the slope $\alpha$ as depicted in FIG. 37. The control circuit can access and/or reference a partial blockage ratio associated with a given filter installed in the filter receptacle of the evacuation system via a cloud such as the cloud 104 (FIG. 39) and/or the cloud 204 (FIG. 46). Alternatively, the partial blockage ratio can be user-defined and/or based on a history of local and/or global pressure data in the cloud.

In one aspect of the present disclosure, increasing the duty cycle of the motor can increase the pump speed such that the pump draws more air through the evacuation system. In other words, an increase in the pressure differential across the filter can trigger a corresponding increase the PWM duty cycle of the motor for the pump.

The pump for the evacuation system is configured to transfer or affect movement of a fluid along the flow path by mechanical action. In action, the pump can increase the pressure of that fluid as the fluid is moved. The pump can have more than one operating pressure. In one aspect of the present disclosure, the pump can operate at a first operating pressure resulting in a first flow rate of fluid through the flow path and the pump can operate at a second operating pressure resulting in a second flow rate of fluid through the flow path. The first and second flow rates of fluid through the flow path can be the same or substantially similar regardless of the difference in the first and second operating pressures of the pump. In one instance, as obstructions accumulate within the flow path, the pump can operate at a higher operating pressure to maintain a constant flow rate.

Referring still to the graphical representation 54200 in FIG. 37, the control circuit can increase the PWM duty cycle of the motor to increase the current supplied to the motor and to increase the operating pressure of the pump. The control circuit can adjust the duty cycle based on detected pressure(s), the pressure differential(s), and/or a ratio of detected pressures, for example. An increased operating pressure can be configured to compensate for the obstructions, such as the obstructions in the filter beginning around time $t_1$ in FIG. 37, while maintaining a constant flow rate of fluid through the flow path. In such instances, the control circuit is able to control the load on the pump as the filter becomes occluded with particles, for example.

In various aspects of the present disclosure, the control circuit can increase the current supplied to the motor up to an established motor current threshold. In one aspect, the control circuit can increase an established motor current threshold to realize a pressure differential required to maintain a desired flow rate. For example, despite obstructions in the flow path, a pressure differential and desired flow rate can be maintained.

In another aspect of the present disclosure, the control circuit can decrease an established motor current threshold for various reasons. For example, the control circuit can decrease the established motor current threshold to protect against inadvertent tissue damages at the surgical site. For example, when a surgical port becomes blocked by patient tissue, the control circuit can reduce the motor current to reduce the pressure in the system and suctioning force applied to the tissue. In one instance, the control circuit can access and/or reference an established motor current threshold via a cloud such as the cloud 104 (FIG. 39) and/or the cloud 204 (FIG. 46). Alternatively, the established motor current threshold can be user-defined and/or based on a history of local and/or global data in the cloud.

In various aspects of the present disclosure, the control circuit can provide increased power and/or motor speed for a limited period of time based on feedback from the pressure sensors. During this time, an indication of the pressure(s) and/or obstructions can be communicated to a user via an interface in the surgical theater, for example. In one instance, a clinician can address the obstruction by clearing the obstruction and/or changing one or more filter(s) in the filter receptacle, for example. The limited period of time can be determined based on data stored in the cloud such as historical data regarding run periods at increase power levels and/or speeds before motor and/or pump failure, for example. After the limited period of time, the power and/or speed can be reduced, as further described herein, until the obstruction is appropriately addressed.

According to various aspects of the present disclosure, the control circuit for an evacuation system can send a drive signal to supply an increased or decreased current to the motor of the evacuation system in order to adjust the speed of the motor and/or the speed of the pump. In one instance, the control circuit can send a drive signal to realize a burst speed at the startup of the evacuation system and/or when transitioning between power levels. For example, the burst speed can be configured to draw the evacuation system up to a specified level at the outset of an active evacuation mode. The specified level can correspond to a specified flow rate and/or specified pressure, for example. In various instances, the burst speed can efficiently draw the evacuation system to a specified level in an energy efficient manner.

In one instance, the burst speed set via the control circuit is different than a constant run speed set via the control circuit. For example, after an initial startup of the evacuation system and/or upon setting an increased power level for the evacuation system, the control circuit can send a drive signal to supply an increased current to the motor to increase the motor speed to a burst speed for a short period of time. The burst speed can be a motor speed that is at least 20% higher than the constant motor speed required to realize a desired flow rate, for example. In one aspect of the present disclosure, the burst speed is at least 50% or at least 100% higher than the constant motor speed required to realize the desired flow rate.

Figure 38:
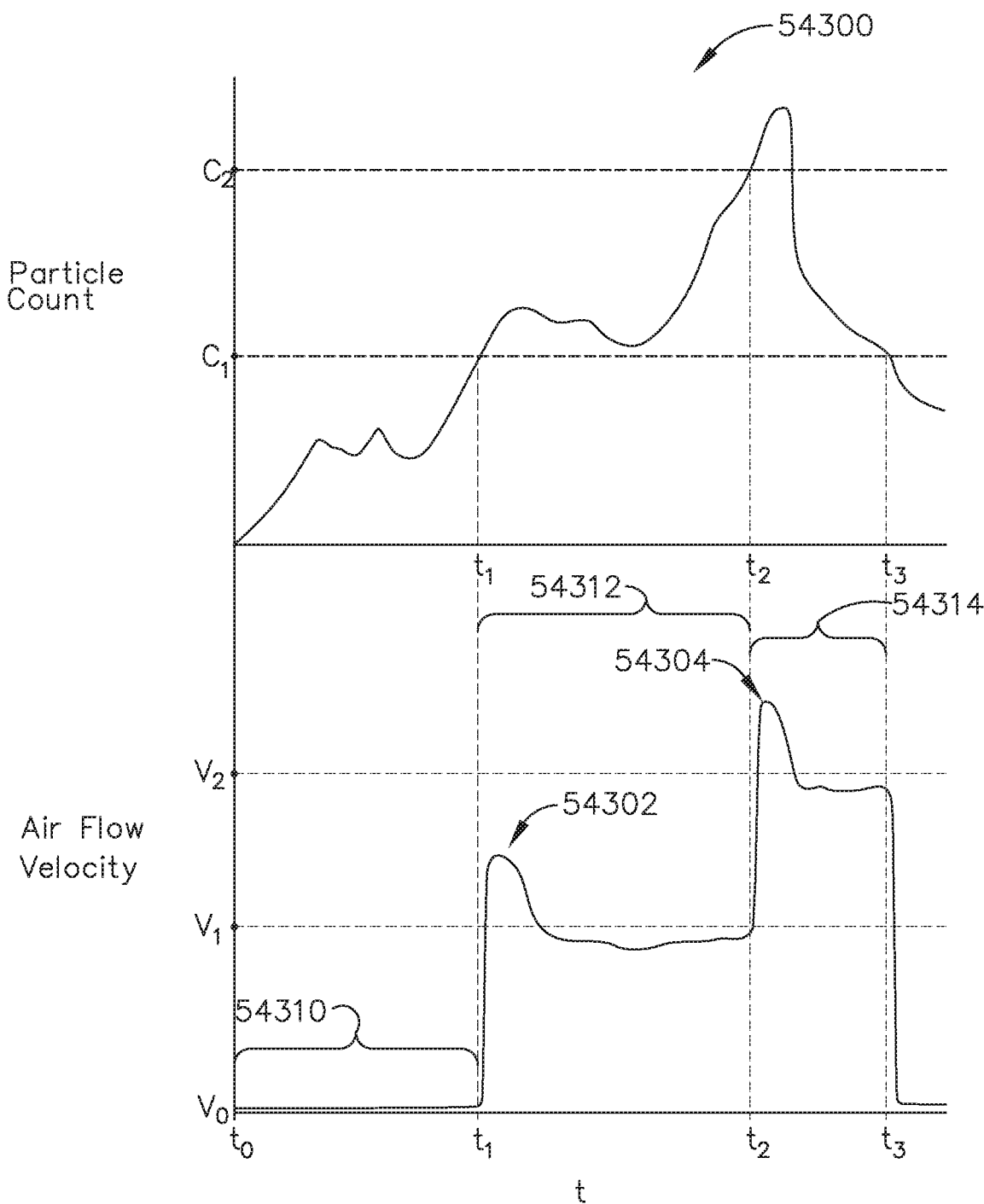
FIG. 38 is a graphical representation of (A) particles counted over time and (C) air flow velocity over time for an evacuation system, in accordance with at least one aspect of the present disclosure.

Referring now to a graphical representation 54300 in FIG. 38, the air flow velocity and particle count over time for a surgical evacuation system is depicted. A control circuit for the surgical evacuation systems 50800 and 50900 (FIGS. 18 and 19) can adjust the air flow velocity as graphically depicted in FIG. 38, for example. More specifically, the air flow velocity comprises burst speeds 54302 and 54304 for a motor of the surgical evacuation system. For example, the burst speed can be a motor speed that is required to realize an air flow velocity that is higher than the desired air flow velocity over a short period of time. As depicted in FIG. 38, the burst speed 54302 can be a motor speed that is required to realize an air flow velocity that is at least 20% higher than the desired air flow velocity $V_1$ between time $t_1$ and time $t_2$ over a fraction (e.g., ⅕) of the period between time $t_1$ and time $t_2$, for example Similarly, the burst speed 54304 can be a motor speed that is required to realize an air flow velocity at least 20% higher than the desired air flow velocity $V_2$ between time $t_2$ and time $t_3$ over a fraction (e.g., ¼) of the period between time $t_2$ and time $t_3$. In various instances, the air flow velocity can depend on the particle count within the evacuation system, as further described herein.

According to various aspects of the present disclosure, a transition of the evacuation system from a first air flow rate to a second air flow rate can be accompanied by an increase in air flow rate directly before or directly after the transition and prior to the adjustment to the second air flow rate. For example, the first air flow rate and the second air flow rate can correspond to a constant, or substantially constant, motor speed and correspondingly constant, or substantially constant, air flow speed. Referring again to the graphical display in FIG. 38, the air flow velocity is substantially constant between time $t_1$ and time $t_2$ and again between time $t_2$ and time $t_3$ with the exception of the burst speeds 54302 and 54304 shortly after time $t_1$ and time $t_2$, respectively. The substantially constant air flow velocities depicted in FIG. 38 can correspond to respective constant motor speeds in respective operating modes of the evacuation system.

Referring still to FIG. 38, at time $t_0$, the air flow velocity can be a non-zero value between $V_0$ and $V_1$, which can correspond to a "quiet" mode 54310 motor speed. In the "quiet" mode 54310, the evacuation system can be configured to sample fluid from the surgical site. The sampled fluid can by utilized to determine an operating state of the smoke evacuation system, an energy device, and/or another component of the surgical system, for example. At time $t_1$, the evacuation system can enter an "active" mode 54312. In certain instances, the "active" mode 54312 can be triggered by one or more sensors in the evacuation system, as further described herein. The increase in air flow velocity to velocity $V_1$ at time $t_1$ and/or to velocity $V_2$ at time $t_2$ can be accompanied by an additional increase in the air flow velocity directly after the transition or initiation to the new velocity level. More specifically, the air flow velocity spikes shortly after time $t_1$ and prior to the subsequent adjustment at time $t_2$ in FIG. 38. Additionally, the air flow velocity spikes shortly after time $t_2$ when the air flow transitions from the velocity $v_1$ to the velocity $v_2$ in a second "active" mode 54314.

Additionally or alternatively, a reduction in the power level of the evacuation system from a first air flow velocity to a second air flow velocity can be accompanied by an initial increase in the air flow velocity directly before the reduction. For example, when decreasing the air flow velocity from a first constant, or substantially constant, level to a second constant, or substantially constant, level, the air flow velocity can experience an air flow velocity spike similar to those illustrated in FIG. 38. In one instance, the control circuit can affect an air flow velocity spike directly before returning to a constant "quiet mode" motor speed from an "active mode". In various instances, a burst speed prior to a quiet mode can flush the surgical system and/or the evacuation system of smoke, for example.

According to aspects of the present disclosure, various particle sensors, such as the particle sensors 50838 and 50848 in FIGS. 18 and 19, for example, can be positioned and configured to count particles flowing through and/or within the evacuation systems 50800 and 50900. Similarly, an air quality particle sensor, such as the particle sensor 50852 in FIGS. 18 and 19, for example, can be positioned and configured to count particles in the ambient air about the evacuation systems 50800 and 50900 and/or within the surgical theater. The various particle sensors (e.g. the particle sensors 50838, 50848, 50852, etc.) can be further configured to transmit signals indicative of the particle concentration to the control circuit in order to adjust the air flow velocity, for example.

Referring again to FIG. 38, the motor for the evacuation system can run at a constant "quiet" mode 54310 speed between time $t_0$ and time $t_1$. Between time $t_0$ and time $t_1$, at least one particle sensor (e.g., the particle sensors 50838 and/or 50848) can be actively counting particles flowing through the evacuation system. In certain instances, at least one particle sensor (e.g., the particle sensor 50852) can be actively counting particles in the ambient air. In at least one instance, the control circuit can compare particles counted at the particle sensor 50838 and/or the particle sensor 50848 to particles counted at particle sensor 50852. The control circuit can determine that the particulate concentration detected by the particle sensor 50838 and/or the particle sensor 50848 exceed a first threshold, such as the threshold $C_1$ in FIG. 38, for example. The threshold $C_1$ can correspond to a particulate concentration level and/or to a ratio of particles counted at various sensors along the flow path, for example. In response to the particle concentration exceeding the first threshold $C_1$, the control circuit can increase the motor speed from the "quiet" mode 54310 speed associated with a first non-zero air flow velocity to a second motor speed, or "active" mode 54312, associated with a second air flow velocity (e.g., $V_1$) at time $t_1$. As discussed above, the increase in air flow velocity can be accompanied by an air flow velocity spike or burst 54302 shortly after time $t_1$.

Referring still to FIG. 38, the control circuit can continue to detect particulate concentration from at least one of the particle sensors 50838, 50848, and/or 50852 while maintaining the motor speed associated with the air flow velocity $V_1$ from time $t_1$ to time $t_2$. At time $t_2$, the control circuit can determine that particle concentration and/or ratio detected by at least one of the particle sensors 50838, 50848, and/or 50852 exceeds a second threshold, such as the threshold $C_2$ in FIG. 38. The threshold $C_2$ can correspond to a particulate concentration level and/or to a ratio of particles counted at various sensors along the flow path that is greater than the first threshold $C_1$. In response to the second threshold $C_2$ being exceeded at time $t_2$, the control circuit is configured to increase the motor speed from the motor speed associated with the air flow velocity $V_1$, or first "active" mode 54314, to a motor speed associated with an increased air flow velocity $V_2$, or second "active" mode 54314. Again, the increase from the air flow velocity $V_1$ to the air flow velocity $V_2$ can be accompanied by an air flow velocity spike or burst 54304 shortly after time $t_2$.

In various instances, the control circuit can continue to receive inputs indicative of the particulate concentration by the particle sensors 50838, 50848, and/or 50852, for example, while maintaining the motor speed associated with the air flow velocity $V_2$ between time $t_2$ and time $t_3$. At time $t_3$, the control circuit can determine that the particulate concentration and/or ratio detected by at least one of the particle sensors 50838, 50848, and/or 50852 has decreased to below the first threshold $C_1$. In response, the control circuit can decrease the motor speed from the motor speed associated with the air flow velocity $V_2$ back to the "quiet" mode speed associated with a first non-zero air flow velocity. As discussed above, in certain instances, the decrease from the air flow velocity $V_2$ back to a non-zero air flow velocity can be accompanied by an air flow velocity spike shortly after time $t_3$. The control circuit can continue to detect and/or compare particulate concentration detected by particle sensors 50838, 50848, and/or 50852, for example, while maintaining the "quiet" mode speed after time $t_3$.

In various aspects of the present disclosure, the motor can be a variable speed motor. For example, the motor 50512 (FIG. 4) can be a variable speed motor. In such an instance, a speed of the motor can be controlled based on an externally-measured parameter. For example, a speed of the variable speed motor can be increased, decreased or maintained based on a parameter measured external to the evacuation system.

According to aspects of the present disclosure, the motor 50512 (FIG. 4) can be regulated by varying a supply of electrical current to the motor 50512. For instance, a first amount of current can be supplied to the motor 50512 to cause the motor 50512 to operate at a first operating level. Alternatively, a second amount of current can be supplied to the motor 50512 to cause the motor 50512 to operate at a second operating level. More specifically, the varying supply of current can be accomplished by varying a pulse width modulation (PWM) duty cycle of an electrical input to the motor 50512. In other aspects, the current can be varied by adjusting a frequency of the current supplied to the motor. In various aspects of the present disclosure, the motor 50512 is coupled to a rotary mechanism or pump 50506 (e.g., compressor, blower, etc. as described herein) such that decreasing the duty cycle or frequency of a current input to the motor 50512 decreases the rotational speed of the pump 50506. In a similar manner, increasing the duty cycle or frequency of the current input to the motor 50512 can increase the rotational speed of the pump 50506.

In various aspects of the present disclosure, a lower operating level of the motor 50512 can be more advantageous than turning the motor 50512 completely off when evacuation and/or suction is not needed, and then switching the motor 50512 back on when suction is needed. For example, a clinician may only need to use the suction intermittently during long periods of surgery. In such aspects, turning the motor 50512 on from a completely turned-off state requires high start-up torques in order to overcome the standstill inertia of the motor 50512. Repeatedly turning the motor 50512 on from a completely off mode in this manner is inefficient and can decrease the lifespan of the motor 50512. Alternatively, employing a lower operating level allows the motor 50512 to remain on during intermittent use of the evacuation system during surgery and adjustment to the higher operating level (e.g., when additional suction is needed) is possible without the higher torques needed to overcome the motor's standstill inertia.

In various aspect of the present disclosure, a range of variation can be established or pre-determined for a motor parameter. In one example, a motor speed range can be pre-determined for the variable speed motor. In various aspects, a control circuit, as discussed above, can determine that a particular flow rate or that an increase or decrease in flow rate is needed at a surgical site based on feedback from one or more sensors. For example, a processor 50308 and/or 50408 in a control circuit can be configured to receive input from one or more sensors and implement an adjustment to the flow rate based, at least in part, on the sensor input(s). The adjustments can be determined in real-time or near real-time.

In one aspect, the control circuit can determine the need for an adjustment to the motor based on a measurement detected by a sensor in the surgical system, such as at least one sensor positioned and configured to detect a fluid (e.g. the fluid detection sensor 50830 in FIGS. 18 and 19), and/or particles in the fluid (e.g. the particle sensors 50838 and/or 50848 in FIGS. 18 and 19), and/or a separate sensor on the electrosurgical instrument positionable at/near the surgical site (e.g. the electrosurgical instrument 50630 in FIG. 7). In response to a determined need, the control circuit can send a drive signal to supply a drive current to the motor 50512 (FIG. 4) to adjust its speed to an adjusted motor speed. This adjusted motor speed can correspond to the particular flow rate desired.

Alternatively, in response to a determined need, the control circuit can send a drive signal to supply a drive current to the motor 50512 to increase or decrease the motor speed to a speed within a pre-determined motor speed range.

In such instances, the control circuit limits a speed increase or decrease of the variable speed motor to within the pre-determined motor speed range. This adjusted motor speed may or may not correspond to the adjusted flow rate desired. For example, due to a pre-determined motor speed range, the control circuit may be unable to adjust the motor speed to realize the desired flow rate.

In another aspect of the present disclosure, a motor speed can be selected by a clinician in the surgical theater, such as when the motor is being operated in a manual mode. For example, the clinician can manually alter a variable speed motor to a desired motor speed via a user interface. The user interface can be on the housing of the evacuation system and/or a surgical hub interface, for example. In various aspects, the user interface can display an externally-measured parameter (e.g., the amount of smoke and/or particles measured via a sensor at or near the surgical site) to the clinician and the clinician can manually set the motor speed based on the externally-measured parameter. In such an aspect, the user interface can send a drive signal to supply a drive current to the motor to set, increase, or decrease the motor speed to the selected motor speed.

In one aspect of the present disclosure, the control circuit can alter a first drive signal to a second drive signal based on pressure conditions detected and/or measured within the evacuation system. For example, referring again to FIGS. 18 and 19, the pressure sensors 50840, 50846, 50850 and 50854 can transmit their respective pressures to the control circuit, which can alter the first drive signal to the second drive signal based on one or more of the detected pressures. Notably, in such an aspect, the actual motor speed may not equal the motor speed selected by the user via the user interface. For example, if a pressure measured within the evacuation system exceeds a threshold pressure, permitting an increased motor speed associated with a user-selected motor speed can damage the motor and/or other components of the evacuation system. As such, the control circuit can override a user-selected motor speed to prevent damage to the evacuation system and components thereof.

In another aspect of the present disclosure, a motor speed can be automatically selected by the control circuit, such as when the motor is being operated in an automatic mode. In such an aspect, the control circuit can send a drive signal to supply a drive current to the motor to set, increase, or decrease the motor speed to an appropriate motor speed based on an externally-measured parameter(s) (e.g., the amount of smoke and/or particles measured at or near the surgical site). In an alternative aspect, the control circuit can send a drive signal to supply a drive current to the motor to set, increase, or decrease the motor speed based on parameters measured within the evacuation system including at least one of pressure and particulate concentration detected by the various sensors therein. In one example, the pressure sensors 50840, 50846, 50850 and 50854 can transmit their respective detected and/or measured pressures to the control circuit. Additionally or alternatively, the particle sensors 50838, 50848 and 50852 can transmit their respective detected and/or measured particle counts to the control circuit.

Figure 35:
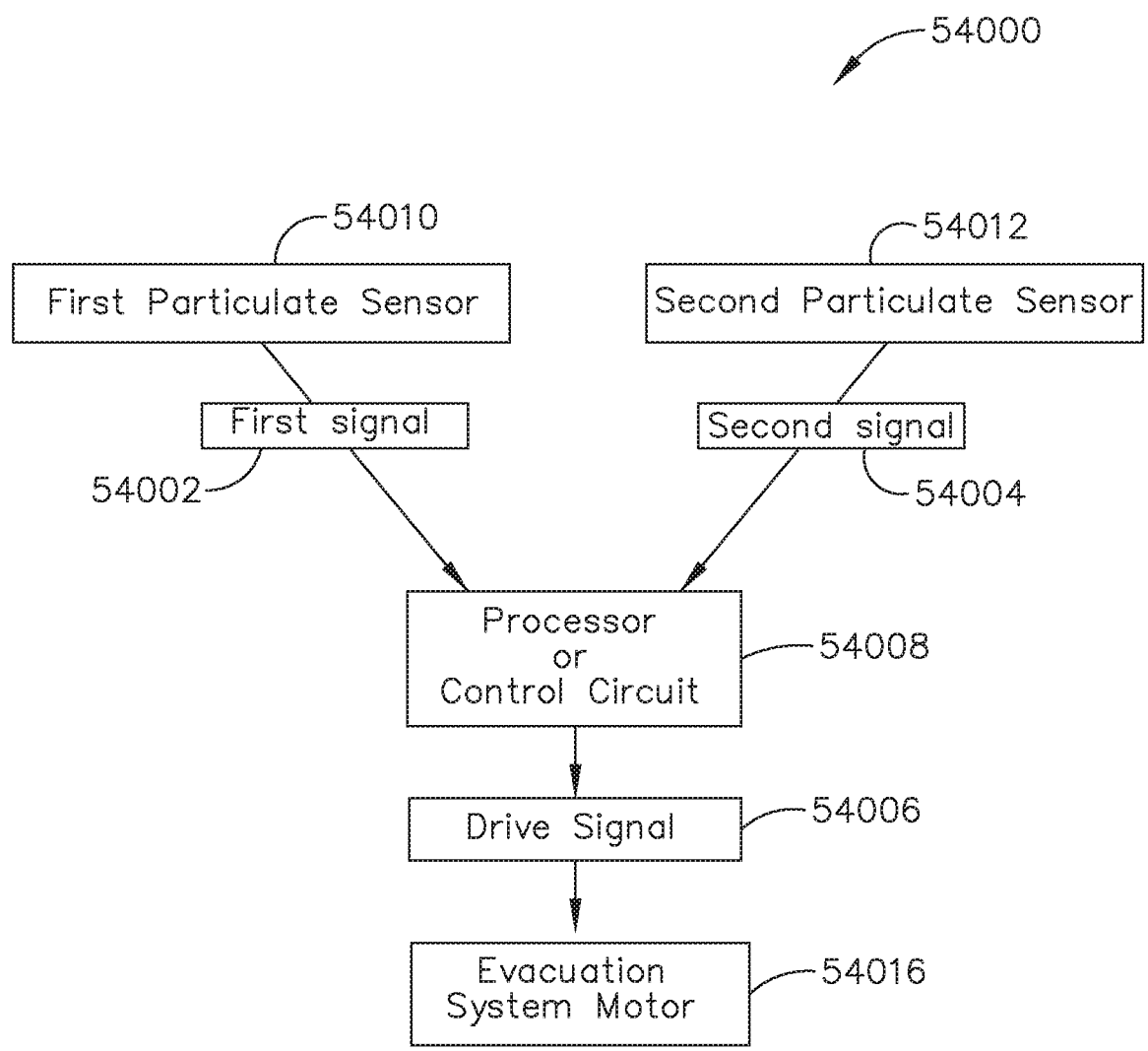
FIG. 35 is a flowchart for controlling a motor based on at least one of a first signal received from a first sensor of an evacuation system and a second signal received from a second sensor of the evacuation system, according to at least one aspect of the present disclosure.

Referring now to FIG. 35, an adjustment algorithm 54000 for a surgical evacuation system is depicted. Various surgical evacuation systems disclosed herein can utilize the adjustment algorithm 54000 of FIG. 35. Moreover, the reader will readily appreciate that the adjustment algorithm 54000 can be combined with one or more additional adjustment algorithms described herein in certain instances. The adjustments to the surgical evacuation system can be implemented by a processor, which is in signal communication with the motor of the evacuator pump (see, e.g. the processors and pumps in FIGS. 5 and 6). For example, the processor 50408 can implement the adjustment algorithm 54000. Such a processor can also be in signal communication with one or more sensors in the surgical evacuation system.

In one instance, a control circuit 54008 can be communicatively coupled to a first particulate sensor 54010, which can be similar to the particle sensor 50838 in FIGS. 18 and 19, and can transmit a first signal comprising its detected and/or measured particle count at block 54002. Additionally, the control circuit 54008 can be coupled to a second particulate sensor 54012, which can be similar in many respects to particle sensor 50848 in FIGS. 18 and 19), and can transmit a second signal comprising its detected and/or measured particle count to the control circuit at block 54004. The control circuit 54008 can then transmit a drive signal at block 54006 to apply a determined drive current to the evacuation system motor at block 54016. For example, the control circuit 54008 can be similar in many respects to the control schematics in FIGS. 5 and 6, and can include a processor communicatively coupled to a memory. In yet another aspect, any combination of sensors 50840, 50846, 50850, 50854, 50838, 50848, and 50852 (FIGS. 18 and 19) can transmit their respective detected and/or measured parameters to the control circuit 54008. In such an alternative aspect, the control circuit can determine an appropriate motor speed based on the internally-measured parameters. In either case, a user interface can display the current motor speed in various instances.

In various aspects of the present disclosure, an appropriate motor speed can be an ideal motor speed determined based on historical data stored in a cloud such as the cloud 104 (FIG. 39) and/or the cloud 204 (FIG. 46). The ideal motor speed can be the most efficient speed given the measured external and/or internal parameter(s), for example. In other aspects, the appropriate motor speed can be an ideal motor speed determined such that all measured pressures are below threshold pressures. In other words, to avoid damage to evacuation system components and to minimize the particulate concentration, such as the concentration measured at the particle sensor 50848, for example. In further aspects, the motor speed automatically selected by the control circuit can be manually adjusted. In such a manual override mode, a user can select a desired motor speed that is different from the automatically-selected motor speed. In such an aspect, a user interface can display the selected motor speed. In further aspects of the present disclosure, the user interface can display the ideal motor speed determined by the control circuit such that the user is informed that a less than (or more than) ideal motor speed and/or flow rate has been set and/or selected.

In yet another aspect of the present disclosure, the externally-measured parameter supplied to the control circuit can comprise a power level of an electrosurgical signal supplied to an electrosurgical instrument by a generator, such as the electrosurgical instrument 50630 by the generator 50640 in FIG. 6. In such an aspect, the control circuit can increase the motor speed in proportion to an increase in the power level. For example, various increased power levels can be correlated to increased levels of smoke in a cloud database. In a similar manner, the control circuit can decrease the motor speed in proportion to a decrease in the power level. Here, in an alternative aspect, a motor speed can be set (e.g., automatically and/or manually as discussed herein) at the evacuation system. Further, in such an aspect, a power level set at the generator 50640 can influence the set motor speed.

In one aspect, a manually-set motor speed can be altered based on the power level set at the generator 50640. In another aspect, an automatically-set motor speed can be altered based on the power level set at the generator 50640.

Figure 36:
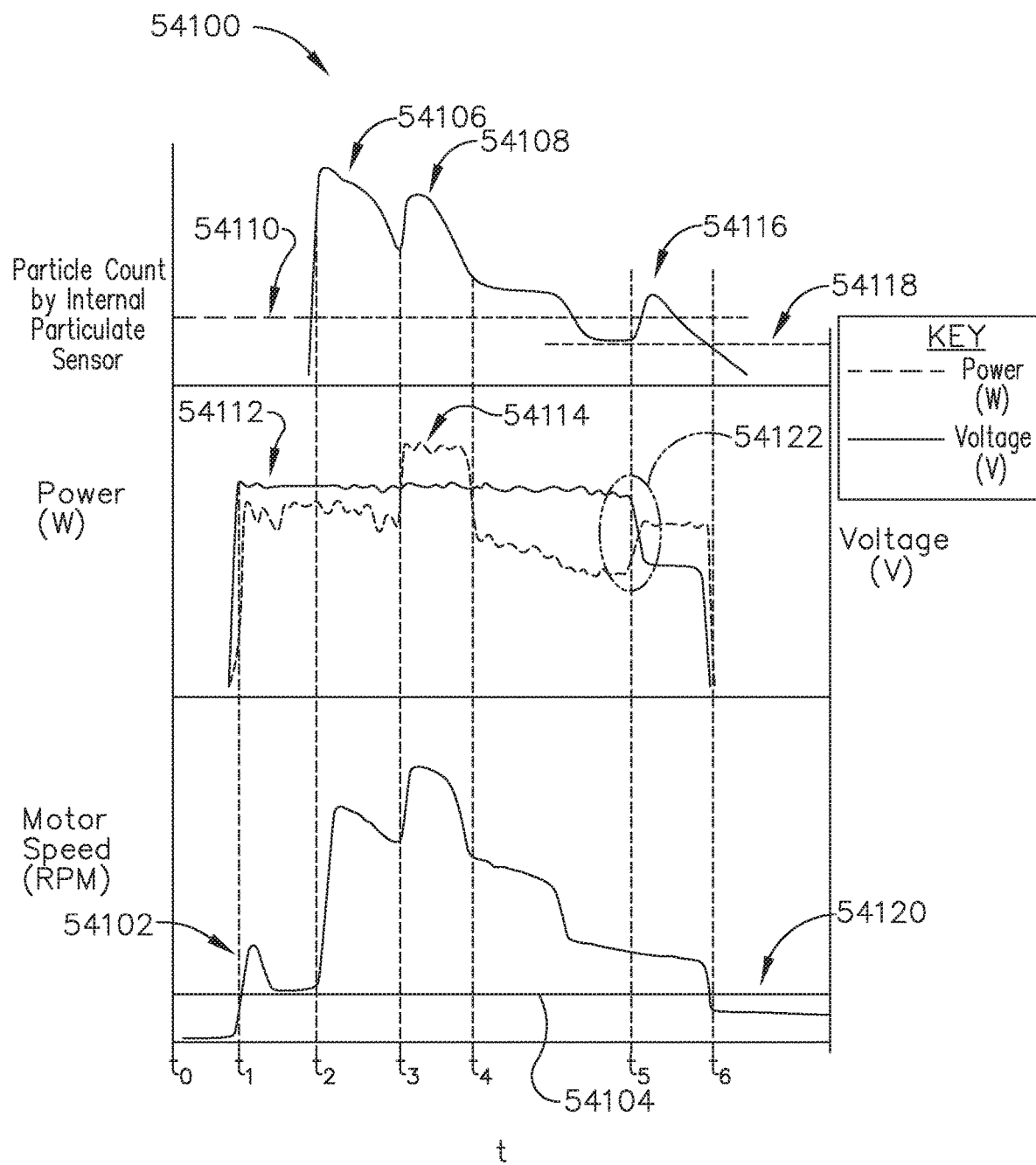
FIG. 36 is a graphical representation of (A) particles counted over time, (B) power and voltage of a generator over time, and (C) motor speed over time for an evacuation system, in accordance with at least one aspect of the present disclosure.

FIG. 36 illustrates a graphical display 54100 of particle count, power, voltage, and motor speed for a surgical evacuation system, such as the evacuation systems 50800 and 50900, for example. A control circuit for the evacuation system is configured to regulate the motor speed based on an externally-measured parameter and an internally-measured parameter. In one aspect of the present disclosure, the control circuits in FIGS. 5 and 6 can implement the depicted motor speed adjustments. In FIG. 36, the externally-measured parameter is the power level of an electrosurgical signal supplied to an electrosurgical instrument by a generator (e.g. the electrosurgical instrument 50630 by the generator 50640 in FIG. 7) used in a surgical procedure. The internally-measured parameter is the particle count detected by the evacuation system, such as the laser particle count counter 50838 in FIGS. 18 and 19, for example. The reader will readily appreciate that, in certain instances, the motor speed can be adjusted based on one of the externally-measured parameter or the internally-measured parameter. In certain instances, additional internal or external parameters can be utilized to adjust the motor speed.

At time $t_0$, the motor speed is zero, the power level supplied to the electrosurgical instrument is zero, and the particle count detected by the particle sensor 50838 is zero. At time $t_1$, a first power level is supplied by the generator to an electrosurgical instrument. In one example, the first power level can correspond to a coagulation mode. In parallel with the power level increase at time $t_1$ or shortly thereafter, the control circuit sends a drive signal to supply a startup current to the motor. The startup current results in a burst 54102 in motor speed before the motor settles to a baseline (e.g., idle) motor speed 54104 between $t_1$ and $t_2$. The baseline motor speed 54104 can correspond to the minimum torque required to turn the pump, for example. For example, as the time approaches $t_2$, the motor speed can correspond to a sleep or a quiet mode, in which the smoke evacuator is powered in anticipation of the generation of smoke. At time $t_1$, the particle sensor 50838 does not affect the motor speed.

At time $t_2$, the particle sensor 50838 detects a first spike 54106 in particulate concentration, which increases the particle count above a minimum threshold 54110, which corresponds to an "active" mode for smoke evacuation. In response to this first spike 54106, shortly after time $t_2$, the control circuit sends a second drive signal to supply an increased current to the motor to increase the flow rate through the evacuation system from a "quiet" mode to the "active" mode, for example. In response to the increased flow rate, the particulate concentration counted by the particle sensor 50838 begins to decline between time $t_2$ and time $t_3$. The control circuit actively monitors the output from the particle sensor 50838 and, because the particulate concentration declines, sends a third drive signal to supply a reduced current to the motor 50512 in proportion to the decrease particulate concentration detected by the particle sensor 50838. In other words, the motor speed between time $t_2$ and time $t_3$ is proportional to the particulate concentration detected by the particle sensor 50838.

At time $t_3$, the first power level supplied by the generator 50640, which remained relatively constant between times $t_1$ and $t_3$, is increased from a first power level 54112 to a second power level 54114. In one example, the second power level 54114 can correspond to a cutting mode. In response to the increased power level of the generator, shortly after time $t_3$, the control circuit sends a third drive signal to supply an increased current to the motor to yet again increase the flow rate through the evacuation system. For example, the motor speed can be changed in response to the waveform change at time $t_3$. Additionally, due to the increased power level, the particle sensor 50838 detects a second spike 54108 in particles counted. The third drive signal can address the increased particulate concentration in the smoke. In response to the increased motor speed, particles counted by the particle sensor 50838 decrease between times $t_3$ and $t_4$. Again, the control circuit actively monitors the particle sensor 50838 and sends a fourth drive signal to supply a reduced current to the motor in proportion to decreases in particulate concentration detected by the particle sensor 50838.

At time $t_4$, the second power level 54114 supplied by the generator, which remained relatively constant between times $t_3$ and $t_4$, decreases at a steady rate between times $t_4$ and $t_5$. In response, after time $t_4$, the particulate concentration detected by the particle sensor 50838 also decreases. In fact, the particulate concentration drops to a level slightly below the minimum threshold 54110 and above a shutoff threshold 54118 between time $t_4$ and time $t_5$ and remains relatively constant near the shutoff threshold 54118 through time $t_5$. In one instances, this can correspond to the evacuation of residual smoke from the surgical site. The control circuit continues to monitor the particle sensor 50838 between times $t_4$ and $t_5$ and sends subsequent drive signals to reduce the current to the motor in proportion to the decrease in particulate concentration between time $t_4$ and time $t_5$.

At time $t_5$, a third spike 54116 in particulate concentration can be detected by the particle sensor 50838, which again increases the particle count above the minimum threshold 54110. In one instance, additional smoke generated during the surgical procedure and detected by the particle sensor 50838 can be a result of the state of the tissue. For example, as the tissue dries out during the procedure, additional smoke can be generated. In response to the increased smoke at time $t_5$, the generator waveform automatically adjusts to minimize the smoke. For example, a third power level can be supplied by the generator. Moreover, the voltage, which remained at a relatively constant first level between time $t_1$ and time $t_5$, drops to a relatively constant second level after time $t_5$ until time $t_6$. The waveform adjustment 54122 at time $t_5$ in which the power is increased the voltage is decreased can be configured to generate less smoke in certain instances.

In response to the power level adjustment to the generator at time $t_5$, the particulate concentration detected by the particle sensor 50838 steadily decreases between times $t_5$ and $t_6$. At time $t_6$, the power level and voltage of the generator is decreased to zero corresponding to a powered down state, such as upon the completion of a surgical step, for example. Furthermore, the particulate concentration detected by the particle sensor 50838 drops below the shutoff threshold 54118 at time $t_6$. In response, the control circuit sends a drive signal to supply a reduced current to the motor to reduce the motor speed to the sleep or quiet mode 54120.

In various instances, an evacuation system can automatically sense and compensate for laparoscopic use. For example, an evacuation system can automatically detect a laparoscopic mode of a surgical system. For laparoscopic surgical procedures, a body cavity of a patient is insufflated with a gas (e.g., carbon dioxide) to inflate the body cavity and create a working and/or viewing space for a practitioner during the surgical procedure. Inflating the body cavity creates a pressurized cavity. In such instances, an evacuation system, as disclosed herein, can be configured to sense the pressurized cavity and adjust a parameter of the evacuation system parameter, such as the motor speed, for example, in response to the pressurized cavity parameters.

For example, referring again to FIGS. 18 and 19, the pressure sensor 50840 can detect a pressure above a certain threshold pressure, which can correspond to pressures conventionally utilized for insufflation. In such instances, the control circuit can initially determine whether the surgical procedure being performed is a laparoscopic surgical procedure. In certain instances, a control circuit of the smoke evacuation system (e.g. the processors 50308 and/or 50408 in FIGS. 5 and 6) can query a communicatively-coupled surgical hub and/or cloud to determine whether a laparoscopic surgical procedure is being performed. For example, situational awareness, as further described herein, can determine and/or confirm whether a laparoscopic procedure is being performed.

In certain instances, an external control circuit, such as the control circuit associated with a surgical hub, for example, can query a communicatively-coupled cloud. In another aspect, a user interface of the evacuation system can receive an input from a practitioner. The control circuit can receive a signal from the user interface indicating that the surgical procedure being performed is a laparoscopic surgical procedure. If it is not a laparoscopic surgical procedure, the control circuit can determine whether the filter is clogged and/or partially clogged as described herein. If it is a laparoscopic surgical procedure, the control circuit can adjust the pressure detected at the pressure sensor 50840 by a predetermined amount to realize a laparoscopy-adjusted pressure at sensor 50840. This laparoscopy-adjusted pressure at sensor 50840 can be utilized in accordance with the various aspects described herein in lieu of the actual pressure detected at sensor 50840. In such aspects, this can avoid an inappropriate and/or premature indication that the filter is clogged and/or partially clogged. Further, the foregoing adjustment can avoid unnecessary motor speed adjustments.

According to various aspects, the evacuation system can further sense such a pressurized cavity and adjust an evacuation system parameter (e.g., motor speed) in response to a determination that the surgical procedure being performed is a laparoscopic surgical procedure. In such aspects, after a pressure sensor such as the pressure sensor 50840, for example, detects that the evacuation system is being used within a pressurized environment, the control circuit can send a drive signal to change one or more operational parameters of the motor to an effective evacuation rate for laparoscopic procedures. In one example, a baseline (e.g., idle) motor speed and/or an upper limit motor speed can be adjusted down to compensate for the added pressure supplied by the pressurized cavity (e.g., see FIG. 7, through the distal conduit opening 50634 near the tip of the surgical instrument 50630 and the suction hose 50636). In such instances, after the pressure sensor, such as the pressure sensor 50840, for example, detects that the evacuation system is being used within a pressurized environment, the control circuit can set a secondary threshold and/or monitor an established secondary threshold with respect to pressure losses at the pressure sensor.

If the pressure detected at the pressure sensor 50840 drops below such a secondary threshold, the evacuation system can negatively impact the insufflation of the surgical site. For example, adjustments to the motor speed could drop the pressure at the pressure sensor 50840 to below a secondary threshold. In certain instances, a separate pressure sensor can be positioned on the electrosurgical instrument (i.e., such that it is within the body cavity during the laparoscopic procedure) to initially detect a pressurized cavity and/or monitor pressures within the body cavity during the laparoscopic surgical procedure. In such an aspect, such a pressure sensor would send signals to the control circuit to appropriately adjust an evacuation system parameter (e.g., motor speed) as described herein.

The reader will readily appreciate that various surgical evacuation systems and components described herein can be incorporated into a computer-implemented interactive surgical system, a surgical hub, and/or a robotic system. For example, a surgical evacuation system can communicate data to a surgical hub, a robotic system, and/or a computer-implanted interactive surgical system and/or can receive data from a surgical hub, robotic system, and/or a computer-implemented interactive surgical system. Various examples of computer-implemented interactive surgical systems, robotic systems, and surgical hubs are further described below.

Computer-Implemented Interactive Surgical System

Figure 39:
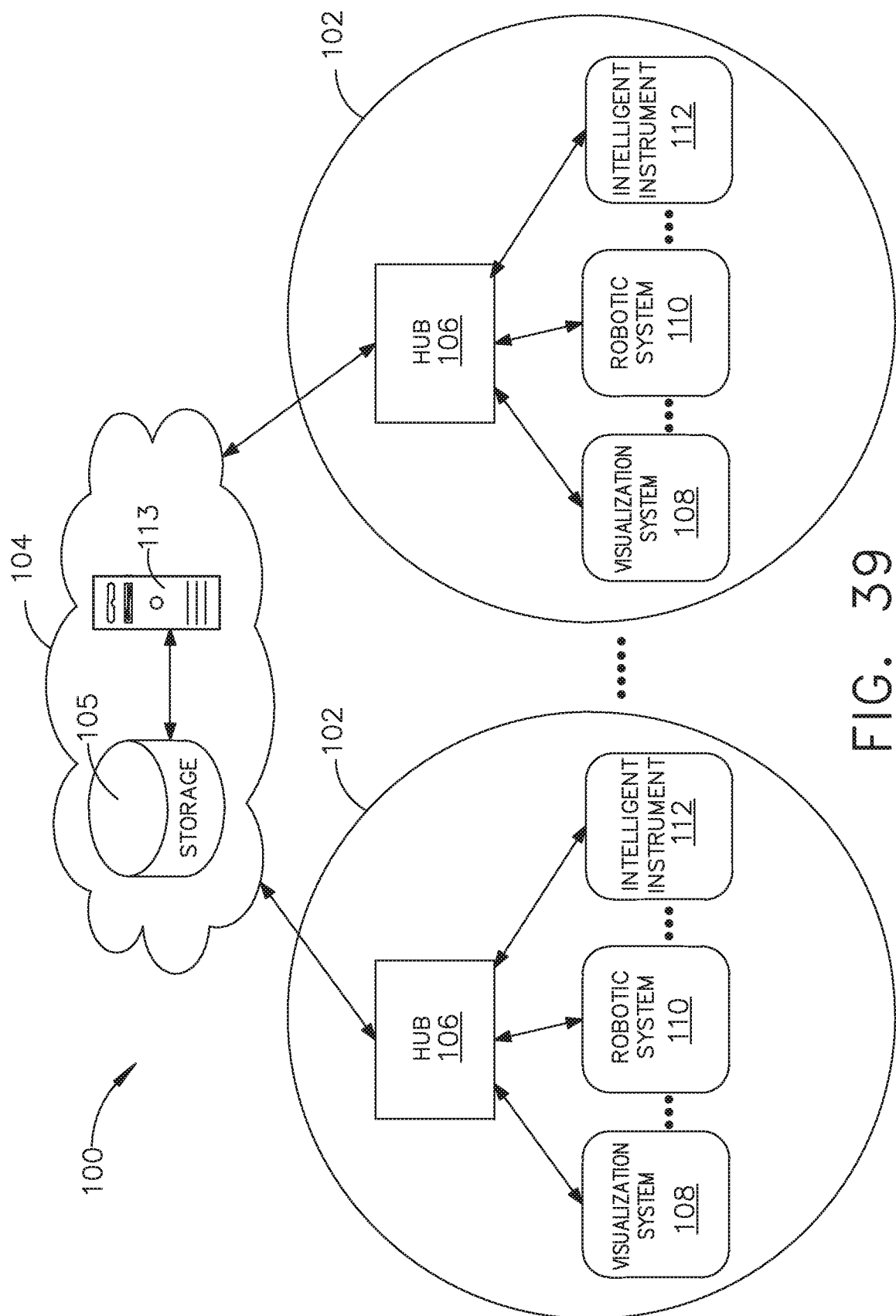
FIG. 39 is a block diagram of a computer-implemented interactive surgical system, in accordance with at least one aspect of the present disclosure.

Referring to FIG. 39, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 39, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 40:
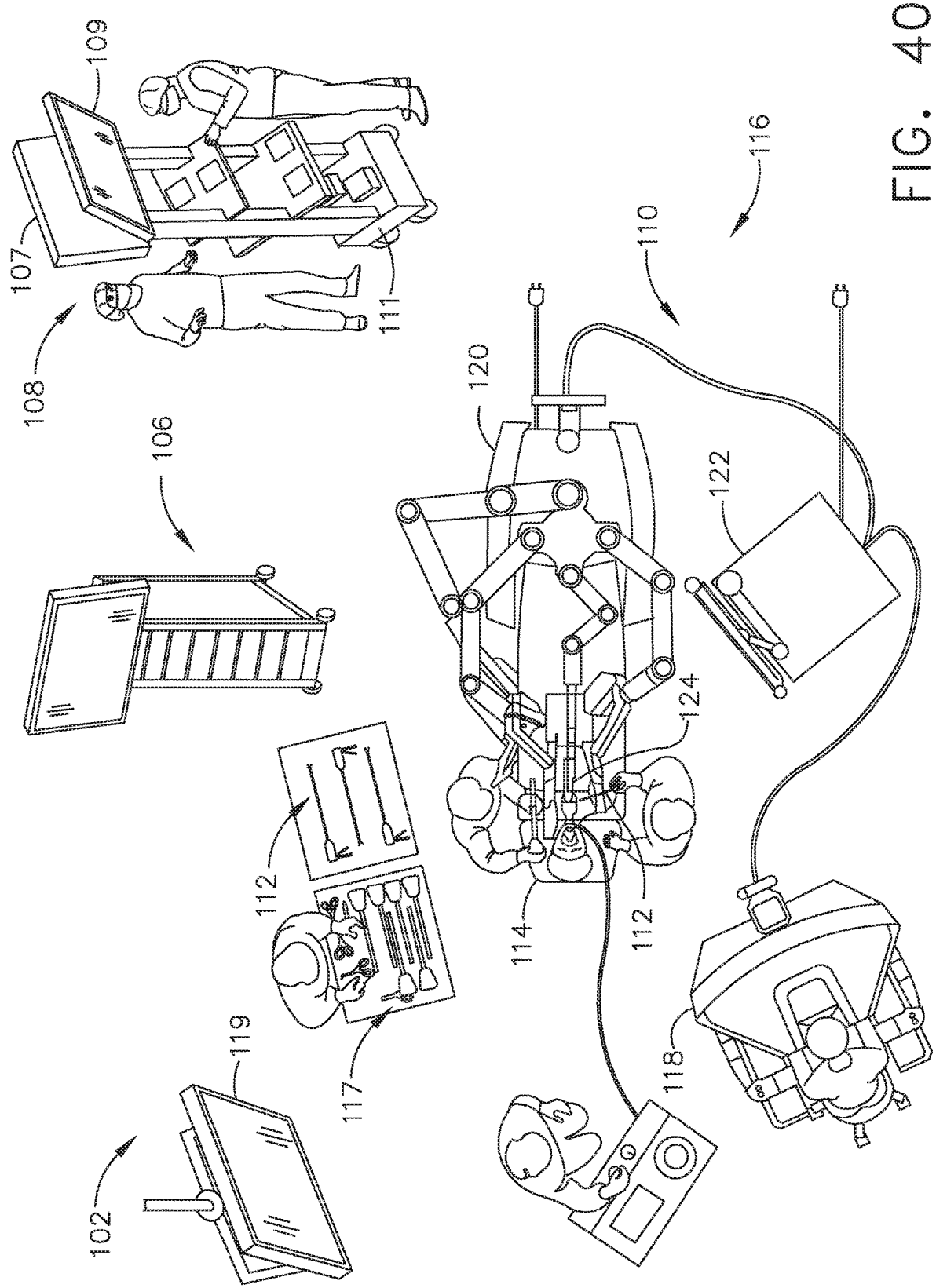
FIG. 40 is a surgical system being used to perform a surgical procedure in an operating room, in accordance with at least one aspect of the present disclosure.

FIG. 40 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image processing units, one or more storage arrays, and one or more displays that are strategically arranged with respect to the sterile field, as illustrated in FIG. 40. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 40, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 40, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 41, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 41, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 42:
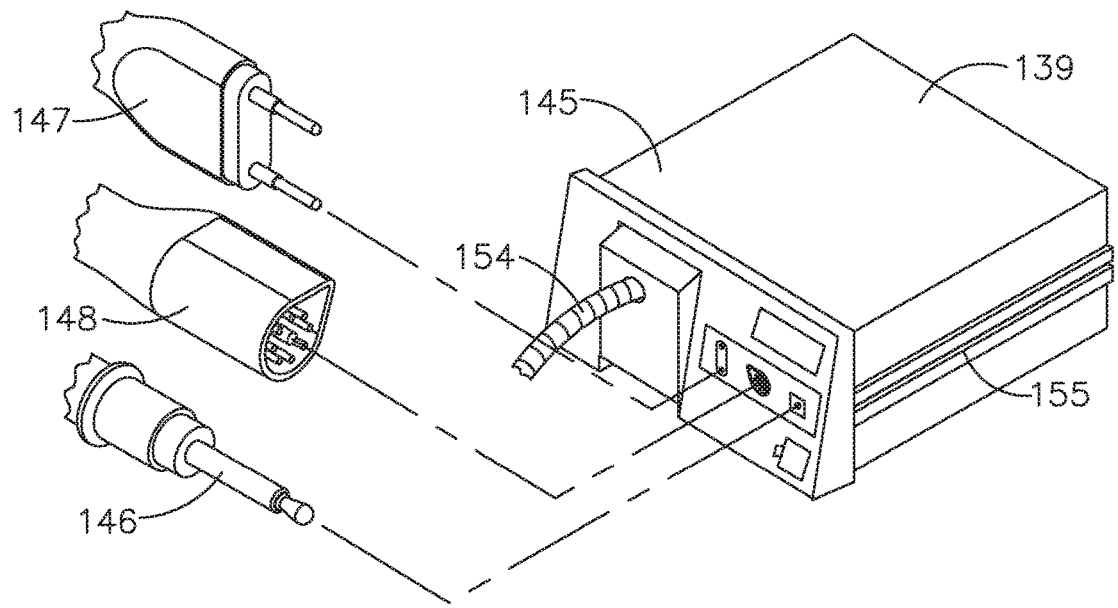
FIG. 42 is a partial perspective view of a surgical hub enclosure, and of a combo generator module slidably receivable in a drawer of the surgical hub enclosure, in accordance with at least one aspect of the present disclosure.
Figure 43:
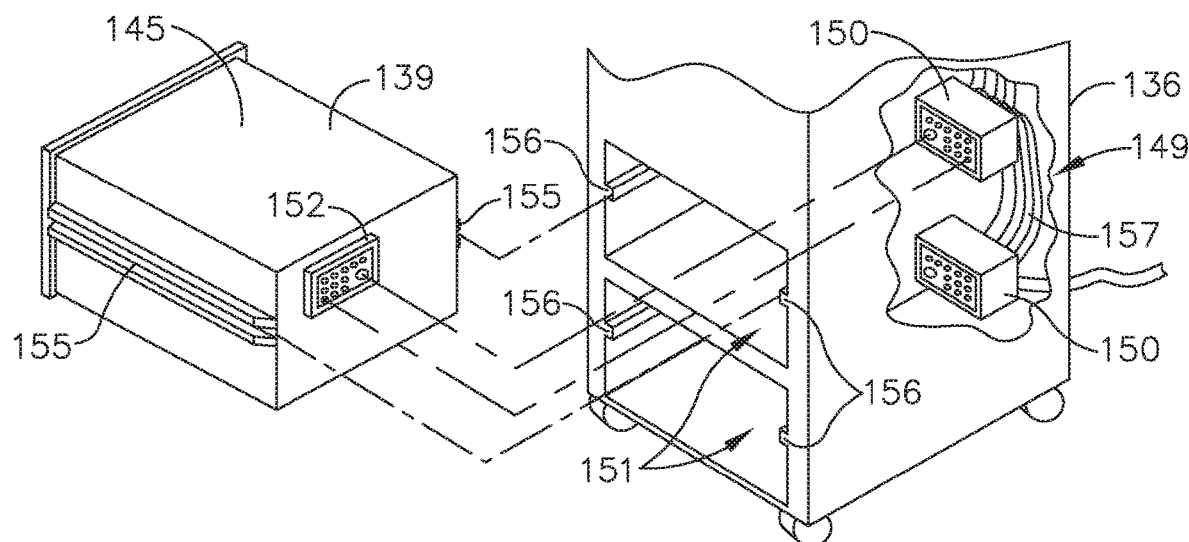
FIG. 43 is a perspective view of a combo generator module with bipolar, ultrasonic, and monopolar contacts and a smoke evacuation component, in accordance with at least one aspect of the present disclosure.

Referring to FIGS. 41-45, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 43, the generator module 140 can be a generator module with integrated monopolar, bipolar, and ultrasonic components supported in a single housing unit 139 slidably insertable into the hub modular enclosure 136. As illustrated in FIG. 42, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

In one aspect, the hub modular enclosure 136 includes docking stations, or drawers, 151, herein also referred to as drawers, which are configured to slidably receive the modules 140, 126, 128. FIG. 43 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 43.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 42, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 43, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 44:
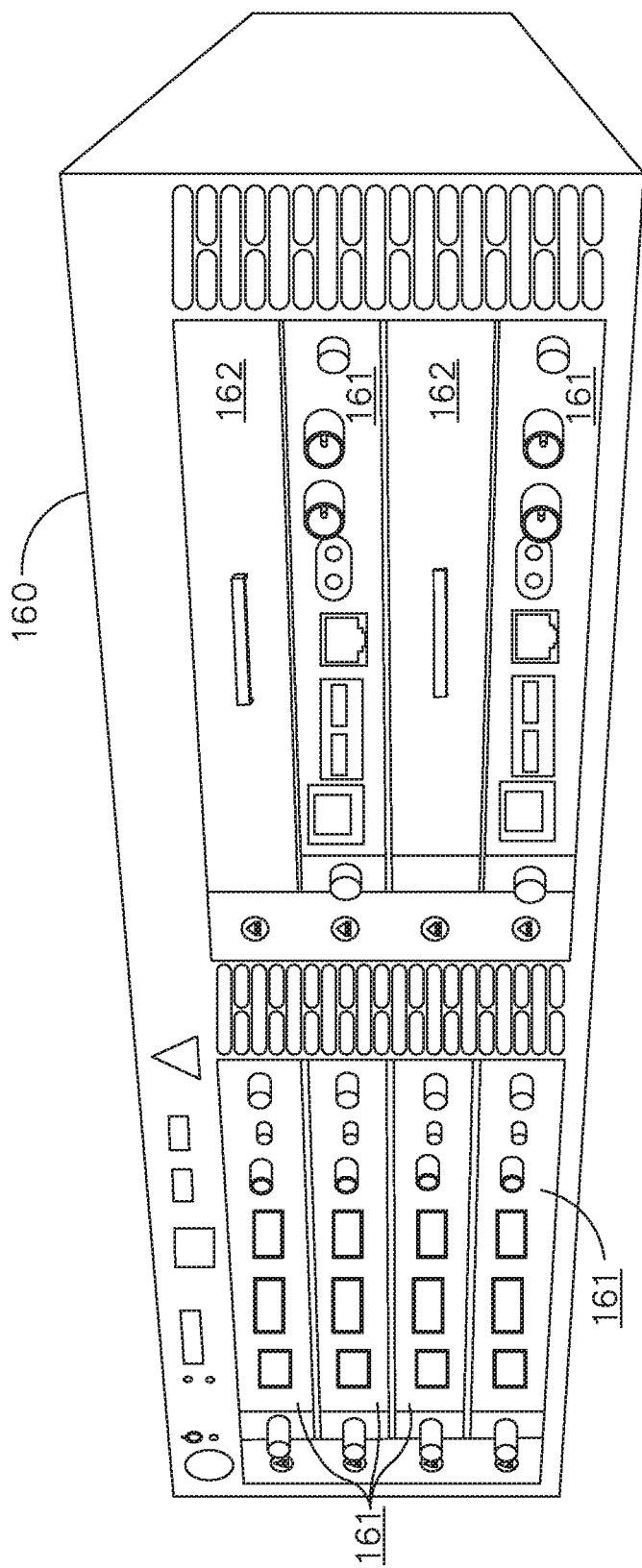
FIG. 44 illustrates individual power bus attachments for a plurality of lateral docking ports of a lateral modular housing configured to receive a plurality of modules, in accordance with at least one aspect of the present disclosure.

FIG. 44 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 44, the modules 161 are arranged laterally in the lateral modular housing 160. Alternatively, the modules 161 may be arranged vertically in a lateral modular housing.

Figure 45:
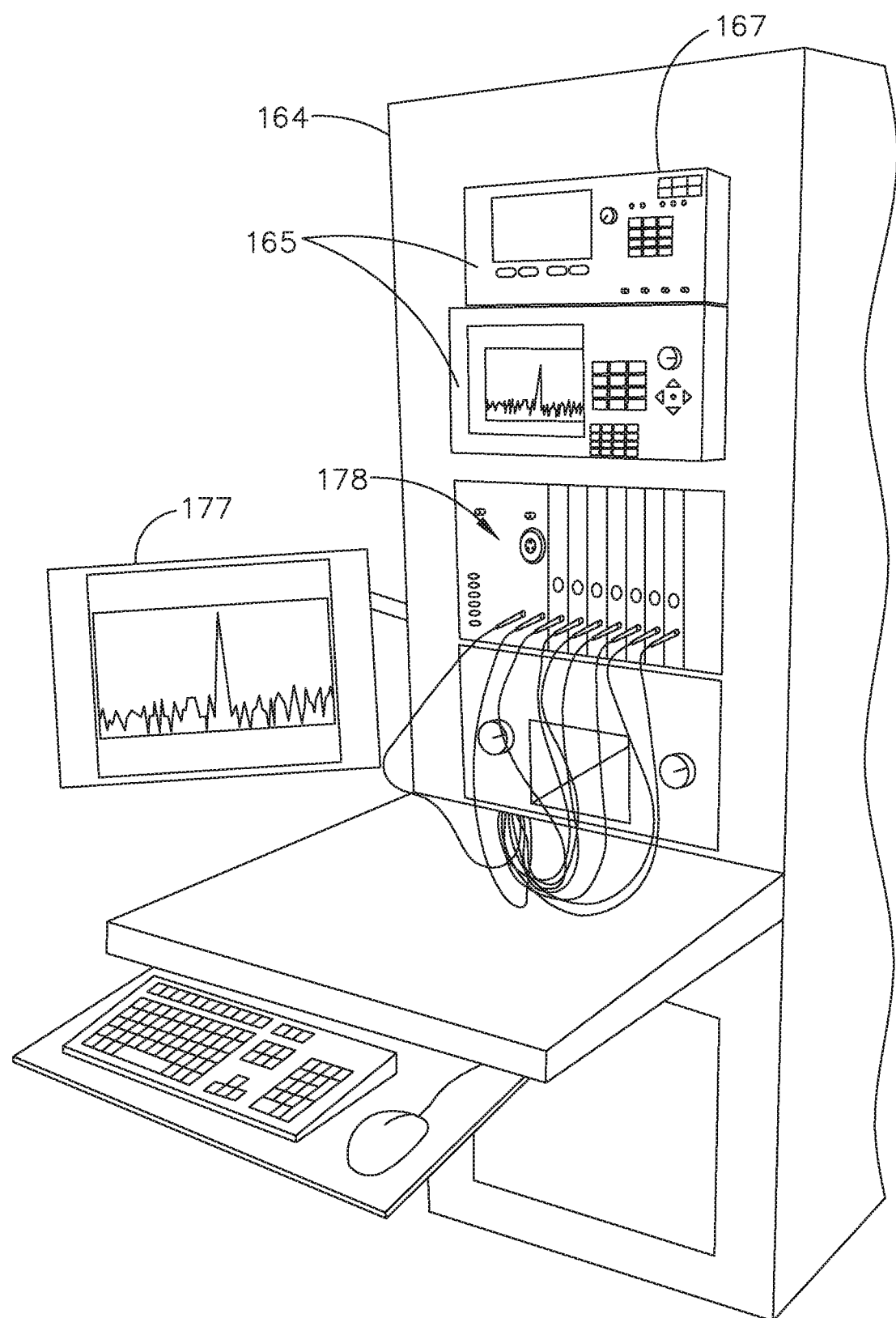
FIG. 45 illustrates a vertical modular housing configured to receive a plurality of modules, in accordance with at least one aspect of the present disclosure.

FIG. 45 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 45, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

FIG. 46 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 47) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 48:
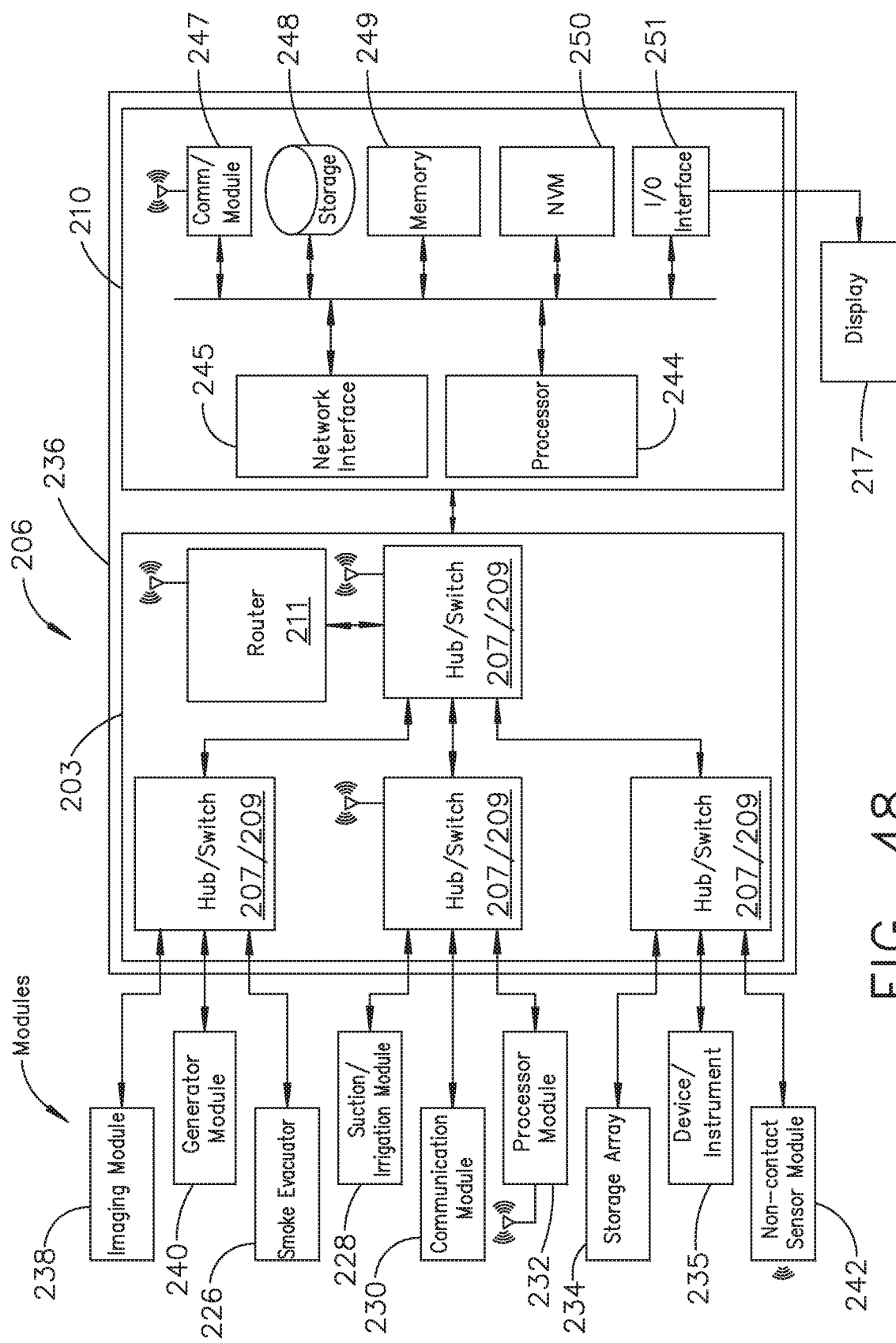
FIG. 48 illustrates a surgical hub comprising a plurality of modules coupled to the modular control tower, in accordance with at least one aspect of the present disclosure.

FIG. 47 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 48, the modular control tower 236 comprises a modular communication hub 203 coupled to a computer system 210. As illustrated in the example of FIG. 47, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 48 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 48, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 48, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 48, the imaging module 238 and/or visualization system 208 of FIG. 48, and/or the processor module 232 of FIGS. 47 and 48, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/ software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 49:
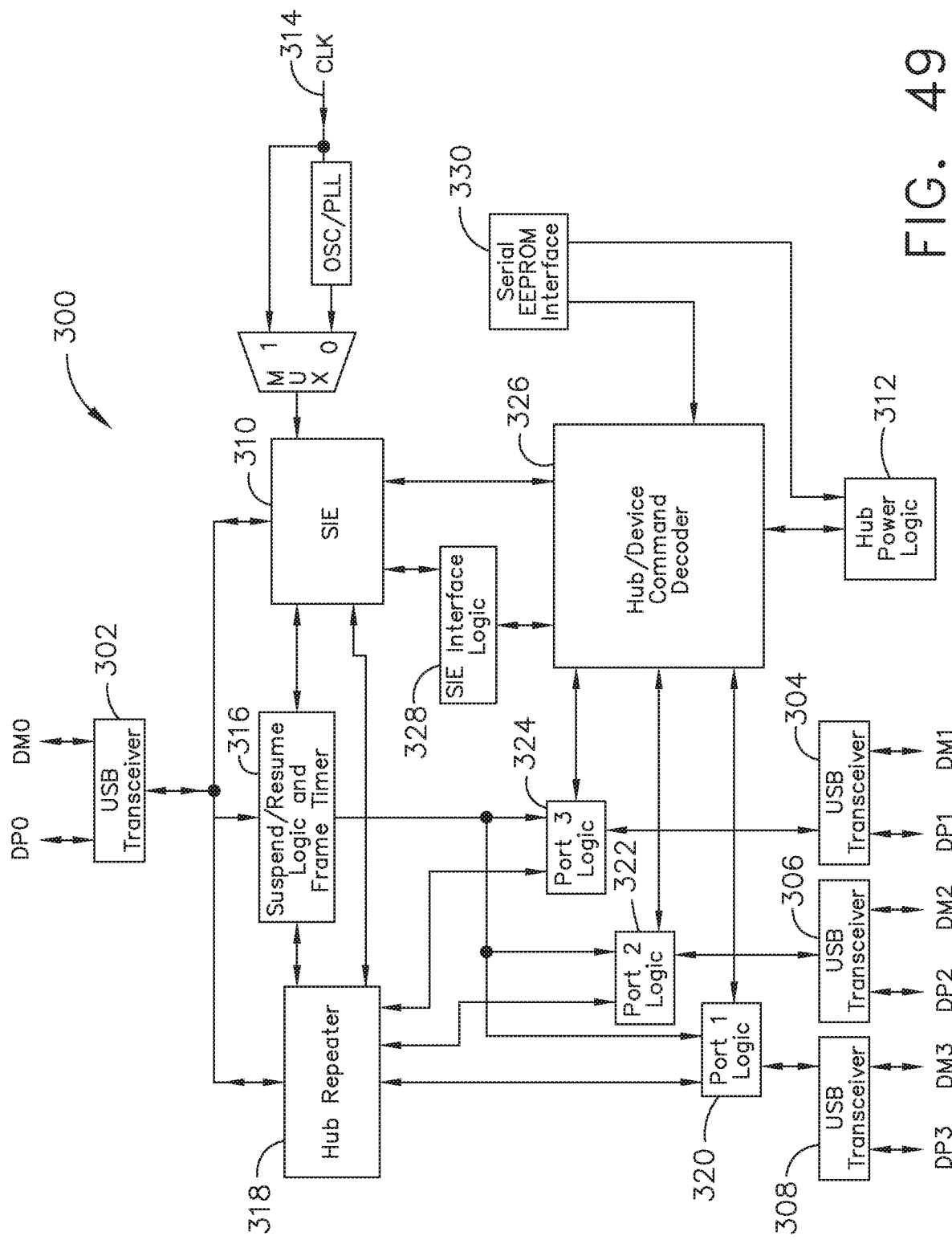
FIG. 49 illustrates one aspect of a Universal Serial Bus (USB) network hub device, in accordance with at least one aspect of the present disclosure.

FIG. 49 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/ data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 50:
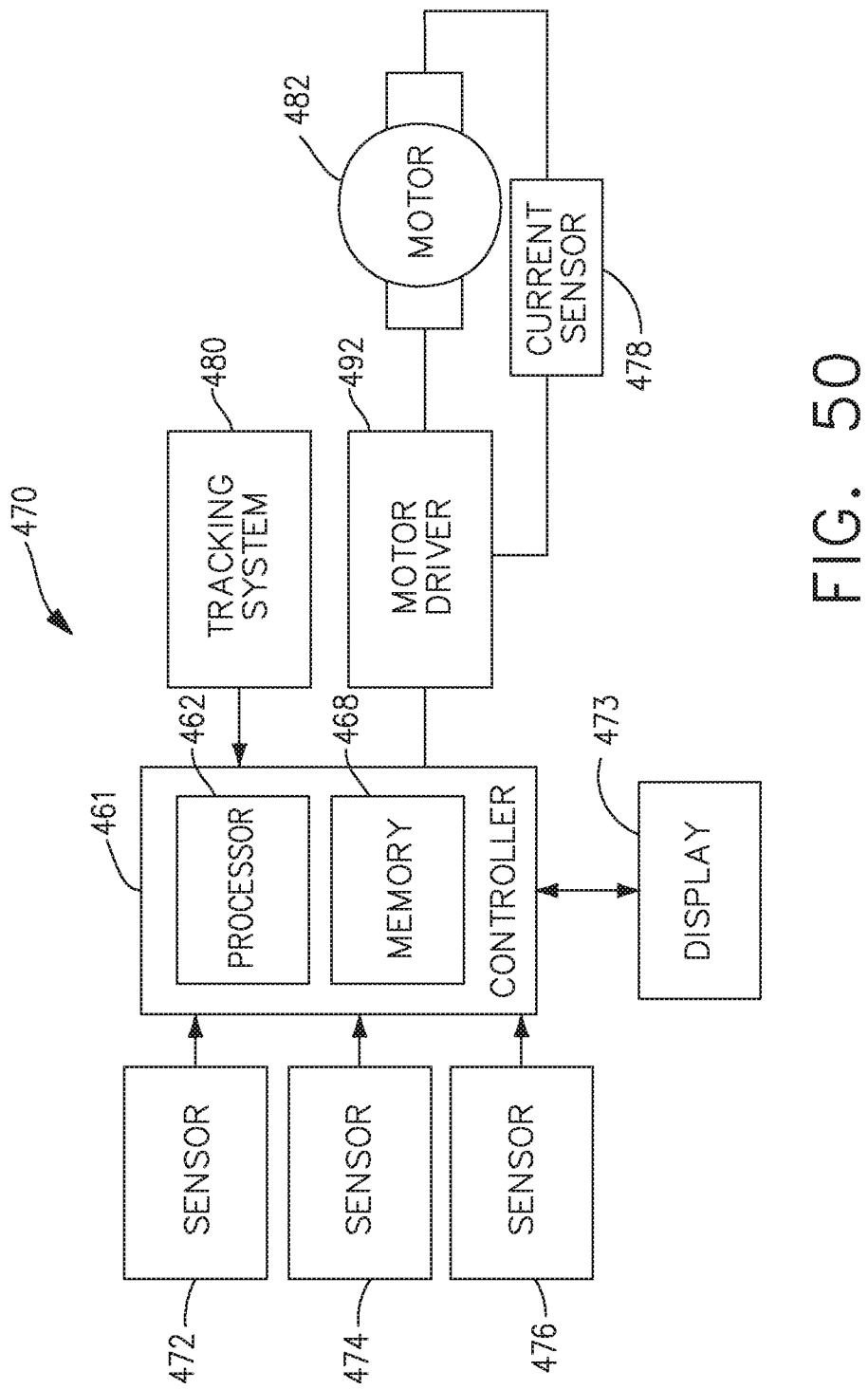
FIG. 50 illustrates a logic diagram of a control system of a surgical instrument or tool, in accordance with at least one aspect of the present disclosure.

FIG. 50 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICK- NESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIG. 50.

Figure 51:
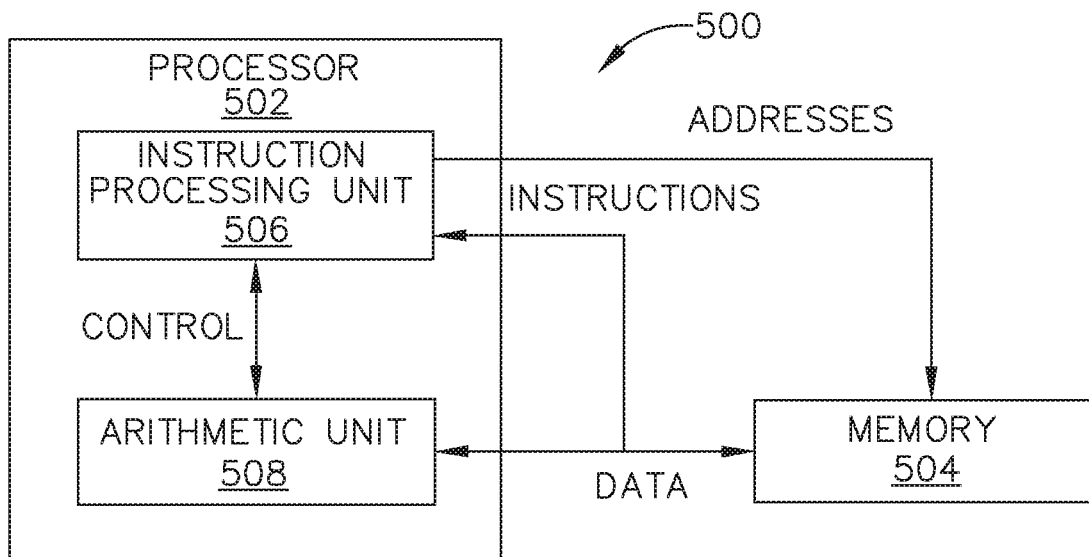
FIG. 51 illustrates a control circuit configured to control aspects of the surgical instrument or tool, in accordance with at least one aspect of the present disclosure.

FIG. 51 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 52:
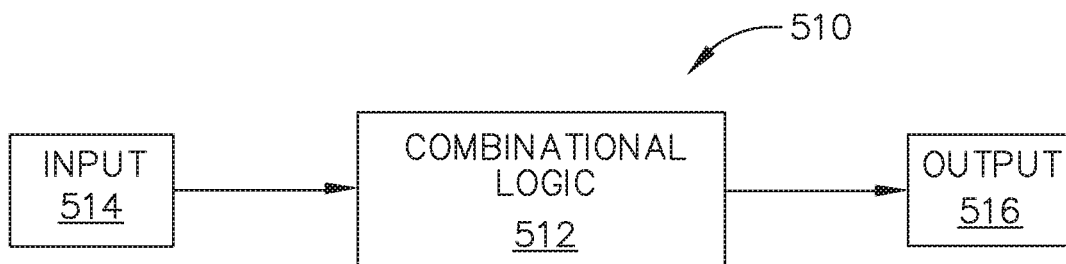
FIG. 52 illustrates a combinational logic circuit configured to control aspects of the surgical instrument or tool, in accordance with at least one aspect of the present disclosure.

FIG. 52 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 53:
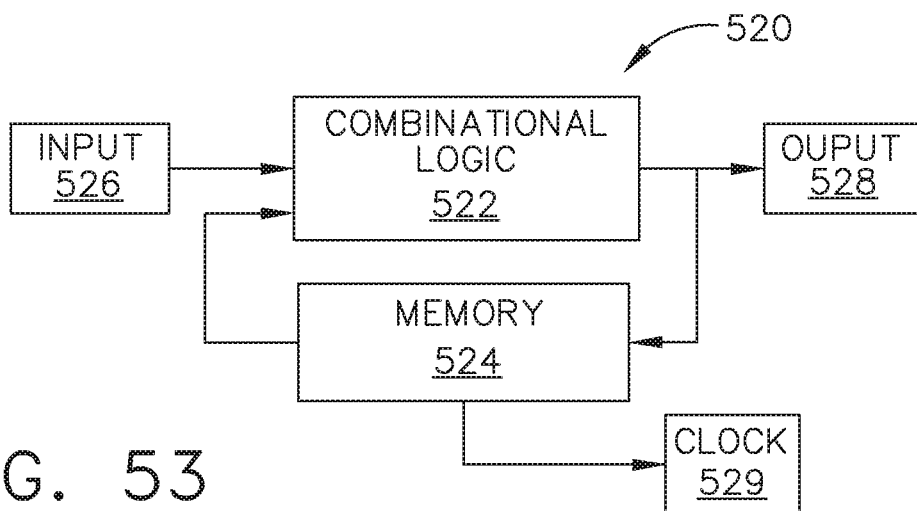
FIG. 53 illustrates a sequential logic circuit configured to control aspects of the surgical instrument or tool, in accordance with at least one aspect of the present disclosure.

FIG. 53 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 51) and a finite state machine to implement various processes herein. In other aspects, the finite state machine may comprise a combination of a combinational logic circuit (e.g., combinational logic circuit 510, FIG. 52) and the sequential logic circuit 520.

Figure 54:
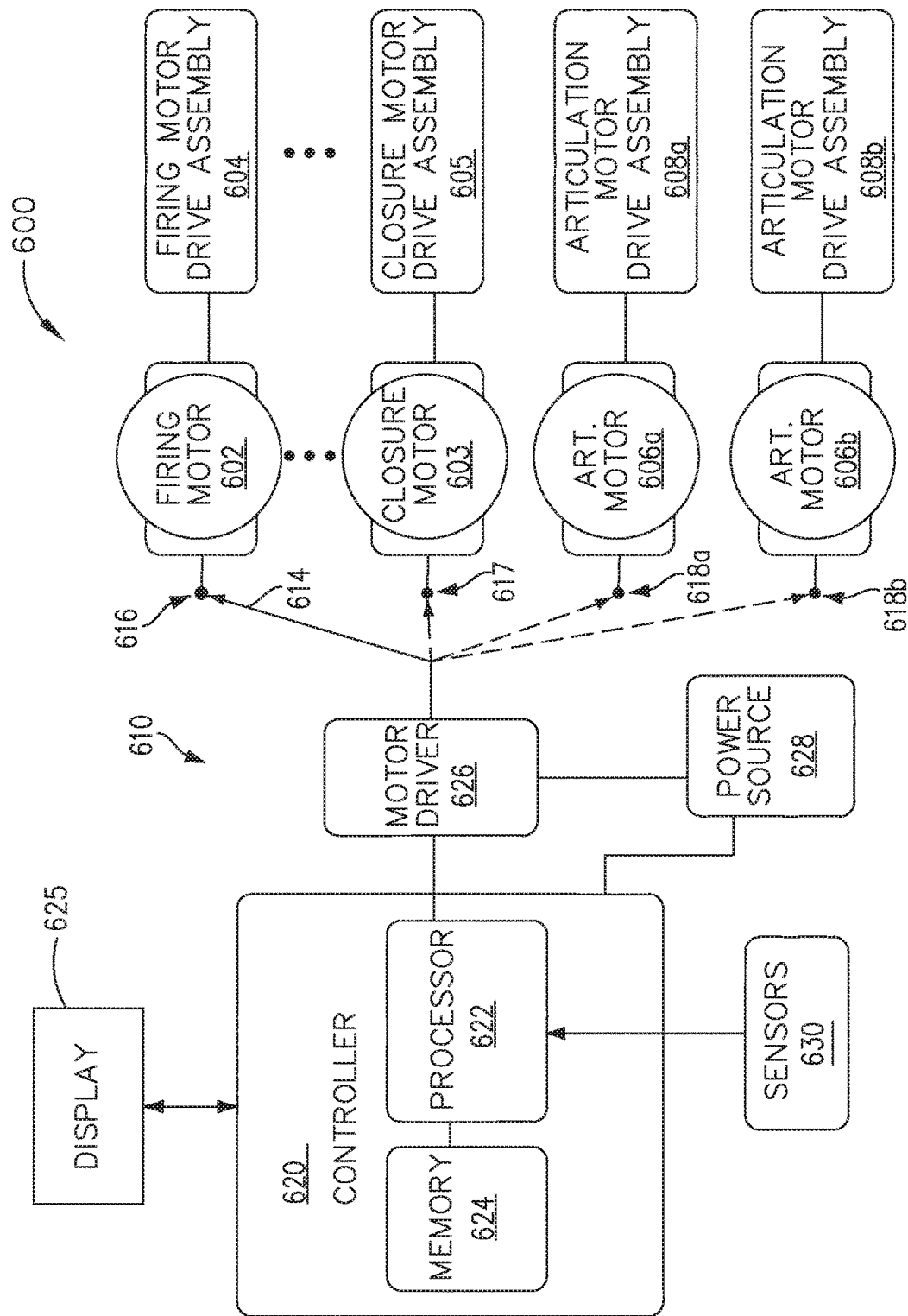
FIG. 54 illustrates a surgical instrument or tool comprising a plurality of motors which can be activated to perform various functions, in accordance with at least one aspect of the present disclosure.

FIG. 54 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 54, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 54, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 55:
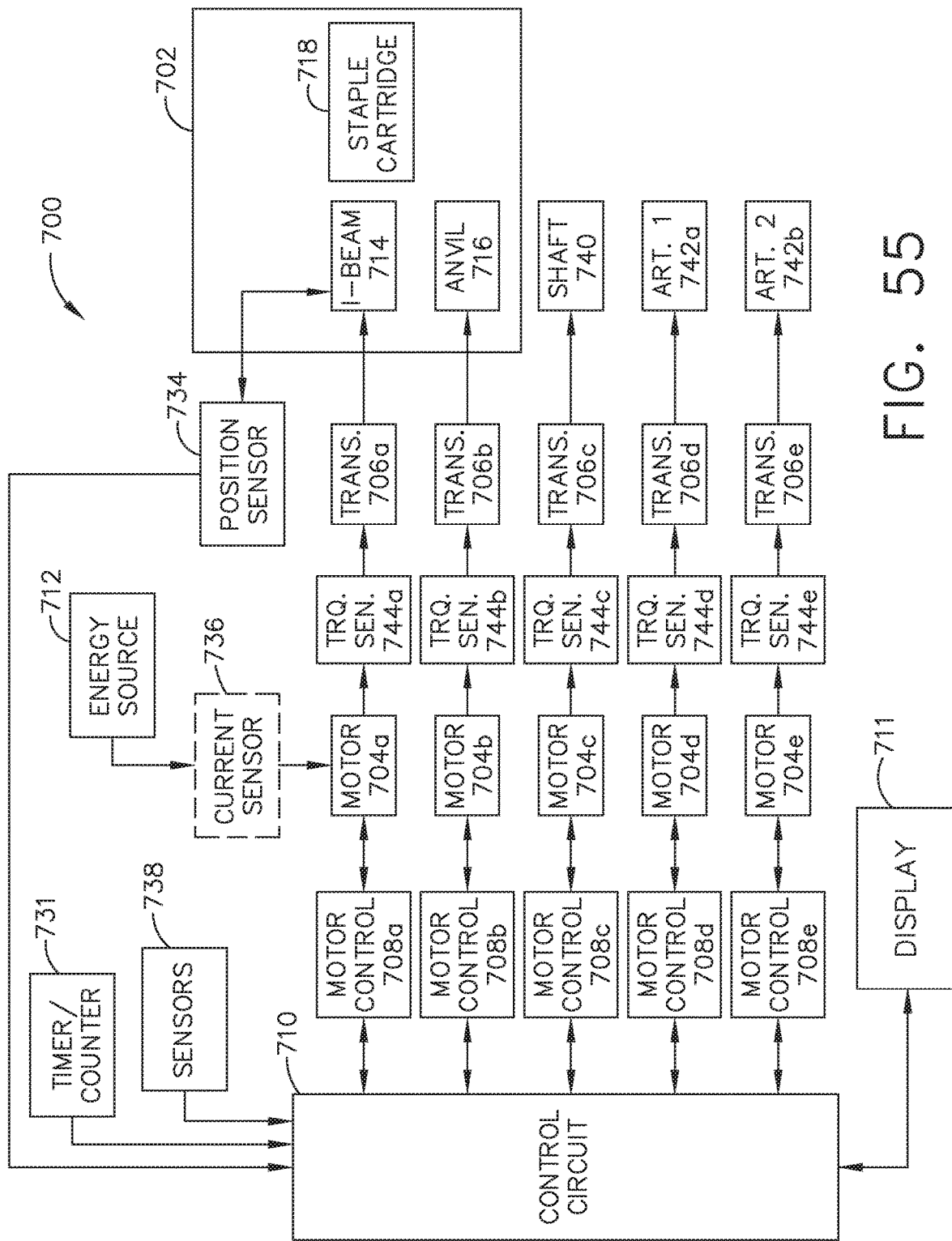
FIG. 55 is a schematic diagram of a robotic surgical instrument configured to operate a surgical tool described herein, in accordance with at least one aspect of the present disclosure.

FIG. 55 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack), which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704*a*-704*e*. The force required to advance any of the movable mechanical elements such as the I-beam 714 corresponds to the current drawn by one of the motors 704*a*-704*e*. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 56:
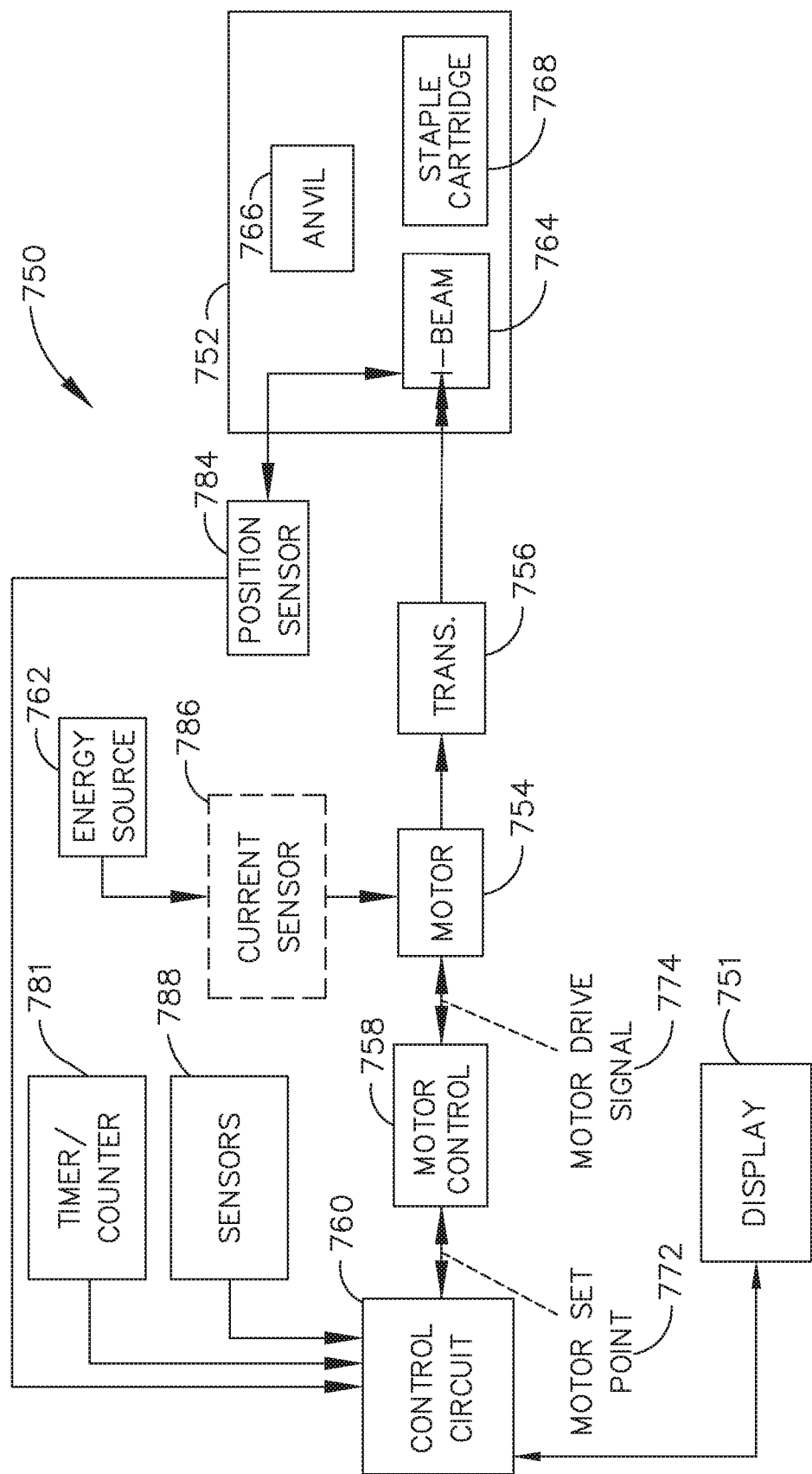
FIG. 56 illustrates a block diagram of a surgical instrument programmed to control the distal translation of a displacement member, in accordance with at least one aspect of the present disclosure.

FIG. 56 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 57:
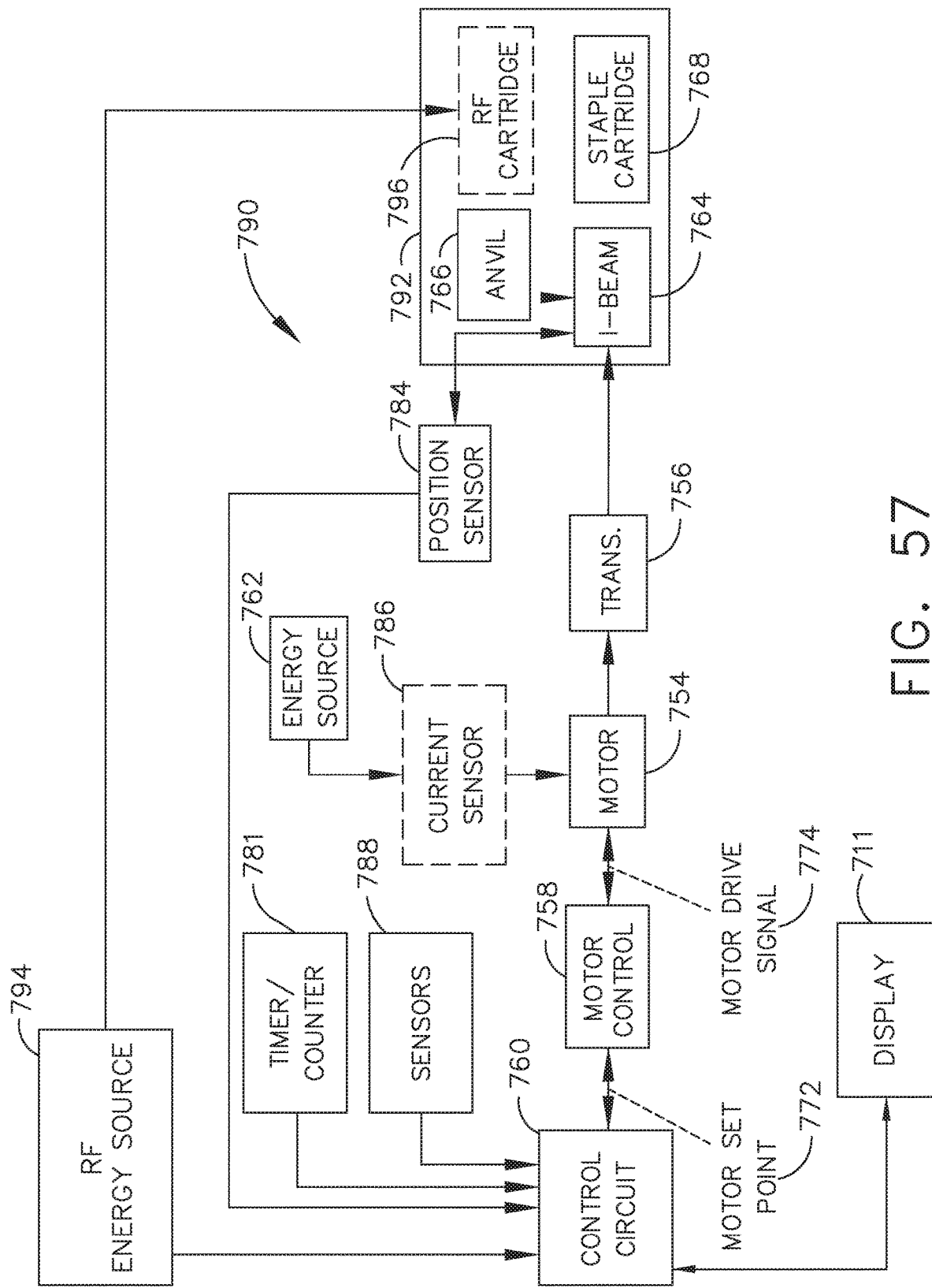
FIG. 57 is a schematic diagram of a surgical instrument configured to control various functions, in accordance with at least one aspect of the present disclosure.

FIG. 57 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

FIG. 58 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 59:
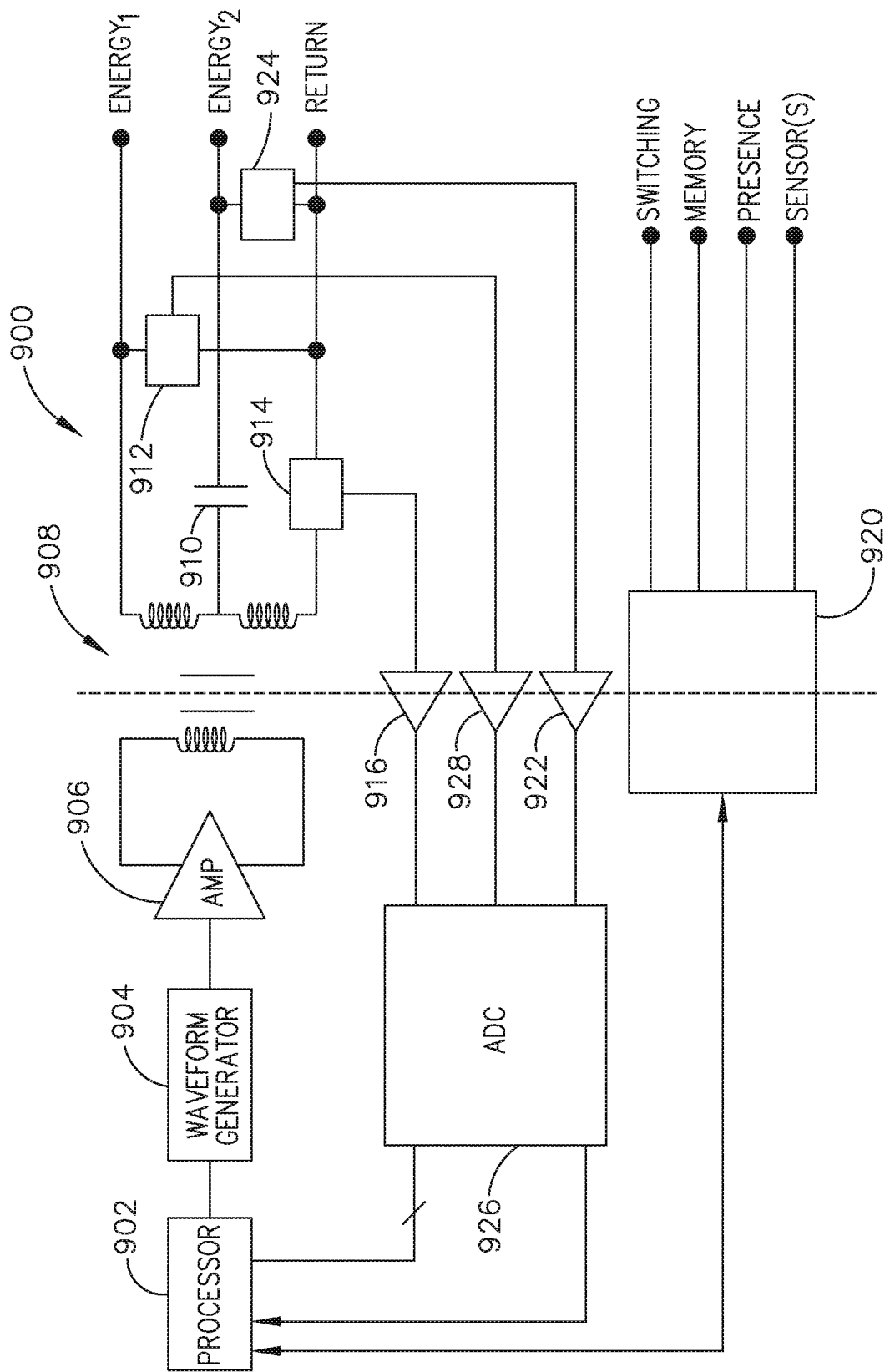
FIG. 59 illustrates an example of a generator, which is one form of the generator of FIG. 20, in accordance with at least one aspect of the present disclosure.

FIG. 59 illustrates an example of a generator 900, which is one form of the generator 800 (FIG. 58). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 59 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 59, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 59. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 41 and 48, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Situational Awareness

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g. a robotic arm and/or robotic surgical tool) that are connected to it and provide contextualized information or suggestions to the surgeon during the course of the surgical procedure.

Figure 60:
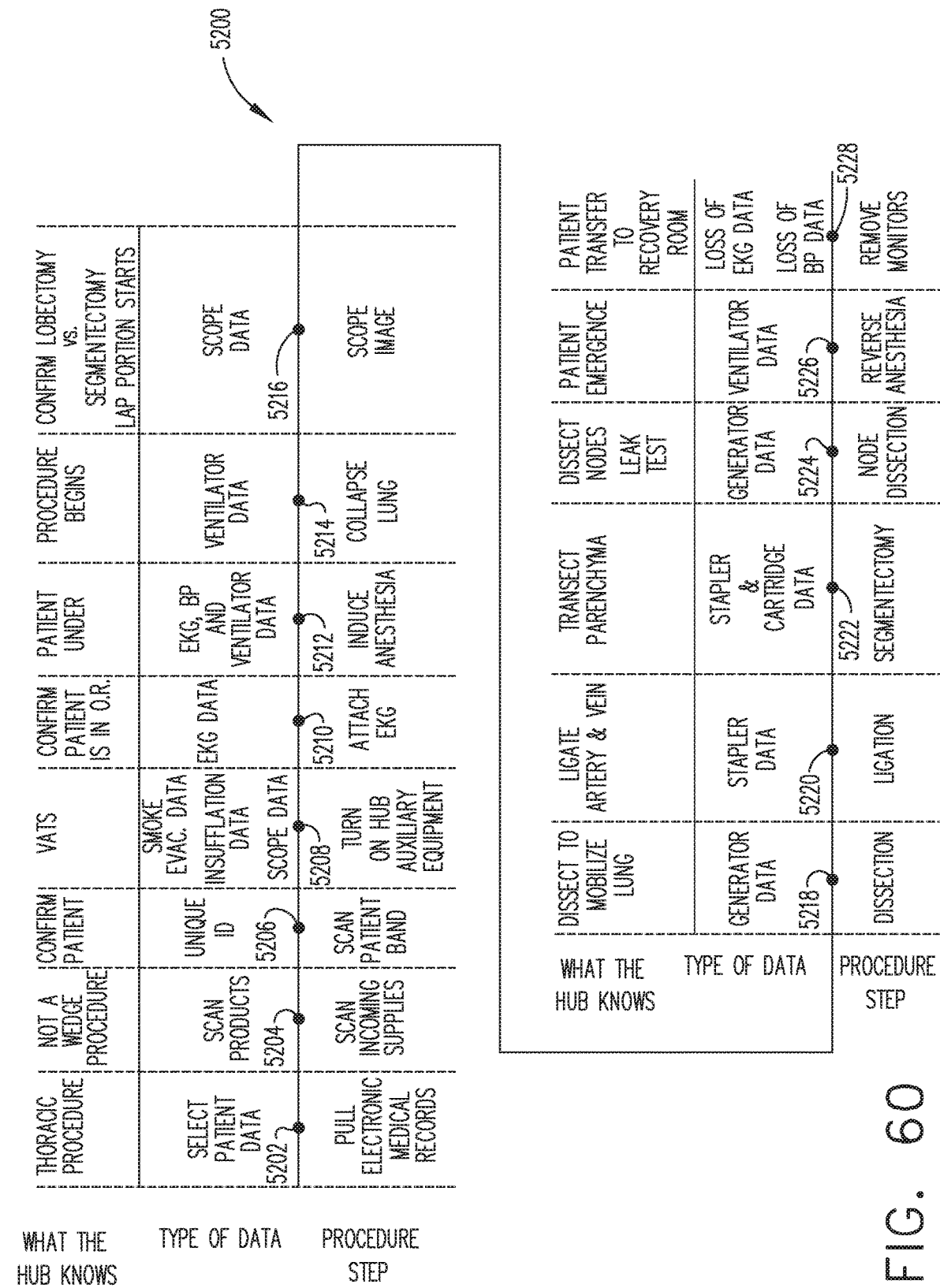
FIG. 60 is a timeline depicting situational awareness of a surgical hub, in accordance with one aspect of the present disclosure.

Referring now to FIG. 60, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's Electronic Medical Record (EMR) from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 40) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, the disclosure of which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

EXAMPLES

Various aspects of the subject matter described herein are set out in the following numbered examples.

Example 1

A surgical evacuation system comprising a pump, a motor operably coupled to the pump, a flow path fluidically coupled to the pump, and a sensor system. The sensor system comprises a first pressure sensor and a second pressure sensor. The first pressure sensor is positioned along the flow path. The second pressure sensor is positioned along the flow path upstream of the first pressure sensor. The surgical evacuation system further comprises a control circuit configured to determine a pressure differential between the first pressure sensor and the second pressure sensor. The control circuit is further configured to adjust an operational parameter of the motor based on the pressure differential.

Example 2

The surgical evacuation system of Example 1, further comprising a receptacle and a filter installed in the receptacle. The first pressure sensor is positioned downstream of the filter and the second pressure sensor is positioned upstream of the filter.

Example 3

The surgical evacuation system of Example 1 or 2, wherein the control circuit is configured to increase the speed of the motor when the pressure differential increases above a threshold amount.

Example 4

The surgical evacuation system of Example 1, 2, or 3, further comprising a fluid trap, wherein the first pressure sensor is positioned downstream of the fluid trap, and wherein the second pressure sensor is positioned upstream of the fluid trap.

Example 5

The surgical evacuation system of Example 4, wherein the pressure differential is indicative of the flow path relative to the fluid trap.

Example 6

The surgical evacuation system of Example 1, 2, 3, 4, or 5, further comprising a housing comprising an inlet and an outlet, wherein the flow path extends between the inlet and the outlet, wherein the first pressure sensor is positioned adjacent to the outlet, and wherein the second pressure sensor is positioned adjacent to the inlet.

Example 7

The surgical evacuation system of Example 1, 2, 3, 4, 5, or 6, wherein the control circuit is configured to maintain a suction load on the pump below a maximum suction load.

Example 8

The surgical evacuation system of Example 1, 2, 3, 4, 5, 6, or 7, wherein the control circuit comprises a processor communicatively coupled to the sensor system. The control circuit further comprises a memory communicatively coupled to the processor, wherein the memory stores instructions executable by the processor.

Example 9

A surgical evacuation system comprising a pump comprising a motor, a flow path fluidically coupled to the pump, and a sensor system. The sensor system comprises a first pressure sensor and a second pressure sensor. The first pressure sensor is positioned along the flow path to detect a first pressure. The second pressure sensor is positioned along the flow path upstream of the first pressure sensor to detect a second pressure. The surgical evacuation system further comprises a control circuit configured to determine a ratio of the second pressure to the first pressure and determine an operating condition of the surgical evacuation system based on the ratio.

Example 10

The surgical evacuation system of Example 9, wherein the control circuit is further configured to adjust an operational parameter of the motor based on the operating condition of the surgical evacuation system.

Example 11

The surgical evacuation system of Example 9 or 10, further comprising a receptacle and a filter installed in the receptacle. The first pressure sensor is positioned downstream of the filter. The second pressure sensor is positioned upstream of the filter.

Example 12

The surgical evacuation system of Example 9, 10, or 11, wherein the control circuit is further configured to increase the speed of the motor in proportion to the ratio.

Example 13

The surgical evacuation system of Example 9, 10, 11, or 12, further comprising a fluid trap, wherein the first pressure sensor is positioned downstream of the fluid trap, wherein the second pressure sensor is positioned upstream of the fluid trap, and wherein the operating condition corresponds to the flow path relative to the fluid trap.

Example 14

The surgical evacuation system of Example 9, 10, 11, 12, or 13, further comprising a housing comprising an inlet and an outlet, wherein the flow path extends between the inlet and the outlet, wherein the first pressure sensor is positioned adjacent to the outlet, wherein the second pressure sensor is positioned adjacent to the inlet, and wherein the control circuit is further configured to maintain a suction load on the pump below a maximum suction load.

Example 15

The surgical evacuation system of Example 9, 10, 11, 12, 13, or 14, wherein the control circuit comprises a processor communicatively coupled to the sensor system. The control circuit further comprises a memory communicatively coupled to the processor, wherein the memory stores instructions executable by the processor.

Example 16

A non-transitory computer readable medium storing computer readable instructions which, when executed, cause a machine to, receive a first signal from a first sensor positioned along a flow path through a surgical evacuation system, receive a second signal from a second sensor positioned along the flow path through the surgical evacuation system, determine an operating condition of the surgical evacuation system based on the first signal and the second signal, and adjust an operational parameter of the surgical evacuation system based on the operating condition.

Example 17

The non-transitory computer readable medium of Example 16, wherein the first sensor comprises a first pressure sensor, and wherein the second sensor comprises a second pressure sensor.

Example 18

The non-transitory computer readable medium of Example 16 or 17, wherein the operating condition corresponds to a state of a filtering system of the surgical evacuation system.

Example 19

The non-transitory computer readable medium Example 18, wherein the computer readable instructions, when executed, cause the machine to increase the speed of a pump motor for the surgical evacuation system when the state of the filtering system comprises a partially blocked state.

Example 20

The non-transitory computer readable medium of Example 16, 17, 18, or 19, wherein the computer readable instructions, when executed, cause the machine to redirect the flow path through the surgical evacuation system.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical evacuation system, comprising:
   a pump;
   a motor operably coupled to said pump;
   a flow path fluidically coupled to said pump;

a housing, comprising an inlet and an outlet, wherein said flow path extends between said inlet and said outlet, and wherein said pump and said motor are positioned within said housing;
a sensor system, comprising:
  a first pressure sensor positioned along said flow path; and
  a second pressure sensor positioned along said flow path upstream of said first pressure sensor; and
a control circuit configured to:
  determine a pressure differential between said first pressure sensor and said second pressure sensor;
  adjust a duty cycle of said motor based on the pressure differential; and
  transmit at least one surgical evacuation system parameter to a surgical hub, wherein the surgical hub is configured to aggregate data from a plurality of data sources comprising the control circuit and sources separate from the surgical evacuation system and is configured to display a plurality of parameters comprising the at least one surgical evacuation parameter.

2. The surgical evacuation system of claim 1, further comprising:
  a receptacle; and
  a filter installed in said receptacle, wherein said first pressure sensor is positioned downstream of said filter, and wherein said second pressure sensor is positioned upstream of said filter.

3. The surgical evacuation system of claim 2, wherein said control circuit is configured to increase the speed of said motor when the pressure differential increases above a threshold amount.

4. The surgical evacuation system of claim 1, further comprising a fluid trap, wherein said first pressure sensor is positioned downstream of said fluid trap, and wherein said second pressure sensor is positioned upstream of said fluid trap.

5. The surgical evacuation system of claim 4, wherein the pressure differential is indicative of said flow path relative to said fluid trap.

6. The surgical evacuation system of claim 1, wherein said first pressure sensor is positioned adjacent to said outlet, and wherein said second pressure sensor is positioned adjacent to said inlet.

7. The surgical evacuation system of claim 6, wherein said control circuit is configured to maintain a suction load on said pump below a maximum suction load.

8. The surgical evacuation system of claim 1, wherein said control circuit comprises:
  a processor communicatively coupled to said sensor system; and
  a memory communicatively coupled to said processor, wherein said memory stores instructions executable by said processor.

9. The surgical evacuation system of claim 1, wherein the control circuit is further configured to receive an input from the surgical hub.

10. The surgical evacuation system of claim 9, wherein the input is based on the aggregated data from the plurality of data sources.

11. A surgical evacuation system, comprising:
  a pump comprising a motor;
  a flow path fluidically coupled to said pump;
  a housing, comprising an inlet and an outlet, wherein said flow path extends between said inlet and said outlet, and wherein said pump is positioned within said housing;
  a sensor system, comprising:
    a first pressure sensor positioned along said flow path to detect a first pressure; and
    a second pressure sensor positioned along said flow path upstream of said first pressure sensor to detect a second pressure; and
  a control circuit configured to:
    determine a ratio of said second pressure to said first pressure;
    determine an operating condition of the surgical evacuation system based on said ratio; and
    transmit the operating condition to a surgical hub, wherein the surgical hub is configured to aggregate data from a plurality of data sources comprising the control circuit and sources separate from the surgical evacuation system and is configured to display a plurality of outputs comprising the operating condition.

12. The surgical evacuation system of claim 11, wherein said control circuit is further configured to adjust an operational parameter of said motor based on said operating condition of the surgical evacuation system.

13. The surgical evacuation system of claim 12, further comprising:
  a receptacle; and
  a filter installed in said receptacle, wherein said first pressure sensor is positioned downstream of said filter, and wherein said second pressure sensor is positioned upstream of said filter.

14. The surgical evacuation system of claim 13, wherein said control circuit is further configured to increase the speed of said motor in proportion to said ratio.

15. The surgical evacuation system of claim 11, further comprising a fluid trap, wherein said first pressure sensor is positioned downstream of said fluid trap, wherein said second pressure sensor is positioned upstream of said fluid trap, and wherein said operating condition corresponds to said flow path relative to said fluid trap.

16. The surgical evacuation system of claim 11, wherein said first pressure sensor is positioned adjacent to said outlet, wherein said second pressure sensor is positioned adjacent to said inlet, and wherein said control circuit is further configured to maintain a suction load on said pump below a maximum suction load.

17. The surgical evacuation system of claim 11, wherein said control circuit comprises:
  a processor communicatively coupled to said sensor system; and
  a memory communicatively coupled to said processor, wherein said memory stores instructions executable by said processor.

18. A non-transitory computer readable medium storing computer readable instructions which, when executed, cause a machine to:
  receive a first signal from a first sensor positioned along a flow path through a surgical evacuation system;
  receive a second signal from a second sensor positioned along the flow path through the surgical evacuation system;
  determine an efficiency ratio of the surgical evacuation system based on the first signal and the second signal;
  redirect the flow path internally through the surgical evacuation system;

adjust an operational parameter of a pump motor of the surgical evacuation system based on the efficiency ratio; and transmit the efficiency ratio to a surgical hub control circuit, wherein the surgical hub control circuit is configured to aggregate data from a plurality of data sources comprising the non-transitory computer readable medium and sources separate from the non-transitory computer readable medium and is configured to display a plurality of outputs comprising the efficiency ratio on a surgical hub display.

19. The non-transitory computer readable medium of claim 18, wherein the first sensor comprises a first pressure sensor, and wherein the second sensor comprises a second pressure sensor.

20. The non-transitory computer readable medium of claim 18, wherein the efficiency ratio corresponds to a state of a filtering system of the surgical evacuation system.

21. The non-transitory computer readable medium claim 20, wherein the computer readable instructions, when executed, cause the machine to increase the speed of the pump motor for the surgical evacuation system when the state of the filtering system comprises a partially blocked state.

* * * * *